(12) United States Patent
Lipkens et al.

(10) Patent No.: US 10,967,298 B2
(45) Date of Patent: Apr. 6, 2021

(54) DRIVER AND CONTROL FOR VARIABLE IMPEDENCE LOAD

(71) Applicant: FloDesign Sonics, Inc., Wilbraham, MA (US)

(72) Inventors: Bart Lipkens, Bloomfield, CT (US); Ronald Musiak, Westfield, MA (US); Dane Mealey, Somers, CT (US); John Artis, Santa Rosa, CA (US); Ali Shajii, Weston, MA (US)

(73) Assignee: FloDesign Sonics, Inc., Wilbraham, MA (US)

(*) Notice: Subject to any disclaimer, the term of this patent is extended or adjusted under 35 U.S.C. 154(b) by 34 days.

(21) Appl. No.: 15/872,984

(22) Filed: Jan. 16, 2018

(65) Prior Publication Data

US 2018/0207551 A1    Jul. 26, 2018

Related U.S. Application Data

(63) Continuation-in-part of application No. 15/621,691, filed on Jun. 13, 2017, now Pat. No. 10,350,514, (Continued)

(51) Int. Cl.
*B01D 17/04* (2006.01)
*B01D 17/06* (2006.01)
(Continued)

(52) U.S. Cl.
CPC ............ *B01D 17/04* (2013.01); *B01D 17/06* (2013.01); *B01D 21/00* (2013.01); *B01D 21/283* (2013.01)

(58) Field of Classification Search
CPC ...... B01D 29/115; B01D 37/00; B01D 29/52; B01D 29/865; B01D 2201/0415; B01D 2201/0446; B01D 2201/127; B01D 17/04
See application file for complete search history.

(56) References Cited

U.S. PATENT DOCUMENTS 2,473,971 A    6/1949 Ross
2,667,944 A    2/1954 Crites
(Continued)

FOREIGN PATENT DOCUMENTS

AU    2002236405    9/2002
CN    105 087 788 A    11/2015
(Continued)

OTHER PUBLICATIONS

Alvarez et al.; Shock Waves, vol. 17, No. 6, pp. 441-447, 2008.
(Continued)

*Primary Examiner* — Cameron J Allen
(74) *Attorney, Agent, or Firm* — FloDesign Sonics, Inc.

(57) ABSTRACT

An acoustic standing wave is utilized to separate components from a multi-component fluid, such as oil from an oil-water mixture, or cells entrained in a fluid, in a fluid flow scheme with an acoustophoresis device. For example, the flow scheme and device allows for trapping of the oil as the oil coalesces, agglomerates, and becomes more buoyant than the water. A driver and controller for the acoustophoretic device accommodate variable loading as the components are separated, thereby improving separation efficiency.

10 Claims, 80 Drawing Sheets

Related U.S. Application Data which is a continuation of application No. 15/000,573, filed on Jan. 19, 2016, now Pat. No. 9,675,902, which is a continuation of application No. 13/943,529, filed on Jul. 16, 2013, now Pat. No. 9,272,234, which is a continuation-in-part of application No. 13/844,754, filed on Mar. 15, 2013, now Pat. No. 10,040,011.

(60) Provisional application No. 61/754,792, filed on Jan. 21, 2013, provisional application No. 61/708,641, filed on Oct. 2, 2012, provisional application No. 61/611,159, filed on Mar. 15, 2012, provisional application No. 61/611,240, filed on Mar. 15, 2012, provisional application No. 62/446,356, filed on Jan. 13, 2017, provisional application No. 61/671,856, filed on Jul. 16, 2012.

(51) Int. Cl.
*B01D 21/00* (2006.01)
*B01D 21/28* (2006.01)

(56) References Cited

U.S. PATENT DOCUMENTS

| | | | |
|---|---|---|---|
| 3,372,370 | A | 3/1968 | Cyr |
| 3,555,311 | A | 1/1971 | Weber |
| 4,055,491 | A | 10/1977 | Porath-Furedi |
| 4,065,875 | A | 1/1978 | Srna |
| 4,118,649 | A | 10/1978 | Schwartzman et al. |
| 4,158,629 | A | 6/1979 | Sawyer |
| 4,165,273 | A | 8/1979 | Azarov et al. |
| 4,173,725 | A | 11/1979 | Asai et al. |
| 4,204,096 | A | 5/1980 | Barcus et al. |
| 4,254,661 | A | 3/1981 | Kossoff et al. |
| 4,320,659 | A | 3/1982 | Lynnworth et al. |
| 4,344,448 | A | 8/1982 | Potts |
| 4,398,325 | A | 8/1983 | Piaget et al. |
| 4,484,907 | A | 11/1984 | Sheeran, Jr. |
| 4,552,669 | A | 11/1985 | Sekellick |
| 4,666,595 | A | 5/1987 | Graham |
| 4,673,512 | A | 6/1987 | Schram |
| 4,699,588 | A | 10/1987 | Zinn et al. |
| 4,743,361 | A | 5/1988 | Schram |
| 4,759,775 | A | 7/1988 | Peterson et al. |
| 4,800,316 | A | 1/1989 | Wang |
| 4,821,838 | A | 4/1989 | Chen |
| 4,836,684 | A | 6/1989 | Javorik et al. |
| 4,860,993 | A | 8/1989 | Goode |
| 4,878,210 | A | 10/1989 | Mitome |
| 4,983,189 | A | 1/1991 | Peterson et al. |
| 5,059,811 | A | 10/1991 | King et al. |
| 5,062,965 | A | 11/1991 | Bernou et al. |
| 5,085,783 | A | 2/1992 | Feke et al. |
| 5,164,094 | A | 11/1992 | Stuckart |
| 5,225,089 | A | 7/1993 | Benes et al. |
| 5,371,429 | A | 12/1994 | Manna |
| 5,395,592 | A | 3/1995 | Bolleman et al. |
| 5,431,817 | A | 7/1995 | Braatz et al. |
| 5,443,985 | A | 8/1995 | Lu et al. |
| 5,452,267 | A | 9/1995 | Spevak |
| 5,475,486 | A | 12/1995 | Paoli |
| 5,484,537 | A | 1/1996 | Whitworth |
| 5,527,460 | A | 6/1996 | Trampler et al. |
| 5,560,362 | A | 10/1996 | Sliwa, Jr. et al. |
| 5,562,823 | A | 10/1996 | Reeves |
| 5,594,165 | A | 1/1997 | Madanshetty |
| 5,604,301 | A | 2/1997 | Mountford et al. |
| 5,626,767 | A | 5/1997 | Trampler et al. |
| 5,688,405 | A | 11/1997 | Dickinson et al. |
| 5,711,888 | A | 1/1998 | Trampler et al. |
| 5,779,911 | A * | 7/1998 | Haug ............... B01D 61/12 210/143 |
| 5,831,166 | A | 11/1998 | Kozuka et al. |
| 5,834,871 | A | 11/1998 | Puskas |
| 5,902,489 | A | 5/1999 | Yasuda et al. |
| 5,912,182 | A | 6/1999 | Coakley et al. |
| 5,947,299 | A | 9/1999 | Vazquez et al. |
| 5,951,456 | A | 9/1999 | Scott |
| 6,029,518 | A * | 2/2000 | Oeftering ............ B01D 17/041 210/748.02 |
| 6,090,295 | A | 6/2000 | Raghavarao et al. |
| 6,161,435 | A * | 12/2000 | Bond ............... B01D 61/12 210/785 |
| 6,166,231 | A | 12/2000 | Hoeksema |
| 6,216,538 | B1 | 4/2001 | Yasuda et al. |
| 6,205,848 | B1 | 6/2001 | Faber et al. |
| 6,273,262 | B1 | 8/2001 | Yasuda et al. |
| 6,286,370 | B1 * | 9/2001 | Sinha ............... G01N 5/02 73/579 |
| 6,332,541 | B1 | 12/2001 | Coakley et al. |
| 6,391,653 | B1 | 5/2002 | Letcher et al. |
| 6,475,151 | B2 | 11/2002 | Koger et al. |
| 6,482,327 | B1 | 11/2002 | Mori et al. |
| 6,487,095 | B1 | 11/2002 | Malik et al. |
| 6,592,821 | B1 | 7/2003 | Wada et al. |
| 6,641,708 | B1 | 11/2003 | Becker et al. |
| 6,649,069 | B2 | 11/2003 | DeAngelis |
| 6,699,711 | B1 | 3/2004 | Hahn et al. |
| 6,727,451 | B1 | 4/2004 | Fuhr et al. |
| 6,763,722 | B2 | 7/2004 | Fjield et al. |
| 6,881,314 | B1 | 4/2005 | Wang et al. |
| 6,929,750 | B2 | 8/2005 | Laurell et al. |
| 6,936,151 | B1 | 8/2005 | Lock et al. |
| 7,008,540 | B1 | 3/2006 | Weavers et al. |
| 7,010,979 | B2 | 3/2006 | Scott |
| 7,061,163 | B2 | 6/2006 | Nagahara et al. |
| 7,081,192 | B1 | 7/2006 | Wang et al. |
| 7,093,482 | B2 | 8/2006 | Berndt |
| 7,108,137 | B2 | 9/2006 | Lal et al. |
| 7,150,779 | B2 | 12/2006 | Meegan, Jr. |
| 7,186,502 | B2 | 3/2007 | Vesey |
| 7,191,787 | B1 | 3/2007 | Redeker et al. |
| 7,322,431 | B2 | 1/2008 | Ratcliff |
| 7,331,233 | B2 | 2/2008 | Scott |
| 7,340,957 | B2 | 3/2008 | Kaduchak et al. |
| 7,373,805 | B2 | 5/2008 | Hawkes et al. |
| 7,541,166 | B2 | 6/2009 | Belgrader et al. |
| 7,601,267 | B2 | 10/2009 | Haake et al. |
| 7,673,516 | B2 | 3/2010 | Janssen et al. |
| 7,674,630 | B2 | 3/2010 | Siversson |
| 7,837,040 | B2 | 11/2010 | Ward et al. |
| 7,846,382 | B2 | 12/2010 | Strand et al. |
| 7,968,049 | B2 | 6/2011 | Takahashi et al. |
| 8,075,786 | B2 | 12/2011 | Bagajewicz |
| 8,080,202 | B2 | 12/2011 | Takahashi et al. |
| 8,134,705 | B2 | 3/2012 | Kaduchak et al. |
| 8,256,076 | B1 | 9/2012 | Feller |
| 8,263,407 | B2 * | 9/2012 | Goddard ............ G01N 15/1404 210/748.01 |
| 8,266,950 | B2 | 9/2012 | Kaduchak et al. |
| 8,273,253 | B2 | 9/2012 | Curran |
| 8,273,302 | B2 | 9/2012 | Takahashi et al. |
| 8,309,408 | B2 | 11/2012 | Ward et al. |
| 8,319,398 | B2 | 11/2012 | Vivek et al. |
| 8,334,133 | B2 | 12/2012 | Fedorov et al. |
| 8,387,803 | B2 | 3/2013 | Thorslund et al. |
| 8,592,204 | B2 | 11/2013 | Lipkens et al. |
| 8,679,338 | B2 | 3/2014 | Rietman et al. |
| 8,691,145 | B2 | 4/2014 | Dionne et al. |
| 8,873,051 | B2 | 10/2014 | Kaduchak et al. |
| 8,889,388 | B2 | 11/2014 | Wang et al. |
| 9,272,234 | B2 | 3/2016 | Lipkens et al. |
| 9,357,293 | B2 | 5/2016 | Claussen |
| 9,365,815 | B2 | 6/2016 | Miyazaki et al. |
| 9,368,110 | B2 | 6/2016 | Hershey et al. |
| 9,388,363 | B2 | 7/2016 | Goodson et al. |
| 9,391,542 | B2 | 7/2016 | Wischnewskiy |
| 9,403,114 | B2 | 8/2016 | Kusuura |
| 9,410,256 | B2 | 8/2016 | Dionne et al. |
| 9,416,344 | B2 | 8/2016 | Lipkens et al. |
| 9,421,553 | B2 | 8/2016 | Dionne et al. |

(56) References Cited

U.S. PATENT DOCUMENTS

| | | |
|---|---|---|
| 9,422,328 B2 | 8/2016 | Kennedy, III et al. |
| 9,457,139 B2 | 10/2016 | Ward et al. |
| 9,457,302 B2 | 10/2016 | Lipkens et al. |
| 9,458,450 B2 | 10/2016 | Lipkens et al. |
| 9,464,303 B2 | 10/2016 | Burke |
| 9,476,855 B2 | 10/2016 | Ward et al. |
| 9,480,375 B2 | 11/2016 | Marshall et al. |
| 9,480,935 B2 | 11/2016 | Mariella, Jr. et al. |
| 9,488,621 B2 | 11/2016 | Kaduchak et al. |
| 9,504,780 B2 | 11/2016 | Spain et al. |
| 9,512,395 B2 | 12/2016 | Lipkens et al. |
| 9,513,205 B2 | 12/2016 | Yu et al. |
| 9,514,924 B2 | 12/2016 | Morris et al. |
| 9,517,474 B2 | 12/2016 | Mao et al. |
| 9,532,769 B2 | 1/2017 | Dayton et al. |
| 9,533,241 B2 | 1/2017 | Presz, Jr. et al. |
| 9,550,134 B2 | 1/2017 | Lipkens et al. |
| 9,550,998 B2 | 1/2017 | Williams |
| 9,556,271 B2 | 1/2017 | Blumberg et al. |
| 9,556,411 B2 | 1/2017 | Lipkens et al. |
| 9,566,352 B2 | 2/2017 | Holmes et al. |
| 9,567,559 B2 | 2/2017 | Lipkens et al. |
| 9,567,609 B2 | 2/2017 | Paschon et al. |
| 9,572,897 B2 | 2/2017 | Bancel et al. |
| 9,573,995 B2 | 2/2017 | Schurpf et al. |
| 9,574,014 B2 | 2/2017 | Williams et al. |
| 9,580,500 B2 | 2/2017 | Schurpf et al. |
| 9,587,003 B2 | 3/2017 | Bancel et al. |
| 9,597,357 B2 | 3/2017 | Gregory et al. |
| 9,597,380 B2 | 3/2017 | Chakraborty et al. |
| 9,605,074 B2 | 3/2017 | Shah |
| 9,605,266 B2 | 3/2017 | Rossi et al. |
| 9,606,086 B2 | 3/2017 | Ding et al. |
| 9,608,547 B2 | 3/2017 | Ding et al. |
| 9,611,465 B2 | 4/2017 | Handa et al. |
| 9,616,090 B2 | 4/2017 | Conway et al. |
| 9,623,348 B2 | 4/2017 | McCarthy et al. |
| 9,629,877 B2 | 4/2017 | Cooper et al. |
| D787,630 S | 5/2017 | Lipkens et al. |
| 9,644,180 B2 | 5/2017 | Kahvejian et al. |
| 9,645,060 B2 | 5/2017 | Fiering |
| 9,656,263 B2 | 5/2017 | Laurell et al. |
| 9,657,290 B2 | 5/2017 | Dimov et al. |
| 9,662,375 B2 | 5/2017 | Jensen et al. |
| 9,663,756 B1 | 5/2017 | Lipkens et al. |
| 9,670,477 B2 | 6/2017 | Lipkens et al. |
| 9,670,938 B2 | 6/2017 | Beliavsky |
| 9,675,668 B2 | 6/2017 | Bancel et al. |
| 9,675,902 B2 | 6/2017 | Lipkens et al. |
| 9,675,906 B2 | 6/2017 | Lipkens et al. |
| 9,677,055 B2 | 6/2017 | Jones et al. |
| 9,685,155 B2 | 6/2017 | Hershey et al. |
| 9,686,096 B2 | 6/2017 | Lipkens et al. |
| 9,688,958 B2 | 6/2017 | Kennedy, III et al. |
| 9,689,234 B2 | 6/2017 | Gregory et al. |
| 9,689,802 B2 | 6/2017 | Caseres et al. |
| 9,695,063 B2 | 7/2017 | Rietman et al. |
| 9,695,442 B2 | 7/2017 | Guschin et al. |
| 9,810,665 B2 | 11/2017 | Fernald et al. |
| 9,833,763 B2 | 12/2017 | Fernald et al. |
| 9,869,659 B2 | 1/2018 | Buckland et al. |
| 9,872,900 B2 | 1/2018 | Ciaramella et al. |
| 9,873,126 B2 | 1/2018 | Mao et al. |
| 9,873,894 B2 | 1/2018 | Conway et al. |
| 9,878,056 B2 | 1/2018 | Bancel et al. |
| 9,878,536 B2 | 1/2018 | Foresti et al. |
| 9,879,087 B2 | 1/2018 | DeSander et al. |
| 9,990,297 B2 | 1/2018 | Conway et al. |
| 9,907,846 B2 | 3/2018 | Morein et al. |
| 9,908,288 B2 | 3/2018 | Harkness |
| 9,909,117 B2 | 3/2018 | Kaduchak |
| 9,909,313 B1 | 3/2018 | Grubbs |
| 9,913,656 B2 | 3/2018 | Stulen |
| 9,913,866 B2 | 3/2018 | O'Shea et al. |
| 9,925,277 B2 | 3/2018 | Almarsson et al. |
| 9,926,382 B2 | 3/2018 | Fischer et al. |
| 9,937,207 B2 | 4/2018 | Gregory et al. |
| 9,938,390 B2 | 4/2018 | Storti et al. |
| 9,943,599 B2 | 4/2018 | Gehl et al. |
| 9,944,702 B2 | 4/2018 | Galetto |
| 9,944,709 B2 | 4/2018 | Galetto |
| 9,947,431 B2 | 4/2018 | El-Zahab |
| 9,974,898 B2 | 5/2018 | Spain et al. |
| 2002/0038662 A1 | 4/2002 | Schuler et al. |
| 2002/0134734 A1 | 9/2002 | Campbell et al. |
| 2003/0015035 A1 | 1/2003 | Kaduchak et al. |
| 2003/0028108 A1 | 2/2003 | Miller et al. |
| 2003/0195496 A1 | 10/2003 | Maguire |
| 2003/0209500 A1 | 11/2003 | Kock et al. |
| 2003/0230535 A1 | 12/2003 | Affeld et al. |
| 2004/0016699 A1 | 1/2004 | Bayevsky |
| 2004/0035208 A1 | 2/2004 | Diaz et al. |
| 2004/0057866 A1 | 3/2004 | Zumeris et al. |
| 2004/0112841 A1 | 6/2004 | Scott |
| 2004/0124155 A1 | 7/2004 | Meegan, Jr. |
| 2004/0149039 A1 | 8/2004 | Cardelius |
| 2005/0031499 A1 | 2/2005 | Meier |
| 2005/0121269 A1 | 6/2005 | Namduri |
| 2005/0145567 A1 | 7/2005 | Quintel et al. |
| 2005/0196725 A1 | 9/2005 | Fu |
| 2006/0037915 A1 | 2/2006 | Strand et al. |
| 2006/0037916 A1 | 2/2006 | Trampler |
| 2006/0050615 A1 | 3/2006 | Swisher |
| 2007/0053795 A1 | 3/2007 | Laugharn, Jr. et al. |
| 2007/0138108 A1 | 6/2007 | Hadfield et al. |
| 2007/0224676 A1 | 9/2007 | Haq |
| 2007/0267351 A1 | 11/2007 | Roach et al. |
| 2007/0272618 A1 | 11/2007 | Gou et al. |
| 2007/0284299 A1 | 12/2007 | Xu et al. |
| 2008/0011693 A1 | 1/2008 | Li et al. |
| 2008/0067128 A1 | 3/2008 | Hoyos et al. |
| 2008/0105625 A1 | 5/2008 | Rosenberg et al. |
| 2008/0181838 A1 | 7/2008 | Kluck |
| 2008/0217259 A1 | 9/2008 | Siversson |
| 2008/0245709 A1 | 10/2008 | Kaduchak et al. |
| 2008/0245745 A1 | 10/2008 | Ward et al. |
| 2008/0264716 A1 | 10/2008 | Kuiper et al. |
| 2008/0272034 A1 | 11/2008 | Ferren et al. |
| 2008/0272065 A1 | 11/2008 | Johnson |
| 2008/0316866 A1 | 12/2008 | Goodemote et al. |
| 2009/0029870 A1 | 1/2009 | Ward et al. |
| 2009/0048805 A1 | 2/2009 | Kaduchak et al. |
| 2009/0053686 A1 | 2/2009 | Ward et al. |
| 2009/0087492 A1 | 4/2009 | Johnson et al. |
| 2009/0098027 A1 | 4/2009 | Tabata et al. |
| 2009/0104594 A1 | 4/2009 | Webb |
| 2009/0126481 A1 | 5/2009 | Burris |
| 2009/0178716 A1 | 7/2009 | Kaduchak et al. |
| 2009/0194420 A1 | 8/2009 | Mariella, Jr. et al. |
| 2009/0227042 A1 | 9/2009 | Gauer et al. |
| 2009/0045107 A1 | 12/2009 | Ward et al. |
| 2009/0295505 A1 | 12/2009 | Mohammadi et al. |
| 2010/0000945 A1 | 1/2010 | Gavalas |
| 2010/0078323 A1 | 4/2010 | Takahashi et al. |
| 2010/0078384 A1 | 4/2010 | Yang |
| 2010/0124142 A1 | 5/2010 | Laugharn et al. |
| 2010/0139377 A1 | 6/2010 | Huang et al. |
| 2010/0192693 A1 | 8/2010 | Mudge et al. |
| 2010/0193407 A1 | 8/2010 | Steinberg et al. |
| 2010/0206818 A1 | 8/2010 | Leong et al. |
| 2010/0255573 A1 | 10/2010 | Bond et al. |
| 2010/0261918 A1 | 10/2010 | Chianelli et al. |
| 2010/0317088 A1 | 12/2010 | Radaelli et al. |
| 2010/0323342 A1 | 12/2010 | Gonzalez Gomez et al. |
| 2010/0330633 A1 | 12/2010 | Walther et al. |
| 2011/0003350 A1 | 1/2011 | Schafran et al. |
| 2011/0024335 A1 | 2/2011 | Ward et al. |
| 2011/0092726 A1 | 4/2011 | Clarke |
| 2011/0095225 A1 | 4/2011 | Eckelberry et al. |
| 2011/0123392 A1* | 5/2011 | Dionne .............. A61L 2/025 422/1 |
| 2011/0125024 A1 | 5/2011 | Mueller |
| 2011/0146678 A1 | 6/2011 | Ruecroft et al. |
| 2011/0154890 A1 | 6/2011 | Holm et al. |

(56) References Cited

U.S. PATENT DOCUMENTS

| | | |
|---|---|---|
| 2011/0166551 A1 | 7/2011 | Schafer |
| 2011/0189732 A1 | 8/2011 | Weinand et al. |
| 2011/0207225 A1 | 8/2011 | Mehta et al. |
| 2011/0245750 A1 | 10/2011 | Lynch et al. |
| 2011/0262990 A1 | 10/2011 | Wang et al. |
| 2011/0278218 A1 | 11/2011 | Dionne et al. |
| 2011/0281319 A1 | 11/2011 | Swayze et al. |
| 2011/0309020 A1 | 12/2011 | Rietman et al. |
| 2012/0088295 A1 | 4/2012 | Yasuda et al. |
| 2012/0145633 A1 | 6/2012 | Polizzotti et al. |
| 2012/0163126 A1 | 6/2012 | Campbell et al. |
| 2012/0175012 A1 | 7/2012 | Goodwin et al. |
| 2012/0231504 A1 | 9/2012 | Niazi |
| 2012/0267288 A1 | 10/2012 | Chen et al. |
| 2012/0325727 A1 | 12/2012 | Dionne et al. |
| 2012/0325747 A1 | 12/2012 | Reitman et al. |
| 2012/0328477 A1 | 12/2012 | Dionne et al. |
| 2012/0329122 A1 | 12/2012 | Lipkens et al. |
| 2013/0017577 A1 | 1/2013 | Arunakumari et al. |
| 2013/0115664 A1 | 5/2013 | Khanna et al. |
| 2013/0175226 A1 | 7/2013 | Coussios et al. |
| 2013/0217113 A1 | 8/2013 | Srinivasan et al. |
| 2013/0277316 A1 | 10/2013 | Dutra et al. |
| 2013/0277317 A1 | 10/2013 | LoRicco et al. |
| 2013/0284271 A1 | 10/2013 | Lipkens et al. |
| 2013/0292319 A1* | 11/2013 | Fulkerson ............ B01D 61/18 210/321.78 |
| 2014/0011240 A1 | 1/2014 | Lipkens et al. |
| 2014/0017758 A1 | 1/2014 | Kniep et al. |
| 2014/0102947 A1 | 4/2014 | Baym et al. |
| 2014/0141413 A1 | 5/2014 | Laugham, Jr. et al. |
| 2014/0154795 A1 | 6/2014 | Lipkens et al. |
| 2014/0319077 A1 | 10/2014 | Lipkens et al. |
| 2014/0329997 A1 | 11/2014 | Kennedy, III et al. |
| 2014/0377834 A1 | 12/2014 | Presz, Jr. et al. |
| 2015/0053561 A1 | 2/2015 | Ward et al. |
| 2015/0060581 A1 | 3/2015 | Santos et al. |
| 2015/0252317 A1 | 9/2015 | Lipkens et al. |
| 2015/0274550 A1 | 10/2015 | Lipkens et al. |
| 2015/0321129 A1 | 11/2015 | Lipkens et al. |
| 2016/0060615 A1 | 3/2016 | Walther et al. |
| 2016/0089620 A1 | 3/2016 | Lipkens et al. |
| 2016/0102284 A1 | 4/2016 | Lipkens et al. |
| 2016/0121331 A1 | 5/2016 | Kapur et al. |
| 2016/0123858 A1 | 5/2016 | Kapur et al. |
| 2016/0145563 A1 | 5/2016 | Berteau et al. |
| 2016/0153249 A1 | 6/2016 | Mitri |
| 2016/0175198 A1 | 6/2016 | Warner et al. |
| 2016/0184790 A1 | 6/2016 | Sinha et al. |
| 2016/0202237 A1 | 7/2016 | Zeng et al. |
| 2016/0208213 A1 | 7/2016 | Doyle et al. |
| 2016/0230168 A1 | 8/2016 | Kaduchak et al. |
| 2016/0237110 A1 | 8/2016 | Gilmanshin et al. |
| 2016/0237394 A1 | 8/2016 | Lipkens et al. |
| 2016/0237395 A1 | 8/2016 | Lipkens et al. |
| 2016/0252445 A1 | 9/2016 | Yu et al. |
| 2016/0279540 A1 | 9/2016 | Presz, Jr. et al. |
| 2016/0279551 A1 | 9/2016 | Foucault |
| 2016/0312168 A1 | 10/2016 | Pizzi |
| 2016/0314868 A1 | 10/2016 | El-Zahab et al. |
| 2016/0319270 A1 | 11/2016 | Lipkens et al. |
| 2016/0325039 A1 | 11/2016 | Leach et al. |
| 2016/0325206 A1 | 11/2016 | Presz, Jr. et al. |
| 2016/0332159 A1 | 11/2016 | Dual et al. |
| 2016/0339360 A1 | 11/2016 | Lipkens et al. |
| 2016/0347628 A1 | 12/2016 | Dionne et al. |
| 2016/0355776 A1 | 12/2016 | Lipkens et al. |
| 2016/0361670 A1 | 12/2016 | Lipkens et al. |
| 2016/0363579 A1 | 12/2016 | Lipkens et al. |
| 2016/0368000 A1 | 12/2016 | Dionne et al. |
| 2016/0369236 A1 | 12/2016 | Kennedy, III et al. |
| 2016/0370326 A9 | 12/2016 | Kaduchak et al. |
| 2017/0000413 A1 | 1/2017 | Clymer et al. |
| 2017/0002060 A1 | 1/2017 | Bolen et al. |
| 2017/0002839 A1 | 1/2017 | Burkland et al. |
| 2017/0007679 A1 | 1/2017 | Maeder et al. |
| 2017/0008029 A1 | 1/2017 | Lipkens et al. |
| 2017/0016025 A1 | 1/2017 | Poirot et al. |
| 2017/0016027 A1 | 1/2017 | Lee et al. |
| 2017/0020926 A1 | 1/2017 | Mata-Fink et al. |
| 2017/0029802 A1 | 2/2017 | Lipkens et al. |
| 2017/0035866 A1 | 2/2017 | Poirot et al. |
| 2017/0037386 A1 | 2/2017 | Jones et al. |
| 2017/0038288 A1 | 2/2017 | Ward et al. |
| 2017/0042770 A1 | 2/2017 | Warner et al. |
| 2017/0044517 A1 | 2/2017 | Lipkens et al. |
| 2017/0049949 A1 | 2/2017 | Gilmanshin et al. |
| 2017/0056448 A1 | 3/2017 | Glick et al. |
| 2017/0058036 A1 | 3/2017 | Ruiz-Opazo et al. |
| 2017/0065636 A1 | 3/2017 | Moriarty et al. |
| 2017/0066015 A1 | 3/2017 | Lipkens et al. |
| 2017/0067021 A1 | 3/2017 | Moriarty et al. |
| 2017/0067022 A1 | 3/2017 | Poirot et al. |
| 2017/0072405 A1 | 3/2017 | Mao et al. |
| 2017/0073406 A1 | 3/2017 | Schurpf et al. |
| 2017/0073423 A1 | 3/2017 | Juillerat et al. |
| 2017/0073638 A1 | 3/2017 | Campana et al. |
| 2017/0073684 A1 | 3/2017 | Rossi et al. |
| 2017/0073685 A1 | 3/2017 | Maeder et al. |
| 2017/0080070 A1 | 3/2017 | Weinschenk et al. |
| 2017/0080423 A1 | 3/2017 | Dauson et al. |
| 2017/0081629 A1 | 3/2017 | Lipkens et al. |
| 2017/0088809 A1 | 3/2017 | Lipkens et al. |
| 2017/0088844 A1 | 3/2017 | Williams |
| 2017/0089826 A1 | 3/2017 | Lin |
| 2017/0096455 A1 | 4/2017 | Baric et al. |
| 2017/0107536 A1 | 4/2017 | Zhang et al. |
| 2017/0107539 A1 | 4/2017 | Yu et al. |
| 2017/0119820 A1 | 5/2017 | Moriarty et al. |
| 2017/0128523 A1 | 5/2017 | Ghatnekar et al. |
| 2017/0128857 A1 | 5/2017 | Lipkens et al. |
| 2017/0130200 A1 | 5/2017 | Moriarty et al. |
| 2017/0136168 A1 | 5/2017 | Spain et al. |
| 2017/0137491 A1 | 5/2017 | Matheson et al. |
| 2017/0137774 A1 | 5/2017 | Lipkens et al. |
| 2017/0137775 A1 | 5/2017 | Lipkens et al. |
| 2017/0137802 A1 | 5/2017 | Lipkens et al. |
| 2017/0145094 A1 | 5/2017 | Galetto |
| 2017/0151345 A1 | 6/2017 | Shah |
| 2017/0152502 A1 | 6/2017 | Scharenberg et al. |
| 2017/0152503 A1 | 6/2017 | Scharenberg et al. |
| 2017/0152504 A1 | 6/2017 | Scharenberg et al. |
| 2017/0152505 A1 | 6/2017 | Scharenberg et al. |
| 2017/0152527 A1 | 6/2017 | Paschon et al. |
| 2017/0152528 A1 | 6/2017 | Zhang et al. |
| 2017/0158749 A1 | 6/2017 | Cooper |
| 2017/0159005 A1 | 6/2017 | Lipkens et al. |
| 2017/0159007 A1 | 6/2017 | Lipkens et al. |
| 2017/0166860 A1 | 6/2017 | Presz, Jr. et al. |
| 2017/0166877 A1 | 6/2017 | Bayle et al. |
| 2017/0166878 A9 | 6/2017 | Thanos et al. |
| 2017/0166903 A1 | 6/2017 | Zhang et al. |
| 2017/0173080 A1 | 6/2017 | Lee et al. |
| 2017/0173128 A1 | 6/2017 | Hoge et al. |
| 2017/0173498 A9 | 6/2017 | Lipkens et al. |
| 2017/0175073 A1 | 6/2017 | Lipkens et al. |
| 2017/0175125 A1 | 6/2017 | Welstead et al. |
| 2017/0175139 A1 | 6/2017 | Wu et al. |
| 2017/0175144 A1 | 6/2017 | Zhang et al. |
| 2017/0175509 A1 | 6/2017 | Abdel-Fattah et al. |
| 2017/0175720 A1 | 6/2017 | Tang et al. |
| 2017/0183390 A1 | 6/2017 | Springer et al. |
| 2017/0183413 A1 | 6/2017 | Galetto |
| 2017/0183418 A1 | 6/2017 | Galetto |
| 2017/0183420 A1 | 6/2017 | Gregory et al. |
| 2017/0184486 A1 | 6/2017 | Mach et al. |
| 2017/0189450 A1 | 7/2017 | Conway et al. |
| 2017/0190767 A1 | 7/2017 | Schurpf et al. |
| 2017/0191022 A1 | 7/2017 | Lipkens et al. |
| 2017/0232439 A1 | 8/2017 | Suresh et al. |
| 2017/0374730 A1 | 12/2017 | Flores |
| 2018/0000311 A1 | 1/2018 | Lipkens et al. |
| 2018/0000870 A1 | 1/2018 | Britt |
| 2018/0000910 A1 | 1/2018 | Chakraborty et al. |

(56) References Cited

U.S. PATENT DOCUMENTS

| | | |
|---|---|---|
| 2018/0008707 A1 | 1/2018 | Bussmer et al. |
| 2018/0009158 A1 | 1/2018 | Harkness et al. |
| 2018/0009888 A9 | 1/2018 | Baumeister et al. |
| 2018/0009895 A1 | 1/2018 | Smith et al. |
| 2018/0010085 A1 | 1/2018 | Lipkens et al. |
| 2018/0010117 A1 | 1/2018 | Paschon et al. |
| 2018/0014846 A1 | 1/2018 | Rhee |
| 2018/0015128 A1 | 1/2018 | Britt |
| 2018/0015392 A1 | 1/2018 | Lipkens et al. |
| 2018/0016570 A1 | 1/2018 | Lipkens et al. |
| 2018/0016572 A1 | 1/2018 | Tang |
| 2018/0020295 A1 | 1/2018 | Pander et al. |
| 2018/0021379 A1 | 1/2018 | Galetto et al. |
| 2018/0022798 A1 | 1/2018 | Shurpf et al. |
| 2018/0028683 A1 | 2/2018 | Wong et al. |
| 2018/0043473 A1 | 2/2018 | Helvajian et al. |
| 2018/0049767 A1 | 2/2018 | Gee et al. |
| 2018/0051089 A1 | 2/2018 | Galettto et al. |
| 2018/0051265 A1 | 2/2018 | Cooper |
| 2018/0052095 A1 | 2/2018 | Cumbo et al. |
| 2018/0052147 A1 | 2/2018 | Zeng |
| 2018/0055529 A1 | 3/2018 | Messerly et al. |
| 2018/0055530 A1 | 3/2018 | Messerly et al. |
| 2018/0055531 A1 | 3/2018 | Messerly et al. |
| 2018/0055532 A1 | 3/2018 | Messerly et al. |
| 2018/0055997 A1 | 3/2018 | Cabrera et al. |
| 2018/0056095 A1 | 3/2018 | Messerly et al. |
| 2018/0057810 A1 | 3/2018 | Zhang et al. |
| 2018/0058439 A1 | 3/2018 | Locke et al. |
| 2018/0066223 A1 | 3/2018 | Lim |
| 2018/0066224 A1 | 3/2018 | Lipkens et al. |
| 2018/0066242 A1 | 3/2018 | Zhang |
| 2018/0067044 A1 | 3/2018 | Kaduchak et al. |
| 2018/0071363 A1 | 3/2018 | Ghatnekar et al. |
| 2018/0071981 A1 | 3/2018 | Collino et al. |
| 2018/0078268 A1 | 3/2018 | Messerly |
| 2018/0080026 A1 | 3/2018 | Rossi et al. |
| 2018/0085743 A1 | 3/2018 | Yavorsky et al. |
| 2018/0087044 A1 | 3/2018 | Lipkens et al. |
| 2018/0088083 A1 | 3/2018 | Sinha |
| 2018/0092338 A1 | 4/2018 | Hering et al. |
| 2018/0092660 A1 | 4/2018 | Ethicon |
| 2018/0094022 A1 | 4/2018 | Bracewell et al. |
| 2018/0095067 A1 | 4/2018 | Huff et al. |
| 2018/0098785 A1 | 4/2018 | Price et al. |
| 2018/0100134 A1 | 4/2018 | Lim |
| 2018/0100204 A1 | 4/2018 | O'Shea |
| 2018/0130491 A1 | 5/2018 | Mathur |

FOREIGN PATENT DOCUMENTS

| | | |
|---|---|---|
| CN | 104722106 B | 4/2016 |
| DE | 30 27 433 A1 | 2/1982 |
| DE | 32 18 488 A1 | 11/1983 |
| DE | 196 48 519 A1 | 6/1998 |
| DE | 103 19 467 B3 | 7/2004 |
| DE | 10 2008 006 5 | 9/2008 |
| DE | 10 2014 206 823 A1 | 10/2015 |
| EP | 0 292 470 B1 | 11/1988 |
| EP | 0 167 406 B1 | 7/1991 |
| EP | 0 641 606 | 3/1995 |
| EP | 1 175 931 A1 | 1/2002 |
| EP | 1 254 669 B1 | 11/2002 |
| EP | 1 308 724 A2 | 5/2003 |
| EP | 2 209 545 | 7/2010 |
| EP | 270152 A1 | 1/2018 |
| EP | 2419511 | 1/2018 |
| EP | 3068888 | 1/2018 |
| EP | 3257600 | 1/2018 |
| EP | 3274453 | 1/2018 |
| EP | 3274454 | 1/2018 |
| EP | 3275894 | 1/2018 |
| EP | 278108 | 2/2018 |
| EP | 3279315 | 2/2018 |
| EP | 3286214 | 2/2018 |
| EP | 2289535 | 3/2018 |
| EP | 2545068 | 3/2018 |
| EP | 2675540 | 3/2018 |
| EP | 2750683 | 3/2018 |
| EP | 2796102 | 3/2018 |
| EP | 3066201 | 3/2018 |
| EP | 3066998 | 3/2018 |
| EP | 3107552 | 3/2018 |
| EP | 3288660 | 3/2018 |
| EP | 3288683 | 3/2018 |
| EP | 3289362 | 3/2018 |
| EP | 3291842 | 3/2018 |
| EP | 3291852 | 3/2018 |
| EP | 3292142 | 3/2018 |
| EP | 3292195 | 3/2018 |
| EP | 3292515 | 3/2018 |
| EP | 3294343 | 3/2018 |
| EP | 3294764 | 3/2018 |
| EP | 3294857 | 3/2018 |
| EP | 3294871 | 3/2018 |
| EP | 3294888 | 3/2018 |
| EP | 3294896 | 3/2018 |
| EP | 3296302 | 3/2018 |
| EP | 3297740 | 3/2018 |
| EP | 3298046 | 3/2018 |
| EP | 3164488 | 4/2018 |
| EP | 3301115 | 4/2018 |
| EP | 3302783 | 4/2018 |
| EP | 3302789 | 4/2018 |
| EP | 3303558 | 4/2018 |
| EP | 3306310 | 4/2018 |
| GB | 2 420 510 A | 5/2006 |
| JP | 9-136090 | 5/1997 |
| KR | 1442486 | 9/2014 |
| RU | 2037327 C1 | 6/1995 |
| RU | 2085933 | 7/1997 |
| SU | 629496 | 10/1978 |
| WO | WO 1987/07178 A1 | 12/1987 |
| WO | WO 89/11899 A1 | 12/1989 |
| WO | WO 90/05008 | 3/1990 |
| WO | WO 95/01214 A1 | 1/1995 |
| WO | WO 97/34643 | 9/1997 |
| WO | WO 1998/017373 | 4/1998 |
| WO | WO 98/50133 A1 | 11/1998 |
| WO | WO 00/41794 | 7/2000 |
| WO | WO 02/072234 A1 | 9/2002 |
| WO | WO 02/072236 A1 | 9/2002 |
| WO | WO 03/089567 | 10/2003 |
| WO | WO 2004/079716 A1 | 9/2004 |
| WO | WO 2009/063198 | 5/2009 |
| WO | WO 2009/111276 A1 | 9/2009 |
| WO | WO 2009/144709 A1 | 12/2009 |
| WO | WO 2010/024753 A1 | 4/2010 |
| WO | WO 2010/040394 A1 | 4/2010 |
| WO | WO 2011/023949 A2 | 3/2011 |
| WO | WO 2011/025890 A1 | 3/2011 |
| WO | WO 2011/027146 A2 | 3/2011 |
| WO | WO 2011/131947 A2 | 10/2011 |
| WO | WO 2011/161463 A2 | 12/2011 |
| WO | WO 2013/043044 A1 | 3/2013 |
| WO | WO 2013/043297 A1 | 3/2013 |
| WO | WO 2013/049623 A1 | 4/2013 |
| WO | WO 2013/055517 A1 | 4/2013 |
| WO | WO 2013/138797 A1 | 9/2013 |
| WO | WO 2013/148376 | 10/2013 |
| WO | WO 2013/159014 A1 | 10/2013 |
| WO | WO 2014/014941 A1 | 1/2014 |
| WO | WO 2014/029505 | 2/2014 |
| WO | WO 2014/046605 A1 | 3/2014 |
| WO | WO 2014/055219 A2 | 4/2014 |
| WO | WO 2014/124306 A1 | 8/2014 |
| WO | WO 2014/153651 | 10/2014 |
| WO | WO 2015/006730 | 1/2015 |
| WO | WO 2015/102528 | 7/2015 |
| WO | WO 2016/004398 A2 | 1/2016 |
| WO | WO 2016/124542 | 8/2016 |
| WO | WO 2016/176663 | 11/2016 |
| WO | WO 2016/209082 | 12/2016 |
| WO | WO 2017/041102 | 3/2017 |

(56) References Cited

FOREIGN PATENT DOCUMENTS

| | | |
|---|---|---|
| WO | WO 20174201349 | 11/2017 |
| WO | WO 2017218714 | 12/2017 |
| WO | WO 2018/009894 A1 | 1/2018 |
| WO | WO 2018002036 | 1/2018 |
| WO | WO 2018005873 | 1/2018 |
| WO | WO 2018013558 | 1/2018 |
| WO | WO 2018013629 A1 | 1/2018 |
| WO | WO 2018013840 | 1/2018 |
| WO | WO2018014174 | 1/2018 |
| WO | WO2018015561 | 1/2018 |
| WO | WO 20180011600 | 1/2018 |
| WO | WO2018018958 | 2/2018 |
| WO | WO2018021920 | 2/2018 |
| WO | WO2018022158 | 2/2018 |
| WO | WO2018022513 | 2/2018 |
| WO | WO2018022619 | 2/2018 |
| WO | WO2018022651 | 2/2018 |
| WO | WO2018022930 | 2/2018 |
| WO | WO2018023114 | 2/2018 |
| WO | WO2018024639 | 2/2018 |
| WO | WO2018026644 | 2/2018 |
| WO | WO2018026941 | 2/2018 |
| WO | WO2018028647 | 2/2018 |
| WO | WO 2018034343 | 2/2018 |
| WO | WO2018034885 | 2/2018 |
| WO | WO 2018035141 | 2/2018 |
| WO | WO 2018035423 | 2/2018 |
| WO | WO20180202691 | 2/2018 |
| WO | WO 2018034655 | 3/2018 |
| WO | WO 2018038711 | 3/2018 |
| WO | WO 2018039119 | 3/2018 |
| WO | WO 2018039407 | 3/2018 |
| WO | WO 2018039408 | 3/2018 |
| WO | WO 2018039410 | 3/2018 |
| WO | WO 2018039412 | 3/2018 |
| WO | WO 2018039515 | 3/2018 |
| WO | WO 2018045284 | 3/2018 |
| WO | WO 2018049226 | 3/2018 |
| WO | WO 2018050738 | 3/2018 |
| WO | WO 2018057825 | 3/2018 |
| WO | WO 2018063291 | 4/2018 |
| WO | WO 2018081476 | 5/2018 |
| WO | WO 20180814701 | 5/2018 |

OTHER PUBLICATIONS

Augustsson et al., Acoustophoretic microfluidic chip for sequential elution of surface bound molecules from beads or cells, Biomicrofluidics, Sep. 2012, 6(3):34115.

Benes et al.; Ultrasonic Separation of Suspended Particles, 2001 IEEE Ultrasonics Symposium; Oct. 7-10, 2001; pp. 649-659; Atlanta, Georgia.

Castilho et al.; Animal Cell Technology: From Biopharmaceuticals to Gene Therapy; 11—Animal Cell Separation; 2008.

Castro; Tunable gap and quantum quench dynamics in bilayer graphene; Jul. 13, 2010; Mathematica Summer School.

Chitale et al.; Understanding the Fluid Dynamics Associated with Macro Scale Ultrasonic Separators; Proceedings of Meetings on Acoustics, May 2015.

Cravotto et al.; Ultrasonics Sonochemistry, vol. 15, No. 5, pp. 898-902, 2008.

Garcia-Lopez, et al; Enhanced Acoustic Separation of Oil-Water Emulsion in Resonant Cavities. The Open Acoustics Journal. 2008, vol. 1, pp. 66-71.

Grenvall et al.; Concurrent Isolation of Lymphocytes and Granulocytes Using Prefocused Free Flow Acoustophoresis; Analytical Chemistry; vol. 87; pp. 5596-5604; 2015.

Higginson et al.; Tunable optics derived from nonlinear acoustic effects; Journal of Applied Physics; vol. 95; No. 10; pp. 5896-5904; 2004.

Hill et al.; Ultrasonic Particle Manipulation; Microfluidic Technologies for Miniaturized Analysis Systems, Jan. 2007, pp. 359-378.

Ilinskii et al.; Acoustic Radiation Force on a Sphere in Tissue; AIP Conference Proceedings; 2012.

Kuznetsova et al.; Microparticle concentration in short path length ultrasonic resonators: Roles of radiation pressure and acoustic streaming; Journal of the Acoustical Society of America, American Institute of Physics for the Acoustical Society of America, vol. 116, No. 4, Oct. 1, 2004, pp. 1956-1966, DOI: 1.1121/1.1785831.

Latt et al.; Ultrasound-membrane hybrid processes for enhancement of filtration properties; Ultrasonics sonochemistry 13.4 (2006): 321-328.

Li et al.; Electromechanical behavior of PZT-brass unimorphs; J. Am. Ceram. Soc. vol. 82; No. 7; pp. 1733-1740, 1999.

Lipkens et al.; The effect of frequency sweeping and fluid flow on particle trajectories in ultrasonic standing waves; IEEE Sensors Journal, vol. 8, No. 6, pp. 667-677, 2008.

Lipkens et al.; Frequency sweeping and fluid flow effects on particle trajectories in ultrasonic standing waves; Acoustics 08, Paris, Jun. 29-Jul. 4, 2008.

Lipkens et al.; Prediction and measurement of particle velocities in ultrasonic standing waves; J. Acoust. Soc. Am., 124 No. 4, pp. 2492 (A) 2008.

Lipkens et al.; Separation of micron-sized particles in macro-scale cavities by ultrasonic standing waves; Presented at the International Congress on Ultrasonics, Santiago; Jan. 11-17, 2009.

Lipkens et al.; Separation of bacterial spores from flowering water in macro-scale cavities by ultrasonic standing waves; submitted/uploaded to http://arxiv.org/abs/1006.5467 on Jun. 28, 2010.

Lipkens et al., Macro-scale acoustophoretic separation of lipid particles from red blood cells, The Journal of the Acoustical Society of America, vol. 133, Jun. 2, 2013, p. 045017, XP055162509, New York, NY.

Meribout et al.; An Industrial-Prototype Acoustic Array for Real-Time Emulsion Layer Detection in Oil Storage Tanks; IEEE Sensors Journal, vol. 9, No. 12, Dec. 2009.

Musiak et al.; Design of a Control System for Acoustophoretic Separation, 2013 IEEE 56th International Midwest Symposium on Circuits and Systems (MWSCAS), Aug. 2013, pp. 1120-1123.

Nilsson et al.; Review of cell and particle trapping in microfluidic systems; Department of Measurement Technology and Industrial Electrical Engineering, Div. of Nanobiotechnology, Lund University, P.O. Box 118. Lund, Sweden, Analytica Chimica Acta 649, Jul. 14, 2009, pp. 141-157.

Pangu et al.; Droplet transport and coalescence kinetics in emulsions subjected to acoustic fields; Ultrasonics 46, pp. 289-302 (2007).

Phys. Org. "Engineers develop revolutionary nanotech water desalination membrane." Nov. 6, 2006. http://phys.org/news82047372.html.

Ponomarenko et al.; Density of states and zero Landau level probed through capacitance of graphene; Nature Nanotechnology Letters, Jul. 5, 2009; DOI: 10.1038/NNAN0.2009.177.

"Proceedings of the Acoustics 2012 Nantes Conference," Apr. 23-27, 2012, Nantes, France, pp. 278-282.

Ryll et al.; Performance of Small-Scale CHO Perfusion Cultures Using an Acoustic Cell Filtration Device for Cell Retention: Characterization of Separation Efficiency and Impact of Perfusion on Product Quality; Biotechnology and Bioengineering; vol. 69; Iss. 4; pp. 440-449; Aug. 2000.

Seymour et al, J. Chem. Edu., 1990, 67(9), p. 763, published Sep. 1990.

Volpin et al.; Mesh simplification with smooth surface reconstruction; Computer-Aided Design; vol. 30; No. 11; 1998.

Wang et al.; Retention and Viability Characteristics of Mammalian Cells in an Acoustically Driven Polymer Mesh; Biotechnol. Prog. 2004, pp. 384-387 (2004).

Wicklund et al.; Ultrasonic Manipulation of Single Cells; Methods in Molecular Biology; vol. 853; pp. 1777-196; 2012.

Annex to Form PCT/ISA/206—Communication Relating to the Results of the Partial International Search Report dated Jul. 18, 2013.

European Search Report of European Application No. 11769474.5 dated Sep. 5, 2013.

(56) References Cited

OTHER PUBLICATIONS

European Search Report of European Application No. 11796470.0 dated Jan. 5, 2016.
European Search Report of European Application No. 13760840.2, dated Feb. 4, 2016.
European Search Report of European Application No. 13721179.3 dated Mar. 23, 2016.
European Search Report for European Application No. 14749278.9 dated Jan. 13, 2017.
Extended European Search Report for European Application No. EP 12833859.7 dated Mar. 20, 2015.
Extended European Search Report for European Application No. EP 14787587.6 dated Jan. 2, 2017.
International Search Report and Written Opinion for International Application No. PCT/US2011/032181 dated Dec. 20, 2011.
International Search Report and Written Opinion for International Application No. PCT/US2011/040787 dated Feb. 27, 2012.
International Search Report and Written Opinion for International Application No. PCT/US2012/051804 dated Nov. 16, 2012.
International Search Report and Written Opinion for International Application No. PCT/US2013/037404 dated Jun. 21, 2013.
International Search Report and Written Opinion for International Application No. PCT/US2013/032705 dated Jul. 26, 2013.
International Search Report and Written Opinion for International Application No. PCT/US2013/059640 dated Feb. 18, 2014.
International Search Report and Written Opinion for International Application No. PCT/US2013/050729 dated Sep. 25, 2013.
International Search Report and Written Opinion for International Application No. PCT/US2014/015382 dated May 6, 2014.
International Search Report and Written Opinion for International Application No. PCT/US2014/035557 dated Aug. 27, 2014.
International Search Report and Written Opinion for International Application No. PCT/US2014/043930 dated Oct. 22, 2014.
International Search Report and Written Opinion for International Application No. PCT/US2014/046412 dated Oct. 27, 2014.
International Search Report and Written Opinion for International Application No. PCT/US2014/064088 dated Jan. 30, 2015.
International Search Report and Written Opinion for International Application No. PCT/US2015/010595 dated Apr. 15, 2015.
International Search Report and Written Opinion for International Application No. PCT/US2015/019755 dated May 4, 2015.
International Search Report and Written Opinion for International Application No. PCT/US2015/030009 dated Jul. 30, 2015.
International Search Report and Written Opinion for International Application No. PCT/US2015/039125 dated Sep. 30, 2015.
International Search Report and Written Opinion for International Application No. PCT/US2015/053200 dated Dec. 28, 2015.
International Search Report and Written Opinion for International Application No. PCT/US2015/066884, dated Mar. 22, 2016.
International Search Report and Written Opinion for International Application No. PCT/US2016/024082 dated Jun. 27, 2016.
International Search Report and Written Opinion for International Application No. PCT/US2016/031357 dated Jul. 26, 2016.
International Search Report and Written Opinion for International Application No. PCT/US2016/038233 dated Sep. 26, 2016.
International Search Report and Written Opinion for International Application No. PCT/US2015/024365 dated Oct. 13, 2016.
International Search Report and Written Opinion for International Application No. PCT/US2016/041664 dated Oct. 18, 2016.
International Search Report and Written Opinion for International Application No. PCT/US2016/044586 dated Oct. 21, 2016.
International Search Report and Written Opinion for International Application No. PCT/US2016/049088 dated Nov. 28, 2016.
International Search Report and Written Opinion for International Application No. PCT/US2016/050415 dated Nov. 28, 2016.
International Search Report and Written Opinion for International Application No. PCT/US2016/037104 dated Dec. 16, 2016.
International Search Report and Written Opinion for International Application No. PCT/US2017/015197 dated Apr. 3, 2017.
International Search Report and Written Opinion for International Application No. PCT/US2017/015450 dated Apr. 10, 2017.
International Search Report and Written Opinion for International Application No. PCT/US2016/047217 dated Apr. 11, 2017.
International Search Report and Written Opinion for International Application No. PCT/US2016/048243 dated Apr. 20, 2017.
International Search Report and Written Opinion for International Application No. PCT/US2017/017788 dated May 8, 2017.
International Search Report and Written Opinion for International Application No. PCT/US2017/030903 dated Jul. 19, 2017.
International Search Report and Written Opinion for International Application No. PCT/US2017/025108 dated Jul. 20, 2017.
International Search Report and Written Opinion for International Application No. PCT/US2017/031425 dated Aug. 30, 2017.
Sony New Release: <http://www.sony.net/SonyInfo/News/Press/201010/10-137E/index.html>.
International Search Report and Written Opinion for International Application No. PCT/US2017/031425 dated Oct. 23, 2017.

* cited by examiner

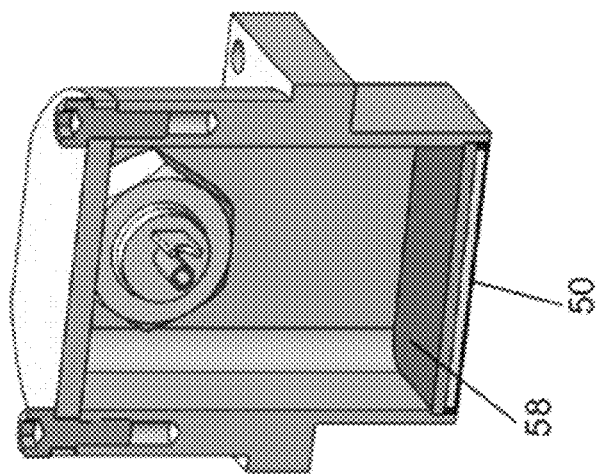
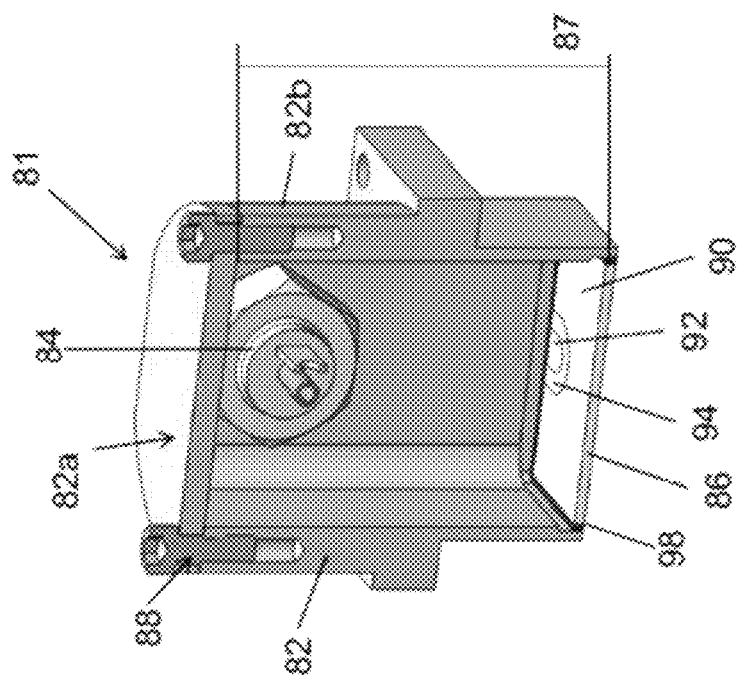
FIG. 11A
FIG. 11B

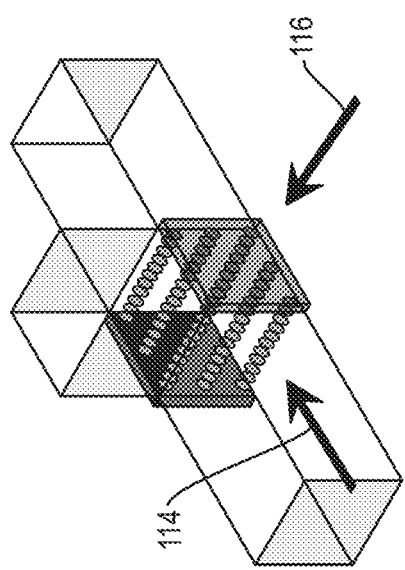
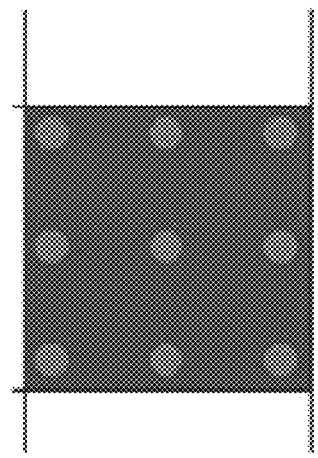
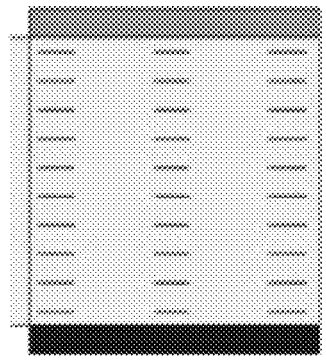
FIG. 14A
FIG. 14B
FIG. 14C

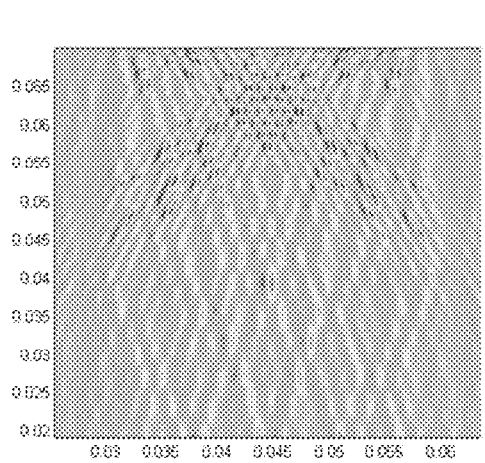 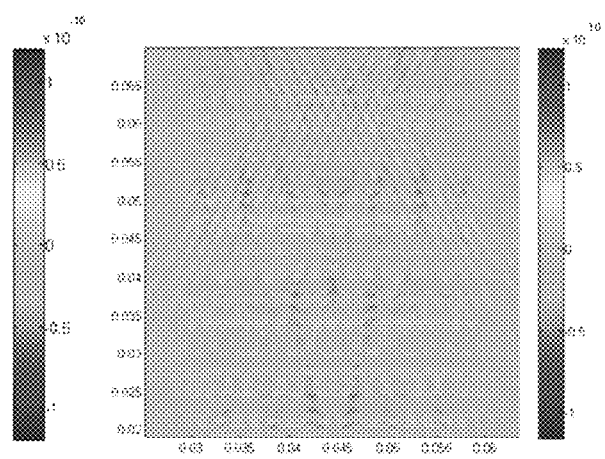
FIG. 23          FIG. 24
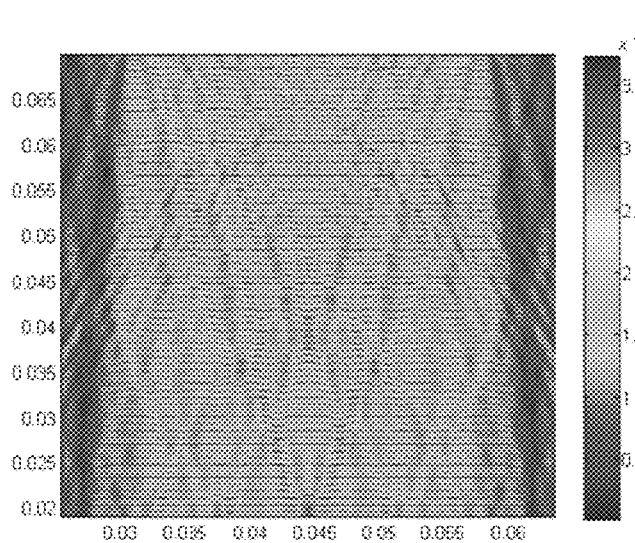
FIG. 25

- 1x1x1
- 3% Yeast
- 2 MHz
- 60 ml/min, 10W
- Each frequency ran for 20 minutes to reach a steady state
- Average values plotted

- 1x1x2
- 3% Yeast
- 2 MHz
- 90 ml/min, 10W
- Each frequency ran for 20 minutes to reach a steady state
- Average values plotted

- 1x1x2
- 3% Yeast
- 2 MHz
- 90 ml/min, 10W
- Each frequency ran for 20 minutes to reach a steady state
- Average values plotted

- 1x1x2
- 6% Yeast
- 1 MHz
- 90 ml/min, 10W
- Each frequency ran for 20 minutes to reach a steady state
- Average values plotted

How It Works

- After the scan, the system will set the frequency to the resonance frequency and wait 10 seconds before monitoring.
- Current data is continually monitored at 5Hz and a running average of 20 points is calculated
  - If the running average stays above the Upper Cutoff Limit, the system will continue to monitor
  - If the running average drops below the Upper Cutoff Limit, the frequency is increased by 1000Hz
  - If the running average drops below the Lower Cutoff Limit, a scan is commenced
- Frequency can be changed at any point. The system will change the frequency, wait 10 seconds, and continue monitoring at the new frequency
- When the voltage is changed a new scan will be initiated
- Tracking range is set from 2.2 MHz to 2.26 MHz
  - If tracking algorithm moves frequency out of this range, it resets the frequency to 2.23 MHz

FIG. 84

DRIVER AND CONTROL FOR VARIABLE IMPEDENCE LOAD

CROSS-REFERENCE TO RELATED APPLICATIONS

This application claims the benefit of U.S. Provisional Application Ser. No. 62/446,356, filed Jan. 13, 2017, and is a continuation-in-part of U.S. patent application Ser. No. 15/621,691, filed Jun. 13, 2017, which is a continuation of U.S. patent application Ser. No. 15/000,573, filed Jan. 19, 2016, now U.S. Pat. No. 9,675,902, which is a continuation of U.S. patent application Ser. No. 13/943,529, filed Jul. 16, 2013, now U.S. Pat. No. 9,272,234, which claims priority to U.S. Provisional Patent Application Ser. No. 61/671,856, filed on Jul. 16, 2012; and is also a continuation-in-part of U.S. Ser. No. 13/844,754, filed Mar. 15, 2013, which claimed the benefit of U.S. Provisional Patent Application Ser. No. 61/611,159, filed Mar. 15, 2012, and of U.S. Provisional Patent Application Ser. No. 61/611,240, also filed Mar. 15, 2012, and of U.S. Provisional Patent Application Ser. No. 61/708,641, filed Oct. 2, 2012, and of U.S. Provisional Patent Application Ser. No. 61/754,792, filed Jan. 21, 2013. The entire disclosures of all of these applications are hereby incorporated herein by reference.

STATEMENT REGARDING FEDERALLY SPONSORED RESEARCH OR DEVELOPMENT

Not Applicable

BACKGROUND

Acoustophoresis is the separation of materials using acoustic waves. For example, particles and secondary fluids can be separated from a primary or host fluid using acoustics, such as acoustic standing waves. Acoustic standing waves can exert forces on particles in a fluid when there is a differential in density and/or compressibility, otherwise known as the acoustic contrast factor. The pressure profile in a standing wave contains areas of local minimum pressure amplitudes at standing wave nodes and local maxima at standing wave anti-nodes. Depending on their density and compressibility, the particles can be trapped at the nodes or anti-nodes of the standing wave. Generally, the higher the frequency of the standing wave, the smaller the particles that can be trapped.

At a micro scale, for example with structure dimensions on the order of micrometers, conventional acoustophoresis systems tend to use half or quarter wavelength acoustic chambers, which at frequencies of a few megahertz are typically less than a millimeter in thickness, and operate at very slow flow rates (e.g., µL/min). Such systems are not scalable since they benefit from extremely low Reynolds number, laminar flow operation, and minimal fluid dynamic optimization.

At the macro-scale, planar acoustic standing waves have been used in separation processes. However, a single planar wave tends to trap the particles or secondary fluid such that separation from the primary fluid is achieved by turning off or removing the planar standing wave. The removal of the planar standing wave may hinder continuous operation. Also, the amount of power that is used to generate the acoustic planar standing wave tends to heat the primary fluid through waste energy, which may be disadvantageous for the material being processed. Conventional drivers and controllers used to generate acoustic waves may be designed for static impedance loads with relatively low power output.

A number of industrial applications generate wastewater that is contaminated with undesirable or hazardous fluid materials, such as oil. These operations include oil drilling, mining and natural gas fracking. Also, spills from oil rigs into seawater generate emulsified oil in the water that is difficult to separate. The use of methods such as hydrocyclones, absorptive media, mechanical filtration, and chemical dispersion to separate the oil from the water are both cost prohibitive and possibly injurious to the environment.

SUMMARY

The present disclosure relates to systems, devices and/or methods for acoustophoresis on preferably a large scale. The devices use one or more distinct ultrasonic transducers as described herein, or an array of such transducers. In some examples, a transducer is driven at frequencies that produce multi-dimensional standing waves. Acoustophoresis can employ high intensity standing waves of sound to exert forces on particles. An acoustic standing wave has a pressure profile that appears to "stand" still in time. The pressure profile in a standing wave varies from areas of low pressure (nodes) to areas of high pressure (anti-nodes). Acoustic standing waves can be produced in acoustic resonators. Acoustophoresis can be achieved using a piezoelectric element as an ultrasonic transducer. The piezoelectric element represents a variable impedance load during acoustophoretic operations. In addition, the piezoelectric element may be driven at radio frequencies (RF) to generate the desired acoustic waves that influence material in the micrometer or smaller range.

A disclosed driver for such transducers produces relatively high power at variable RF frequencies with a flexibility for handling variable impedance loads. The driver includes a DC-DC converter and an inverter. The converter provides a variable output that is proportional to the input. The inverter produces an RF drive signal given a DC input. The converter and inverter are controlled with a controller that provides a desired level of power and a desired frequency. A feedback loop from the load to the controller provides feedback signals that permit the controller to formulate control signals supplied to the driver to obtain a desired output. The load can be a piezoelectric element in an ultrasonic transducer, or can be an ultrasonic transducer in combination with an acoustic chamber, which can be a resonant chamber or system.

The load can be driven by the driver to obtain certain characteristics, such as operating at a low or minimum reactance point. As the load is driven, the impedance characteristics of the load can change. The change in impedance can be due to a number of factors, including temperature, fluid characteristics (e.g., density, compressibility, velocity), particle or fluid trapping in an acoustic wave generated by the transducer, frequency, resonance and any other variable that might influence the load. The driver can be controlled based on feedback data from the load to adjust output parameters such as frequency, power, voltage, current, phase or any other parameter the driver can produce under control of the controller.

Disclosed in some embodiments is an acoustophoresis device, which includes a chamber with an inlet, an outlet, an ultrasonic transducer coupled to the chamber, the ultrasonic transducer including a piezoelectric material being configured to generate a multi-dimensional standing wave in the flow chamber.

In some embodiments, a reflector may be provided on an opposite side of the chamber from the ultrasonic transducer. The chamber may be a flow chamber for accommodating a fluid flow that transits past the ultrasonic transducer.

The device may include a plurality of device inlets spaced about a first end of the device. The device may include a longitudinal sidewall that is spaced apart from a contoured wall.

The piezoelectric material of the ultrasonic transducer can have a rectangular shape. The reflector can have a non-planar surface.

In particular embodiments, the first end of the device has a circular cross-section and the flow chamber has a rectangular cross-section.

The multi-dimensional standing wave generated by the transducer can result in an acoustic radiation force having an axial force component and a lateral force component that are of the same order of magnitude.

In some embodiments, the transducer comprises: a housing having a top end, a bottom end, and an interior volume; and a piezoelectric element at the bottom end of the housing having an exposed exterior surface and an interior surface, the piezoelectric element being able to vibrate when excited. The piezoelectric element may be excited by application of an electrical signal.

Sometimes, no backing layer is present within the housing, and a gap is present in the interior volume between the piezoelectric element and a top plate at the top end of the housing.

In other devices, the transducer includes a backing layer contacting the interior surface of the piezoelectric element, the backing layer being made of a substantially acoustically transparent material. The substantially acoustically transparent material can be balsa wood, cork, or foam. The substantially acoustically transparent material may have a thickness of up to 1 inch.

The flow chamber can further comprise a transparent window for viewing the interior of the flow chamber.

In particular embodiments, the device has a length L from the at least one device inlet to a bottom of the longitudinal sidewall, and a ratio of the length L to the first diameter is less than 1.

Also disclosed herein are acoustophoresis devices for retaining or trapping particles from a particle/host fluid mixture. The particles may be cells. In some embodiments, an acoustophoresis device comprises: a chamber; at least one ultrasonic transducer coupled to the chamber, the at least one ultrasonic transducer including a piezoelectric material configured to be excited to generate a multi-dimensional acoustic standing wave in the chamber; and a reflector coupled to the chamber opposite from the at least one ultrasonic transducer; wherein the particles are continuously trapped in the multi-dimensional acoustic standing wave, agglomerate, aggregate, clump, or coalesce, and settle out of the host fluid due to enhanced gravity forces, and exit the flow chamber; and wherein the multi-dimensional standing wave results in an acoustic radiation force having an axial force component and a lateral force component that are of the same order of magnitude.

Acoustophoretic systems are also disclosed. In particular embodiments, an acoustophoresis system includes a chamber for receiving a fluid mixture that includes cells or particles in a fluid, an ultrasonic transducer coupled to the chamber and configured to be excited to generate an acoustic wave in the chamber, and a driver electrically connected to the ultrasonic transducer and configured to provide an excitation to the ultrasonic transducer to generate the acoustic wave in the chamber, the driver including an amplifier.

In certain embodiments, the at least one ultrasonic transducer can comprise a plurality of transducers, and each of the plurality of transducers can be individually electrically connected to its own amplifier.

In certain embodiments of the acoustophoretic system, a function generator can be provided that drives the amplifier by generating a signal (e.g., a low voltage sinusoidal voltage signal) that is sent to the amplifier. A power resistor and/or a capacitor can be electrically connected between the amplifier and the at least one ultrasonic transducer. An oscilloscope can be provided for measuring a first voltage before the power resistor and a second voltage after the power resistor. Further yet, a particle analyzer located downstream of the one or more flow chamber outlets for characterizing the particles.

Further disclosed herein are methods for continuously separating particles from a host fluid. In particular embodiments, such a method comprises: flowing a mixture of the host fluid and particles through an acoustophoresis device, the acoustophoresis device comprising: a flow chamber including one or more inlets and outlets; at least one ultrasonic transducer coupled to the flow chamber; a reflector coupled to the flow chamber opposite from the at least one ultrasonic transducer; and an amplifier electrically connected to the at least one ultrasonic transducer. The method further comprises driving the amplifier to produce an output signal that drives the at least one ultrasonic transducer to create a multi-dimensional acoustic standing wave in the flow chamber; measuring a first voltage between the amplifier and a predetermined first impedance; measuring a second voltage between the first impedance and the at least one ultrasonic transducer; measuring a current from the output signal between the measured first and second voltages; determining an impedance of the at least one ultrasonic transducer from the measured current and measured first and second voltages.

In certain embodiments, the particles are continuously trapped in the multi-dimensional acoustic standing wave, then agglomerate, aggregate, clump, or coalesce, and eventually settle out of the host fluid due to enhanced gravity forces, and exit the flow chamber. In further embodiments, the multi-dimensional standing wave results in an acoustic radiation force having an axial force component and a lateral force component that are of the same order of magnitude.

The impedance of the at least one ultrasonic transducer can be proportional to the measured current. The impedance of the at least one ultrasonic transducer can additionally be proportional to the first impedance. The impedance of the at least one ultrasonic transducer can be inversely proportional to the measured first and second voltages. The method can further comprise determining the phase angle of the impedance of the at least one ultrasonic transducer. In some embodiments, the first impedance can be predetermined across a power resistor electrically connected between the amplifier and the at least one ultrasonic transducer. In such embodiments, the predetermined first impedance across the power resistor can be proportional to the first voltage and can be inversely proportional to the second voltage.

The method can further comprise determining an electrical power consumed by the at least one ultrasonic transducer from the measured second voltage and the impedance of the at least one ultrasonic transducer. The electrical power consumed by the at least one ultrasonic transducer can be proportional to the measured second voltage. The electrical power consumed by the at least one ultrasonic transducer can be inversely proportional to the impedance of the at least one ultrasonic transducer.

The amplifier can be driven by a function generator that generates a signal (e.g., a low voltage sinusoidal voltage signal) that is sent to the amplifier. The first and second voltages can be measured by an oscilloscope. A particle analyzer located downstream of the acoustophoretic device can be used for characterizing the particles.

Discussed herein are systems and methods for acoustophoresis for generating optimized particle clusters to improve gravity separation and collection efficiency. Improved, continuous, acoustophoresis devices using improved fluid dynamics are also discussed, as well as control of the devices for desired performance.

Control of the acoustic transducer can be implemented on the basis of power setpoints. For example, a user can set a desired power level for power delivered to the transducer. Performance of acoustophoresis in an acoustic chamber using the acoustic transducer can be modulated on the basis of modulated input power to the acoustic transducer. In some instances, a power setpoint is desired for operation, while other parameters, such as frequency, for example, are modified. The power setpoint determines the power output of an RF power supply or RF power amplifier. A power control is provided to maintain the power setpoint, while other parameters associated with operation of the acoustophoresis device are varied. The power control senses signals provided to the acoustic transducer, such as, for example, voltage and current. These feedback signals are used to determine frequency and phase angle for the power delivered to the transducer. In some examples, a buck converter is used as the DC power supply. The buck converter has a response bandwidth, which may influence the responsiveness of the RF power control. For example, if the buck converter bandwidth is relatively narrow, the system response for the RF power control may be relatively slow for the desired operational performance environment for the acoustophoresis device.

A number of different materials may be processed through the acoustophoresis device, each of which may provide different load characteristics on the acoustic transducer and acoustic chamber. The RF power supply thus may be subjected to a wide range of loads, which may place demands on both the Buck and RF power supply supplies that are challenging to meet. For example, heavy loading of the acoustic transducer and/or acoustic chamber experienced with certain types of materials being processed may cause power supply components to be overloaded, and/or overheated, or may cause trip point thresholds to be met or exceeded. The heavy loading or trip point thresholds crossings may cause faults to be identified in the power control, causing the power supply to be shut down. In addition, the power demands on the RF power supply may change significantly with changes in other operational parameters, such as temperature, frequency or loading characteristics, including reactance. Power control based on a desired power level set levels the point may thus imply other operational setpoints, such as frequency, to manage operation of the power supply and acoustophoresis device to handle a range of loads.

In some implementations, an RF linear amplifier is used to supply RF power to the transducer. The linear amplifier may operate by receiving an input AC signal, which may be AC or DC, and amplifying the input signal in accordance with the operational characteristics of the linear amplifier. Linear amplifiers are typically designed to have a linear response, such that any input signal is amplified by the same gain, regardless of the magnitude of the input signal, within the operating parameters or specifications of the linear amplifier. This linear operation can be achieved through the use of techniques that contribute to linearizing the response of the linear amplifier, potentially in areas where non-ideal conditions tend to impose nonlinearities on the response. However, linear operation is attained at the cost of power regulation, usually generating significant heat losses as well as incurring inefficient operation. Accordingly, linear amplifiers tend to consume significant amounts of power, even when the magnitude of the input signal is relatively small and/or when the gain is relatively small. When demands are placed on the linear amplifier to supply power in response to changing system conditions, such as frequency or loading, challenges are presented in terms of responsiveness and avoiding overloads.

In addition, linear amplifiers are designed for nominal applications, for example, where a 50 ohm load is specified. The load applied to the linear amplifier is thus intended to be composed of mostly real impedance, or resistance, and tolerates a relatively small amount of reactive impedance. In the case of providing power to an acoustic transducer that is composed of a piezoelectric material, the power supply sees a highly reactive load, which limits the usefulness of an RF linear amplifier as the source of RF power supply.

Discussed herein is a RF acoustic driver power supply and method for providing power to an acoustic transducer composed of a piezoelectric material, such as PZT-8. The piezoelectric material may be formed as a poly-crystal, which is also referred to as a crystal herein. The driver power supply provides RF power with a relatively wide bandwidth of operation to permit responsive operation with relatively high efficiency and with the ability to accommodate a wide range of loads. The driver contains power supply is a DC-DC converter that combines a power converter, such as a buck, buck-boost or boost power converter, with an RF frequency inverter which supplies RF AC to the PZT.

The system can be driven by a function generator and an amplifier. The system performance can be monitored and controlled by a computer. Excitation frequencies can be in the range of from about hundreds of kilohertz to several megahertz.

The generation of an acoustic standing wave in a fluid medium may be accomplished with the use of an oscillator or function generator and an amplifier, which may be a linear amplifier. The function generator or oscillator linear amplifier provides an electronic input to a piezoelectric device such that the piezoelectric device vibrates at the frequency that is set by the function generator or oscillator connected to the input of the amplifier. The amplifier also generates provides a certain amount of power that is provided to the piezoelectric material, which power can determine the strength of the acoustic wave that is set by the frequency of the function generator or oscillator. A controller implementing a control scheme is provided for the amplifier and the function generator or oscillator to control the generated and applied power.

A function generator is utilized to generate the initial wave pattern that is imparted to the acoustic resonator system that includes at least one acoustic transducer that is composed, for example, of a piezoelectric material. The system may include another transducer and/or one or more reflectors that are coupled to an acoustic chamber. The signal from the function generator is controlled for various parameters, such as, for example, amplitude. For example, the signal from the function generator is amplified to increase the amount of power applied to the transducer. The power applied to the transducer determines, at least in part, the power of the acoustic standing wave. The control of power applied to the transducer can thus control the power of the acoustic standing wave. The parameters of the signal from the function generator, such as frequency, amplitude and phase, can be controlled with a controller. The amplification of the signal from the function generator can also be controlled by a controller, which may be the same or different from the function generator controller.

The characteristics of the waveform oscillator input to the piezoelectric material of the acoustic transducer can be modified to permit various vibration modes of the piezoelectric material. For example, a pure sine wave can induce a very succinct vibration of the piezoelectric material, while a signal with harmonic content can cause parasitic vibrations of the piezoelectric material. The input to the piezoelectric material may influence the heat generated or input into the fluid in which the acoustic standing wave is formed. The input may generate more complicated motion in the fluid coupled with the piezoelectric material.

Additionally, driving a piezoelectric material with a current source rather than a voltage source may permit greater electro-mechanical freedom in supporting and sustaining desirable vibratory modes in the piezoelectric material. A drive and control scheme can be provided to generate a low harmonic signal into the piezoelectric material. The control of the acoustic transducer that generates the acoustic standing wave in the fluid medium can utilize a feedback loop and a computational processor. An inductor-capacitor-inductor (LCL) or LC circuit configuration may be used to generate a low harmonic function wave, such as a sine wave, into the piezoelectric material. The low harmonic sine wave permits less parasitic vibrations of the piezoelectric material. Such a sine wave may also permit the piezoelectric material to generate less heat when it vibrates.

An LCL configuration can act on the signal from the amplifier as a filter to reduce the harmonic content speed of response of the amplifier output. The LCL may thus act, at least in part, as a low pass filter for the amplifier output. In some examples, the LCL may cause the amplifier output to be filtered to a pure sine wave form. As a result, the perturbation of the piezoelectric material does not generate extra, parasitic vibrations of the material. The output L of the LCL structure provides a current source drive to the piezoelectric material. The LCL input, and thus the current source, is controlled to improve the piezoelectric material's performance in generating an acoustic wave.

The acoustic transducer can be driven to create a multi-dimensional acoustic standing wave in a coupled medium, where the wave has at least non-zero acoustic forces in a direction transverse to the propagation direction of the wave. The multi-dimensional acoustic standing wave generation process takes advantage of the higher-order vibratory modes of a loosely suspended piezoelectric plate.

Piezoelectric material changes shape based on an electrical signal applied to it, such as a voltage or current signal, or based on a corresponding electric field permeating the material. The electric field from external charges affects the fields of the bound charges in the material and thereby affects the shape of the material. The electrical signal can be from a voltage source. In that case the amount of material deformation is related to the voltage applied. For example, the deformation may be 'voltage clamped' or 'voltage damped'. The amount of charge induced is related to the applied voltage and the properties of the material. This relationship can be expressed mathematically as Q=C*V, where Q is charge, C is material capacitance, and V is the voltage of the applied signal. Electrodes may be attached to the piezoelectric material to provide a conduit for the applied charges signal. In that case the resultant voltage, and the corresponding electric field, is a function of the externally applied charges. Using the above equation, the voltage can be express as V=Q/C. The resultant voltage may be 'unconstrained' in relation to operation of the piezoelectric device. The 'C' of the piezoelectric device is due to its physical geometry and material properties. Since the material changes shape as a function of the electric field permeating it, the 'C' of the device is a function of the electric field permeating it. For a given Q, and driving the material with a current source that is a time varying source of charge, C changes as a function of electric field, which changes the voltage across the device to 'accommodate' the changed C. In a voltage driven system, the electric field can determine the amount of charge, which can determine the degree of deformation and correspondingly the amount of change in C. To encourage multimode behavior in piezoelectric material, the piezoelectric material can be configured to be 'free floating', and in some examples, is made to be as free floating as possible in both a mechanical and electrical sense.

The LCL circuit can be implemented as an impedance matching network which can amplify either current or voltage depending on the value of the impedance being matched. One operation implementation technique is to amplify voltage. In this case, power may be transmitted through the LCL with little power loss with the use of low loss inductors (L) and capacitors (C).

The harmonic frequencies are reduced or eliminated due the arrangement of the elements used in the circuit and independent of whether or not there is voltage amplification. The circuit arrangement can be implemented as a low pass filter. Low pass filters allow signals below a certain frequency, called the corner frequency, to pass through the filter while blocking signals with frequencies above the corner frequency. A square wave input into such a network produces a sine wave output when the harmonics of the square wave are at frequencies above the filter's corner frequency.

Voltage amplification may or may not occur at certain frequencies. Amplification can take place if the input impedance of the LCL is smaller than the impedance the LCL is connected to, within a certain range of frequencies. If a voltage gain is applied, then there will be a corresponding current loss since the voltage times the current (V*I) product going into the network must equal the V*I product leaving that network, provided there are negligible losses within the network itself. There is voltage amplification when the system is operated at a piezoelectric material's anti-resonance frequency, which produces large impedances and the LCL is designed to present the inverse of those impedances at its input. For example, suppose the piezoelectric material or crystal's resistance at a particular frequency is 100 ohms and is absorbing 25 watts. The voltage at the crystal is 50 volts with a corresponding current of 0.5 amps (V*I=25). If the LCL translates that 100 ohms to 9 ohms at its input then the drive voltage is 15 volts with a corresponding current of 1.67 amps, which equates to 25 watts. Thus, for a particular driver power, the voltage into the LCL can be low and the current can be high, while the current at the output of the LCL can be low and the voltage output can be high, where the input and output V*I products are equal, assuming negligible losses.

The control of the multi-dimensional acoustic standing wave and the acoustic resonator or transducer is an important part of an acoustophoresis process. For example, as a multi-dimensional acoustic standing wave is utilized to trap biologic cells and cell debris from a bioreactor process, the reactance of the resonator changes. By sensing the voltage and current of the RF transmission line to the piezoelectric element, the resonator can be properly tuned to optimize the acoustophoresis process. The reactance and power can be extracted from the voltage and current signals on the piezoelectric element. For example, voltage and current signals can be provided to a digital signal processor (DSP), which can be used to calculate RF reactance and power. The measured and calculated parameters of operation for the piezoelectric element can be used to provide feedback for the tuning process. This tuning process may consist of adjusting the gain of the amplifier to achieve a desired power that is provided to the piezoelectric element and/or adjusting the frequency of the drive signal to achieve a desired reactance of the resonator, as examples.

The multi-dimensional acoustic standing wave is generated through a multimode perturbation of the piezoelectric material by electronic signal generated by a function generator or oscillator and modified by an amplifier. The generation of the multi-dimensional acoustic standing wave and the multimode perturbation of the piezoelectric material is described in U.S. Pat. No. 9,228,183 which is incorporated herein by reference.

An RF power driver or converter is provided to drive the acoustic transducer. In some implementations, the driver power converter is composed of a DC-DC converter coupled to a DC-AC inverter. A filter is provided between the converter and inverter. The output of the inverter may be supplied to the LCL matching filter. The RF driver power converter has a number of advantages over the linear amplifiers discussed above, including more efficient operation, better responsiveness and the ability to drive highly reactive loads.

The DC-DC converter may be a buck, buck-boost or boost converter, as examples, although any type of DC-DC converter may be used. The amplifier used in conjunction with the function generator or oscillator discussed above can be can be implemented as the converter can be implemented with a and filter. The filter can be implemented as an RLC filter with a bandwidth that permits the filter output, such as output voltage, to respond to dynamic changes of the transducer and/or the acoustic cavity.

The function generator or oscillator discussed above can be implemented as the DC-AC inverter. The inverter receives a DC input and provides an RF frequency output. The inverter output can be applied to a the LCL or LC matching filter, which smoothes the output of the inverter and provides an impedance match for the output of the inverter to permit efficient electrical power transfer.

A control, which may be a digital or analog control, is provided that can receive inputs fed back from the acoustic transducer or other system components and provide control signals to various components of the RF driver power converter. The control can provide control signals to vary the DC output of the converter, and/or modify and control the amplitude of the power of the drive signal for the acoustic transducer. Control signals provided by the control can vary the operation of the inverter to modify and control the frequency of the drive signal. The RF driver power converter with the control permits control and modulation of the acoustic transducer as a highly reactive load, while maintaining desired transducer and acoustic chamber performance.

A control technique provides a system and method for locating desired operating points for an acoustic transducer-cavity combination, with or without loading, which loading may be highly reactive. Feedback from the acoustic transducer can be used to locate the resonance and anti-resonance frequencies of transducer operation. According to some implementations, an operating frequency less than the transducer anti-resonance is inspected for minimum reactance as a point of operation. Some implementations locate a frequency above the anti-resonance frequency, which frequency is inspected for maximum reactance as a point of operation. According to these implementations, a desired level of efficiency can be obtained for acoustophoresis using the acoustic transducer to generate an acoustic standing wave through fluid in the acoustic chamber or cavity to which the transducer is coupled. The points of operation that are determined according to a control technique discussed herein can be frequency setpoints, which can be dynamically maintained. For example, a desired point of operation may change with characteristics of operation of the acoustic chamber, such as a degree of material separation, temperature, power delivered to the transducer, and other phenomena that may influence or modify a desired operating point.

These and other non-limiting characteristics are more particularly described below.

BRIEF DESCRIPTION OF THE DRAWINGS

The following is a brief description of the drawings, which are presented for the purposes of illustrating embodiments disclosed herein and not for the purposes of limiting the same.

FIG. 11A is a cross-sectional side view of an acoustic transducer with a free piezoelectric element;

FIG. 11B is a cross-sectional view of an acoustic transducer with a damped piezoelectric element;

FIG. 14A is an isometric view of an acoustic chamber;

FIG. 14B is a left side elevation view of the acoustic chamber in FIG. 14A;

FIG. 14C is a front elevation view of the acoustic chamber in FIG. 14A;

FIG. 23 shows the lateral (horizontal) acoustic radiation force at 1.9964 MHz.

FIG. 24 shows the axial (vertical) component for a resonance frequency of 1.9964 MHz.

FIG. 25 shows the acoustic pressure amplitude at 1.9964 MHz.

FIG. 84 is text illustrating an example control technique; and

DETAILED DESCRIPTION

Figure 1:
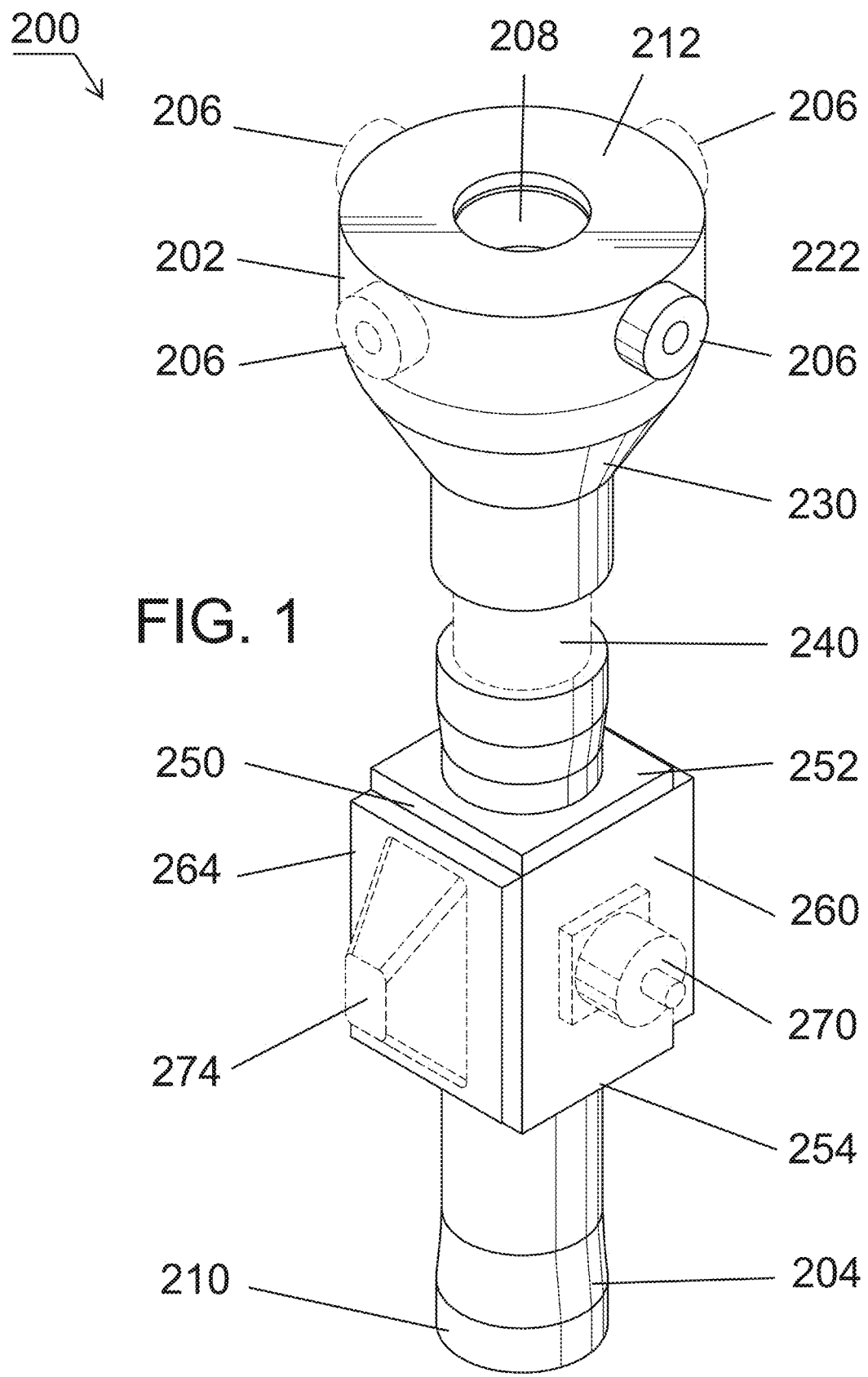
FIG. 1 is a front top perspective view of an exemplary embodiment of a device of the present disclosure.
Figure 2:
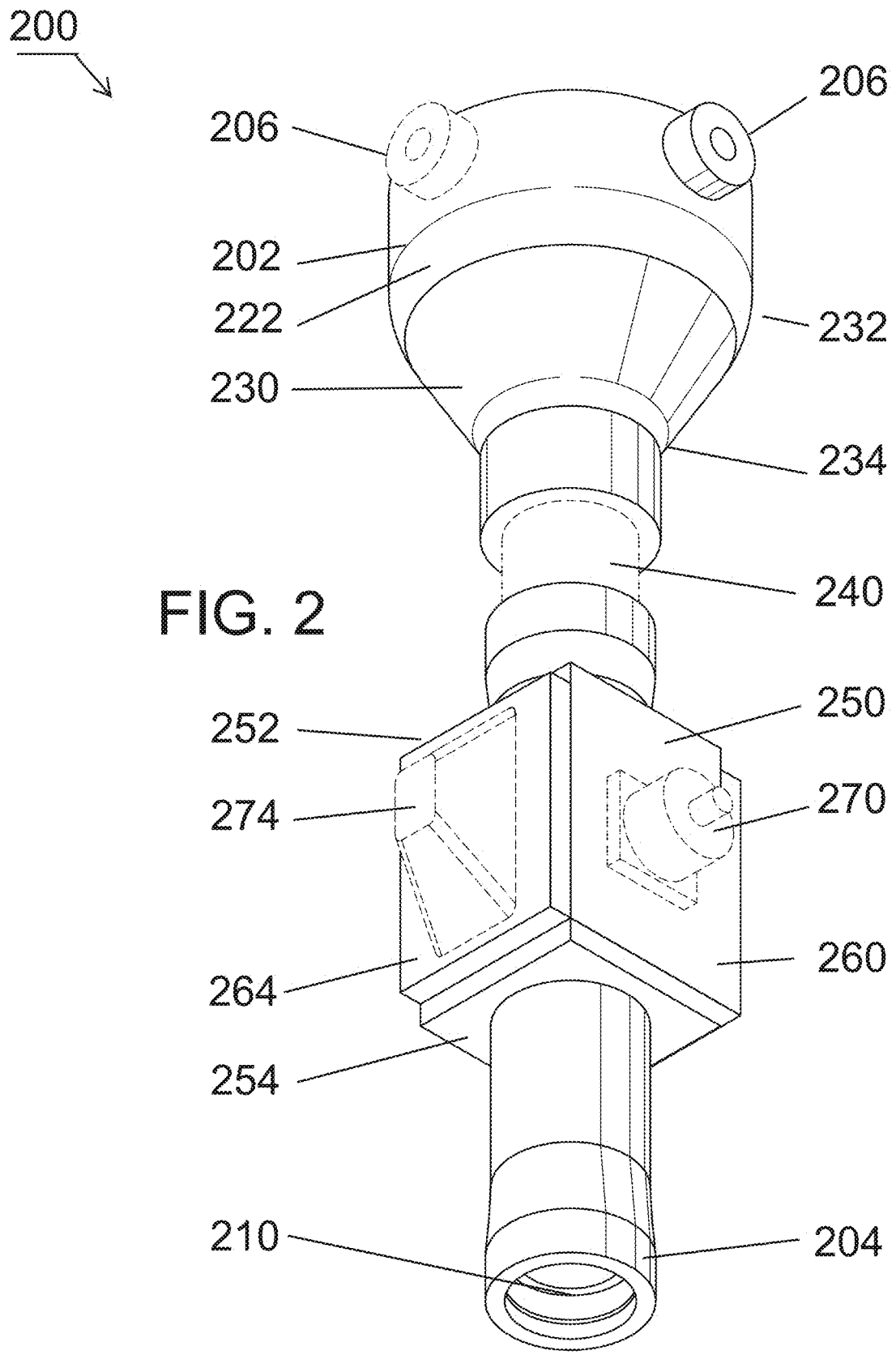
FIG. 2 is a front bottom perspective view of the device of FIG. 1.
Figures 3, 4:
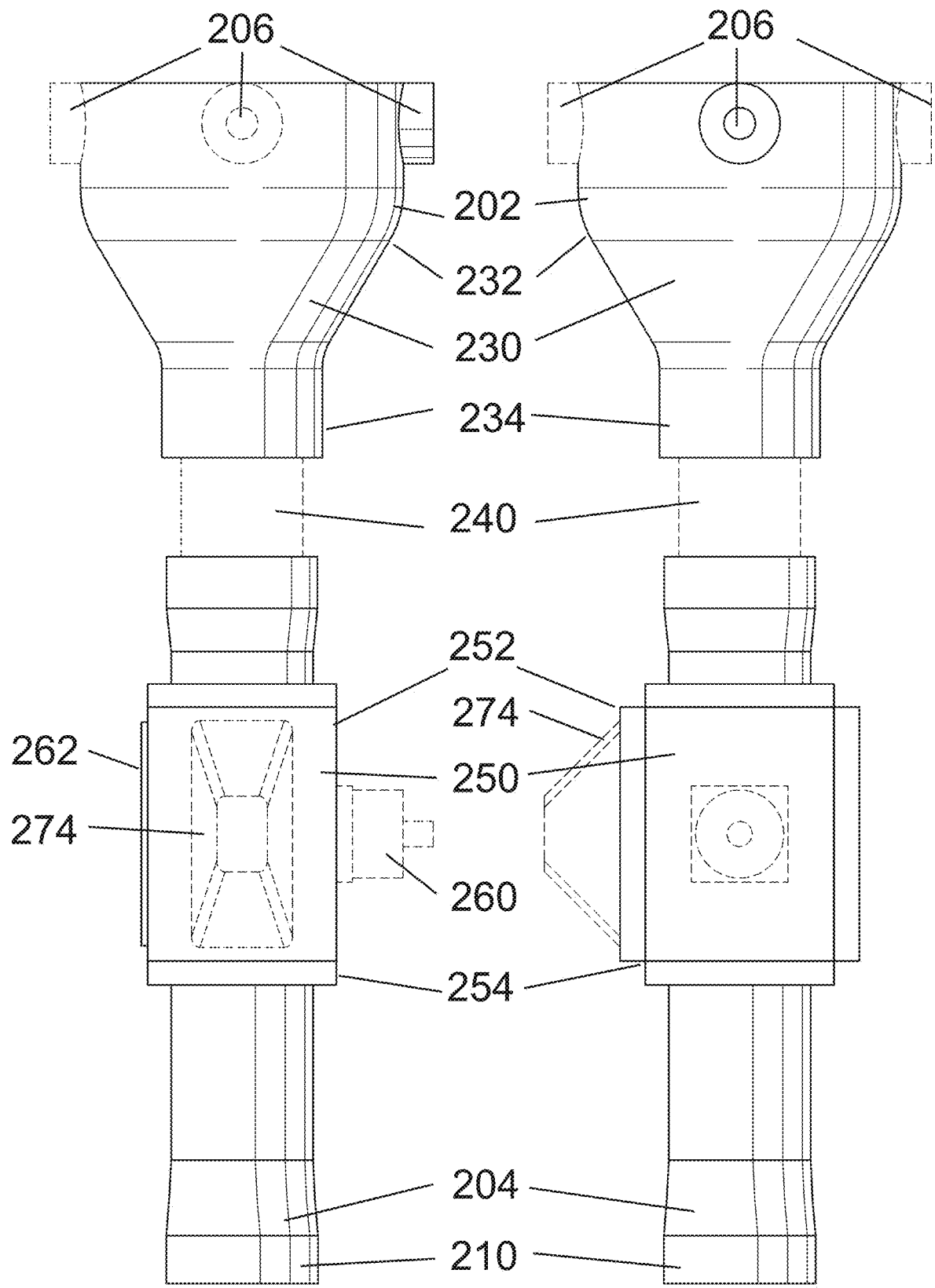
FIG. 3 is a right side view of the device of FIG. 1.
FIG. 4 is a front view of the device of FIG. 1.
Figures 5, 6:
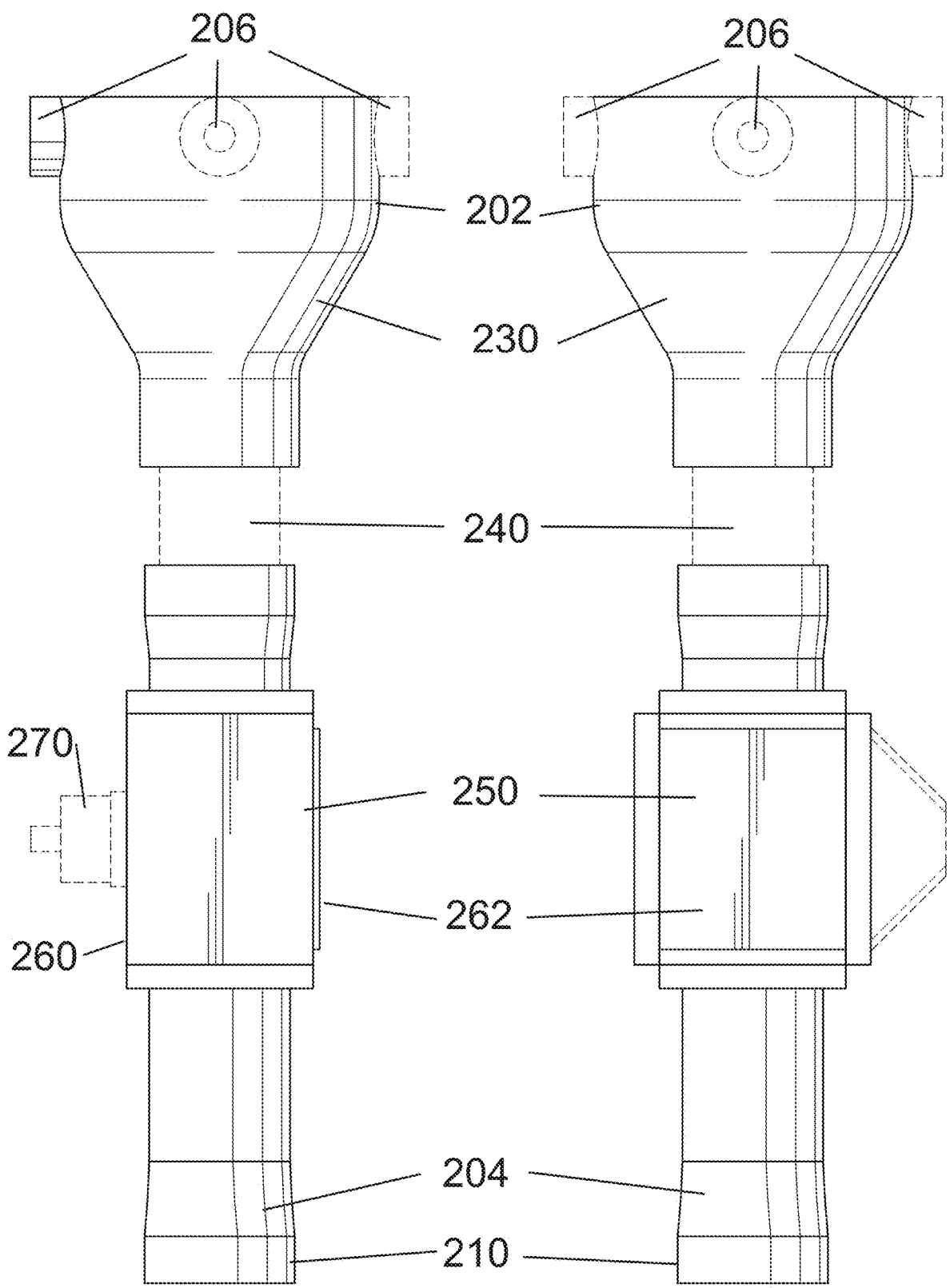
FIG. 5 is a rear view of the device of FIG. 1.
FIG. 6 is a left side view of the device of FIG. 1.
Figure 7:
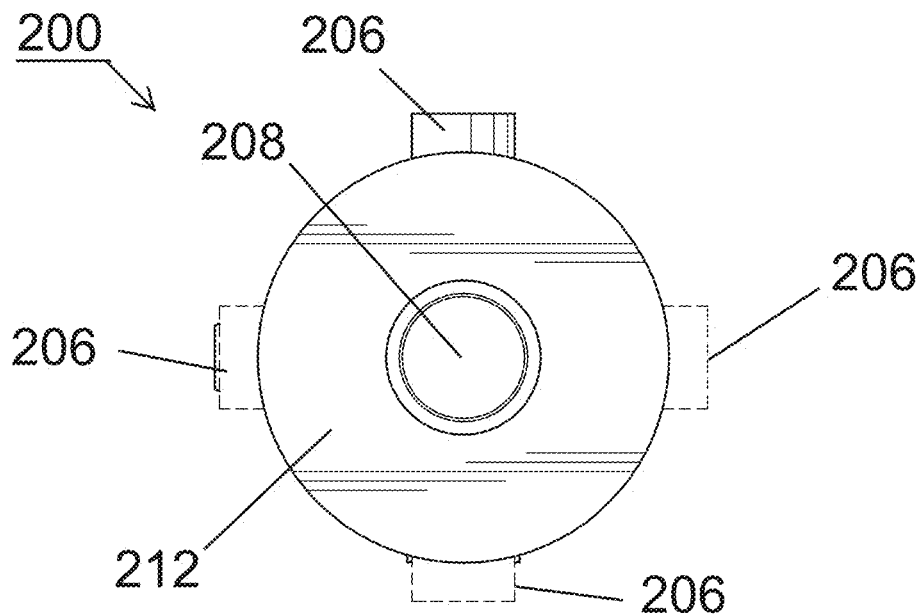
FIG. 7 is a top view of the device of FIG. 1.
Figure 8:
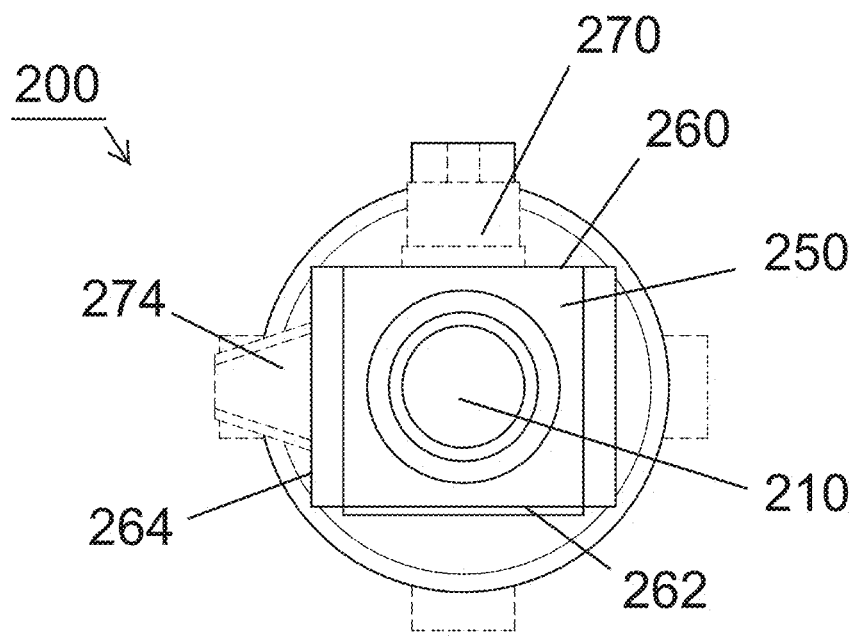
FIG. 8 is a bottom view of the device of FIG. 1.
Figure 9:
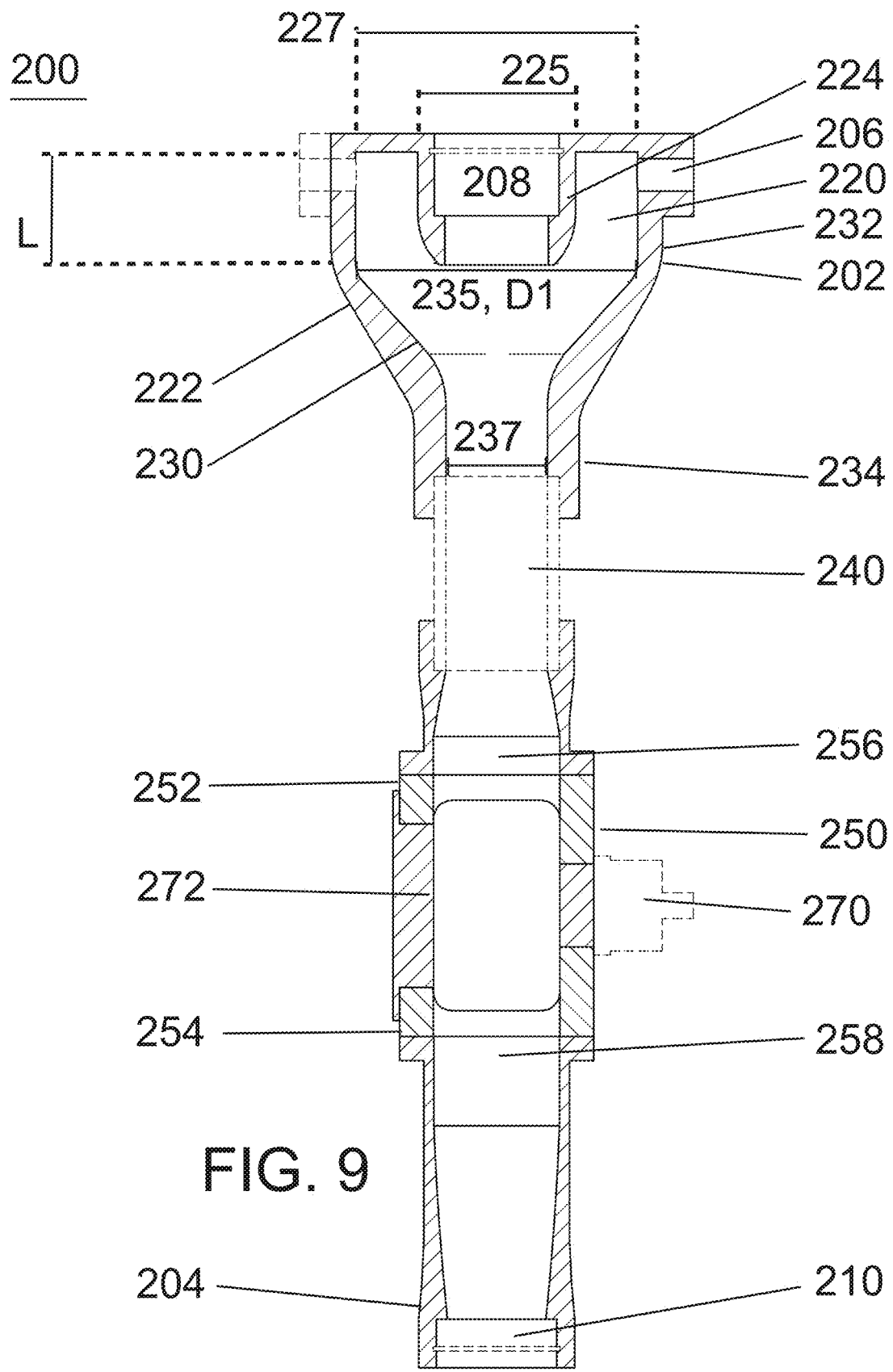
FIG. 9 is a right side cross-sectional view of the device of FIG. 1.

The present disclosure may be understood more readily by reference to the following detailed description of desired embodiments and the examples included therein. In the following specification and the claims which follow, reference will be made to a number of terms which shall be defined to have the following meanings.

The singular forms "a," "an," and "the" include plural referents unless the context clearly dictates otherwise.

As used in the specification and in the claims, the term "comprising" may include the embodiments "consisting of" and "consisting essentially of."

Numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

As used herein, approximating language may be applied to modify any quantitative representation that may vary without resulting in a change in the basic function to which it is related. Accordingly, a value modified by a term or terms, such as "about" and "substantially," may not be limited to the precise value specified. The modifier "about" should also be considered as disclosing the range defined by the absolute values of the two endpoints. For example, the expression "from about 2 to about 4" also discloses the range "from 2 to 4."

It should be noted that many of the terms used herein are relative terms. For example, the terms "upper" and "lower" are relative to each other in location, i.e. an upper component is located at a higher elevation than a lower component in a given orientation, but these terms can change if the device is flipped. The terms "inlet" and "outlet" are relative to a fluid flowing through them with respect to a given structure, e.g. a fluid flows through the inlet into the structure and flows through the outlet out of the structure. The terms "upstream" and "downstream" are relative to the direction in which a fluid flows through various components, i.e. the flow fluids through an upstream component prior to flowing through the downstream component. It should be noted that in a loop, a first component can be described as being both upstream of and downstream of a second component.

The terms "horizontal" and "vertical" are used to indicate direction relative to an absolute reference, i.e. ground level. However, these terms should not be construed to require structures to be absolutely parallel or absolutely perpendicular to each other. For example, a first vertical structure and a second vertical structure are not necessarily parallel to each other. The terms "top" and "bottom" or "base" are used to refer to surfaces where the top is always higher than the bottom/base relative to an absolute reference, i.e. the surface of the earth. The terms "upwards" and "downwards" are also relative to an absolute reference; an upwards flow is always against the gravity of the earth.

The present application refers to "the same order of magnitude." Two numbers are of the same order of magnitude if the quotient of the larger number divided by the smaller number is a value of at least one and less than 10.

Example large volume flow rate acoustophoretic phase separators using ultrasonic standing wave technology can be configured to provide the benefit of having little or no consumables, little or no generated waste, and/or low energy usage or cost. The technology is efficient at removal of particles of greatly varying sizes, including separation of micron and sub-micron sized particles. Examples of acoustic filters/collectors utilizing acoustophoresis can be found in commonly owned U.S. patent application Ser. Nos. 12/947,757; 13/085,299; 13/216,049; and Ser. No. 13/216,035, the entire disclosure of each being hereby fully incorporated herein by reference. Generally, the acoustophoretic systems discussed herein employ ultrasonic standing waves to trap (i.e. hold stationary) secondary phase particles, gases, or liquids that are suspended in a host fluid stream. The secondary phase can be continuously separated out of the host fluid as the mixture flows through the acoustophoretic system.

The acoustic radiation force is proportional to the particle volume (e.g. the cube of the radius) when the particle is small relative to the wavelength. It is proportional to frequency and the acoustic contrast factor. It also scales with acoustic energy (e.g. the square of the acoustic pressure amplitude). For harmonic excitation, the sinusoidal spatial variation of the force is what drives the particles to the stable positions within the standing waves. When the acoustic radiation force exerted on the particles is stronger than the combined effect of fluid drag force and buoyancy/gravitational force, the particle is trapped within the acoustic standing wave field. The action of the acoustic forces on the trapped particles results in concentration, agglomeration and/or coalescence of particles and droplets. Particles which are denser than the host fluid are separated through enhanced gravitational settling, and particles which are less dense than the host fluid are separated through enhanced buoyancy.

Efficient and economic particle separation processes can be useful in many areas of energy generation, e.g., producing water, hydro-f racking, and bio-fuels, e.g., harvesting and dewatering. Acoustophoretic technology can be used to target accelerated capture of bacterial spores in water, oil-recovery, and dewatering of bio-oil derived from micro-algae. Current technology used in the oil recovery field does not perform well in recovery of small, i.e., less than 20 micron, oil droplets. However, the acoustophoretic systems described herein can enhance the capture and coalescence of small oil droplets, thereby shifting the particle size distribution resulting in an overall increased oil capture. Practical, useful, large flow rates at a level of 15-20 gallons per minute (GPM) per square foot (cross-sectional area) are desired. Another goal is the increased capture of oil droplets with a diameter of less than 20 microns. Much prior work on acoustophoretics only occurred at the microscale, in MEMS applications in research settings. Industrial processes use high flow rates and continuous operation.

Acoustophoretic separation can also be used to aid such applications as advanced bio-refining technology to convert low-cost readily available non-food biomass (e.g. municipal solid waste and sewage sludge) into a wide array of chemicals and secondary alcohols that can then be further refined into renewable gasoline, jet fuel, or diesel. A water treatment technology is used to de-water the fermentation broth and isolate valuable organic salts for further processing into fuels. The dewatering process is currently done through an expensive and inefficient ultra-filtration method that suffers from frequent fouling of the membranes, a relatively low concentration factor, and a high capital and operating expense. Acoustophoretic separation can filter out particles with an incoming particle size distribution that spans more than three orders of magnitude, namely from 600 microns to 0.3 microns, allowing improvements in the concentration of the separated broth with a lower capital and operational expense.

Acoustophoretic separation is also useful for the harvesting, oil-recovery, and dewatering of micro-algae for conversion into bio-oil. Current harvesting, oil recovery, and dewatering technologies for micro-algae suffer from high operational and capital expenses. Current best estimates put the price of a barrel of bio-oil derived from micro-algae at a minimum of $200.00 per barrel. There is a desire in the art of micro-algae biofuel for technologies that improve the harvesting, oil-recovery, and dewatering steps of this process. Acoustophoretic separation is one such technology.

Some other applications are in the areas of wastewater treatment, grey water recycling, and water production. Other applications are in the area of biopharmaceuticals, life sciences, and medical applications, such as the separation of lipids from red blood cells. This can be of critical importance during cardiopulmonary bypass surgery, which involves suctioning shed mediastinal blood. Lipids are unintentionally introduced to the bloodstream when blood is re-transfused to the body. Lipid micro-emboli can travel to the brain and cause various neuro-cognitive disorders. Efforts have been undertaken to remove the lipids and cleanse the re-transfused blood, however existing methods can be relatively inefficient and/or harmful to red blood cells.

Particular embodiments focus on the capture and growth of sub 20 micron oil droplets. At least 80% of the volume of sub-20-micron droplets are captured and then grown to droplets that are bigger than 20 microns. The process involves the trapping of the oil droplets in the acoustic standing wave, coalescence of many small trapped droplets, and eventually release of the larger droplets when the acoustic trapping force becomes smaller than the buoyancy force.

Desirably, the ultrasonic transducers generate a three-dimensional standing wave in the fluid that exerts a lateral force on the suspended particles/secondary fluid to accompany the axial force so as to increase the particle trapping capabilities of a acoustophoretic system. Typical results published in literature state that the lateral force is two orders of magnitude smaller than the axial force. In contrast, the technology disclosed in this application provides for a lateral force to be of the same order of magnitude as the axial force.

The present disclosure relates to the use of an acoustic standing wave generated by an ultrasonic transducer or transducers to separate oil from processed water on a macro scale. The oil may be partially emulsified with the water. The separation occurs by trapping the oil particles at the pressure nodes and anti-pressure nodes in a standing wave. As the oil is trapped at these nodes, it agglomerates and, due to buoyancy, will move to an area of trapped, concentrated oil. The buoyancy separation is accomplished through fluid dynamics with the main fluid stream flowing in a downward direction and the trapped, agglomerated and coalesced oil particles floating upward, due to buoyancy, into a trap.

The oil particles are separated from the fluid stream at the anti-pressure nodes of the acoustic standing wave due to the difference in their acoustic contrast factors from the fluid stream. The equation for determining the acoustic contrast factor of an oil in a fluid is known, and is related to the density of the fluid, the density of the oil in the fluid, the compressibility of the fluid, and the compressibility of the oil in the fluid. Both oil and emulsified oil typically have a negative contrast factor ($\phi$).

In the present disclosure, a 3-D acoustic standing wave is generated by causing the ultrasonic transducer to act in a "drumhead" fashion as opposed to a "piston" fashion. The "drumhead" operation of the piezoelectric element in the ultrasonic transducer causes multiple standing waves to be generated in a 3-D space. This is opposed to the action of the piezoelectric element in the ultrasonic transducer acting in a "piston" fashion n where a single standing wave is produced. Through the use of a 3-D multi-standing wave, macro-scale trapping of oil particles may be accomplished. This allows for high volumes of processed water to be treated and the oil to be separated from the water, The piezoelectric element in the ultrasonic transducer may be directly interfaced with the fluid stream or may have a protective layer or matching layer over the surface of the piezoelectric element that is interfaced with the fluid stream, The protective layer may be a coating, such as a polyurethane or epoxy. The protective layer may also be plated onto the surface of the piezoelectric element that is interfaced with the fluid stream. The plated layer may be added to the surface of the piezoelectric element through either electrolytic or electroless plating. The plating material may be nickel, chrome, copper, indium or combination of layers of these materials. Also, the secondary material or matching layer may be adhered to the surface of the piezoelectric element such that the matching layer is now interfaced with the fluid stream. The matching layer may be a material such as a stainless steel that is adhered to the piezoelectric element through the use of a two-part epoxy system.

FIGS. 1-9 show various views of an acoustophoresis device of the present disclosure. Generally, the acoustophoresis device uses the ultrasonic transducer to separate suspended oil particles/droplets in a fluid stream into ordered, coalesced and agglomerated particles trapped in a standing wave of the acoustophoresis device. The flow of the fluid stream is from the upper end downward (i.e. with gravity). The fluid stream can enter the device through one of many inlets that surround a central trapping device for the agglomerated and separated oil. The fluid stream flows into the acoustophoresis separation device from a pump through the inlet. The agglomerated and coalesced oil gains buoyancy and rises into the central oil trapping device. The device is shown here in an orientation where the flow direction is downwards, which is used for separating less-dense particles from the host fluid. However, the device may be essentially turned upside down to allow separation of particles which are heavier than the host fluid. Instead of a buoyant force in an upward direction, the weight of the agglomerated particles due to gravity pulls them downward.

The initial fluid stream is made up of a host fluid (e.g. water) and a suspended phase (e.g. oil droplets/articles). The fluid stream enters the device 200 through one or more device inlets 206 into an annular plenum 220 at a first end 202 of the device. The first end 202 includes an outer sidewall 222 and an inner longitudinal sidewall 224. An end wall 212 is also visible, from which the longitudinal sidewall extends. The term "annular," as used herein, only designates the area or volume between the outer sidewall and the inner longitudinal sidewall, and should not be construed as requiring the first end of the device to have a circular cross-section. However, in contemplated embodiments the first end of the device has a circular cross-section. The annular plenum has an inner diameter 225 and an outer diameter 227. This construction guides the fluid stream flow downwards in the direction of the centerline, i.e. with little to no radial or circumferential motion component. This helps to create laminar/plug flow later downstream. One device inlet 206 is shown here, with three other inlets spaced about the first end being shown in dotted line. It is contemplated that any number of inlets may be provided as desired. In particular embodiments, four inlets are used. The inlets are radially oriented.

A contoured nozzle wall 230 reduces the outer diameter of the flow path, which generates higher velocities near the wall and reduces turbulence, producing near plug flow as the fluid velocity profile develops and the fluid passes through the connecting duct and into a flow/separation chamber. The contoured wall also adds a radial motion component to the suspended particles, moving the particles closer to the centerline of the device and generating more collisions with rising, buoyant agglomerated particles. This radial motion will allow for optimum scrubbing of the particles from the fluid in the connecting duct prior to reaching the separation chamber. The term scrubbing is used to describe the process of particle/droplet agglomeration, aggregation, clumping or coalescing, that occurs when a larger particle/droplet travels in a direction opposite to the fluid flow and collides with smaller particles, in effect scrubbing the smaller particles out of the suspension. The contoured nozzle wall directs the fluid in a manner that generates large scale vortices at the entrance of the first device outlet to also enhance particle collection. Generally, the flow area of the device is designed to be continually decreasing from the device inlets to the separation chamber to assure low turbulence and eddy formation for better particle separation, agglomeration, and collection. Put another way, the contoured wall 230 has a wide end 232 and a narrow end 234. The first end of the device/the wide end of the nozzle wall has a first diameter 235, and the narrow end of the nozzle wall has a second diameter 237. The second diameter is less than the first diameter. The connecting duct 240 is downstream of the nozzle wall and connects to the inlet 256 of the flow chamber 250.

The flow/separation chamber 250 is downstream of the connecting duct 240 and has an inlet 256 at a first end 252, and an outlet 258 at a second end 254 opposite the first end. At least one ultrasonic transducer 270 is present on a wall 260, and a reflector 272 is located on a wall 262 opposite the transducer. Multiple transducers can be used, as desired. In use, standing waves are created between the transducer 270 and reflector 272. These standing waves can be used to agglomerate particles, and this orientation is used to agglomerate particles that are buoyant (e.g. oil). Fluid, containing residual particles, then exits through the flow chamber outlet 258 and through a second device outlet 210 located at a second end 204 of the device opposite the first end 202 of the device. Also shown here is a transparent window 274 on a third wall 264 of the flow chamber. It is contemplated that in particular embodiments, the flow chamber has a rectangular cross-section. The flow chamber inlet and outlets have a circular cross-section for interfacing with the other components of the device.

As the buoyant particles agglomerate, they eventually overcome the combined effect of the fluid flow drag forces and acoustic radiation force, and their buoyant force is sufficient to cause the buoyant particles to rise upwards. In this regard, a first device outlet or collection duct 208 is present at the first end of the device 202, and is surrounded by the longitudinal sidewall 224, or put another way is separated from the device inlets 206 by the longitudinal sidewall 224, or put yet another way the first device outlet is a hole in the end wall 212. The agglomerated buoyant particles exit the device through the first device outlet 208. The first device outlet and the second device outlet are on opposite ends of the device.

It should be noted that the buoyant particles formed in the separation chamber 250 subsequently pass through the connecting duct 240. This causes the incoming fluid stream flow from the device inlets 206 to flow over the rising agglomerated particles due to the inward radial motion imparted by the contoured wall 230. This allows the rising particles to also trap smaller particles in the incoming flow, increasing scrubbing effectiveness. The length of the connecting duct and the contoured nozzle wall thus increase scrubbing effectiveness. Especially high effectiveness is found for particles with a size of 0.1 microns to 10 microns, where efficiency is very low for conventional methods. As noted here, the distance from the device inlets 206 to the bottom of the longitudinal sidewall 224 is marked as length (L). The first diameter is marked as D1 (reference numeral 235). This length-to-diameter ratio here (i.e. L/D1) is less than 1.

The design here results in low flow turbulence at the flow chamber inlet, a scrubbing length before (i.e. upstream of) the flow chamber to enhance particle agglomeration and/or coalescence before acoustic separation, and the use of the collection vortices to aid particle removal upstream of the flow chamber.

The ultrasonic transducer(s) are arranged to cover the entire cross-section of the fluid stream flowpath. In certain embodiments, the flow chamber has a square cross section of 6 inches×6 inches which operates at flow rates of up to 3 gallons per minute (GPM), or a linear velocity of 8 mm/sec. The transducer can be a PZT-8 (Lead Zirconate Titanate) transducer with a 1-inch diameter and a nominal 2 MHz resonance frequency. Each transducer consumes about 28 W of power for droplet trapping at a flow rate of 3 GPM. This translates in an energy cost of 0.25 kW hr/m3. This is an indication of the very low cost of energy of this technology. Desirably, when multiple transducers are present, each transducer is powered and controlled by its own amplifier. This device shifts the particle size distribution in the host fluid through agglomeration of smaller oil droplets into larger oil droplets.

FIG. 10 is a cross-sectional diagram of a conventional ultrasonic transducer. This transducer has a wear plate/protective layer 50 at a bottom end, epoxy layer 52, piezoelectric material 54 (made of, e.g. PZT), an epoxy layer 56, and a backing layer 58. The epoxy layer 56 attaches backing layer 58 to the crystal 54. The entire assembly is contained in a housing 60 which may be made out of, for example, aluminum. A connector 62 provides connection for wires to pass through the housing and connect to leads (not shown) which attach to the piezoelectric material 54. Typically, backing layers are designed to add damping and to create a broadband transducer with uniform displacement across a wide range of frequency and are designed to suppress excitation at particular vibrational eigen-modes. Wear plates are usually designed as impedance transformers to better match the characteristic impedance of the medium into which the transducer radiates, and face in the direction in which the wave is generated. The piezoelectric material can be, for example, a ceramic crystal.

FIG. 11 is a cross-sectional view of an ultrasonic transducer 81 of the present disclosure, which can be used with the acoustophoretic device of FIGS. 1-9. Transducer 81 has an aluminum housing 82. A PZT crystal 86 defines the bottom end of the transducer, and is exposed from the exterior of the housing. The crystal is supported on its perimeter by the housing, with a small elastic layer, e.g. silicone or similar material, located between the crystal and the housing.

Screws (not shown) attach an aluminum top plate 82a of the housing to the body 82b of the housing via threads 88. The top plate includes a connector 84 to pass power to the PZT crystal 86. The bottom and top surfaces of the PZT crystal 86 each contain an electrode. A wrap-around electrode tab 90 connects to the bottom electrode and is isolated from the top electrode. Electrical power is provided to the PZT crystal 86 through the electrodes, with the wrap-around tab 90 being the ground connection point. Note that the crystal 86 has no backing layer or epoxy layer as is present in FIG. 5. Put another way, there is an air gap 87 in the transducer between aluminum top plate 82a and the crystal 86. A minimal backing may be provided in some embodiments.

The transducer design can affect performance of the system. A typical transducer is a layered structure with the ceramic crystal bonded to a backing layer and a wear plate. Because the transducer is loaded with the high mechanical impedance presented by the standing wave, the traditional design guidelines for wear plates, e.g., half wavelength thickness for standing wave applications or quarter wavelength thickness for radiation applications, and manufacturing methods may not be appropriate. Rather, in one embodiment of the present disclosure the transducers, there is no wear plate or backing, allowing the crystal to vibrate in one of its eigenmodes with a high Q-factor. The vibrating ceramic crystal/disk is directly exposed to the fluid flowing through the flow chamber.

Removing the backing (e.g. making the crystal air backed) also permits the ceramic crystal/piezoelectric material to vibrate higher order modes of vibration (e.g. higher order modal displacement) with little damping. In a transducer having a crystal with a backing, the crystal vibrates with a more uniform displacement, like a piston. Removing the backing allows the crystal to vibrate in a non-uniform displacement mode. The higher order the mode shape of the crystal, the more nodal lines the crystal has. The higher order modal displacement of the crystal creates more trapping lines, although the correlation of trapping line to node is not necessarily one to one, and driving the crystal at a higher frequency will not necessarily produce more trapping lines. In the present disclosure, the transducers are driven so that the piezoelectric element vibrates in higher order modes of the general formula (m, n), where m and n are independently 1 or greater. In practice, the transducers of the present disclosure will vibrate at higher orders than (1,2).

In some embodiments, the crystal may have a backing that minimally affects the Q-factor of the crystal (e.g. less than 5%). The backing may be made of a substantially acoustically transparent material such as balsa wood, foam, or cork which allows the crystal to vibrate in a higher order mode shape and maintains a high Q-factor while still providing some mechanical support for the crystal. In another embodiment, the backing may be a lattice work that follows the nodes of the vibrating crystal in a particular higher order vibration mode, providing support at node locations while allowing the rest of the crystal to vibrate freely. The goal of the lattice work or acoustically transparent material is to provide support without lowering the Q-factor of the crystal or interfering with the excitation of a particular mode shape.

Placing the crystal in direct contact with the fluid also contributes to the high Q-factor by avoiding the dampening and energy absorption effects of the epoxy layer and the wear plate. Other embodiments may have wear plates or a wear surface/protective layer to prevent the PZT, which contains lead, contacting the host fluid. This may be desirable in, for example, biological applications such as separating blood. Such applications might use a wear layer such as chrome, electrolytic nickel, or electroless nickel. Chemical vapor deposition could also be used to apply a layer of poly(p-xylxyene) (e.g. Parylene) or other polymer. Organic and biocompatible coatings such as silicone or polyurethane are also contemplated for use as a wear surface.

Figure 12:
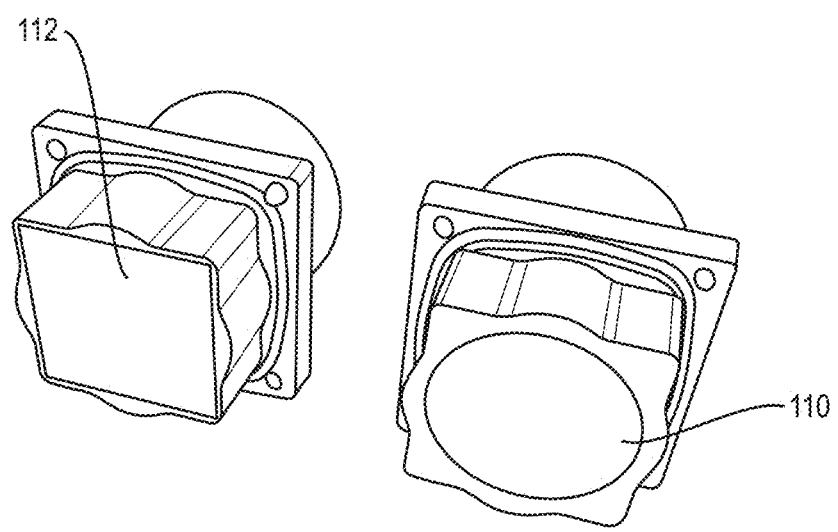
FIG. 12 is a photo of a square transducer and a circular transducer suitable for use in the devices of the present disclosure.

FIG. 12 illustrates two different ultrasonic transducers that can be used in the devices of the present disclosure. The transducer on the right shows a circular-shaped PZT-8 crystal 110 that is 1 inch in diameter. The transducer on the right shows a rectangular-shaped crystal, which here is a square 1 inch by 1 inch crystal. The effect of transducer shape on oil separation efficiency was investigated, and Table 1 shows the results.

TABLE 1

Results of Investigation of Round and Square Transducer Shape

| Transducer Shape | Total Power Input (Watts) | Flowrate (ml/min) | Duration (min) | Capture Efficiency (%) |
|---|---|---|---|---|
| Round | 20 | 500 | 45 | 59% |
| Square | 20 | 500 | 30 | 91% |

The results indicate that the square transducer 112 provides better oil separation efficiencies than the round transducer 110, explained by the fact that the square transducer 112 provides better coverage of the flow channel with acoustic trapping forces, and that the round transducer only provides strong trapping forces along the centerline of the standing wave.

The size, shape, and thickness of the transducer determine the transducer displacement at different frequencies of excitation, which in turn affects oil separation efficiency. Typically, the transducer is operated at frequencies near the thickness resonance frequency (half wavelength). Gradients in transducer displacement typically result in more places for oil to be trapped. Higher order modal displacements generate three-dimensional acoustic standing waves with strong gradients in the acoustic field in all directions, thereby creating equally strong acoustic radiation forces in all directions, leading to multiple trapping lines, where the number of trapping lines correlate with the particular mode shape of the transducer.

Figure 13:
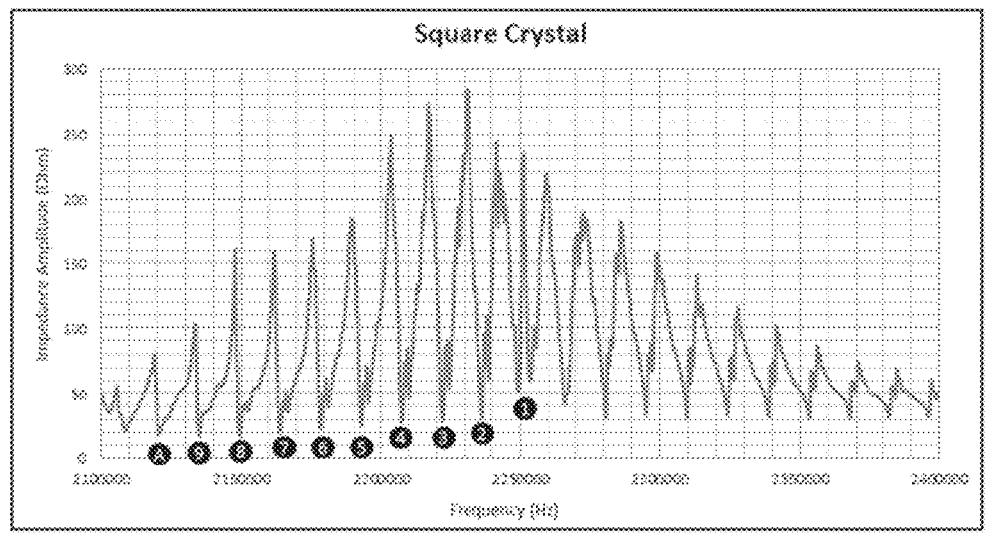
FIG. 13 is a graph of electrical impedance amplitude versus frequency as a square transducer is driven at different frequencies.

FIG. 13 shows the measured electrical impedance amplitude of the transducer as a function of frequency in the vicinity of the 2.2 MHz transducer resonance. The minima in the transducer electrical impedance correspond to acoustic resonances of the water column and represent potential frequencies for operation. Numerical modeling has indicated that the transducer displacement profile varies significantly at these acoustic resonance frequencies, and thereby directly affects the acoustic standing wave and resulting trapping force. Since the transducer operates near its thickness resonance, the displacements of the electrode surfaces are essentially out of phase. The typical displacement of the transducer electrodes is not uniform and varies depending on frequency of excitation. As an example, at one frequency of excitation with a single line of trapped oil droplets, the displacement has a single maximum in the middle of the electrode and minima near the transducer edges. At another excitation frequency, the transducer profile has multiple maxima leading to multiple trapped lines of oil droplets. Higher order transducer displacement patterns result in higher trapping forces and multiple stable trapping lines for the captured oil droplets.

To investigate the effect of the transducer displacement profile on acoustic trapping force and oil separation efficiencies, an experiment was repeated ten times, with all conditions identical except for the excitation frequency. Ten consecutive acoustic resonance frequencies, indicated by circled numbers 1-9 and letter A on FIG. 13, were used as excitation frequencies. The conditions were an experiment duration of 30 min, a 1000 ppm oil concentration, a flow rate of 500 ml/min, and an applied power of 20 W.

Figure 14:
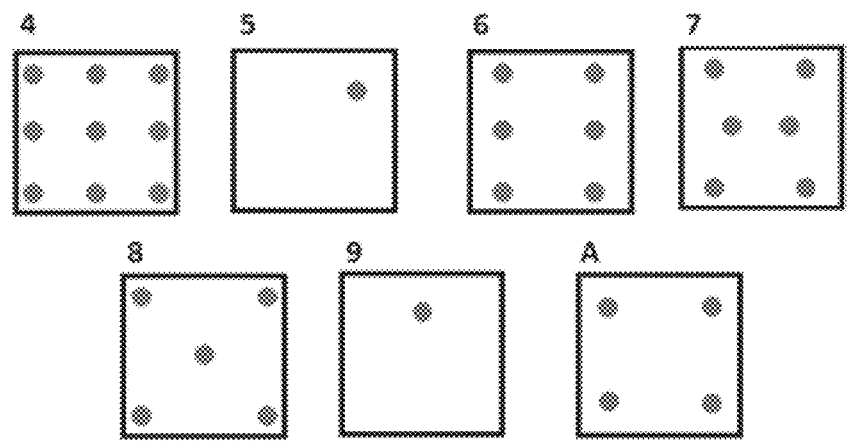
FIG. 14 illustrates the trapping line configurations for seven of the peak amplitudes of FIG. 13.

As the emulsion passed by the transducer, the trapping lines of oil droplets were observed and characterized. The characterization involved the observation and pattern of the number of trapping lines across the fluid channel, as shown in FIG. 14, for seven of the ten resonance frequencies identified in FIG. 13.

The effect of excitation frequency clearly determines the number of trapping lines, which vary from a single trapping line at the excitation frequency of acoustic resonance 5 and 9, to nine trapping lines for acoustic resonance frequency 4. At other excitation frequencies four or five nodal trapping lines are observed. Different displacement profiles of the transducer can produce different (more) trapping lines of the standing waves, with more gradients in displacement profile generally creating higher trapping forces and more trapping lines.

Table 2 summarizes the findings from an oil trapping experiment using a system similar to FIGS. 1-9. An important conclusion is that the oil separation efficiency of the acoustic separator is directly related to the mode shape of the transducer. Higher order displacement profiles generate larger acoustic trapping forces and more trapping lines resulting in better efficiencies. A second conclusion, useful for scaling studies, is that the tests indicate that capturing 5 micron oil droplets at 500 ml/min uses 10 Watts of power per square-inch of transducer area per 1" of acoustic beam span. The main dissipation is that of thermo-viscous absorption in the bulk volume of the acoustic standing wave. The cost of energy associated with this flow rate is 0.667 kWh per cubic meter.

TABLE 2

Trapping Pattern Capture Efficiency Study

| Resonance Peak Location | Total Power Input (Watts) | # of Trapping Lines | Flowrate (ml/min) | Duration (min) | Capture Efficiency (%) |
|---|---|---|---|---|---|
| 4 | 20 | 9 | 500 | 30 | 91% |
| 8 | 20 | 5 | 500 | 30 | 58% |
| A | 20 | 4 | 500 | 30 | 58% |
| 9 | 20 | 2 | 500 | 30 | 37% |

Figure 15A:
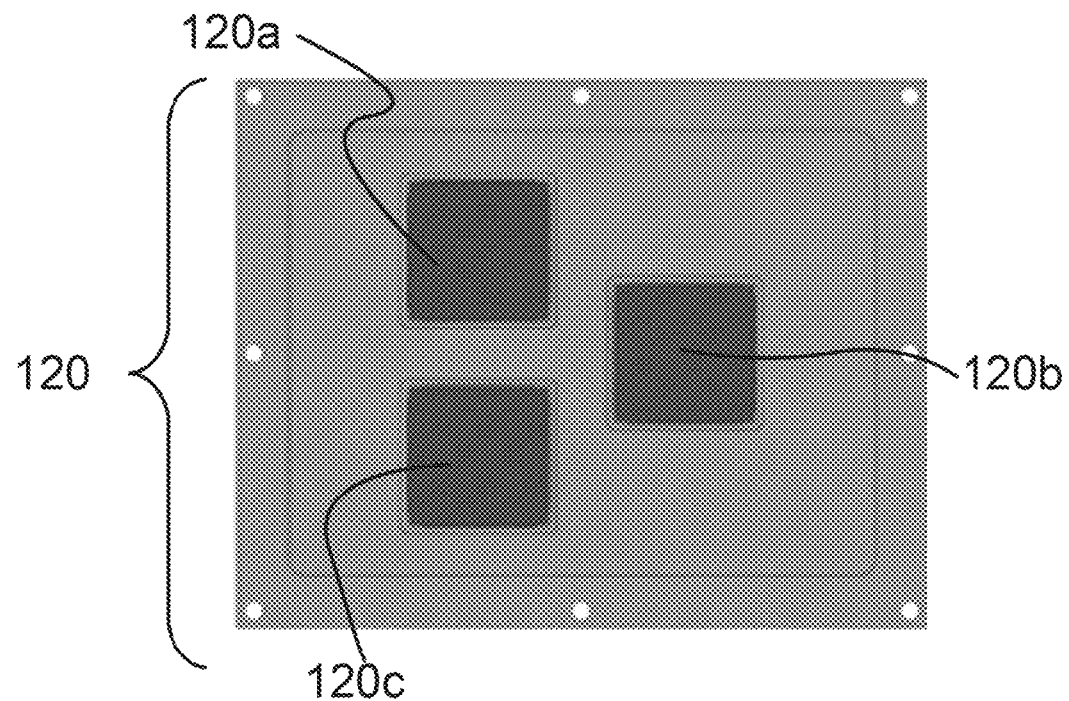
FIG. 15A illustrates a possible array configuration for a group of transducers.
Figure 15B:
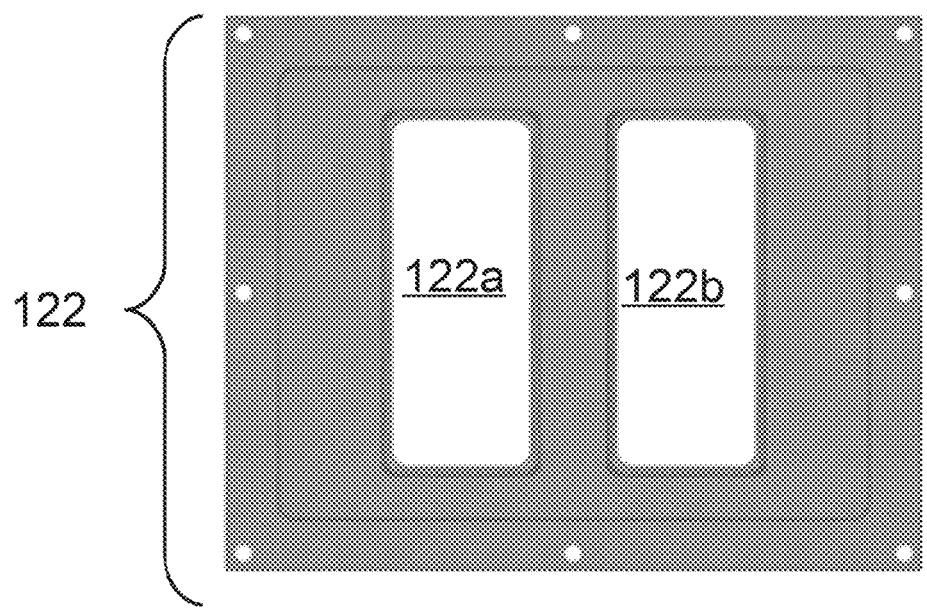
FIG. 15B illustrates another possible array configuration for a group of transducers.

In larger systems, different transducer arrangements are feasible. FIG. 15A shows a transducer array 120 including three square 1"×1" crystals 120a, 120b, 120c. Two squares are parallel to each other, and the third square is offset to form a triangular pattern and get 100% acoustic coverage. FIG. 15B shows a transducer array 122 including two rectangular 1"×2.5" crystals 122a, 122b arranged with their long axes parallel to each other. Power dissipation per transducer was 10 W per 1"×1" transducer cross-sectional area and per inch of acoustic standing wave span in order to get sufficient acoustic trapping forces. For a 4" span of an intermediate scale system, each 1"×1" square transducer consumes 40 W. The larger 1"×2.5" rectangular transducer uses 100 W in an intermediate scale system. The array of three 1"×1" square transducers would consume a total of 120 W and the array of two 1"×2.5" transducers would consume about 200 W. Arrays of closely spaced transducers represent alternate potential embodiments of the technology. Transducer size, shape, number, and location can be varied as desired to generate desired three-dimensional acoustic standing waves.

When multiple transducers are connected in series, the amplifier(s) used to power and control the transducers delivers more voltage at increased current draws. When multiple transducers are connected in parallel, the voltage remains similar to single transducer operation, but the current draw increased proportionally to the number of transducers connected. Typical amplifiers may be more limited in the slew rate of current than in voltage. Also, typical amplifiers only operate up to 100 W, which assumes perfect impedance matching (i.e., a load impedance of 50 Ohm), which may not occur in practice. Another complicating factor is that when multiple transducers are connected to the same amplifier, the transducers are excited at the same frequency. Impedance measurements of the transducers has shown small changes in the resonance frequency of each transducer, which can make it difficult to find an excitation frequency that is optimal for each transducer. Thus, it would be desirable to develop custom-made electronics for powering and controlling the acoustic transducer(s) and the resulting acoustic standing waves of the present disclosure.

Figure 16A:
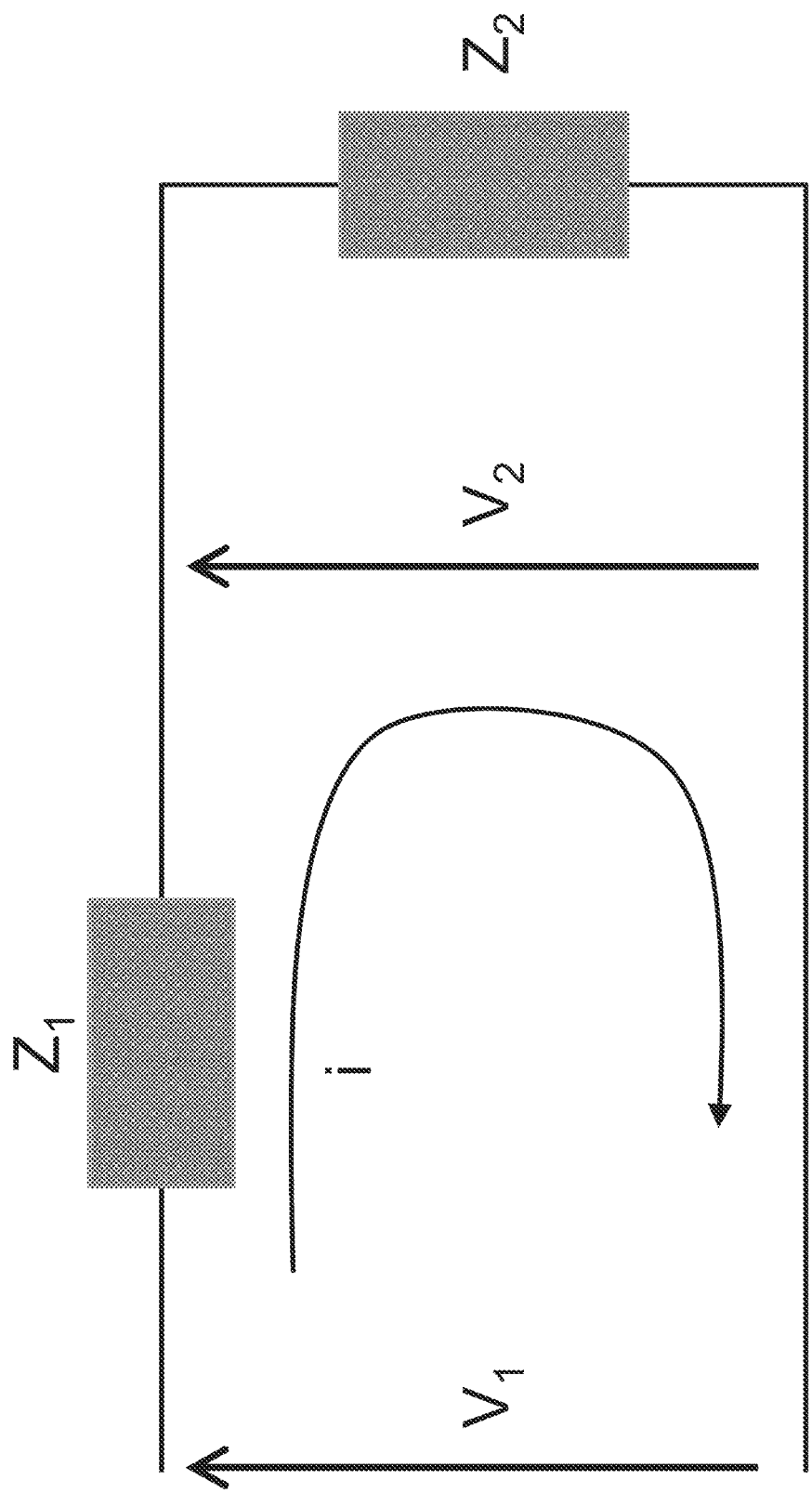
FIG. 16A is a general schematic of an impedance measurement circuit.

A circuit layout of two electrical impedances in series is used to characterize the transducer. From voltage measurements, the electrical impedance and electrical power consumed by the transducer can be derived. The circuit consists of a series combination of two impedances, as shown in FIG. 16A. The impedances can consist of resistances, capacitance, and/or inductance, and are specified later. The voltages are measured before and after impedance Z1. Because resistors are passive devices (i.e., they neither produce nor consume electrical energy), the ratio of voltage to current in these circuits depends upon the frequency and phase angle ($\varphi$) of the supply. Because the AC impedance (Z) is equivalent to DC resistance (R), in these circuits, R=Z.

The measurement between the amplifier and impedance Z1 is voltage V1, and the measurement between impedance Z1 and impedance Z2 is voltage V2. Two cases are distinguished. In the first case, impedance Z2 is a known impedance, typically a pure resistance, and is used along with voltage measurements to obtain impedance Z2. Since the elements can be reactive, the voltages and currents can be treated as vectors (i.e., phasors, with amplitude and phase). In the second case, a known impedance Z1 is used with the voltage measurements to obtain impedance Z2, which is then the unknown transducer. The general circuit equations that can be used to solve the circuit are Kirchoff's equation for voltage:

$$\vec{V}_1 - \vec{V}_2 = Z_1 \vec{\iota}$$

and the relationship between voltage and current:

$$\vec{V}_2 = Z_2 \vec{\iota}$$

When the above equations are combined, the following relationship between the measured voltages and circuit impedances is obtained:

$$\frac{\vec{V_2}}{\vec{V_1}} = \frac{1}{1 + \frac{Z_1}{Z_2}}$$

Figure 16B:
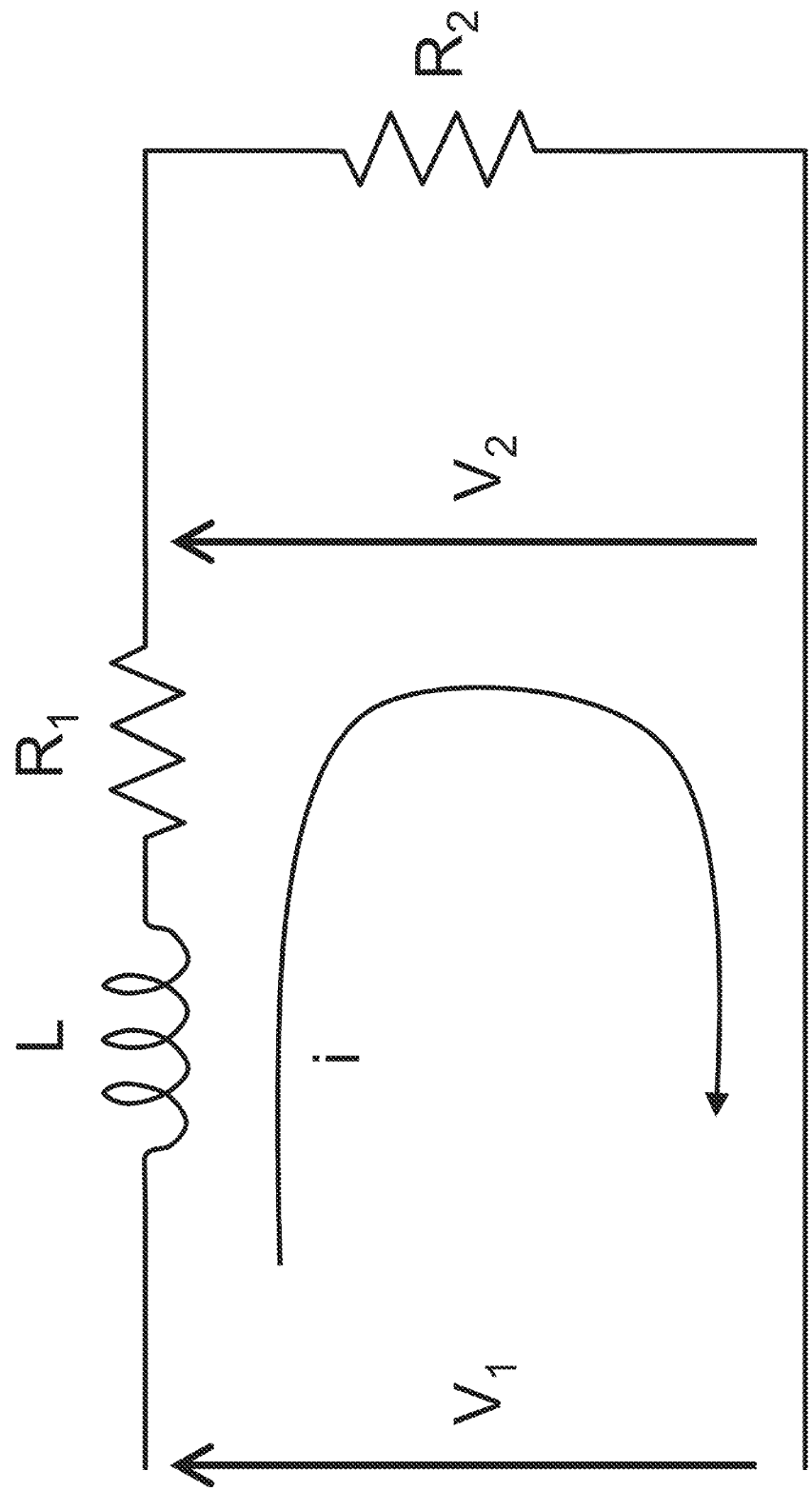
FIG. 16B is a schematic of a circuit used for the calibration of a power resistor.

In a typical setup, a power resistor of a known resistance is used to measure and characterize the transducer. The power resistor behaves like a series combination of a resistor and inductance at typical ultrasonic frequencies because at the ultrasonic frequencies of the present disclosure, the resistor is no longer a pure resistor. As such, the first step in the calibration process is to determine the value of the resistance and inductance of the power resistor. This can be done, for example, by completing the circuit with a known termination resistance, typically 50 or 75 Ohm. Such a circuit is shown in FIG. 16B.

Solving the following relationship between the measured voltages and circuit impedances yields the following equation for impedance Z1:

$$Z_1 = R_2 \left[ \frac{\vec{V_1}}{\vec{V_2}} - 1 \right]$$

From the above equation, the real and imaginary parts representing the resistance and inductance of the power resistor can be obtained. First, the real part of the above equation, represent the resistance of the power resistor, can be found by the following equation:

$$R_1 = \text{Re}\{Z_1\} = R_2 \left[ \frac{V_1}{V_2} \cos\varphi_{12} - 1 \right]$$

and the imaginary part of the above equation, representing the inductance of the power resistor, can be found by the following equation:

$$\omega L = \text{Im}\{Z_1\} = R_2 \left[ \frac{V_1}{V_2} \sin\varphi_{12} - 1 \right]$$

where ω is the work/energy and L is the self-inductance of the power resistor.

From the two above equations, a first estimate of R1 and L can be obtained. The computer program LabVIEW can be used to calculate these values as the average of all of the predicted values at each frequency. Next, a more accurate estimate of these values can be obtained by comparing the measure voltage amplitude ration of V2/V1 and the phase difference between V1 and V2. The voltage amplitude ratio can be obtained by the following equation:

$$\frac{V_2}{V_1} = \frac{1}{\sqrt{\left(1 + \frac{R_1}{R_2}\right)^2 + \left(\frac{\omega L}{R_2}\right)^2}}$$

and the phase difference can be obtained by the following equation:

$$\varphi_{21} = -\alpha\tan 2\left(1 + \frac{R_1}{R_2}, \frac{\omega L}{R_2}\right)$$

Using the LabVIEW computer program, the values of R1 and L can be iterated until the best fit is obtained. At that point, the resistance and inductance values of the power resistor have been determined. For exemplary purposes, typical values for a 10 Ohm power resistor in the frequency range of about 2 MHz are a resistance of 9.6 Ohm and an inductance of 9.7×10-7 Henry.

Figure 16C:
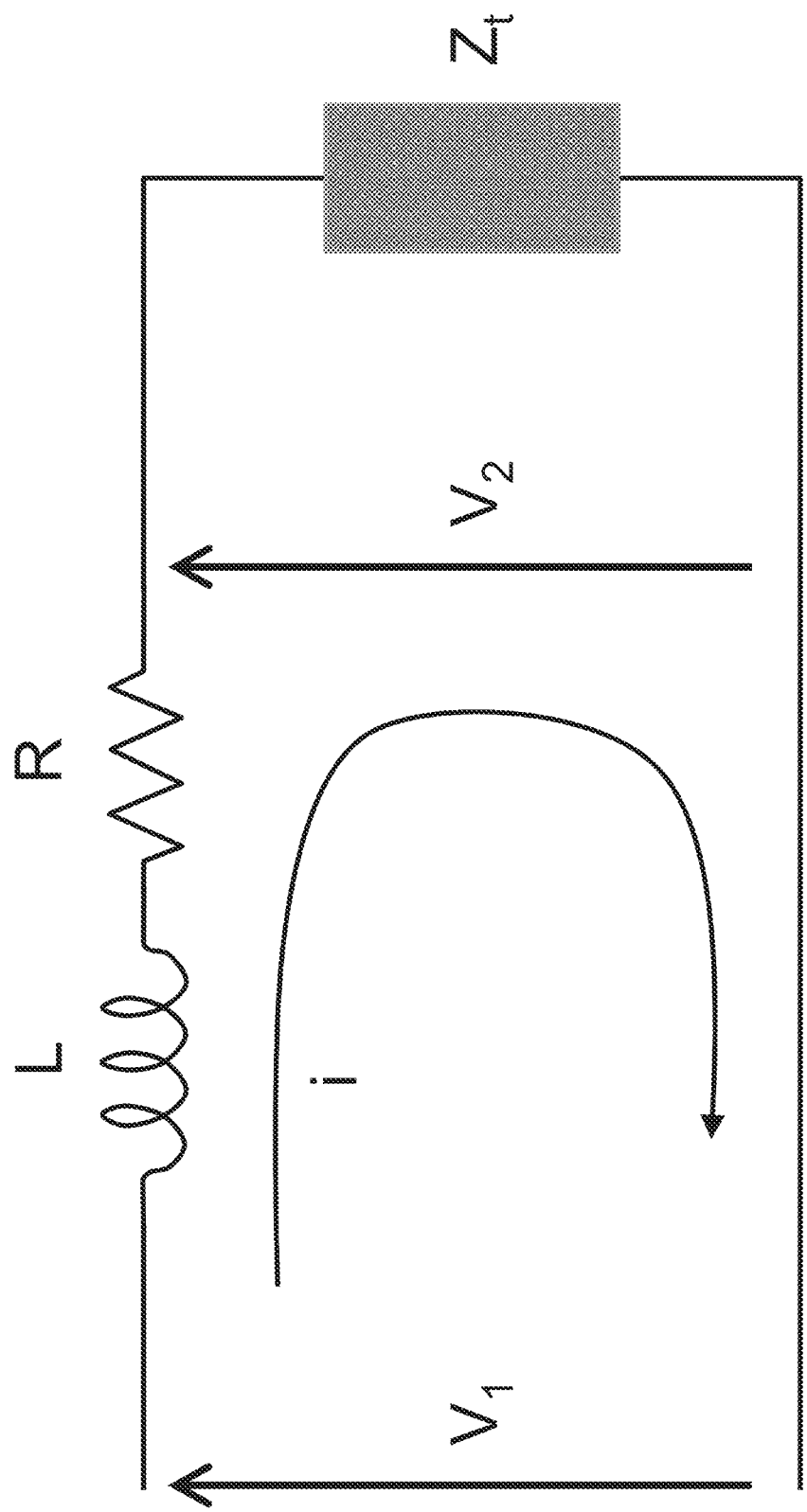
FIG. 16C is a schematic of a circuit used to measure the impedance of a transducer.

Once the power resistor is characterized, the impedance of the transducer can be measured with the schematic shown in FIG. 16C. Impedance Z1 is now known, while impedance Z2 remains unknown, which is the transducer impedance Zt. Using the same equations provided above, the following equations are obtained:

$$Z_t = \frac{Z_1}{\left[\frac{\vec{V_1}}{\vec{V_2}} - 1\right]} \quad Z_1 = R_1 + j\omega L$$

Using these equations, the following equation for $Z_t$ is obtained:

$$Z_t = \frac{\sqrt{R^2 + \omega^2 + L^2}}{\sqrt{\left(\frac{V_1}{V_2}\right)^2 - 2\frac{V_1}{V_2}\cos\varphi_{12} + 1}}$$

and the following equation for the phase of $Z_t$ is obtained:

$$\varphi_{Z_t} = \alpha\tan 2(R, \omega,) - \alpha\tan 2\left(\frac{V_1}{V_2}\cos\varphi_{12} - 1, \frac{V_1}{V_2}\sin\varphi_{12}\right)$$

The electrical power consumed by the transducer is given by the following equation:

$$P_{El} = \frac{V_2^2}{2Z_t}$$

From the power consumed, the real power is given by the following equation:

$$P_{El} = \frac{V_2^2}{2Z_t}\cos\varphi_{Z_t}$$

and the reactive power is given by the following equation:

$$P_{El} = \frac{V_2^2}{2Z_t}\sin\varphi_{Z_t}$$

These equations can be programmed in a LabVIEW computer program that measures the voltages V1 and V2 and deduces therefrom the electrical properties of the transducer.

Figure 16D:
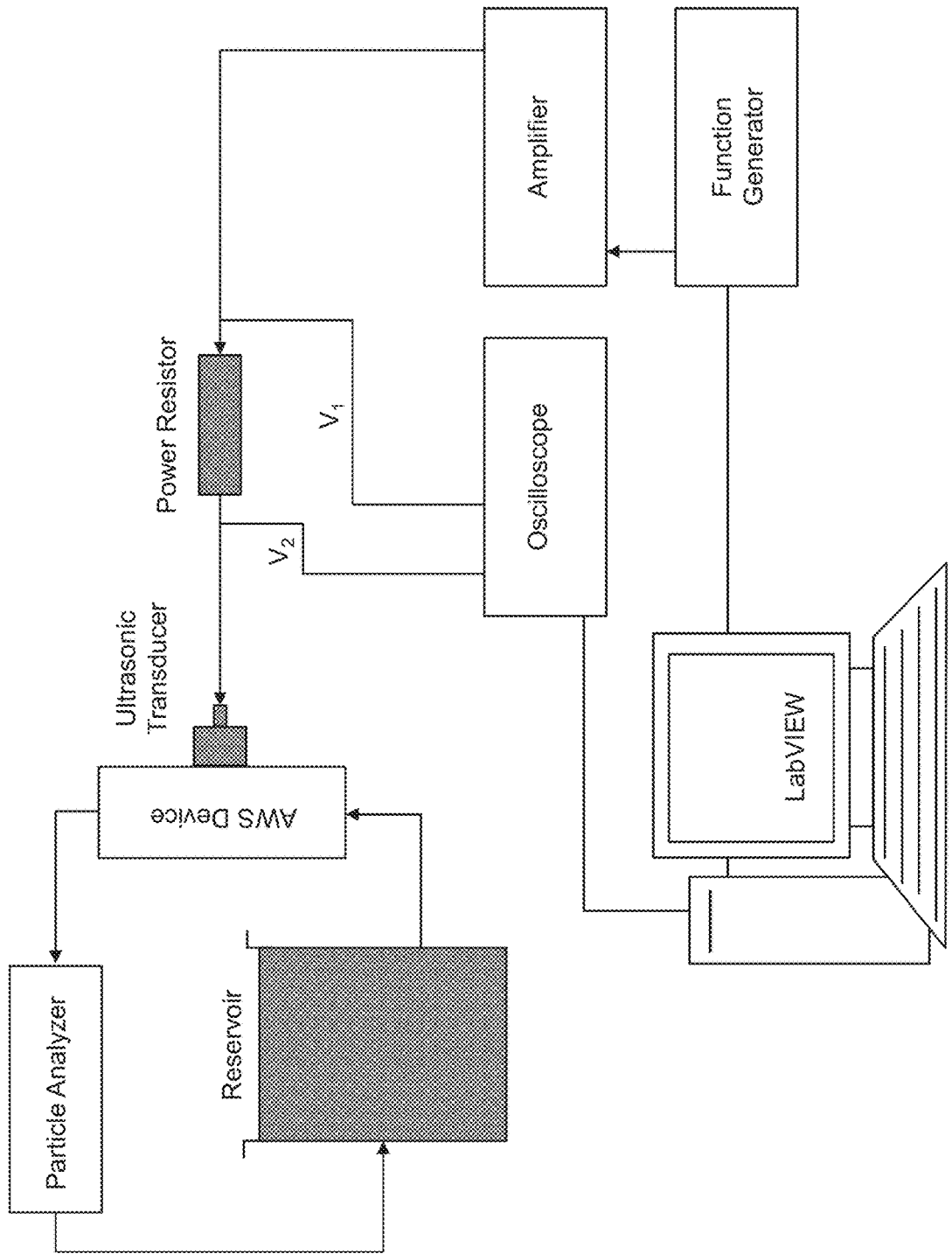
FIG. 16D is a schematic of an electronic system for controlling an acoustophoretic device.

FIG. 16D schematically illustrates an experimental setup for an acoustophoretic device according to the present disclosure and the electronics for controlling the ultrasonic transducer(s) of the device and acoustic standing wave(s) created therein. As seen in FIG. 16D, a function generator (Tektronix AFG 3022B) is used to generate a signal (e.g., a low voltage sinusoidal voltage signal) that is sent to an amplifier (AR Model 100A250A). The amplifier output signal is electrically connected to a power resistor, which is in turn electronically connected to the ultrasonic transducer of the acoustic wave separator (AWS) device. The voltage before the resistor (first voltage V1) and the voltage after the resistor (second voltage V2) are measured. As seen in FIG. 16D, an oscilloscope (Agilent Technologies DSO5014A) is used to measure the voltages. The power resistor is used to measure and characterize the performance of the transducer, as previously explained. A computer running the computer program LabVIEW is used to communicate with the function generator and oscilloscope (e.g., via USB cables). A particle analyzer (Jorin VIPA) is used to characterize the particles in the emulsion.

Figure 17:
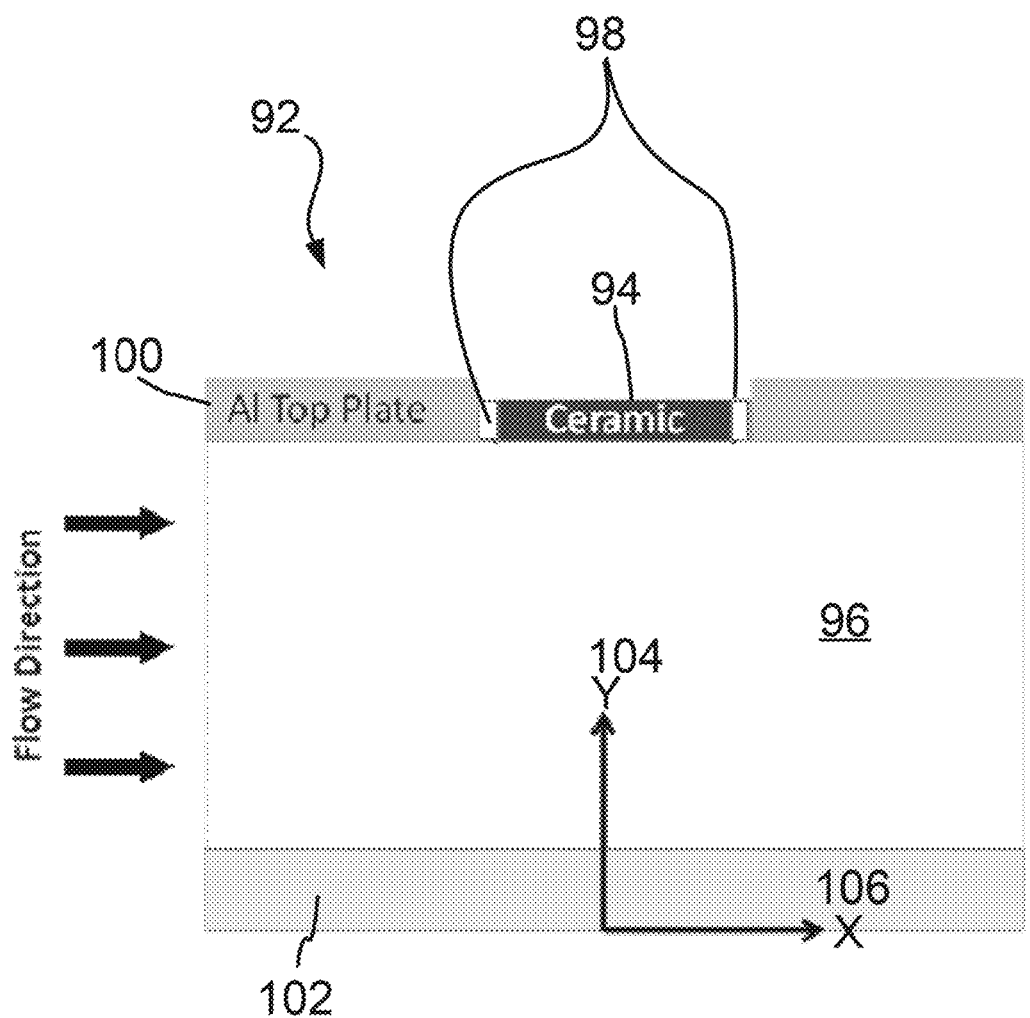
FIG. 17 is a computer model of an acoustophoretic separator simulated to generate FIGS. 18-29.

FIG. 17 is a computer model of an acoustophoretic separator 92 simulated to produce FIGS. 18-29. The piezo ceramic crystal 94 is in direct contact with the fluid in the water channel 96. A layer of silicon 98 is between the crystal 94 and the aluminum top plate 100. A reflector 102 reflects the waves to create standing waves. The reflector is made of a high acoustic impedance material such as steel or tungsten, providing good reflection. For reference, the Y-axis 104 will be referred to as the axial direction. The X-axis 106 will be referred to as the radial or lateral direction. The acoustic pressure and velocity models were calculated in COMSOL including piezo-electric models of the PZT transducer, linear elastic models of the surrounding structure (e.g. reflector plate and walls), and a linear acoustic model of the waves in the water column. The acoustic pressure and velocity was exported as data to MATLAB. The radiation force acting on a suspended particle was calculated in MATLAB using Gor'kov's formulation. The particle and fluid material properties, such as density, speed of sound, and particle size, are entered into the program, and used to determine the monopole and dipole scattering contributions. The acoustic radiation force is determined by performing a gradient operation on the field potential U, which is a function of the volume of the particle and the time averaged potential and kinetic energy of the acoustic field.

Figure 18:
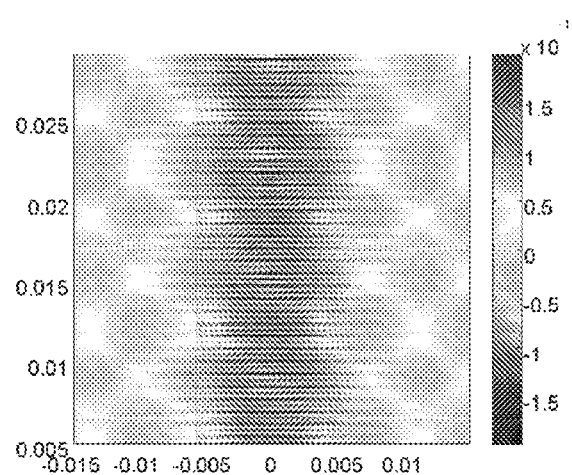
FIG. 18 shows a simulation of the axial forces on a particle in an acoustophoretic separator having a piezoelectric element producing a single standing wave.
Figure 19:
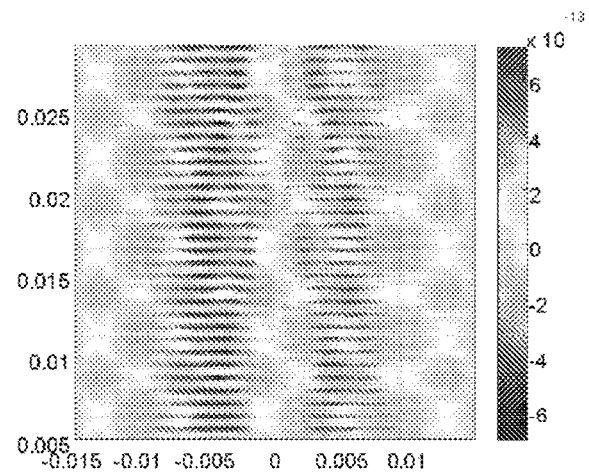
FIG. 19 shows a simulation of the lateral forces on a particle in an acoustophoretic separator having a piezoelectric element producing a single standing wave.
Figure 20:
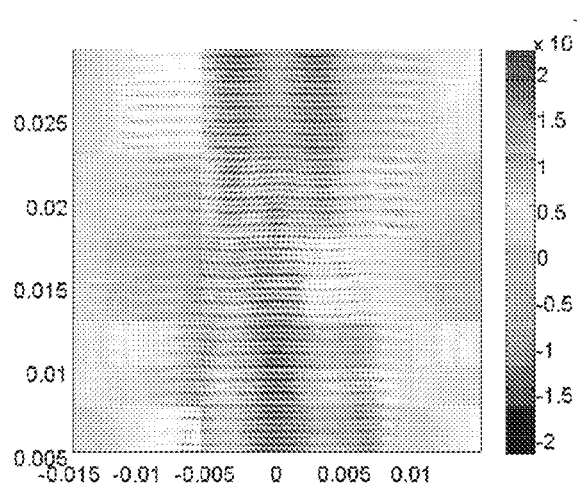
FIG. 20 shows a simulation of the axial forces on a particle in an acoustophoretic separator having a piezoelectric element in a multi-mode excitation.
Figure 21:
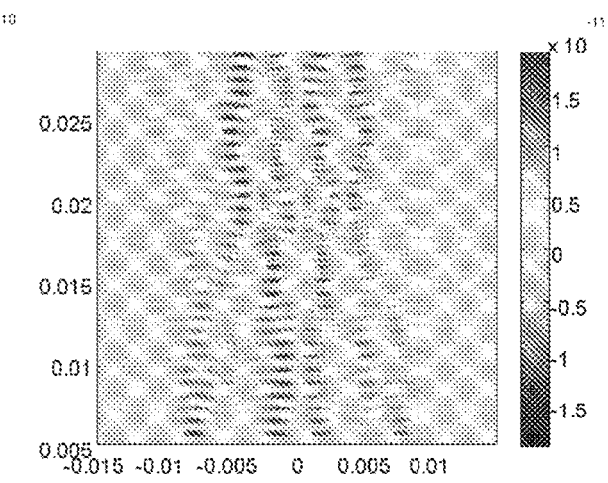
FIG. 21 shows a simulation of the lateral forces on a particle in an acoustophoretic separator a piezoelectric element in a multi-mode excitation.

FIGS. 18-21 show simulations of the difference in trapping pressure gradients between a single acoustic wave and a multimode acoustic wave. FIG. 18 shows the axial force associated with a single standing acoustic wave. FIG. 19 shows the lateral force due to a single standing acoustic wave. FIG. 20 and FIG. 21 show the axial force and lateral force, respectively, in a multi-mode (higher order vibration modes having multiple nodes) piezoelectric element excitation where multiple standing waves are formed. The electrical input is the same as the single mode of FIG. 18 and FIG. 19, but the trapping force (lateral force) is 70 times greater (note the scale to the right in FIG. 19 compared to FIG. 21). The figures were generated by a computer modeling simulation of a 1 MHz piezo-electric transducer driven by 10 V AC potted in an aluminum top plate in an open water channel terminated by a steel reflector (see FIG. 17). The field in FIG. 18 and FIG. 19 is 960 kHz with a peak pressure of 400 kPa. The field in FIG. 20 and FIG. 21 is 961 kHz with a peak pressure of 1400 kPa. In addition to higher forces, the 961 kHz field has more gradients and focal spots.

Figure 22:
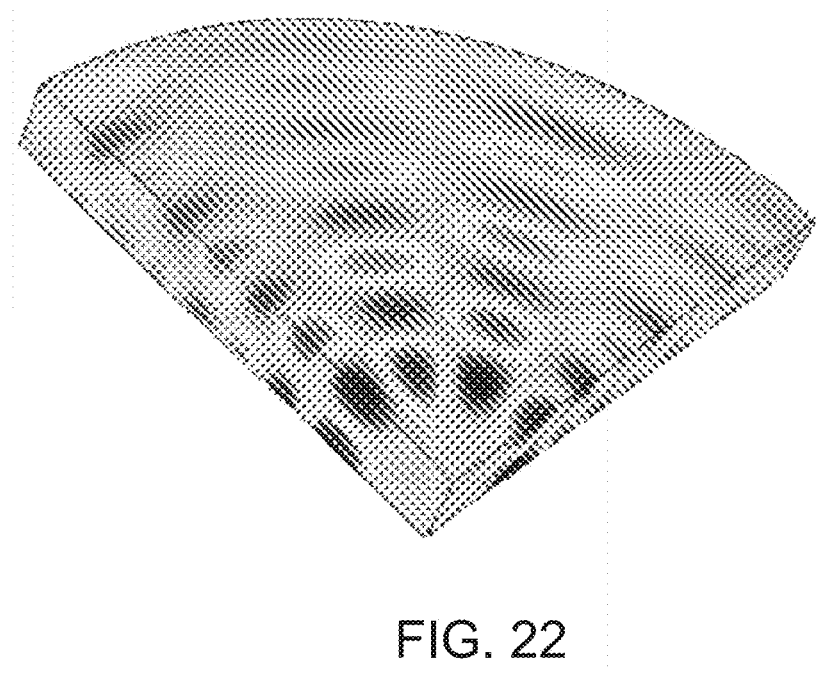
FIG. 22 shows a three dimensional computer generated model of a mode shape calculation for a circular crystal driven at a frequency of 1 MHz.

FIG. 22 shows a three dimensional computer generated model of a mode shape calculation showing the out-of-plane displacement for a circular crystal driven at a frequency of 1 MHz.

FIGS. 23-29 are based on the model of FIG. 17 with a PZT-8 piezo-electric transducer operating at 2 MHz. The transducer is 1" wide and 0.04" thick, potted in an aluminum top plate (0.125" thick) in a 4"×2" water channel terminated by a steel reflector plate (0.180" thick). The acoustic beam spans a distance of 2". The depth dimension, which is 1", is not included in the 2D model. The transducer is driven at 15V and a frequency sweep calculation is done to identify the various acoustic resonances. The results of the three consecutive acoustic resonance frequencies, i.e., 1.9964 MHz (FIGS. 23-25), 2.0106 MHz (FIG. 26 and FIG. 27), and 2.025 MHz (FIG. 28 and FIG. 29), are shown. The acoustic radiation force is calculated for an oil droplet with a radius of 5 micron, a density of 880 kg/m3, and speed of sound of 1700 m/sec. Water is the main fluid with a density of 1000 kg/m3, speed of sound of 1500 m/sec, and dynamic viscosity of 0.001 kg/msec.

FIG. 23 shows the lateral (horizontal) acoustic radiation force. FIG. 24 shows the axial (vertical) component for a resonance frequency of 1.9964 MHz. FIG. 25 shows the acoustic pressure amplitude. FIG. 23 and FIG. 24 show that the relative magnitude of the lateral and axial component of the radiation force are very similar, about 1.2e-10 N, indicating that it is possible to create large trapping forces, where the lateral force component is of similar magnitude or higher than the axial component. This is a new result and contradicts typical results mentioned in the literature.

A second result is that the acoustic trapping force magnitude exceeds that of the fluid drag force, for typical flow velocities on the order of mm/s, and it is therefore possible to use this acoustic field to trap the oil droplet. Of course, trapping at higher flow velocities can be obtained by increasing the applied power to the transducer. That is, the acoustic pressure is proportional to the driving voltage of the transducer. The electrical power is proportional to the square of the voltage.

A third result is that at the frequency shown, high trapping forces associated with this particular trapping mode extend across the entire flow channel, thereby enabling capture of oil droplets across the entire channel width. Finally, a comparison of the minima of the acoustic trapping force field, i.e., the locations of the trapped particles, with the observed trapping locations of droplets in the standing wave shows good agreement, indicating that COMSOL modeling is indeed an accurate tool for the prediction of the acoustic trapping of particles. This will be shown in more detail below.

Figures 26, 27:
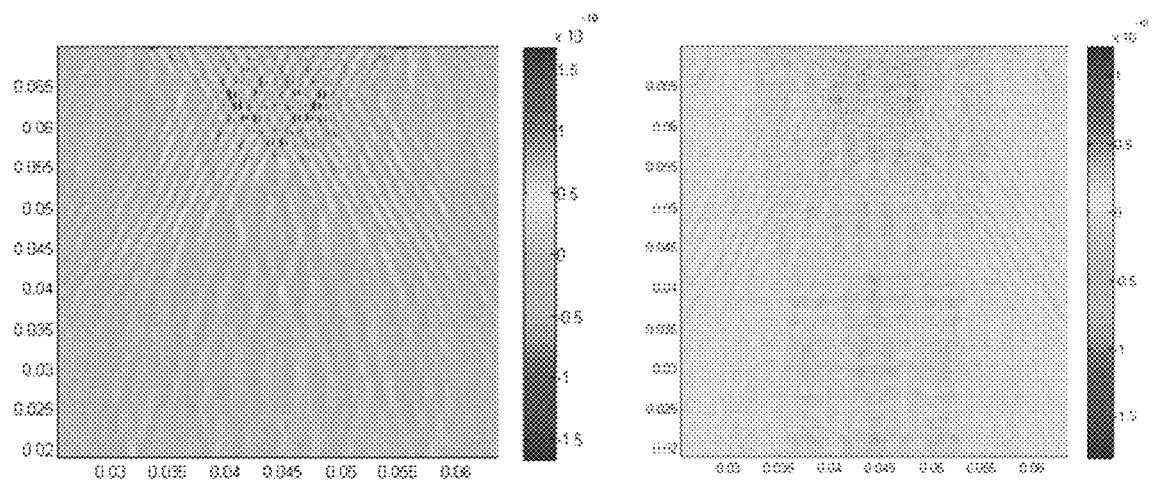
FIG. 26 shows the lateral force component at a resonance frequency of 2.0106 MHz.
FIG. 27 shows the axial acoustic radiation force component at a resonance frequency of 2.0106 MHz.

FIG. 26 shows the lateral force component at a resonance frequency of 2.0106 MHz, and FIG. 27 shows the axial acoustic radiation force component at a resonance frequency of 2.0106 MHz. FIG. 26 and FIG. 27 exhibit higher peak trapping forces than FIG. 23 and FIG. 24. The lateral acoustic radiation forces exceed the axial radiation force. However, the higher trapping forces are located in the upper part of the flow channel, and do not span the entire depth of the flow channel. It would therefore represent a mode that is effective at trapping particles in the upper portion of the channel, but not necessarily across the entire channel. Again, a comparison with measured trapping patterns indicates the existence of such modes and trapping patterns.

Figures 28, 29:
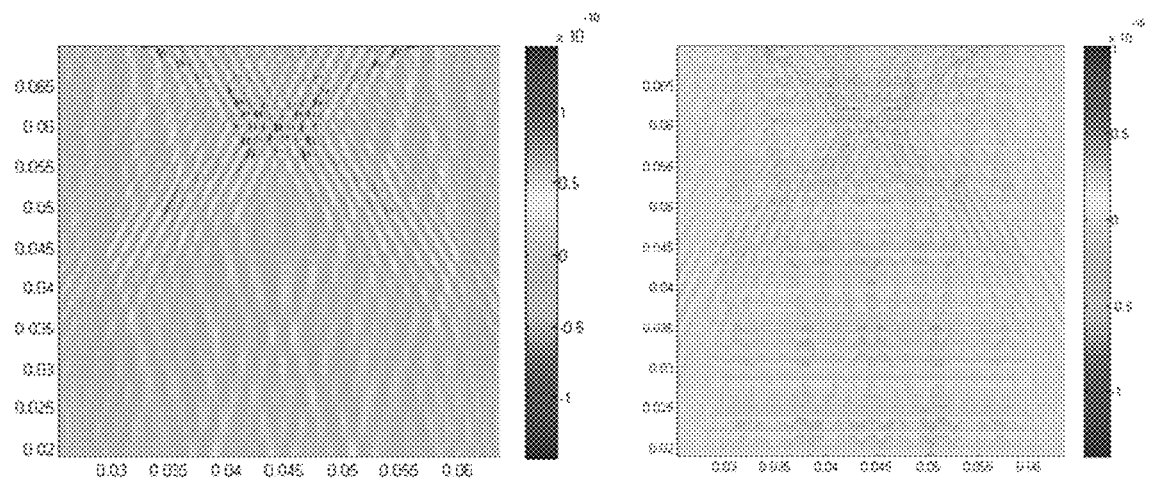
FIG. 28 shows the lateral force component at a resonance frequency of 2.025 MHz.
FIG. 29 shows the axial acoustic radiation force component at a resonance frequency of 2.025 MHz.

FIG. 28 shows the lateral force component at a resonance frequency of 2.025 MHz, and FIG. 29 shows the axial acoustic radiation force component at a resonance frequency of 2.025 MHz. The acoustic field changes drastically at each acoustic resonance frequency, and therefore careful tuning of the system is important. Two-dimensional models are used for relatively accurate prediction of the acoustic trapping forces.

Two-dimensional axisymmetric models were developed to calculate the trapping forces for circular transducers. The models were used to predict acoustic trapping forces on particles, which can then be used to predict particle trajectories in combination with the action of fluid drag and buoyancy forces. The models clearly show that it is possible to generate lateral acoustic trapping forces that can be used to trap particles and overcome the effects of buoyancy and fluid drag. The models also show that circular transducers do not provide for large trapping forces across the entire volume of the standing wave created by the transducer, indicating that circular transducers only yield high trapping forces near the center of the ultrasonic standing wave generated by the transducer, but provide much smaller trapping forces toward the edges of the standing wave. This further indicates that the circular transducer only provides limited trapping for a small section of the fluid flow that would flow across the standing wave of the circular transducer, and no trapping near the edges of the standing wave.

Figure 30:
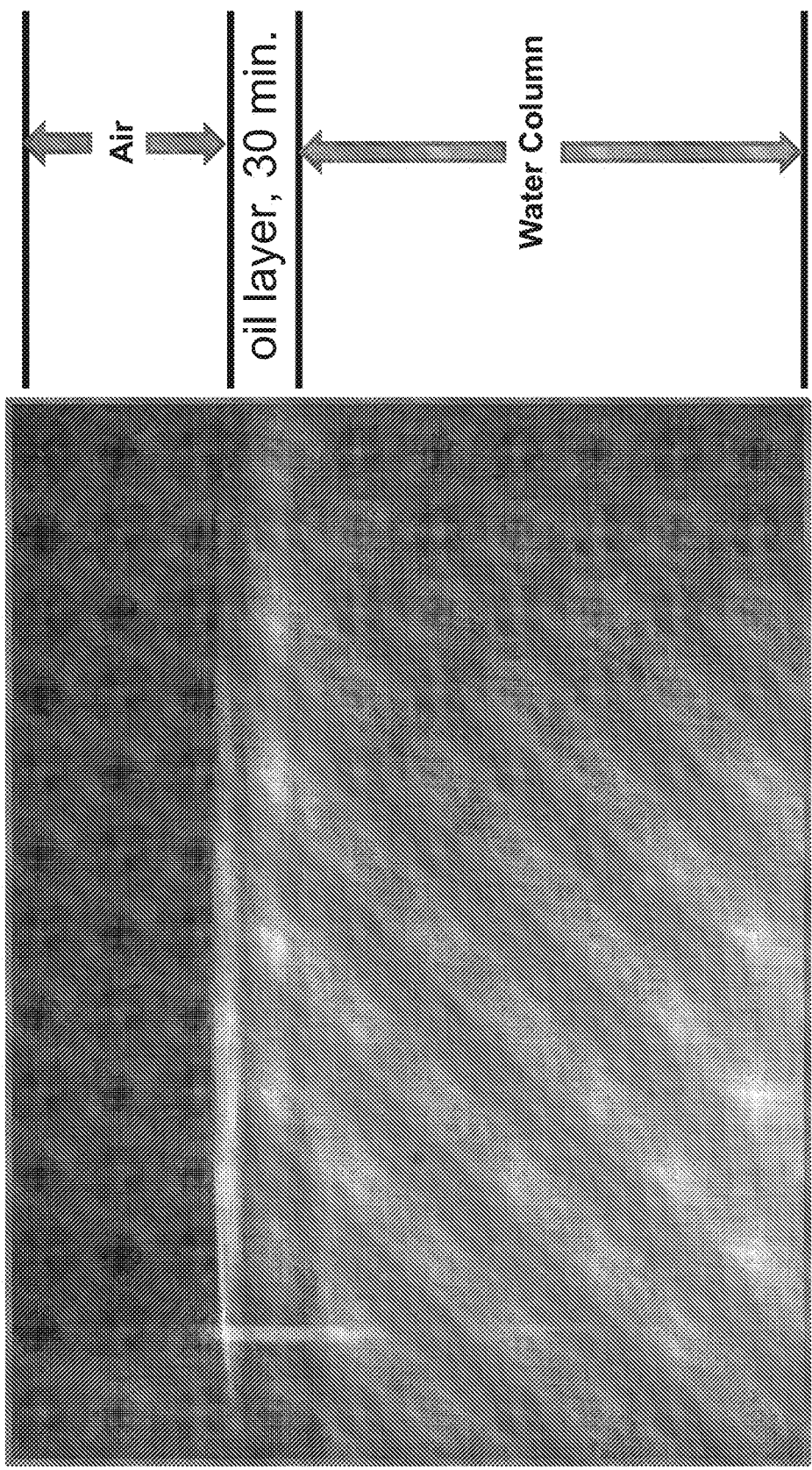
FIG. 30 is a picture showing the results of an oil/water separation experiment.
Figure 31:
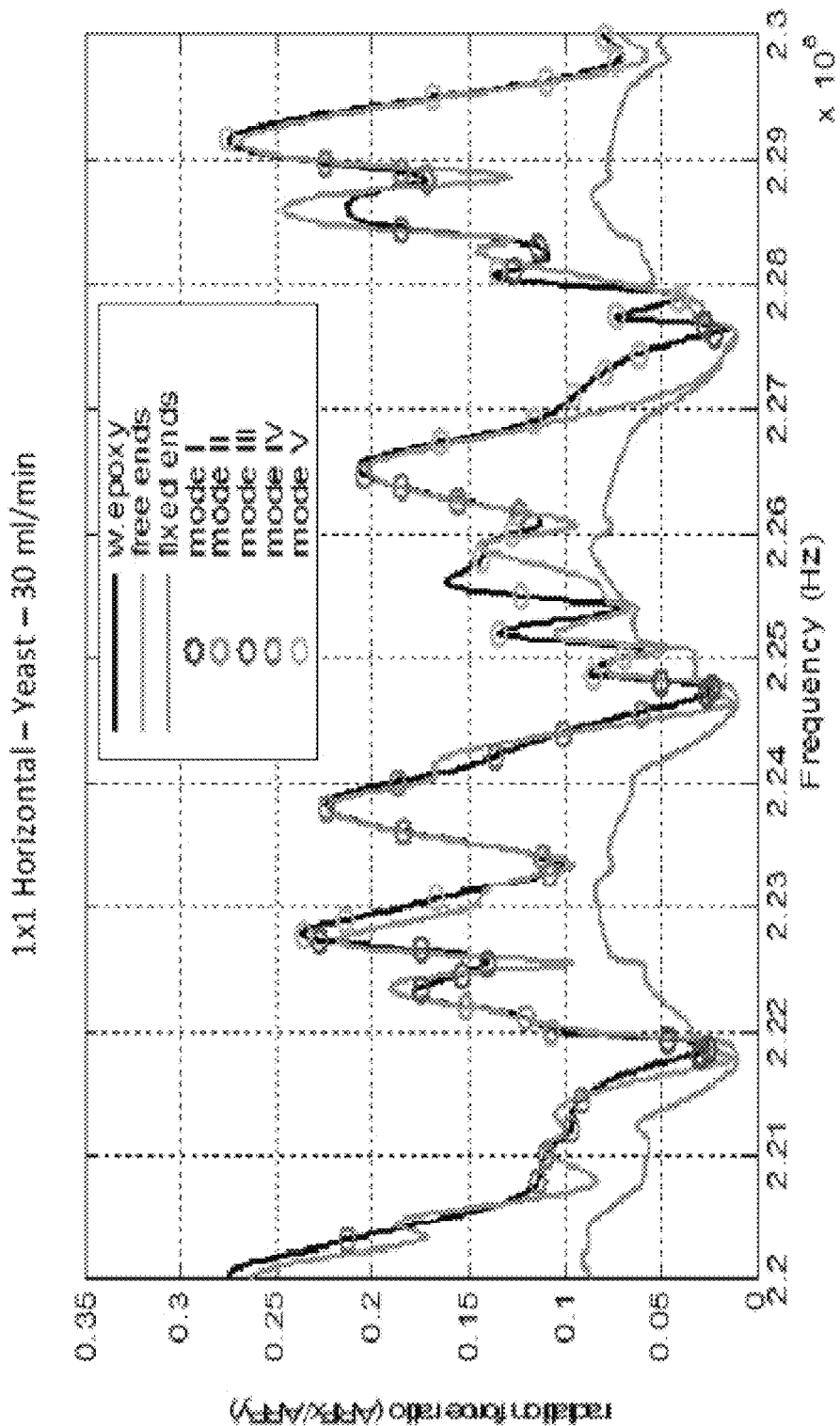
FIG. 31 is a graph illustrating transducer frequency responses and frequencies with dominant modes.

FIG. 30 is a picture showing the separation attained by an apparatus of FIGS. 1-9 after 30 minutes of operation. This picture is taken in a column attached to the first device outlet. An air layer is present at the top, followed by an oil layer and a water column. The oil is clearly separated from the water column.

The acoustophoretic devices of the present disclosure create a three dimensional pressure field which includes standing waves perpendicular to the fluid flow. The pressure gradients are large enough to generate acoustophoretic forces orthogonal to the standing wave direction (i.e., the acoustophoretic forces are parallel to the fluid flow direction) which are of the same order of magnitude as the acoustophoretic forces in the wave direction. This permits better particle trapping and collection in the flow chamber and along well-defined trapping lines, as opposed to merely trapping particles in collection planes as in conventional devices. The particles have significant time to move to nodes or anti-nodes of the standing waves, generating regions where the particles can concentrate, agglomerate, and/or coalesce.

In some embodiments, the fluid flow has a Reynolds number of up to 500, i.e. laminar flow is occurring. For practical application in industry, the Reynolds number is usually from 10 to 500 for the flow through the system. The particle movement relative to the fluid motion generates a Reynolds number much less than 1.0. The Reynolds number represents the ratio of inertial flow effects to viscous effects in a given flow field. For Reynolds numbers below 1.0, viscous forces are dominant in the flow field. This results in significant damping where shear forces are predominant throughout the flow. This flow where viscous forces are dominant is called Stokes flow. The flow of molasses is an example.

Wall contouring and streamlining have very little importance to the flow of very viscous fluids or the flow in very tiny passages, like MEMS devices. The flow of the particles relative to the fluid in MEMS devices will be Stokes flow because both the particle diameters and the relative velocities between the particles and fluid are very small. On the other hand, the Reynolds number for the flow through the present system will be much greater than 1.0 because the fluid velocity and inlet diameter are much larger. For Reynolds numbers much greater than 1.0, viscous forces are dominant only where the flow is in contact with the surface. This viscous region near the surface is called a boundary layer and was first recognized by Ludwig Prandtl (Reference 2). In duct flow, the flow will be laminar if the Reynolds number is significantly above 1.0 and below 2300 for fully developed flow in the duct. The flow velocity starts off uniform. As the flow moves down the duct, the effect of wall viscous forces will diffuse inward towards the centerline to generate a parabolic velocity profile. This parabolic profile may have a peak value that is twice the average velocity. The length of duct or passage for the parabolic profile to develop is a function of the Reynolds number. For a Reynolds number of 20, the development length will be 1.2 duct diameters. Thus, fully developed flow happens very quickly. This peak velocity in the center can be detrimental to acoustic particle separation. Also, turbulence can occur and so flow surface contouring is very important in controlling the flow. Thus, the shape of the contoured nozzle wall will have a large effect on the final velocity profile. The area convergence increases the flow average velocity, but it is the wall contour that determines the velocity profile. The nozzle wall contour will be a flow streamline, and is designed with a small radius of curvature.

The transducer(s) is/are used to create a pressure field that generates forces of the same order of magnitude both orthogonal to the standing wave direction and in the standing wave direction. When the forces are roughly the same order of magnitude, particles of size 0.1 microns to 300 microns will be moved more effectively towards regions of agglomeration ("trapping lines"). Because of the equally large gradients in the orthogonal acoustophoretic force component, there are "hot spots" or particle collection regions that are not located in the regular locations in the standing wave direction between the transducer and the reflector. Such hot spots are located in the maxima or minima of acoustic radiation potential. Such hot spots represent particle collection locations which allow for better wave transmission between the transducer and the reflector during collection and stronger inter-particle forces, leading to faster and better particle agglomeration.

In biological applications, many parts, e.g. the tubing leading to and from the device, may all be disposable, with only the transducer and reflector to be cleaned for reuse. Avoiding centrifuges and filters allows better separation of cells without lowering the viability of the cells. The form factor of the acoustophoretic device is also smaller than a filtering system, allowing cell separation to be miniaturized. The transducers may also be driven to create rapid pressure changes to prevent or clear blockages due to agglomeration of cells. The frequency of the transducers may also be varied to obtain optimal effectiveness for a given power.

One or more multi-dimensional acoustic standing waves are created between an ultrasonic transducer and a reflector. Acoustically transparent or responsive materials may also be used with the transducer or reflector to modify and/or control the standing wave. Two transducers facing each other can be used to generate a standing wave therebetween, e.g., the reflector can be replaced by a transducer. The acoustic waves generated by the transducer(s) are bulk acoustic standing waves that propagate through large volume, e.g., the volume of an acoustic chamber.

As the fluid mixture flows through acoustic chamber with an active ultrasonic transducer, particles or secondary fluid cluster, collect, agglomerate, aggregate, clump, or coalesce at the nodes or anti-nodes of the multi-dimensional acoustic standing wave, depending on the particles' or secondary fluid's acoustic contrast factor relative to the host fluid. The particles form clusters that eventually exit the multi-dimensional acoustic standing wave nodes or anti-nodes when the clusters have grown to a size large enough to overcome the holding force of the multi-dimensional acoustic standing wave (e.g. coalescence or agglomeration overcomes gravity or buoyancy forces). For fluids/particles that are more dense than the host fluid (such as cells), the clusters sink to the bottom and can be collected separately from the clarified host fluid. For fluids/particles that are less dense than the host fluid, the buoyant clusters float upwards and can be collected.

The scattering of the acoustic field off the particles results in a secondary acoustic radiation force that tends to draw particles together. The multi-dimensional acoustic standing wave produces a multi-dimensional acoustic radiation force, which acts as a multi-dimensional trapping field. The multi-dimensional features can be active in at least two or three dimensions. The acoustic radiation force is proportional to the particle volume (e.g. the cube of the radius) when the particle is small relative to the wavelength. The force is proportional to frequency and the acoustic contrast factor. The force scales with acoustic energy (e.g. the square of the acoustic pressure amplitude). When the acoustic radiation force exerted on the particles is stronger than the combined effect of fluid drag force and buoyancy and gravitational force, the particles are trapped within the acoustic standing wave field. The particle trapping in a multi-dimensional acoustic standing wave results in clustering, concentration, agglomeration and/or coalescence of the trapped particles. Relatively large solids of one material can thus be separated from smaller particles of a different material, the same material, and/or the host fluid through enhanced gravitational/buoyancy separation.

The multi-dimensional standing wave generates acoustic radiation forces in both the axial direction (e.g., in the direction of the standing wave, between the transducer and the reflector, which may be at an angle across the flow direction, and in some instances may be perpendicular to the flow direction) and the lateral direction (e.g., in the flow direction or transverse to the direction between the transducer and the reflector). As the mixture flows through the acoustic chamber, particles in suspension experience a strong axial force component in the direction of the standing wave. Since this acoustic force is across (e.g. perpendicular to) the flow direction and the drag force, it quickly moves the particles to pressure nodal planes or anti-nodal planes, depending on the contrast factor of the particle. The lateral acoustic radiation force acts to move the concentrated particles towards the center of each planar node, resulting in clustering, agglomeration or clumping. The lateral acoustic radiation force component can overcome fluid drag for such clumps of particles, to continually grow the clusters, which can exit the mixture due to gravity or buoyancy. The drop in drag per particle as the particle cluster increases in size, as well as the drop in acoustic radiation force per particle as the particle cluster grows in size, may separately or collectively influence operation of the acoustic separator device. In the present disclosure, the lateral force component and the axial force component of the multi-dimensional acoustic standing wave are of the same or different order of magnitude. In this regard, it is noted that in a multi-dimensional acoustic standing wave generated by a single transducer, the axial force is stronger than the lateral force, but the lateral force of such a multi-dimensional acoustic standing wave is much higher than the lateral force of a planar standing wave, usually by two orders of magnitude or more.

Particle drag and acoustic radiation force effects may influence optimal operation of the systems and methods of the present disclosure. At low Reynolds numbers of less than 10, laminar flow dominates, and viscous forces are much stronger than inertial forces.

As the particles are trapped by the multi-dimensional ultrasonic acoustic standing wave, they begin to aggregate and form a clump of particles. The drag on this clump of particles is a function of the geometry of the clump and is not merely the sum of the drag of the individual particles that make up the clump.

For laminar flow, the Navier Stokes equation is expressed as:

$$\rho\left(\frac{\partial V}{\partial t} + (V \cdot \nabla)V\right) = -\nabla P + \mu \nabla^2 V$$

where $$\frac{\partial V}{\partial t}$$

represents unsteady motion, $(V \cdot \nabla)V$ represents inertial motion, $-\nabla P$ represents pressure motion, and $\mu \nabla^2 V$ represents viscous motion.

For low Reynolds numbers, the unsteady motion and inertial motion terms can be ignored (i.e. set equal to zero), and the equation can be simplified to:

$$\nabla P = \mu \nabla^2 V$$

For a particle of diameter a, the following equations hold:

$$\nabla P \propto \mu \frac{V}{a} \quad F = 6\pi \mu a V$$

where P is pressure, $\mu$ is the dynamic viscosity, a is the particle diameter, V is the flow velocity, and F is the Stoke's drag.

Prior to discussing further optimization of the systems, it is helpful to provide an explanation now of how multi-dimensional acoustic standing waves are generated. The multi-dimensional acoustic standing wave used for particle collection is obtained by driving an ultrasonic transducer composed of a piezoelectric material at a frequency that generates the acoustic standing wave and excites a fundamental 3D vibration mode of the transducer. The transducer may be composed of various materials that may be perturbed to generate an ultrasonic wave. For example, the transducer may be composed of a piezoelectric material, including a piezoelectric crystal or poly-crystal. Perturbation of the piezoelectric material, which may be a piezoelectric crystal or poly-crystal, in the ultrasonic transducer to achieve a multimode response allows for generation of a multi-dimensional acoustic standing wave. A piezoelectric material can be specifically designed to deform in a multimode response at designed frequencies, allowing for generation of a multi-dimensional acoustic standing wave. The multi-dimensional acoustic standing wave may be generated with distinct modes of the piezoelectric material such as a 3×3 mode that generates multi-dimensional acoustic standing waves. A multitude of multi-dimensional acoustic standing waves may also be generated by allowing the piezoelectric material to vibrate through many different mode shapes. Thus, the material can be selectively excited to operate in multiple modes such as a 0×0 mode (i.e. a piston mode), 1×1, 2×2, 1×3, 3×1, 3×3, and other higher order modes. The material can be operated to cycle through various modes, in a sequence or skipping past one or more modes, and not necessarily in a same order with each cycle. This switching or dithering of the material between modes allows for various multi-dimensional wave shapes, along with a single piston mode shape to be generated over a designated time.

Some further explanation of the ultrasonic transducers used in the devices, systems, and methods of the present disclosure may be helpful as well. In this regard, the transducers may be composed of a piezoelectric material, such as a piezoelectric crystal or poly-crystal, which may be made of PZT-8 (lead zirconate titanate). Such crystals may have a major dimension on the order of 1 inch and larger. The resonance frequency of the piezoelectric material may nominally be about 2 MHz, and may be operated at one or more frequencies. Each ultrasonic transducer module can have only one crystal, or can have multiple crystals that each act as a separate ultrasonic transducer and are either controlled by one or multiple controllers, which controllers may include signal amplifiers. The piezoelectric material can be square, rectangular, irregular polygon, or generally of any arbitrary shape. The transducer(s) is/are used to create a pressure field that generates forces of the same order of magnitude both orthogonal to the standing wave direction (lateral) and in the standing wave direction (axial).

Figure 10:
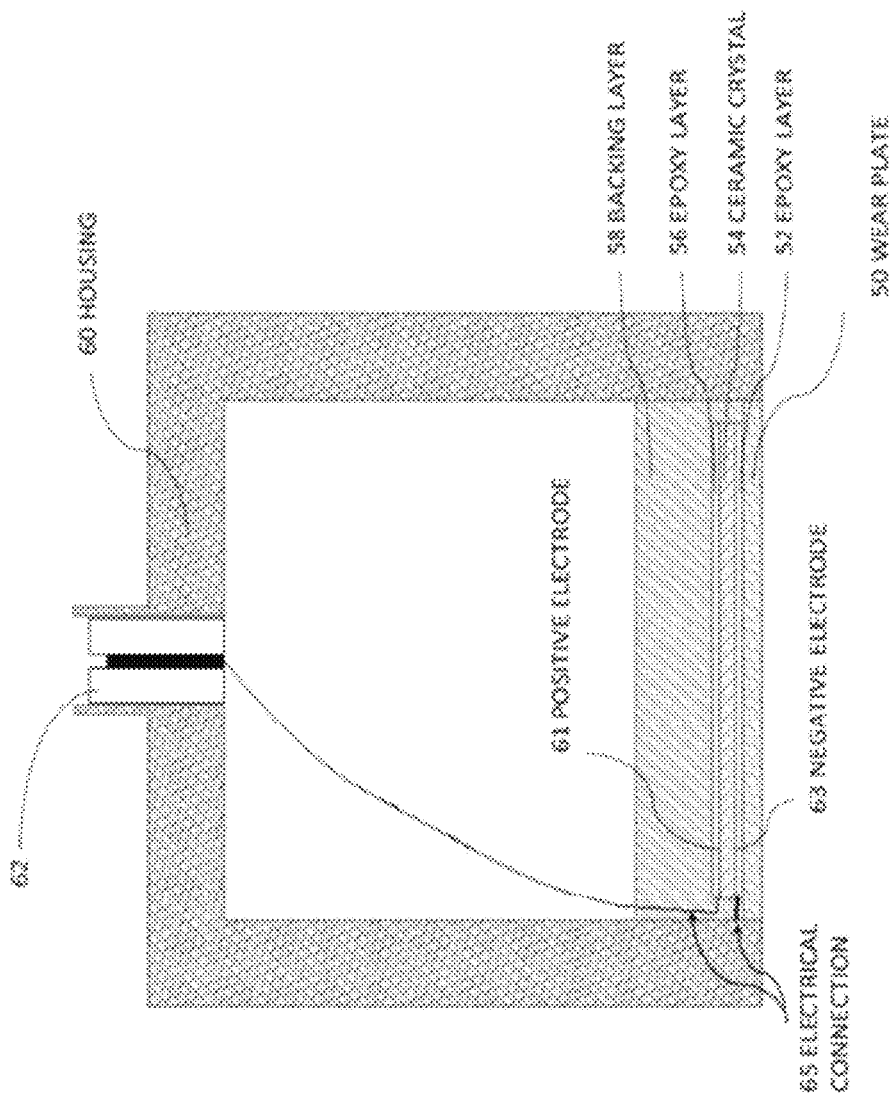
FIG. 10 is a cross-sectional diagram of an ultrasonic transducer.

FIG. 10 is a cross-sectional diagram of a conventional ultrasonic transducer. This transducer has a wear plate 50 at a bottom end, epoxy layer 52, ceramic crystal 54 (made of, e.g. PZT), an epoxy layer 56, and a backing layer 58. On either side of the ceramic crystal, there is an electrode: a positive electrode 61 and a negative electrode 63. The epoxy layer 56 attaches backing layer 58 to the crystal 54. The entire assembly is contained in a housing 60 which may be made out of, for example, aluminum. An electrical adapter 62 provides connection for wires to pass through the housing and connect to leads (not shown) which attach to the crystal 54. Typically, backing layers are designed to add damping and to create a broadband transducer with uniform displacement across a wide range of frequency and are designed to suppress excitation at particular vibrational eigen-modes. Wear plates are usually designed as impedance transformers to better match the characteristic impedance of the medium into which the transducer radiates.

FIG. 11A is a cross-sectional view of an ultrasonic transducer 81 according to an example of the present disclosure. Transducer 81 is shaped as a disc or a plate, and has an aluminum housing 82. The piezoelectric crystal is a mass of perovskite ceramic crystals, each consisting of a small, tetravalent metal ion, usually titanium or zirconium, in a lattice of larger, divalent metal ions, usually lead or barium, and O2-ions. As an example, a PZT (lead zirconate titanate) crystal 86 defines the bottom end of the transducer, and is exposed from the exterior of the housing. The crystal has an interior surface and an exterior surface. The crystal is supported on its perimeter by a small elastic layer 98, e.g. silicone or similar material, located between the crystal and the housing. Put another way, no wear layer is present. In particular embodiments, the crystal is an irregular polygon, and in further embodiments is an asymmetrical irregular polygon.

Screws 88 attach an aluminum top plate 82a of the housing to the body 82b of the housing via threads. The top plate includes a connector 84 for powering the transducer. The top surface of the PZT crystal 86 is connected to a positive electrode 90 and a negative electrode 92, which are separated by an insulating material 94. The electrodes can be made from any conductive material, such as silver or nickel. Electrical power is provided to the PZT crystal 86 through the electrodes on the crystal. Note that the crystal 86 has no backing layer or epoxy layer. Put another way, there is an air gap 87 in the transducer between aluminum top plate 82a and the crystal 86 (i.e. the housing is empty). A minimal backing 58 (on the interior surface) and/or wear plate 50 (on the exterior surface) may be provided in some embodiments, as seen in FIG. 11B.

The transducer design can affect performance of the system. A typical transducer is a layered structure with the ceramic crystal bonded to a backing layer and a wear plate. Because the transducer is loaded with the high mechanical impedance presented by the standing wave, the traditional design guidelines for wear plates, e.g., half wavelength thickness for standing wave applications or quarter wavelength thickness for radiation applications, and manufacturing methods may not be appropriate. Rather, in one embodiment of the present disclosure the transducers, there is no wear plate or backing, allowing the crystal to vibrate in one of its eigenmodes (i.e. near eigenfrequency) with a high Q-factor. The vibrating ceramic crystal/disk is directly exposed to the fluid flowing through the acoustic chamber.

Removing the backing (e.g. making the crystal air backed) also permits the ceramic crystal to vibrate at higher order modes of vibration with little damping (e.g. higher order modal displacement). In a transducer having a crystal with a backing, the crystal vibrates with a more uniform displacement, like a piston. Removing the backing allows the crystal to vibrate in a non-uniform displacement mode. The higher order the mode shape of the crystal, the more nodal lines the crystal has. The higher order modal displacement of the crystal creates more trapping lines, although the correlation of trapping line to node is not necessarily one to one, and driving the crystal at a higher frequency will not necessarily produce more trapping lines.

In some embodiments, the crystal may have a backing that minimally affects the Q-factor of the crystal (e.g. less than 5%). The backing may be made of a substantially acoustically transparent material such as balsa wood, foam, or cork which allows the crystal to vibrate in a higher order mode shape and maintains a high Q-factor while still providing some mechanical support for the crystal. The backing layer may be a solid, or may be a lattice having holes through the layer, such that the lattice follows the nodes of the vibrating crystal in a particular higher order vibration mode, providing support at node locations while allowing the rest of the crystal to vibrate freely. The goal of the lattice work or acoustically transparent material is to provide support without lowering the Q-factor of the crystal or interfering with the excitation of a particular mode shape.

Placing the crystal in direct contact with the fluid also contributes to the high ( ) factor by avoiding the dampening and energy absorption effects of the epoxy layer and the wear plate. Other embodiments may have wear plates or a wear surface to prevent the PZT, which contains lead, from contacting the host fluid. This may be desirable in, for example, biological applications such as separating blood. Such applications might use a wear layer such as chrome, electrolytic nickel, or electroless nickel. Chemical vapor deposition could also be used to apply a layer of poly(p- xylylene) (e.g. Parylene) or other polymers or polymer films. Organic and biocompatible coatings such as silicone or polyurethane are also usable as a wear surface.

Figure 13A:
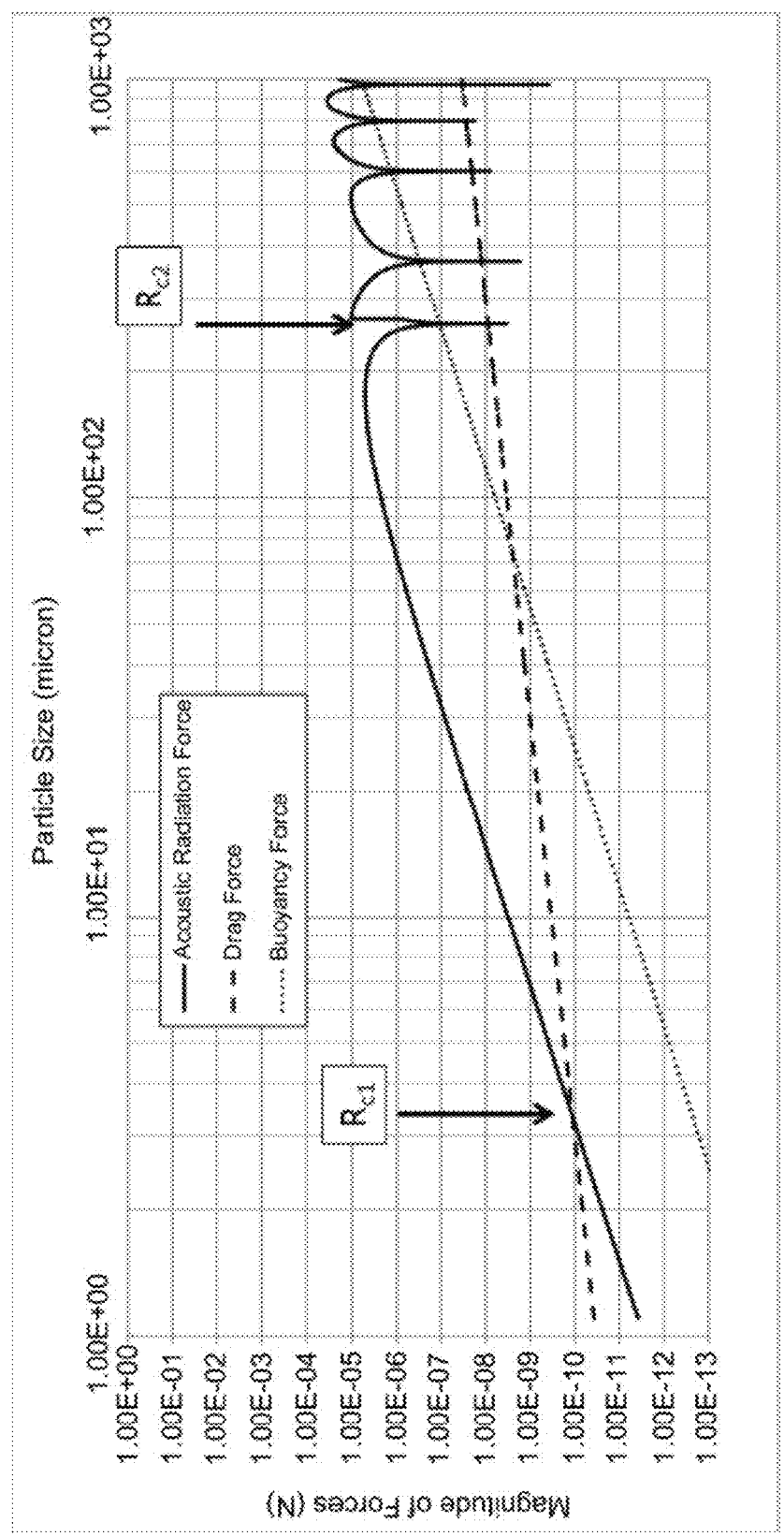
FIG. 13A is a graph illustrating force applied to a particle in a fluid.

FIG. 13A is a log-log graph (logarithmic y-axis, logarithmic x-axis) that shows the scaling of the acoustic radiation force, fluid drag force, and buoyancy force with particle radius, and provides an explanation for the separation of particles using acoustic radiation forces. The buoyancy force is a particle volume dependent force, and may therefore be negligible for particle sizes on the order of micron, but grows, and becomes significant for particle sizes on the order of hundreds of microns. The fluid drag force (Stokes drag force) scales linearly with fluid velocity, and therefore typically exceeds the buoyancy force for micron sized particles, but is negligible for larger sized particles on the order of hundreds of microns. The acoustic radiation force scaling is different. When the particle size is small, Gor'kov's equation is accurate and the acoustic trapping force scales with the volume of the particle. Eventually, when the particle size grows, the acoustic radiation force no longer increases with the cube of the particle radius, and will rapidly vanish at a certain particle size. For further increases of particle size, the radiation force increases again in magnitude but with opposite phase (not shown in the graph). This pattern repeats for increasing particle sizes.

Initially, when a suspension is flowing through the system with primarily small micron sized particles, the acoustic radiation force balances the combined effect of fluid drag force and buoyancy force to permit a particle to be trapped in the standing wave. In FIG. 13A this trapping happens at a particle size labeled as Rc1. FIG. 13A indicates that all larger particles will be trapped as well. Therefore, when small particles are trapped in the standing wave, particle clustering/coalescence/clumping/aggregation/agglomeration takes place, resulting in continuous growth of effective particle size. As particles cluster, the total drag on the cluster is much lower than the sum of the drag forces on the individual particles. In essence, as the particles cluster, they shield each other from the fluid flow and reduce the overall drag of the cluster. As the particle cluster size grows, the acoustic radiation force reflects off the cluster, such that the net acoustic radiation force decreases per unit volume. The acoustic lateral forces on the particles may be larger than the drag forces for the clusters to remain stationary and grow in size.

Particle size growth continues until the buoyancy force becomes dominant, which is indicated by a second particle size, Rc2. The buoyancy force per unit volume of the cluster remains constant with cluster size, since it is a function of the particle density, cluster concentration and gravity constant. Therefore, as the cluster size increases, the buoyancy force on the cluster increases faster than the acoustic radiation force. At the size Rc2, the particles will rise or sink, depending on their relative density with respect to the host fluid. At this size, acoustic forces are secondary, gravity/buoyancy forces become dominant, and the particles naturally drop out or rise out of the host fluid. Some particles may remain in the acoustic wave as clusters of others drop out, and those remaining particles and new particles entering the acoustic chamber with the flow of a fluid mixture continue to move to the three-dimensional nodal locations, repeating the growth and drop-out process. Clusters can grow larger than a half wavelength of the acoustic wave, which results in periodic and sharp changes in acoustic radiation force on the clusters. This phenomenon explains the quick drops and rises in the acoustic radiation force beyond size Rc2. Thus, FIG. 13A explains how small particles can be trapped continuously in a standing wave, grow into larger particles or clumps, and then eventually will rise or settle out because of increased buoyancy/gravity force.

In some examples, the size, shape, and thickness of the transducer can determine the transducer displacement at different frequencies of excitation. Transducer displacement with different frequencies may affect particle separation efficiency. Higher order modal displacements can generate three-dimensional acoustic standing waves with strong gradients in the acoustic field in all directions, thereby creating strong acoustic radiation forces in all directions, which forces may, for example be equal in magnitude, leading to multiple trapping lines, where the number of trapping lines correlate with the particular mode shape of the transducer.

FIG. 14A shows an isometric view of the system in which the trapping line locations are being determined. FIG. 14B is a view of the system as it appears when looking down the inlet, along arrow 114. FIG. 14C is a view of the system as it appears when looking directly at the transducer face, along arrow 116.

The effect of excitation frequency clearly determines the number of trapping lines, which vary from a single trapping line at the excitation frequency of acoustic resonance 5 and 9, to nine trapping lines for acoustic resonance frequency 4. At other excitation frequencies four or five trapping lines are observed. Different displacement profiles of the transducer can produce different (more) trapping lines in the standing waves, with more gradients in displacement profile generally creating higher trapping forces and more trapping lines. It is noted that although the different trapping line profiles shown in FIG. 14 were obtained at the frequencies shown in FIG. 13, these trapping line profiles can also be obtained at different frequencies.

FIG. 14 shows the different crystal vibration modes possible by driving the crystal to vibrate at different fundamental frequencies of vibration. The 3D mode of vibration of the crystal is carried by the acoustic standing wave across the fluid in the chamber all the way to the reflector and back. The resulting multi-dimensional standing wave can be thought of as containing two components. The first component is a planar out-of-plane motion component (uniform displacement across crystal surface) of the crystal that generates a standing wave, and the second component is a displacement amplitude variation with peaks and valleys occurring in lateral directions across the crystal surface. Three-dimensional force gradients are generated by the standing wave. These three-dimensional force gradients result in lateral radiation forces that stop and trap the particles with respect to the flow by overcoming the viscous drag force. In addition, the lateral radiation forces are responsible for creating tightly packed clusters of particles. Therefore, particle separation and gravity-driven collection depends on generating a multi-dimensional standing wave that can overcome the particle drag force as the mixture flows through the acoustic standing wave. Multiple particle clusters are formed along trapping lines in the axial direction of the standing wave, as presented schematically in FIG. 14.

Figure 52:
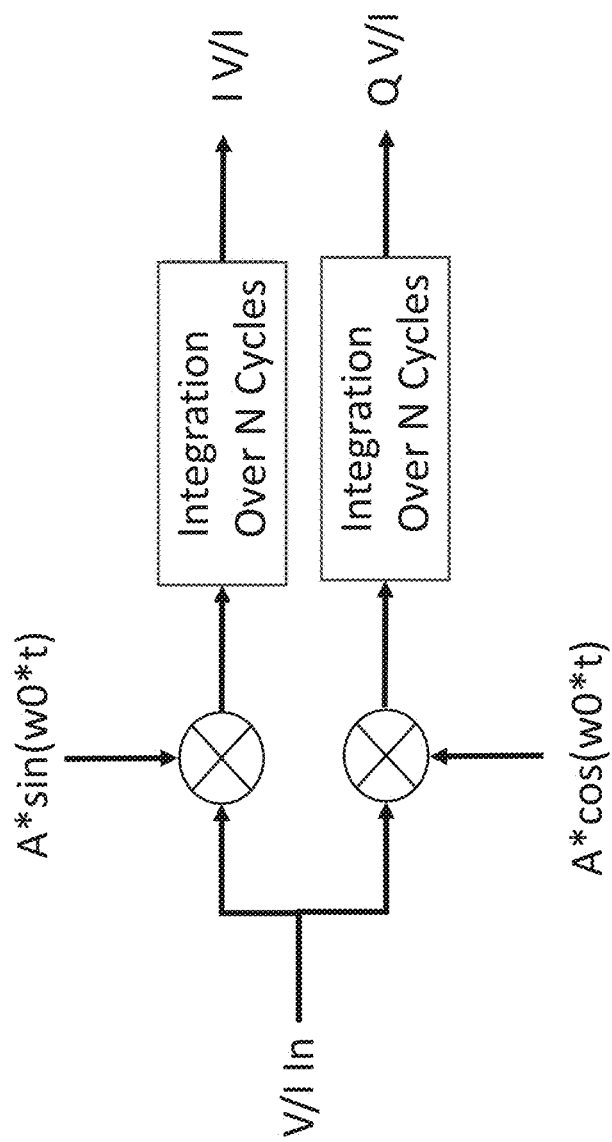
FIG. 52 is a block diagram illustrating demodulation of a voltage or current signal.

The piezoelectric crystals of the transducers described herein can be operated at various modes of response by changing the drive parameters, including frequency, for exciting the crystal. Each operation point has a theoretically infinite number of vibration modes superimposed, where one or more modes are dominant. In practice, multiple vibration modes are present at arbitrary operating points of the transducer, with some modes dominating at a given operating point. FIG. 52 presents COMSOL results for crystal vibration and lateral radiation forces on a typical particle size. The ratio of lateral to axial radiation force is plotted versus operating frequency. Points are labeled on the curve where a specific mode of vibration is dominant. Mode I represents the planar vibration mode of the crystal designed to generate a 2 MHz standing wave in a mixture. Mode III represents the 3×3 mode operation of a 1×1 crystal. These analytical results show that the 3×3 mode can be dominant with different levels of lateral radiation force. More specifically, operating the example system at a frequency of 2.283 MHz generates the lowest lateral force ratio of about 1.11 for a 3×3 mode. This operating point generates the largest cluster size and the best collection operation for the example system. Operating the devices and systems described herein at a frequency for a given configuration that produces a desired 3D mode with the lowest lateral force ratio is desirable to achieve the most efficient separation.

Figure 32:
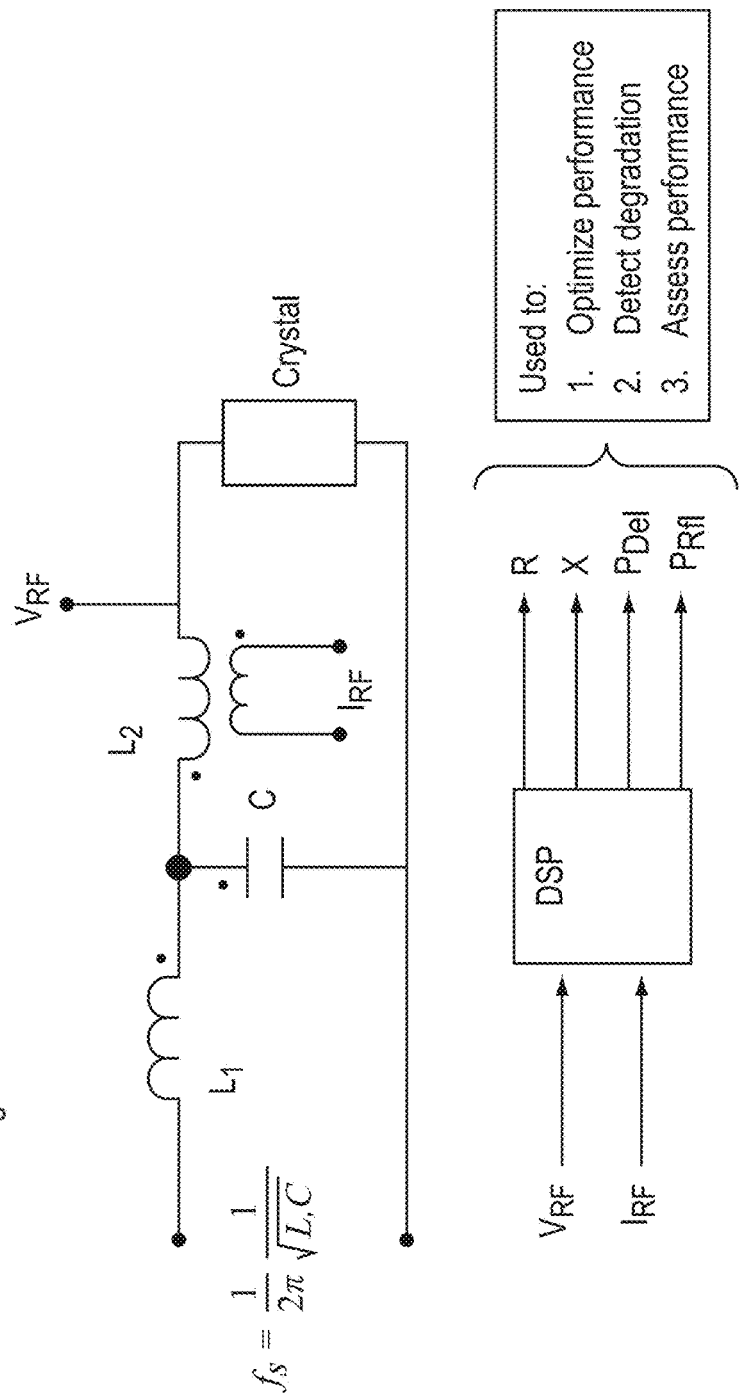
FIG. 32 is a circuit and block diagram of an LCL network.

The description in FIG. 32 shows an inductor-capacitor-inductor system that is utilized to smooth the electronic impulses that are sent to the piezoelectric material. The step is a critical part of the process as otherwise parasitic vibrations of the piezoelectric material will generate heat into the system and reduce the overall efficiency of the acoustic resonator when generating a multidimensional acoustic standing wave. FIG. 32 also shows a digital signal processor (DSP) that may be utilized to optimize the performance of the acoustic resonator by detecting degradation of the acoustic wave and assess the performance of the resonator system, adjusting the system for optimum performance.

Figure 33:
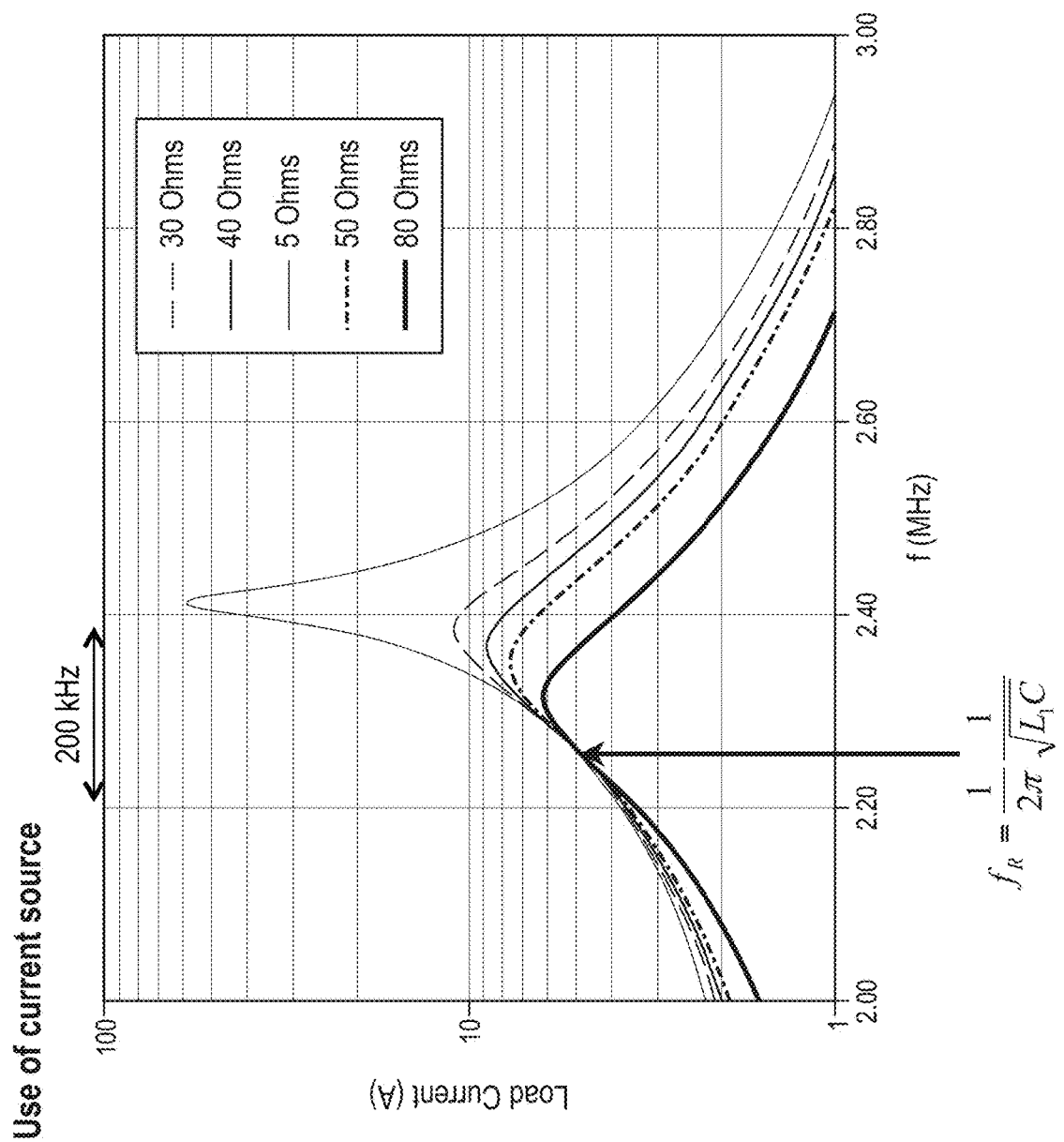
FIG. 33 is a graph illustrating a frequency response for load current.

FIG. 33 shows the use of a load current in amps over various frequencies and at different resistances. The highest current load at about 2.4 MHz is at the lowest resistance of 5 ohms.

Figure 34:
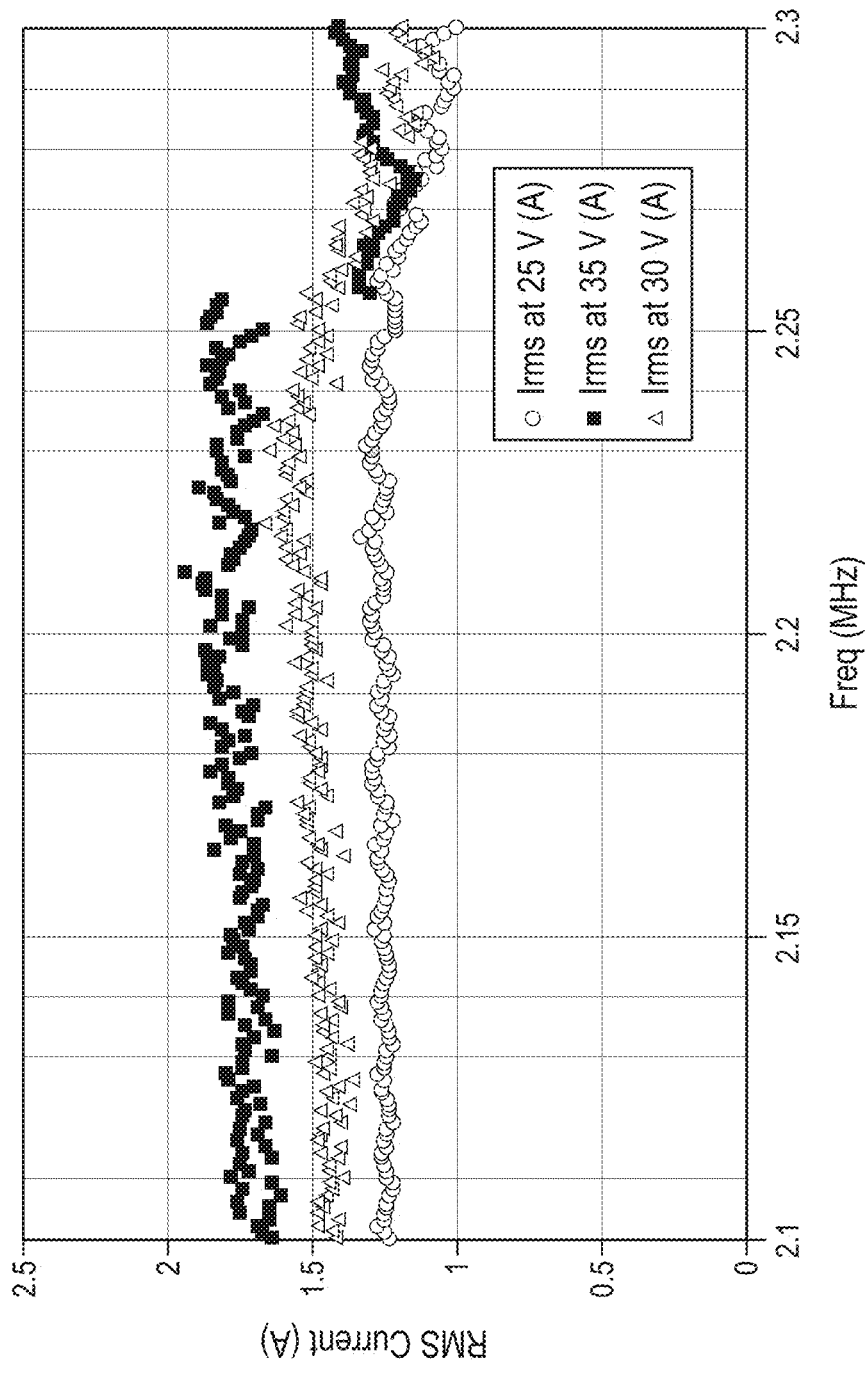
FIG. 34 is a graph illustrating a frequency response for RMS current.

FIG. 34 shows three root mean squared (RMS) currents plotted against frequencies from 2.1 MHz to 2.3 MHz where the currents are at different voltages from 25 V to 35 V.

Figure 35:
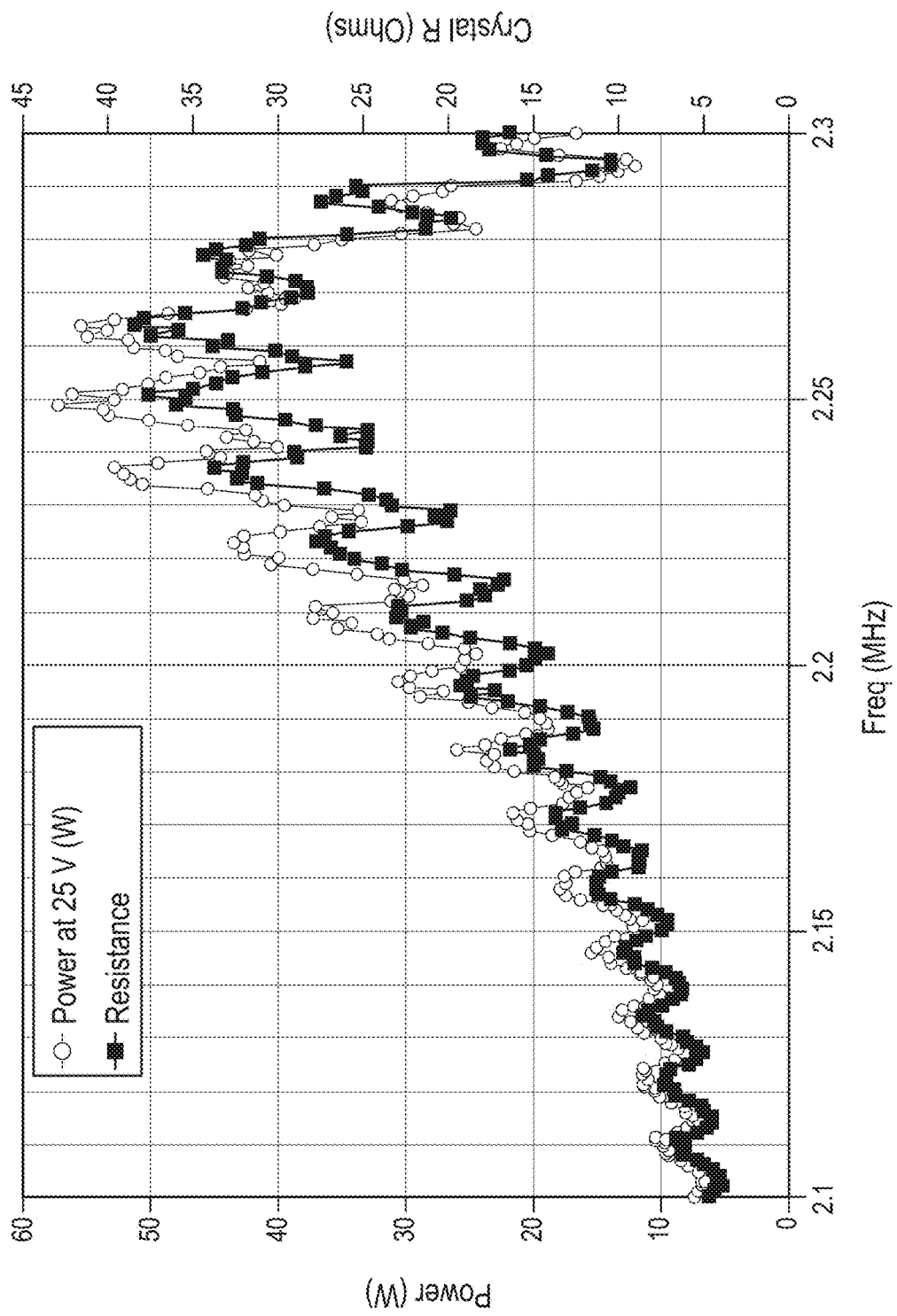
FIG. 35 is a graph illustrating a frequency response for output power.

FIG. 35 shows the output to the crystal in power (measured in Watts) at 25 V over frequencies from 2.1 MHz to 2.3 MHz. The plot also shows the resistance of the piezoelectric material over the same frequency range.

Figure 36:
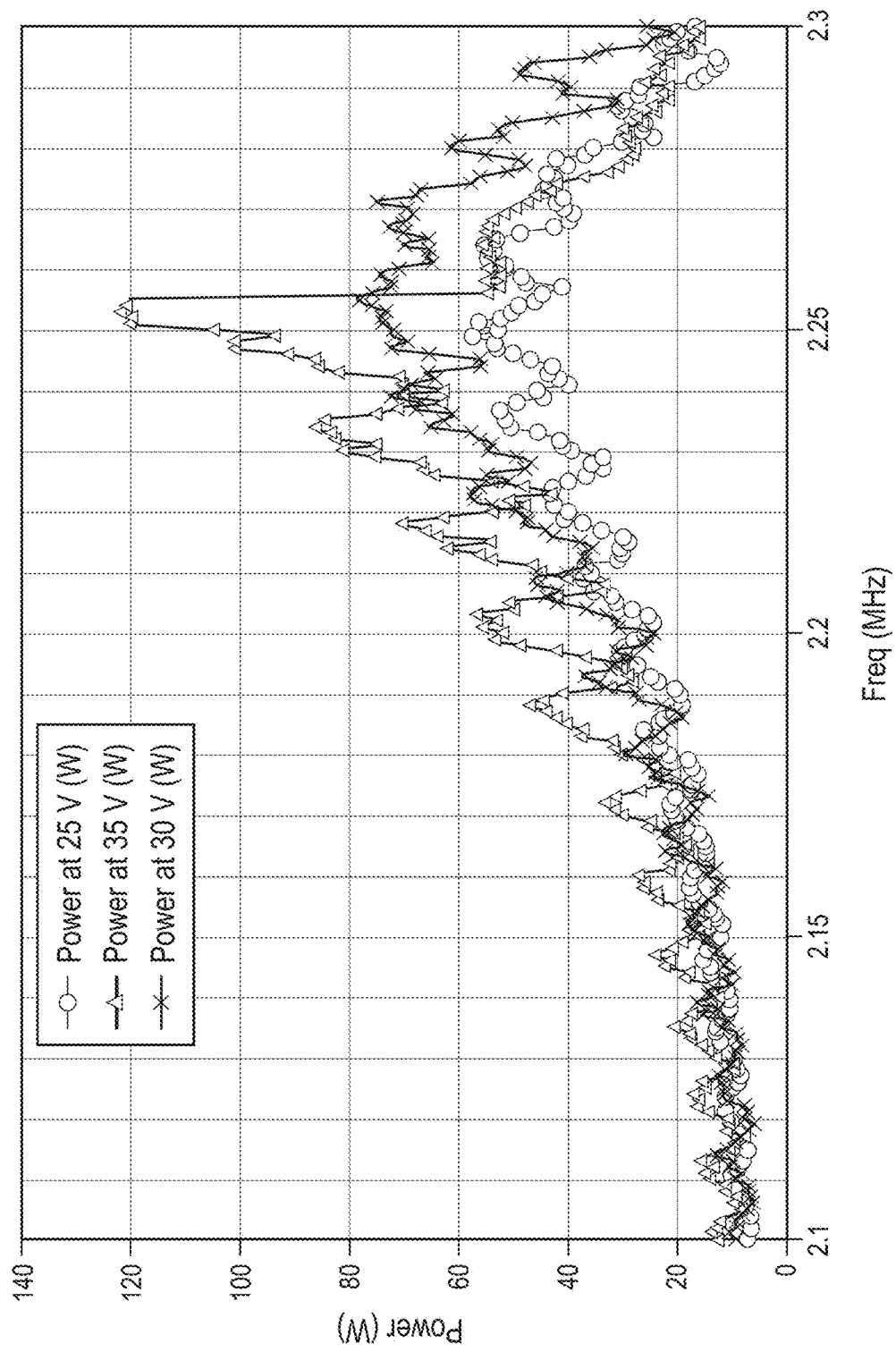
FIG. 36 is a graph illustrating a frequency response for output power.

FIG. 36 shows the output into the piezoelectric material in Watts over a 2.1 MHz to 2.3 MHz range and at three different voltage levels (25 V, 30 V, 35 V).

Figure 37:
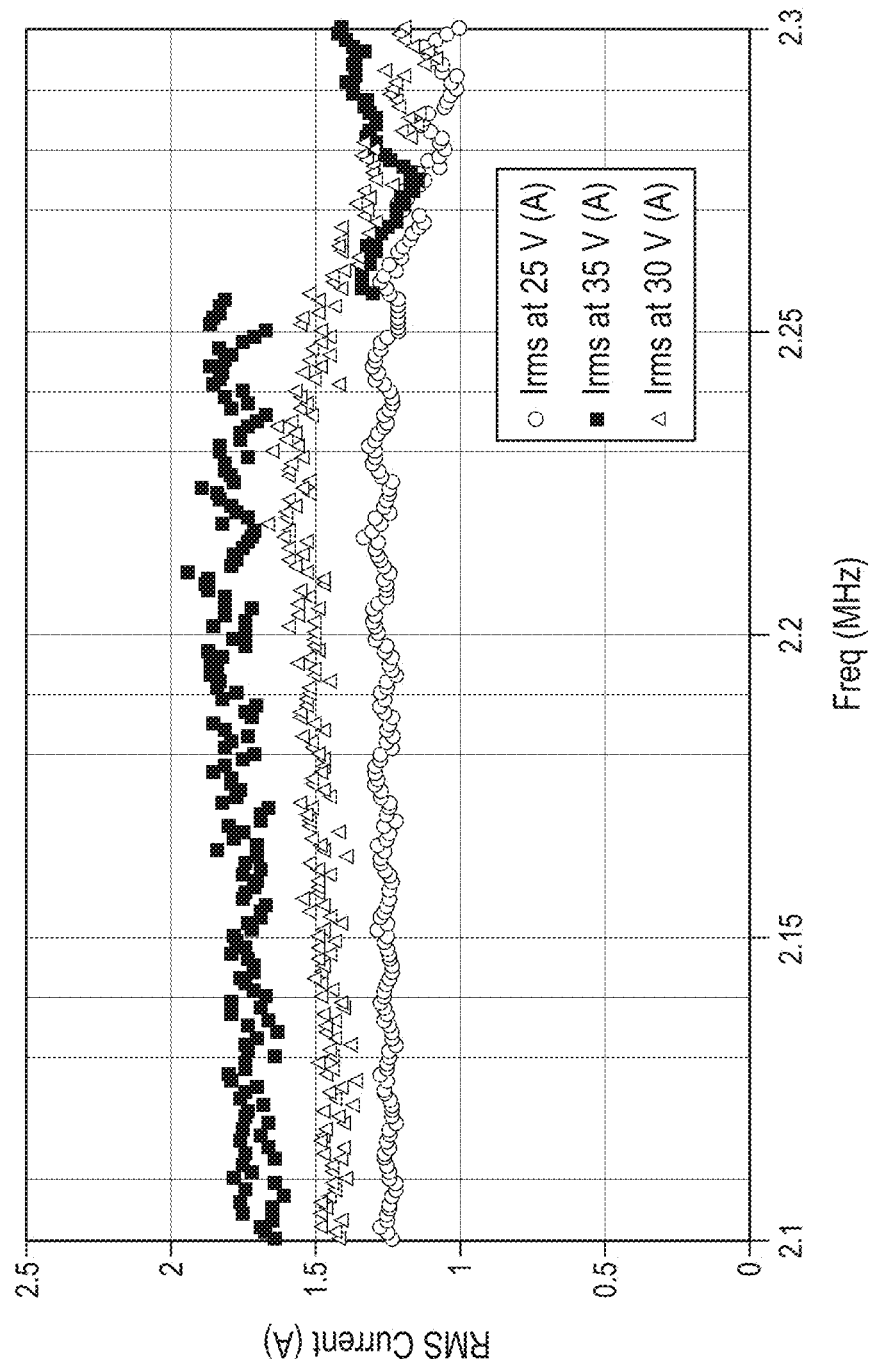
FIG. 37 is a graph illustrating a frequency response for output current.

FIG. 37 shows the output in RMS current to the piezoelectric material over the range of 2.1 MHz to 2.3 MHz at three different voltages (25 V, 30 V, 35 V).

Figure 38:
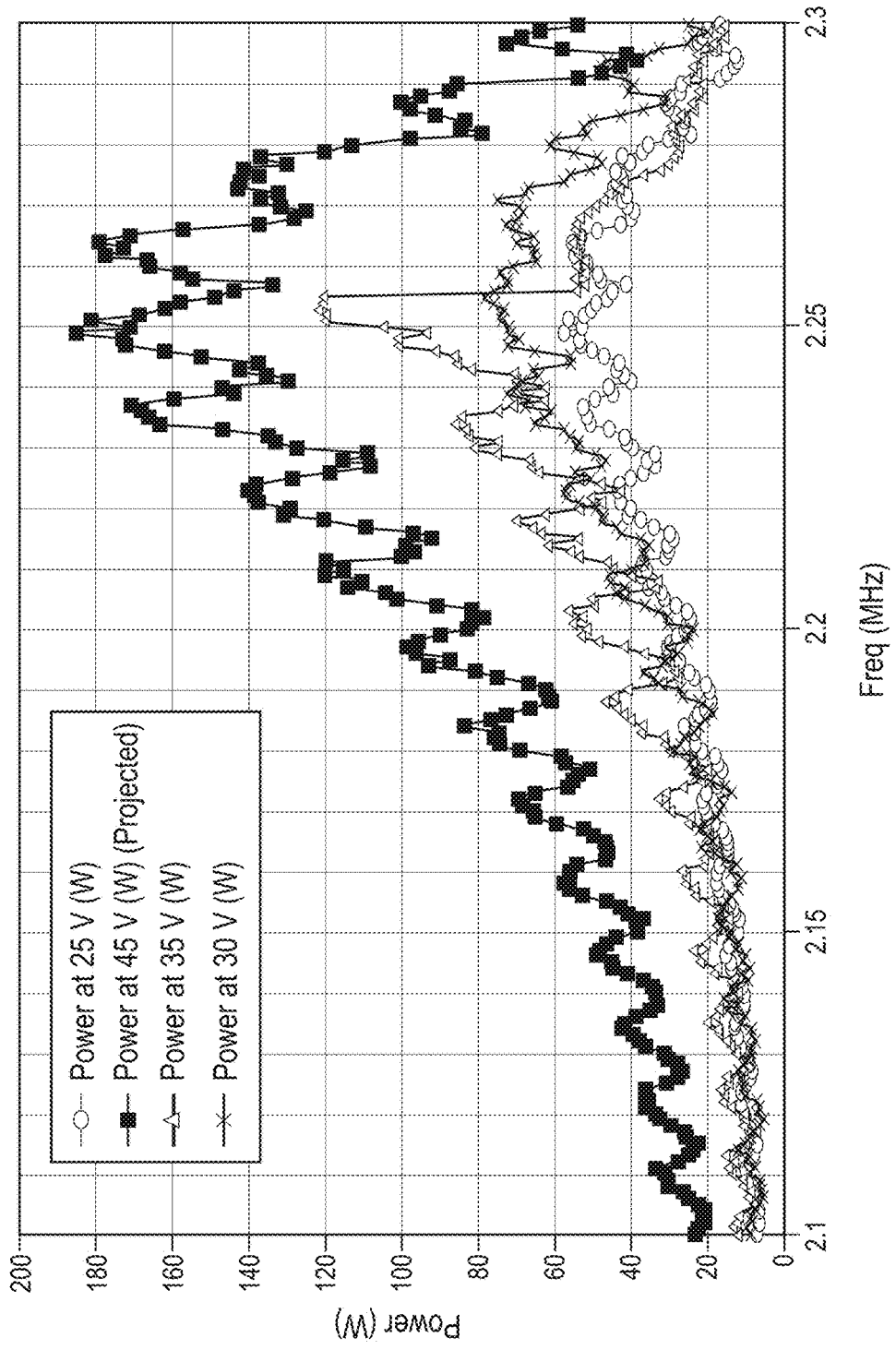
FIG. 38 is a graph illustrating a frequency response for projected output power.

FIG. 38 shows the projected output power into the piezoelectric material where there are three measured power output numbers and a fourth projected power number, the fourth power number being at 45 V over the frequency range of 2.1 MHz to 2.3 MHz.

Figure 39:
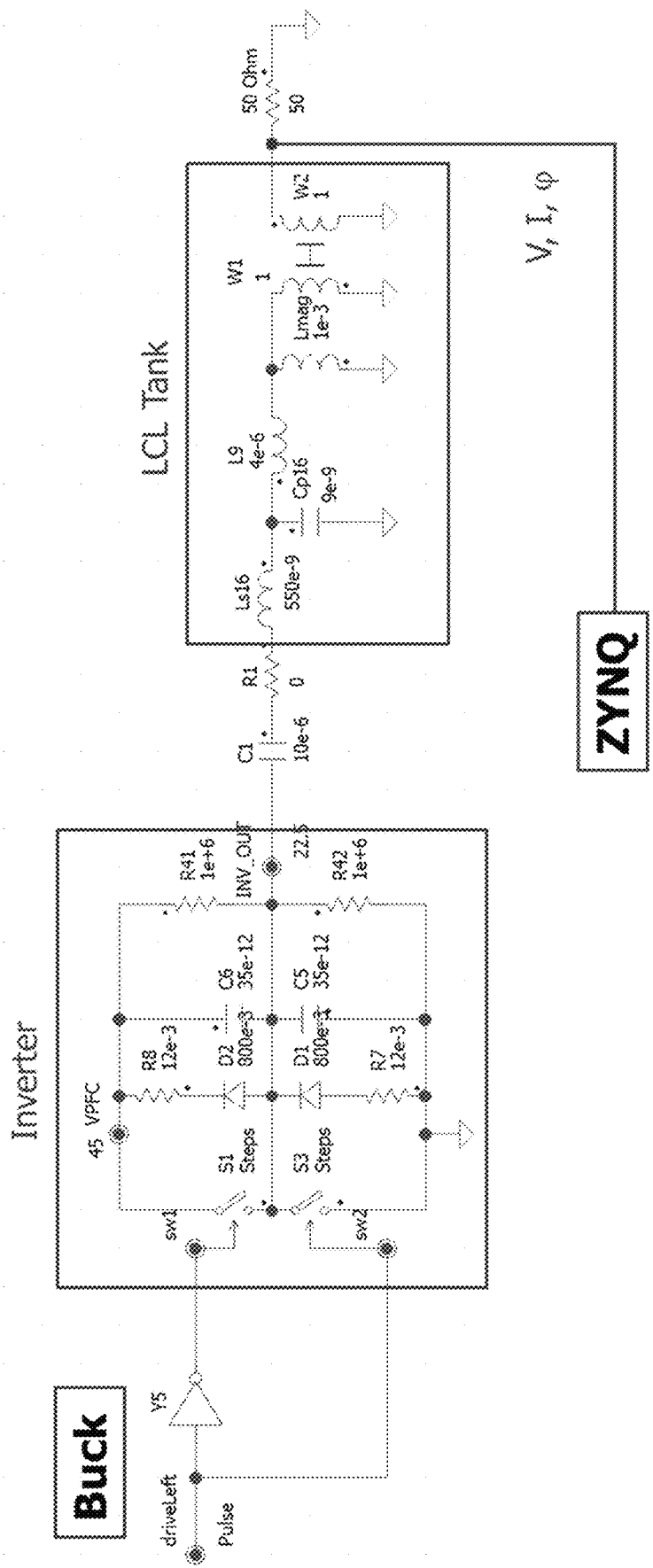
FIG. 39 is a circuit diagram showing an RF power supply with an LCL network.

FIG. 39 shows a schematic of the Buck book voltage, the inverter, and the inductor-capacitor inductor (LCL) tank.

Figure 40:
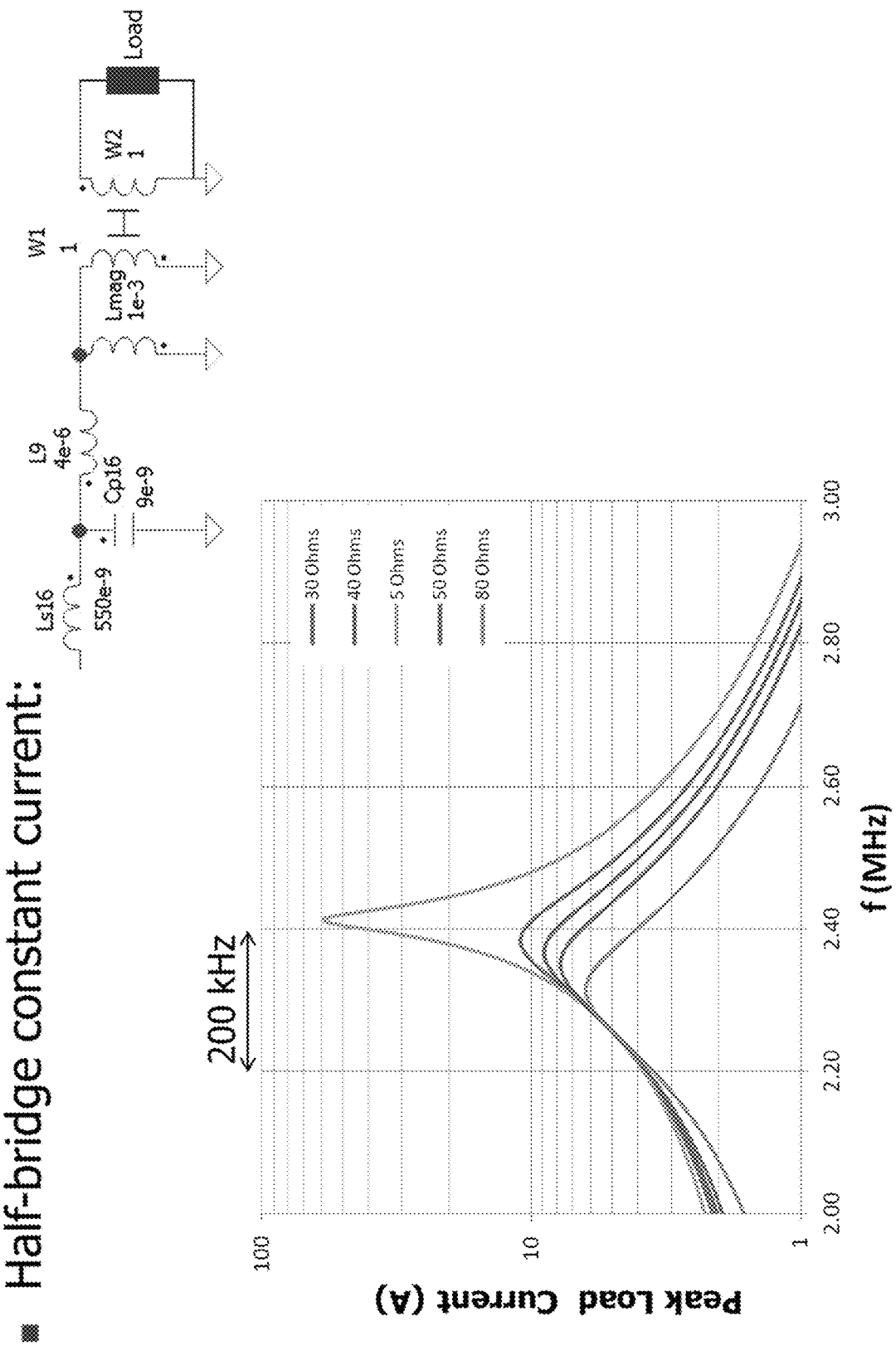
FIG. 40 is a circuit diagram and graph illustrating a frequency response for peak load current.

FIG. 40 shows the configuration of the LCL circuit and plots peak current loads over the range of 2 MHz to 3 MHz.

Figure 41:
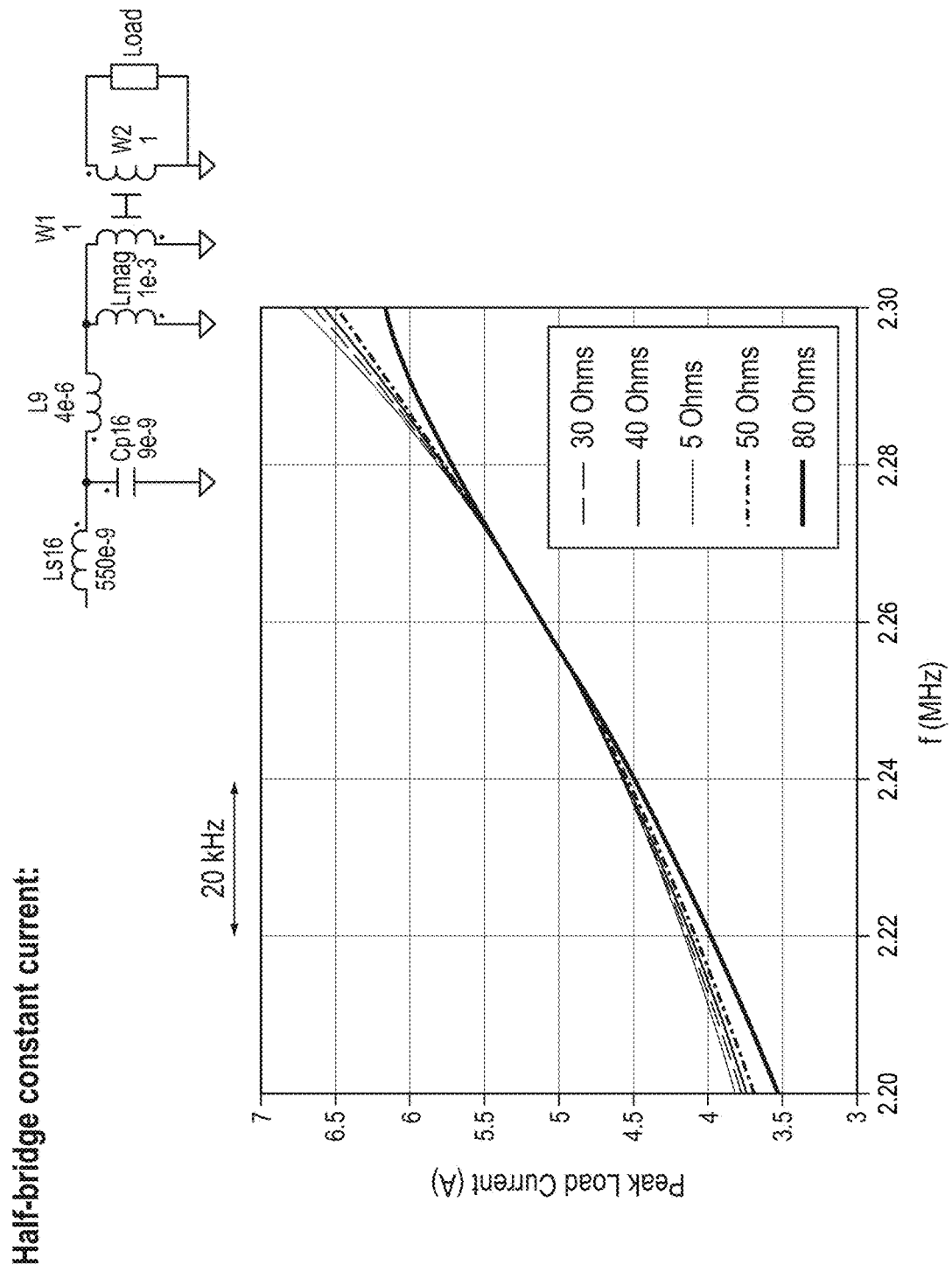
FIG. 41 is a circuit diagram and graph illustrating a frequency response for peak load current.

FIG. 41 shows the LCL circuit and the peak load current plotted over the frequency range of 2.2 MHz to 2.3 MHz at various resistance levels.

Figure 42:
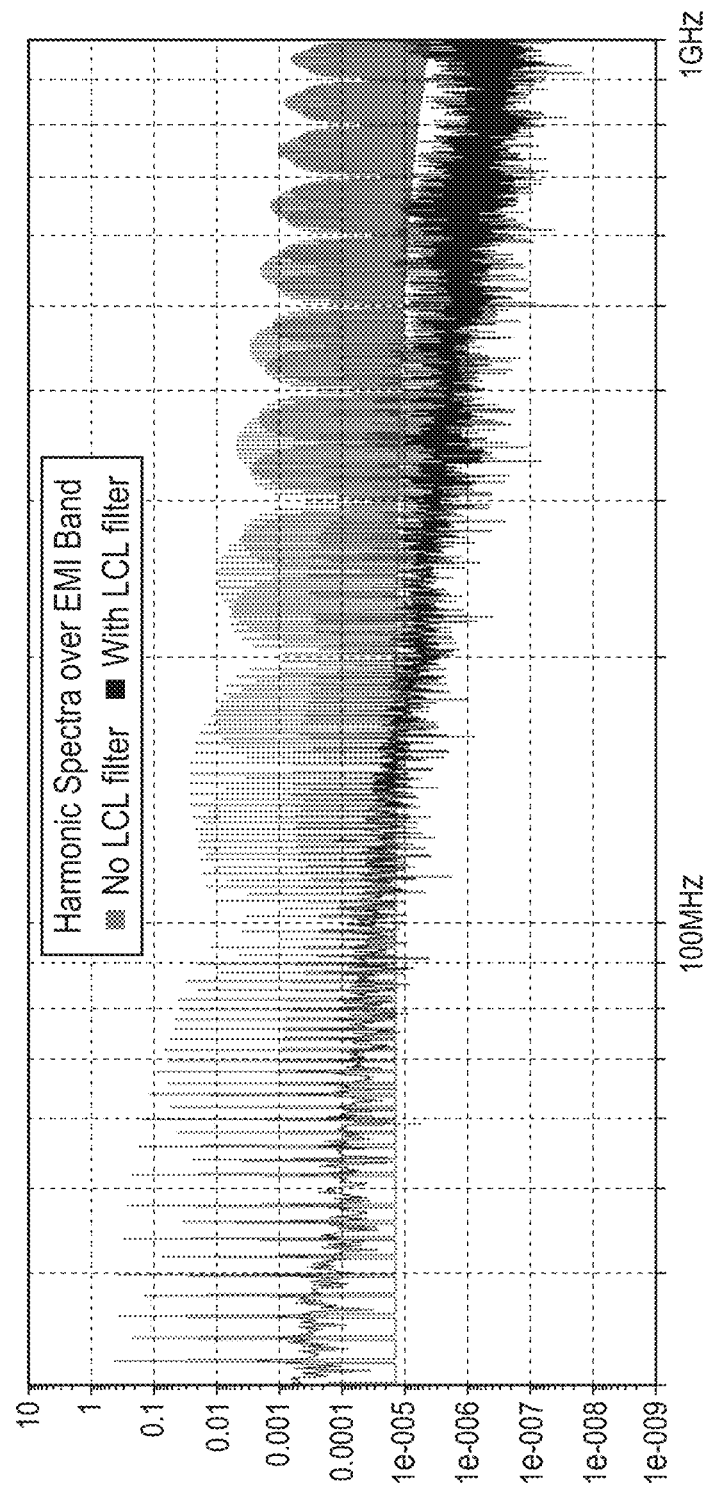
FIG. 42 is a graph illustrating a frequency response with and without an LCL network.

The-effect of the LCL circuit is shown in FIG. 42 which shows the higher frequency harmonics being filtered out of the electronic signal that is sent to the piezoelectric material. The smaller a particular spectral line is the better the filtering operation. As a result, the parasitic vibrations that would have been generated in the piezoelectric material are reduced or eliminated.

Figure 43:
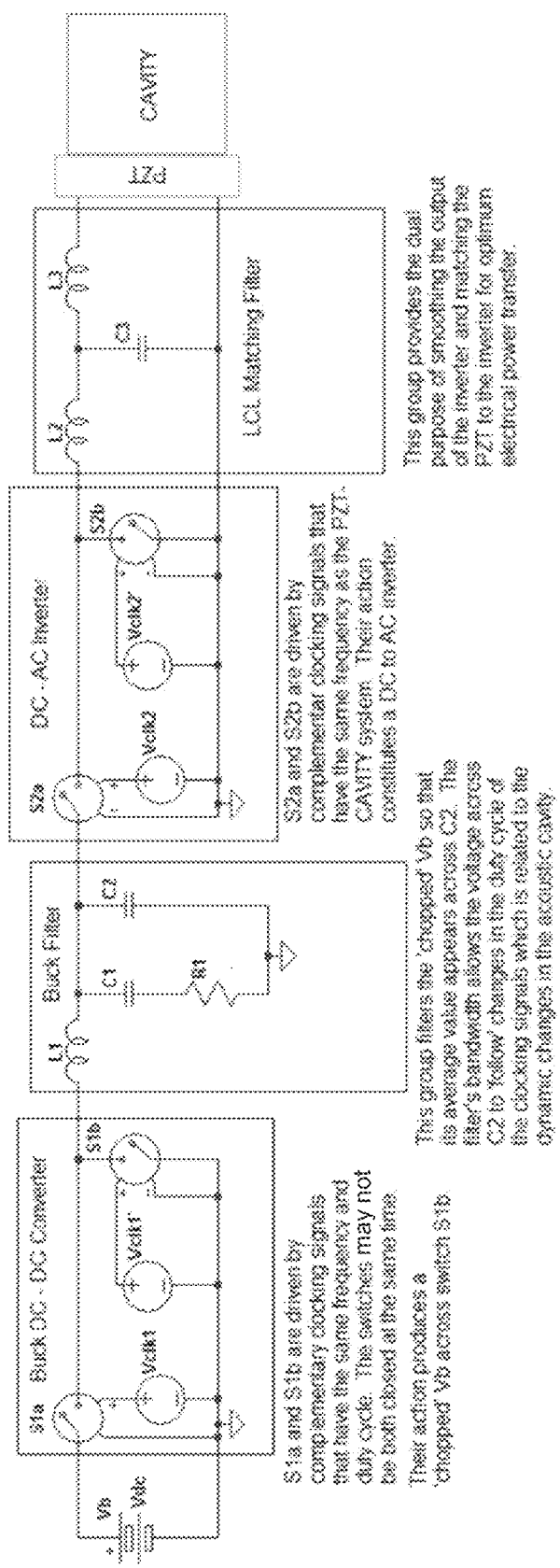
FIG. 43 is a circuit diagram of an RF power supply with an LCL network.

FIG. 43 is a diagram of an RF driver power converter composed of a DC-DC converter, a converter filter, ADC-AC inverter and an LCL matching filter. The switches of the converter are driven by complementary clocking signals that have the same frequency and duty cycle. The switches may be operated to avoid being both closed at the same time. The output of the converter is a chopped signal with an average DC voltage that is dependent on the duty cycle of the switches.

The output of the converter is provided to an RLC filter that averages the output of the converter. The chopped output of the converter appears as an average DC signal across the output of the filter. The filter's bandwidth or response is sufficient to follow or keep up with changes in the duty cycle of the clocking signals provided to the switches of the converter. The duty cycle of the clocking signals, or the DC output of the converter, is related to control of the dynamic characteristics of the acoustic transducer, for example, the reactive nature of the piezoelectric material.

The output of the filter is provided to the DC-AC inverter. The inverter includes switches that are driven by complementary clocking signals that are switched at a frequency that is related to the operation of the acoustic transducer and cavity system. The DC input to the inverter is used as a control signal for RF power conversion, where the inverter provides an RF signal with a power level that is controlled by the DC input.

The output of the inverter is applied to an LCL matching filter, which is connected to the acoustic transducer. The LCL matching filter smoothes the output of the inverter and provides a load match for the inverter output.

Figure 44:
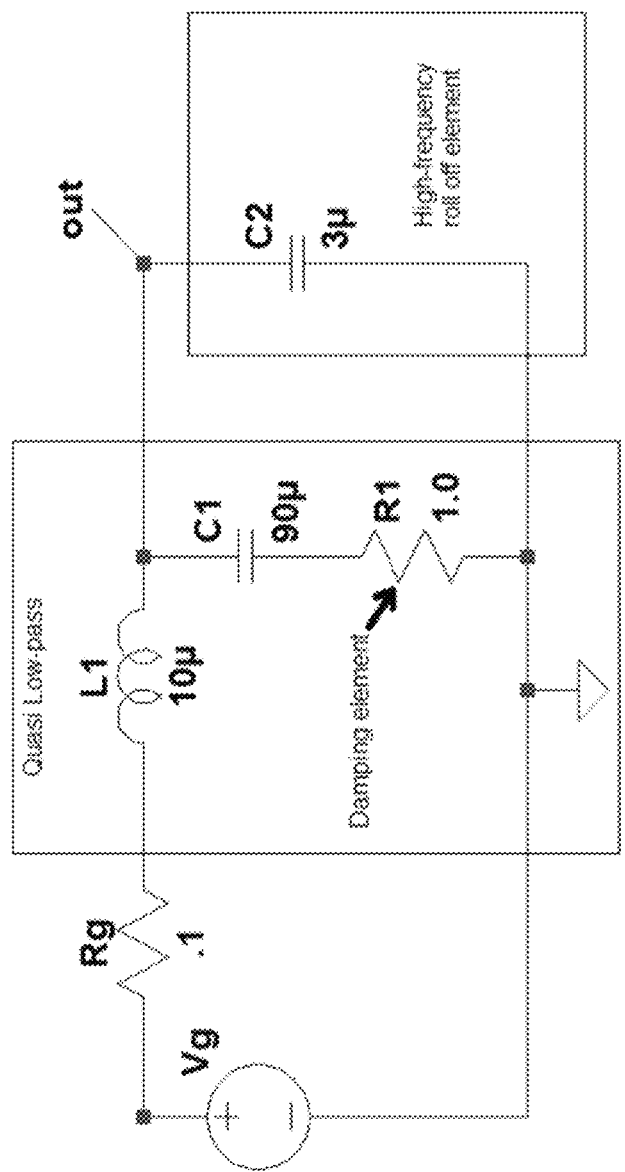
FIG. 44 is a circuit diagram of a low pass filter used with the RF driver power supply of FIG. 43.

An example of the filter interposed between the converter and inverter in the RF driver power converter is illustrated in FIG. 44. The filter may be implemented as a low pass filter, with a response time or bandwidth that is sufficient to react to changes in duty cycle of the complementary signals used to drive the DC-DC converter switches. As can be seen in FIG. 44, resistor Rg is 0.1 ohms, inductor L1 is 10 microhenries, capacitor C1 is 90 µF and resistor R1 is 1.0 ohms. The output of the filter is provided to a high-frequency roll off element, implemented here as capacitor C2, which has a value of 3 µF. The filter contributes to interfacing the DC-DC converter, which operates on a duty cycle basis, with the DC-AC inverter, which operates as a function generator or oscillator that translates the DC input from the converter into an RF amplified signal that can be used to drive the acoustic transducer. The filter thus performs several functions, including smoothing the response of the output of the DC-DC converter and averaging the chopped output of the converter to provide a well-regulated DC signal that is related to the operation, for example, the feedback data, of the acoustic transducer.

Figure 45:
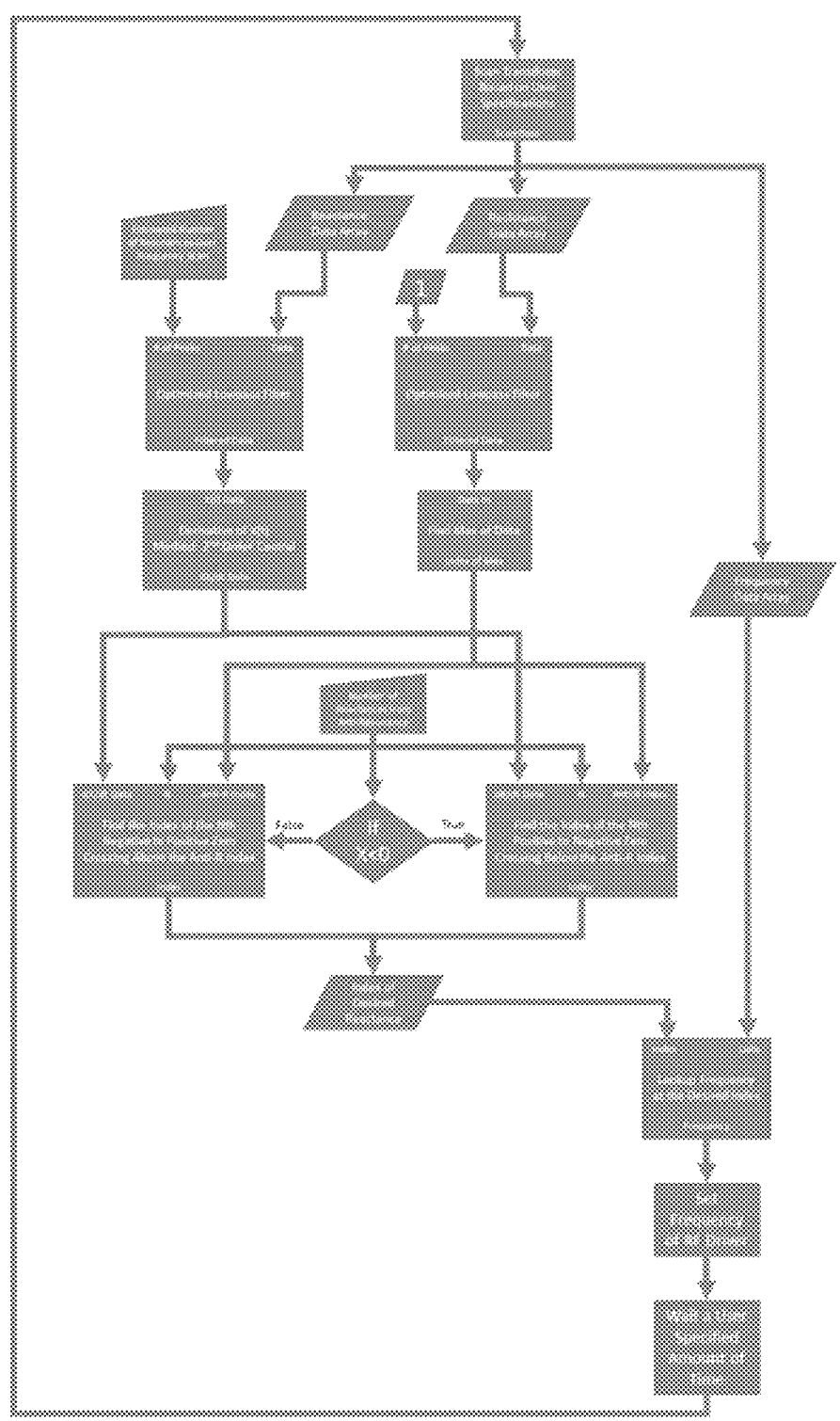
FIG. 45 is a flowchart illustrating a method for controlling an acoustic transducer.

Referring to FIG. 45, a flow chart is illustrated for a process for locating a minimum and/or maximum reactance for the acoustic transducer and/or the transducer/acoustic chamber combination, which may be under load. The load can be a fluid in the acoustic chamber, and/or particulates or a secondary fluid that is separated from the primary or host fluid. As the particulates or secondary fluid is separated from the primary or host fluid, the characteristics of the fluid in the acoustic chamber change, which can impact the operation of the transducer and/or transducer/acoustic chamber combination. The process for locating an operating point for driving the transducer begins by scanning through frequencies applied to the transducer, for example, by applying a range of frequencies to the transducer and measuring feedback data from the transducer. The range of frequencies to be scanned can be provided by user settings. Data for the reactance, X, and resistance, R, of the transducer is collected. One technique for collecting reactance and resistance data is to measure voltage, current and phase angle on the transducer. Resistance is determined as the real part of the voltage divided by the current, while reactance is determined as imaginary part of the voltage divided by the current.

As the data for the frequency scan is collected, a number of resonance and anti-resonance frequencies can be determined. The data can be passed through a low pass filter and peaks can be identified using a derivative function. A maximum peak for the anti-resonance is also identified. The method can accept an input setting of the number of reactances from anti-resonance to locate a minimum reactance. Based on the collected and calculated data, the desired minimum reactance below anti-resonance or desired maximum reactance above anti-resonance is determined, in this case as an index of the minimum or maximum reactances. Once the frequency of the desired reactance is located, the frequency of the RF driver power converter is set to the located frequency. The located frequency can be an operating setpoint for operating the transducer.

After a period of time, such as a number of milliseconds up to a number of tens of seconds, the process is repeated. By repeating the process, variations in the system can be dynamically identified, such as changes to reactance caused by temperature shifts, and the desired operating setpoints can be modified accordingly in keeping with the process.

Figure 46:
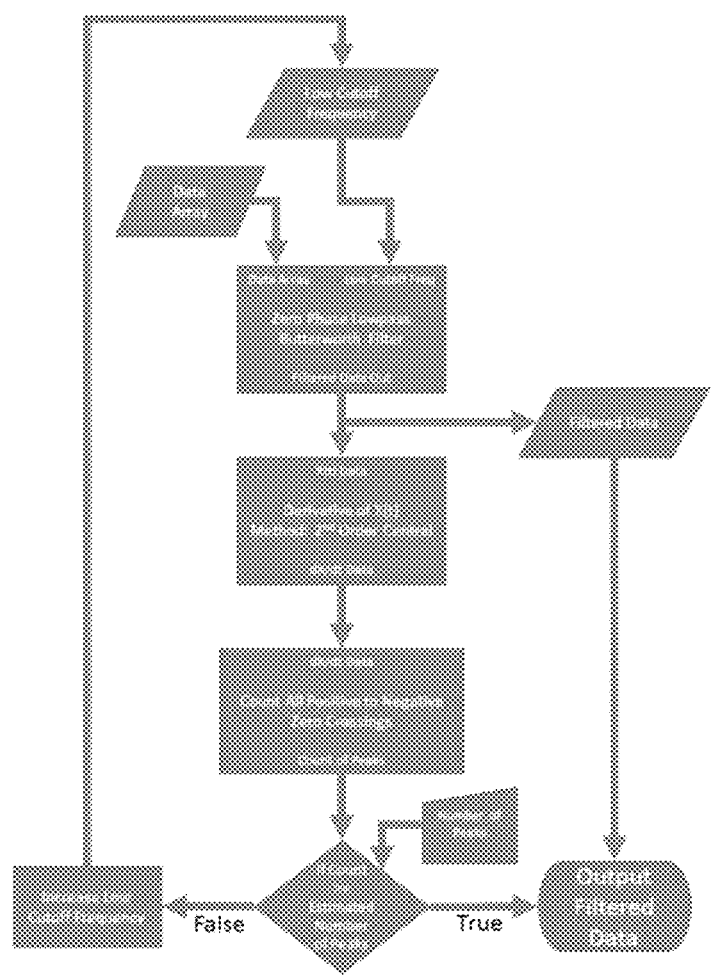
FIG. 46 is a flowchart illustrating a method for implementing an optimized low pass filter.

Referring to FIG. 46, a flow chart illustrates a process for implementing a low-pass filter for use in the frequency determination process described above. The filter characteristics can be modified in accordance with the illustrated process to contribute to optimizing detection of the desired frequency setpoints. The process begins by using an existing cut off or corner frequency in conjunction with the data collected from the frequency scan. A zero phase low-pass Butterworth filter is used to filter the collected data with the cutoff frequency. The derivative of the data is taken to determine minimums and/or maximums, and positive to negative zero crossings are identified and counted. The positive to negative zero crossings are indicative of detected peaks in the frequency response. If the process detects more peaks than expected, the cutoff frequency is increased and the process is repeated. If the count is less than the expected number of peaks, the filtered data is provided to the minimum/maximum reactance detection process.

Figure 47:
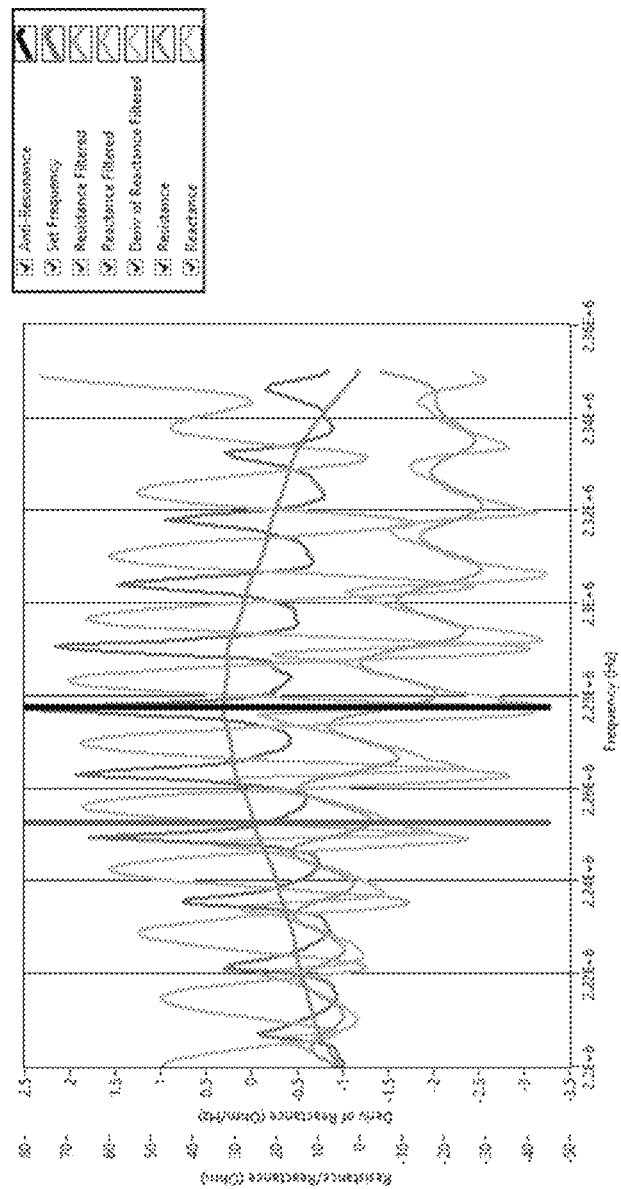
FIG. 47 is a graph illustrating a frequency response for an acoustic transducer.

FIG. 47 illustrates a frequency scan for a slightly damped 1×3 piezoelectric transducer coupled to an acoustic cavity through which a fluid containing CHO (Chinese hamster ovary) cells was flowed. As illustrated, peak anti-resonance is located, and a minimum reactance two away from the anti-resonance is selected for a frequency setpoint. In the figure, anti-resonance is approximately 2.278 MHz, and the selected frequency setpoint is approximately 2.251 MHz.

Figure 48:
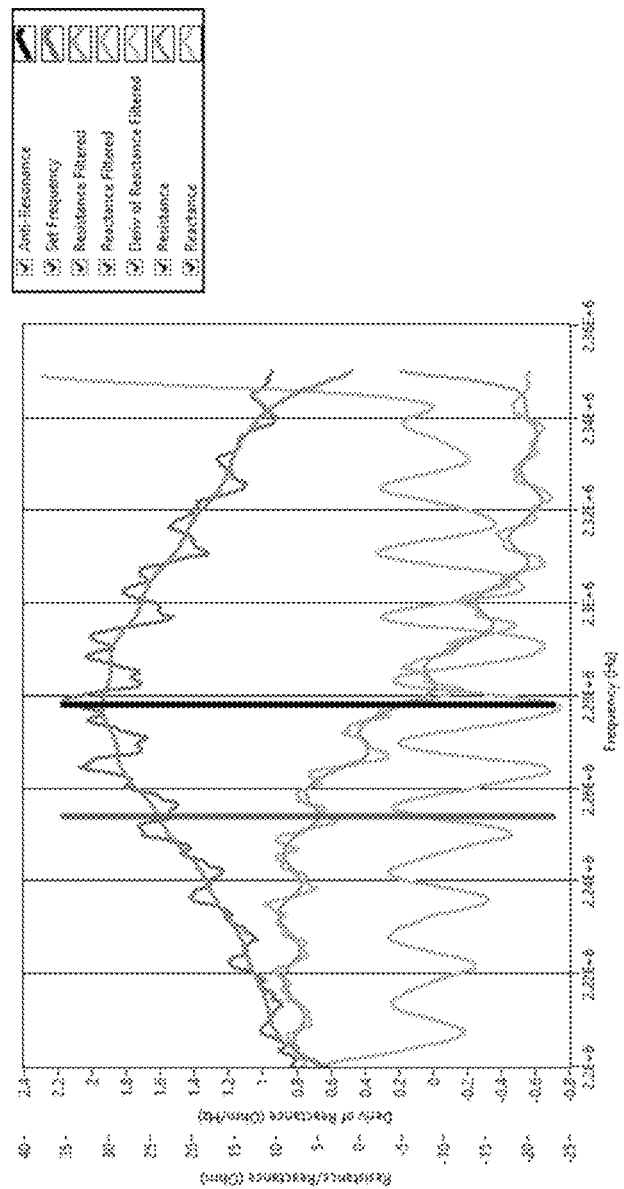
FIG. 48 is a graph illustrating a frequency response for an acoustic transducer.

FIG. 48 illustrates a frequency scan for a highly damped 2 MHz 1×3 transducer coupled to an acoustic chamber containing CHO. The peak anti-resonance is identified and the minimum reactance two away from the anti-resonance frequency is selected for an operating setpoint. Although a minimum reactance two away from the anti-resonance frequency is chosen as an operating setpoint, any reactance or index away from anti-resonance can be chosen for an operating setpoint.

Through experimental testing of the large scale acoustic filtration system, it has been determined that the 1 MHz and 2 MHz 1×3 transducer may have an optimal efficiency when operating at the minimum reactance points at frequencies below the transducer anti-resonances, as well as operating at the maximum reactance points above the anti-resonance of the transducer. The technique described herein provides an automated method to set the frequency of the RF drive to the transducer, so it is operating at a minimum reactance point below the anti-resonance or a maximum reactance above the anti-resonance. According to a feature, the technique maintains the desired operating point. The technique can be used to set the frequency of the RF drive, such as the inverter, function generator or oscillator discussed above.

TABLE 3

Functions and Variable Inputs and Outputs

| Name | Type | Description |
| --- | --- | --- |
| Scan Function | Function | Steps through a range of frequencies and captures Resistance and Reactance data from the Voltage and Current measurements of the RF drive. Inputs: Range (+−50 kHz around anti-res) Step Size (500 Hz) Step Interval (1 ms) Output: Array of Frequency, R, and X |
| Estimated Number of Resonances | Input Double | Expected number of resonances over the full scan range |
| Number of Reactance Minima/ Maxima from Anti-Resonance | Input Signed Integer | If negative the method will pick the frequency of that many minima below the anti-resonance. If positive the method will pick the frequency of that many maxima above the anti-resonance |
| Frequency to Set | Output Double | The frequency that the method picks to set the RF drive |
| Wait Time | Input Double | Specifies the amount of time between scans |

The method begins by running a sweep of frequencies and collecting resistance and reactance data for each frequency step. The resistance and reactance data is extrapolated from the voltage and current measurements of the RF drive. The sweep range is specified by the user, but is targeted to be 50 kHz above and 50 kHz below the anti-resonance of the transducer. The step size and step interval are also variables that can be altered. When the sweep is complete it outputs the frequency, resistance, and reactance at each step.

The data from the sweep is then filtered utilizing a zero-phase low pass Butterworth filter. The reactance enters a loop where the low cutoff frequency of the filter is constantly increased, until the number of peaks of the filtered data, equals the number of estimated peaks. This number of estimated peaks is entered by the user. The resistance data is filtered using a zero-phase low-pass Butterworth filter, however the low cutoff frequency is increased until there is one peak. The peak value of the filtered resistance data is interpreted as the anti-resonance of the transducer.

The derivative of the filtered reactance data is calculated and is used to find all the maximum or minimum points of the reactance curve. If the number of reactance minima/maxima from the anti-resonance data input is negative the method will look for the minimum reactance points below the anti-resonance. The method does this by identifying the negative to positive zero crossings, in other words, the upward slope zero crossings of the derivative of the filtered reactance curve. If this number is positive the method will look for the positive to negative zero crossings above the anti-resonance, which are the maximum points of the reactance curve. The absolute value of the number of reactance minima/maxima from the anti-resonance data input is the number of minimum or maximum points from the anti-resonance. The index of this point is used to determine the frequency to set the RF drive.

The RF drive is set and the method waits for a designated amount of time set by the user. Once this time period has elapsed the method then scans and start the sequence over again. Sample data of both slightly and highly damped data can be seen in FIG. 47 and FIG. 48. In both these examples the method was selected to pick two minimum reactance points below the anti-resonance. The set frequency is indicated by the red line. It can be seen that this line falls on the negative to positive zero crossing of the derivative of the filtered reactance data curve, and at the local minimum of the filtered reactance data curve.

Figure 49:
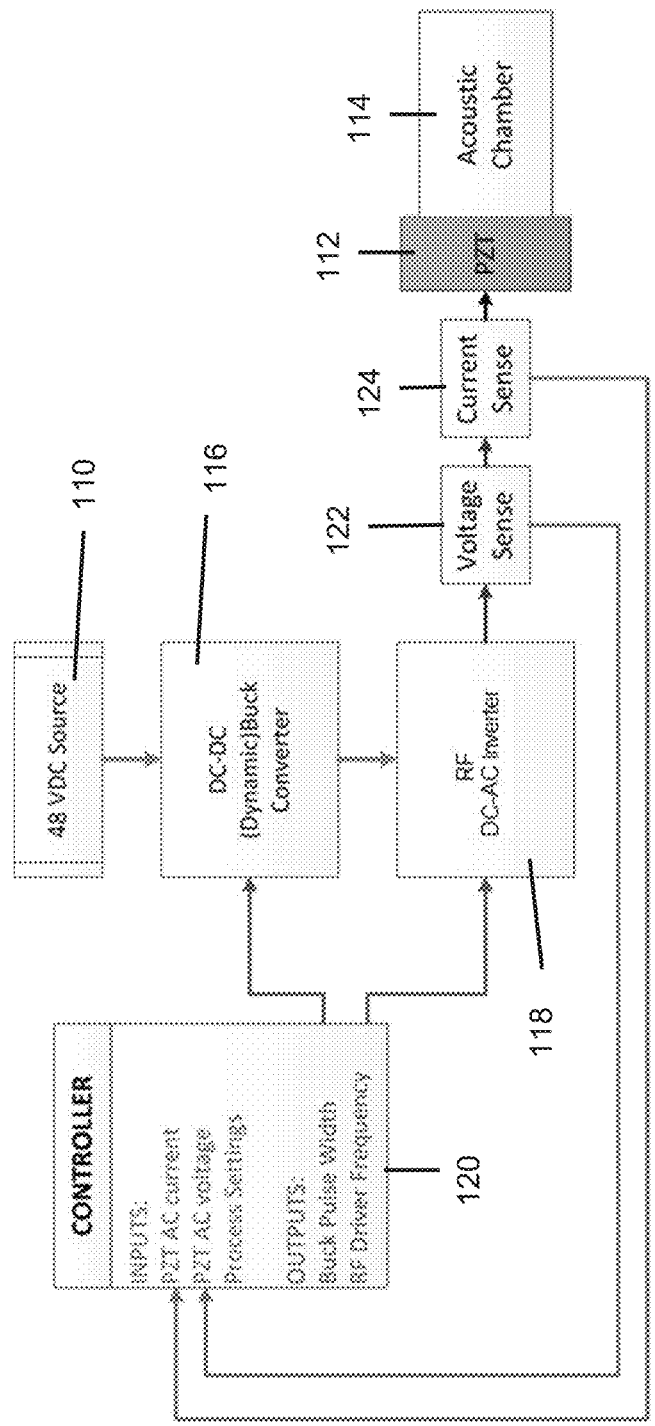
FIG. 49 is a block diagram illustrating a control technique for an acoustic transducer.

Referring to FIG. 49, a diagram of a control configuration for controlling an acoustic transducer 112 coupled to an acoustic chamber 114 is illustrated. Acoustic transducer 112 is driven by an RF driver power converter composed of DC source 110, DC-DC converter 116 and RF DC-AC inverter 118. The output drive signal provided by inverter 118 is inspected or sensed to obtain voltage sense 122 and current sense 124, which are fed back to a controller 120. Controller 120 provides control signals to converter 116 and inverter 118 to modulate the drive signal provided to the acoustic transducer 112.

The signal provided by controller 120 to converter 116 is a pulse width measure, which determines the duty cycle of the switching signals in converter 116. The duty cycle determines the DC level of the output of converter 116, which is applied to inverter 118. For example, the greater the duty cycle, the higher the DC output that is generated by converter 116. Controller 120 also provides control signals to inverter 118 that determine the frequency of operation of inverter 118. The control signals provided to inverter 118 may be switching signals, for switching switches in inverter 118, an example of such switches being shown in FIG. 43. Alternately, or in addition, controller 120 can provide a control signal to inverter 118 that is used to indicate a desired switching frequency, and circuitry internal to inverter 118 interprets the control signal and switches the internal switches in accordance with the interpreted control signal.

Voltage sense 122 and current sense 124 produce signals that are provided to controller 120 as feedback signals to control the drive signal provided to acoustic transducer 112. Controller 120 performs operations and calculations on the signals provided by voltage sense 122 and current sense 124, for example, to obtain a power measure, P=V*I, or to obtain a phase angle, θ=arctan (X/R).

Controller 120 is provisioned with a control scheme that accepts process settings, such as power output, range of frequency operation, or other user selectable parameters, and provides control signals to converter 116 and inverter 118 based on the process settings and the feedback values. For example, as described above, controller 120 can sequence through a number of frequencies in a range of frequencies that are provided to inverter 118 to scan through the frequency range and determine the characteristics of transducer 112 or transducer 112 in combination with acoustic chamber 114, which may be under load. The results of the frequency scan in terms of voltage and current obtained from the voltage sense 122 and current sense 124, respectively, are used to identify characteristics of the impedance curves for the components or the system, such as is illustrated in FIG. 47. The frequency scan can be implemented to occur at set up, and/or at intervals during operation of the illustrated system. During steady-state operation, the frequency scanned can be conducted to identify desired setpoints for operation, such as power or frequency, based on user settings and feedback values. The control scheme implemented by controller 120 is thus dynamic, and responds to changing conditions in the system, such as may be encountered with frequency drift, temperature change, load changes and any other system parameter changes. The dynamic nature of the control scheme permits the controller to respond to or compensate for nonlinearities, such as may be encountered as components age or lose tolerance. Accordingly, the control scheme is adaptive and can accommodate system changes.

Some examples of system operation include driving acoustic transducer 112 to produce a multidimensional acoustic standing wave in the acoustic chamber 114. A 3D acoustic wave is stimulated by driving acoustic transducer 112, which may be implemented as a piezoelectric crystal, sometimes referred to herein as a PZT, near its anti-resonance frequency. Cavity resonances modulate the impedance profile of the PZT as well as affect its resonance modes. Under the influence of the 3D acoustic field, suspended particles in the liquid medium in the acoustic cavity 114 are forced into agglomerated sheets and then into strings of 'beads' of agglomerated material. Once particle concentrations reach a critical size, gravitational forces take over and the agglomerated material drops out of the acoustic field and to the bottom of the chamber. The changing concentrations of agglomerated material as well as the dropping out of that material affects the cavity's resonances which in turn change the acoustic loading on the PZT and its corresponding electrical impedance. The changing dynamics of the collected material detunes the cavity and PZT reducing the effects of the 3D wave in clarifying the medium. Additionally, changes in the medium and cavity temperature also detune the cavity so that clarification is reduced. To track the resonance changes occurring in the cavity, a control technique is used to follow changes in the PZT's electrical characteristics.

A strong 3D acoustic field can be generated by driving the PZT at a frequency where its input impedance is a complex (real and imaginary) quantity. However, cavity dynamics can cause that impedance value to change significantly in an erratic manner. The changes in impedance are due, at least in part, to changes in the load applied to the acoustic transducer 112 and/or acoustic chamber 114. As particles or secondary fluid is separated from a primary or host fluid, the loading on acoustic transducer 112 and/or acoustic chamber 114 changes, which in turn can influence the impedance of the acoustic transducer 112 and/or acoustic chamber 114.

To correct for detuning, controller 120 calculates the PZT impedance from the voltage and current sensed at the PZT using voltage sense 122 and current sense 124 and determines which way to change the operating frequency to compensate for the detuning. Since frequency changes affect power delivered to the chamber, the controller also determines how to adjust the output voltage of (dynamic) buck converter 116 to maintain the desired amount of power output from RF DC-AC inverter 118 and into the acoustic transducer 112 and/or acoustic chamber 114.

Buck converter 116 is an electronically adjustable DC-DC power supply and is the power source for inverter 118. RF DC-AC inverter 118 converts the DC voltage out of converter 116 back to a high-frequency, AC signal to drive the PZT. The dynamics in the chamber occur at rates corresponding to frequencies in the low audio band. Consequently, the converter 116, controller 120, and DC-AC inverter 118 are capable of working at rates faster than the low audio band to permit controller 120 to track chamber dynamics and keep the system in tune.

Controller 120 can simultaneously change the frequency of DC-AC inverter 118 and the DC voltage coming out of buck converter 116 to track cavity dynamics in real time. The control bandwidth of the system is a function of the RF bandwidth of inverter 118 and the cutoff frequency of the filtering system of buck converter 116.

Controller 120 can be implemented as a DSP (digital signal processor) control, or as an FPGA (field programmable gate array) control, as examples. Controller 120 may be implemented with two channels, to permit parallel processing, for example to analyze real and/or reactive impedance, voltage, current and power.

The acoustic dynamics of the cavity affects the electrical characteristics of the PZT which affects the voltage and current drawn the PZT. The sensed PZT voltage and current is processed by the controller to compute the real-time power consumed by the PZT as well as its instantaneous impedance (affected by acoustic dynamics). Based on user set points the controller adjusts, in real-time, the DC power supplied to inverter 118 and the frequency at which inverter 118 is operated to track cavity dynamics and maintain user set points. An LCL network is used to match the output impedance of inverter t 118 to increase power transfer efficiency.

Controller 120 samples sensor signals fast enough to detect changes in cavity performance (via changes in PZT impedance) in real time. For example, controller 120 may sample the feedback values from the voltage sense 122 and current sense 124 at one hundred million samples per second. Signal processing techniques are implemented to permit a wide dynamic range for system operation to accommodate wide variations in cavity dynamics and applications. Converter 116 can be configured to have a fast response time to follow the signal commands coming from controller 120. Inverter 118 can drive a wide range of loads that demand varying amounts of real and reactive power that change over time. The electronics package used to implement the system illustrated in FIG. 49 may be configured to meet or exceed UL and CE requirements for electromagnetic interference (EMI).

Figure 50:
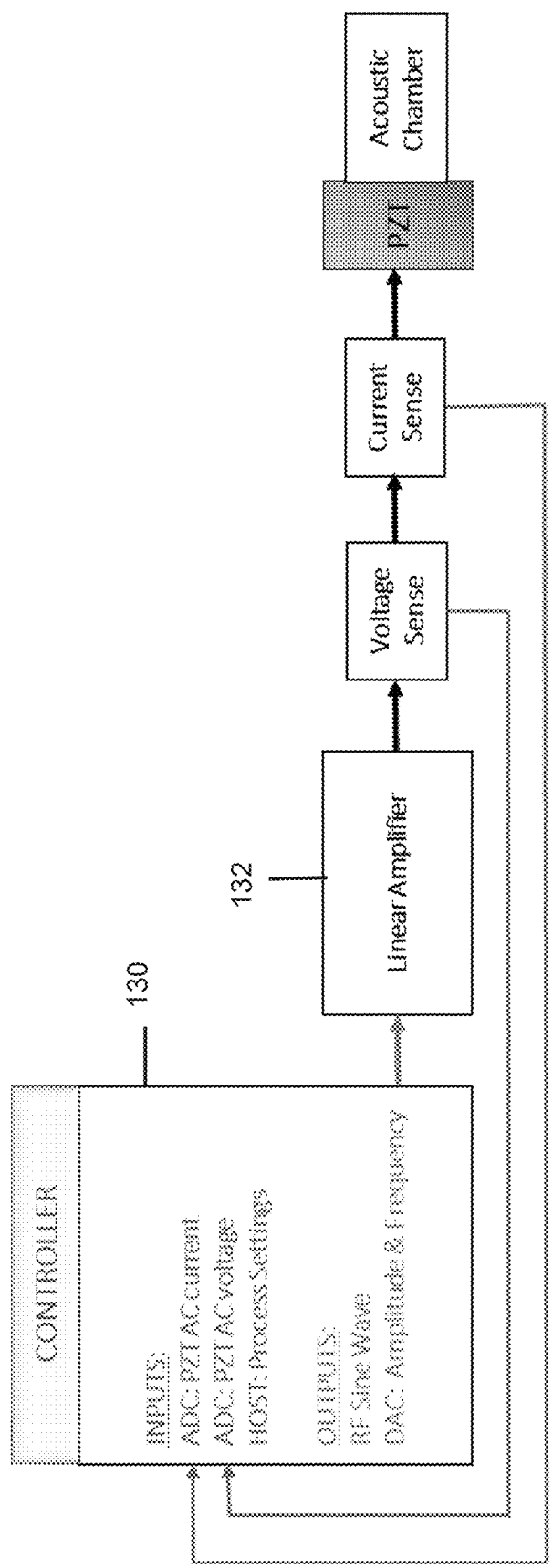
FIG. 50 is a block diagram illustrating a control technique for an acoustic transducer.

Referring to FIG. 50, controller 120 may be implemented with very-high-speed parallel digital-signal-processing loops using RTL (Register Transfer Level) which is realized in actual digital electronic circuits inside a field-programmable-gate-array (FPGA). Two high speed digital proportional integral (PI) loops adjust the frequency and amplitude control signals generated by controller 120 to track power and reactance. A linear amplifier 132 is used to amplify the output signal from controller 130 (which can be implemented as controller 120) in preparation for driving the PZT. The voltage and current sense is used to sense the voltage and current at the transducer. A calculation is performed in series by controller 130 to generate control signals provided to linear amplifier 132. The FPGA can be operated with a clocking signal of 100 MHz. The clocking speed contributes to obtaining fast enough sampling to monitor and adapt to conditions of the PZT in real-time. In addition, the structure of the FPGA permits each gate component to have a propagation delay commensurate with the clocking speed. The propagation delay for each gate component can be less than one cycle, or 10 ns with a clocking speed of 100 MHz.

Figure 51:
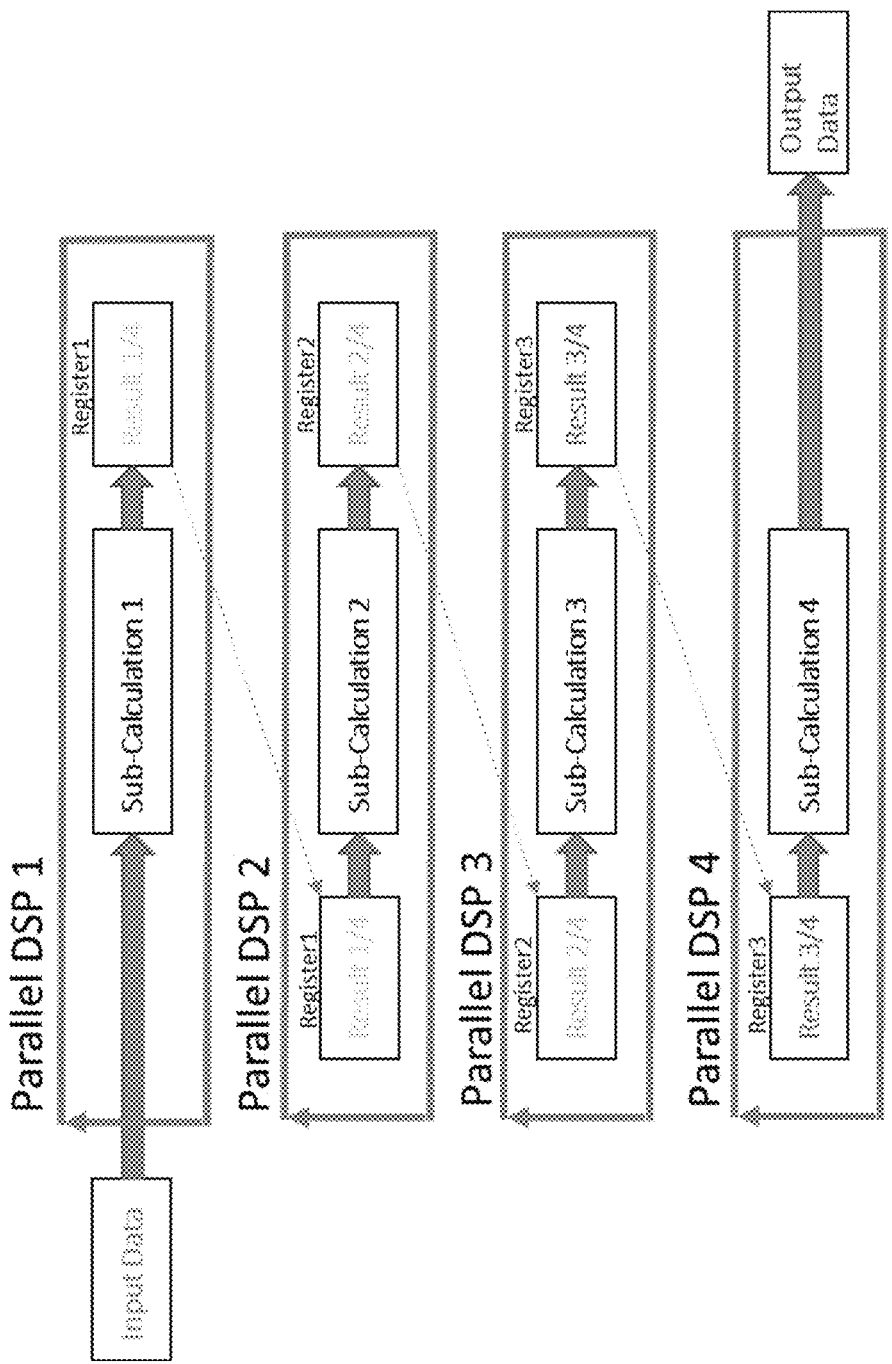
FIG. 51 is a block diagram illustrating a calculation technique for obtaining control parameters for an acoustic transducer.

Referring to FIG. 51, a diagram illustrates parallel and sequential operations for calculating control signals. Controller 130 may be configured to calculate the following parameters.

$V\text{RMS}=\text{sqrt}(V1^2+V2^2+\ldots+Vn^2)$ $I\text{RMS}=\text{sqrt}(I1^2+I2^2+\ldots+In^2)$ Real Power ($P=V$-Inst.$\times I$-Inst Integrated over $N$ Cycles)

Apparent Power ($S=V\text{RMS}\times I\text{RMS}$)

Controller 130 may be configured to calculate reactive power and bipolar phase angle by decomposing sensed voltage and current into in-phase and quadrature-phase components. FIG. 52 illustrates the in-phase and quadrature-phase demodulation of the voltage and current to obtain a four-quadrant phase, reactive power and reactance. The calculations for reactive power and phase angle can be simplified using the in-phase and quadrature-phase components.

$V\text{Phase Angle}=\text{Arctan}(QV/IV)$ $I\text{Phase Angle}=\text{Arctan}(QI/II)$ Phase Angle=$V$Phase−$I$phase Reactive Power=($Q$=Apparent Power$\times$Sine(Phase Angle)

Controller 130 may implement a control scheme that begins with a frequency sweep to determine system performance parameters at discrete frequencies within the frequency sweep range. The control scheme may accept inputs of a start frequency, a frequency step size and number of steps, which defines the frequency sweep range. Controller 130 provides control signals to linear amplifier 132 to modulate the frequency applied to the PZT, and the voltage and current of the PZT are measured using the voltage sense and the current sense. The control scheme of controller 130 may repeat the frequency sweep a number of times to determine the system characteristics, for example, reactance, with a relatively high level of assurance.

A number of reactance minimums can be identified as a result of analysis of the data obtained in the frequency sweep. The control technique can be provided with an input that specifies a certain frequency range where a desired reactance minimum is located, as well as being provided with a resistance slope (+/−) that can be used for tracking a desired point of operation based on resistance tracking that corresponds to a desired minimum reactance. The resistance slope may be constant near the minimum reactance, which may provide a useful parameter for use with a tracking technique. By tracking resistance at a desired frequency, a robust control can be attained for operating at a minimum reactance point.

The control technique may take the derivative of the resistance/reactance values to locate zero slope derivatives, which are indicative of maximums and minimums. A proportional-integral-differential (PID) controller loop may be used to track the resistance to obtain a frequency setpoint at which a desired minimum reactance occurs. In some implementations, the control may be a proportional-integral (PI) loop. With the FPGA operating at 100 MHz, adjustments or frequency corrections can be made every 10 ns to compensate for changes in the tracked resistance. This type of control can be very accurate and implemented in real-time to manage control of the PZT in the presence of a number of changing variables, including reactance, load and temperature, for examples. The control technique can be provided with an error limit for the frequency of the reactance minimum or frequency setpoint, to permit the control to adjust the output to linear amplifier 132 to maintain the frequency within the error limit.

A fluid mixture, such as a mixture of fluid and particulates, may be flowed through the acoustic chamber to be separated. The fluid mixture flow may be provided via a fluid pump, which may impose perturbations on the fluid, as well as the PZT and chamber. The perturbations can create a significant fluctuation in sensed voltage and current amplitudes, indicating that the effective impedance of the chamber fluctuates with pump perturbations. However, owing to the speed of the control technique, the fluctuations can be almost completely canceled out by the control method. For example, the perturbations can be identified in the feedback data from the PZT and can be compensated for in the control output from the controller. The feedback data, for example the sensed voltage and current, may be used to track the overall acoustic chamber pressure. As the characteristics of the transducer and/or acoustic chamber change over time and with various environmental parameters, such as pressure or temperature, the changes can be sensed and the control technique can compensate for the changes to continue to operate the transducer and acoustic chamber at a desired setpoint. Thus, a desired setpoint for operation can be maintained with very high accuracy and precision, which can lead to optimized efficiency for operation of the system.

The FPGA may be implemented as a standalone module and maybe coupled with a class-D driver. Each module may be provided with a hardcoded address so that it can be identified when connected to a system. The module can be configured to be hot-swappable, so that continuous operation of the system is permitted. The module may be calibrated to a particular system and a transducer, or may be configured to perform a calibration at particular points, such as upon initialization. The module may include long-term memory, such as an EEPROM, to permit storage of time in operation, health, error logs and other information associated with operation of the module. The module is configured to accept updates, so that new control techniques can be implemented with the same equipment, for example.

Figure 53:
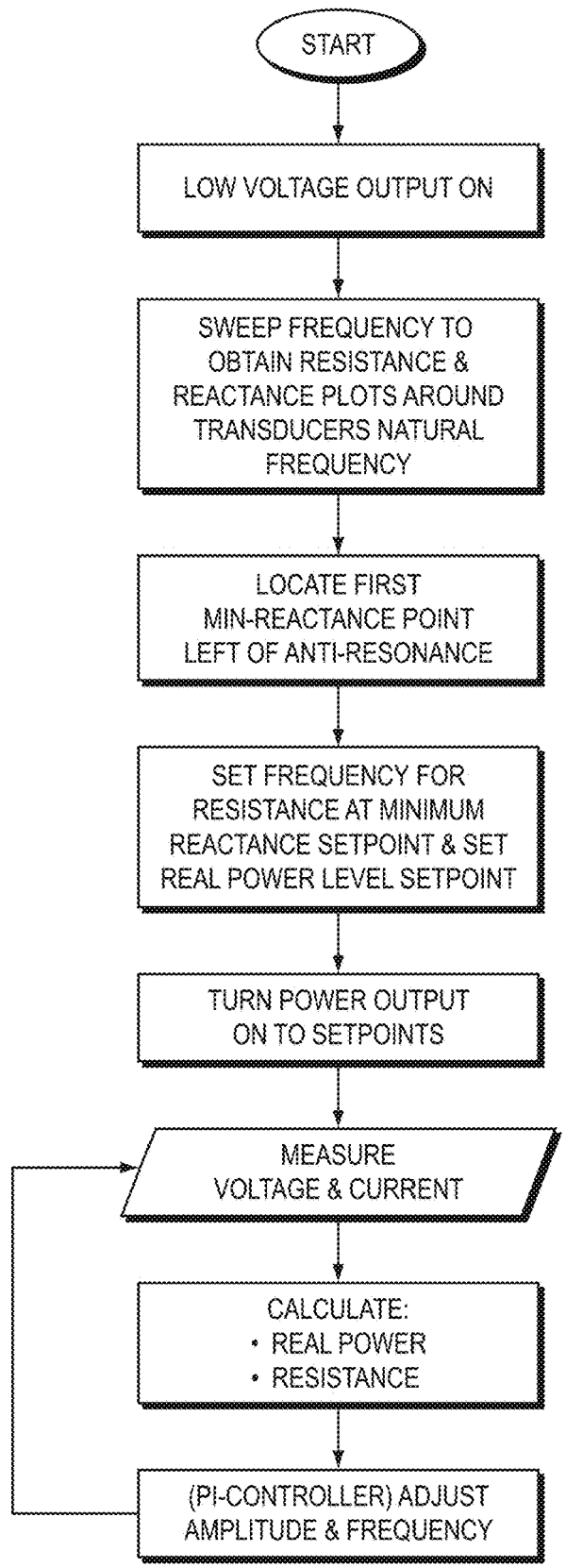
FIG. 53 is a flowchart illustrating a control technique for an acoustic transducer.

Referring now to FIG. 53, a method for controlling an acoustic transducer is illustrated with a flowchart. The illustrated method may be implemented on or with controller 120 or 130. The method uses a low voltage output during a frequency sweep that drives the acoustic transducer over a range of frequencies. Feedback from the acoustic transducer is used to determine the resistance and reactance response of the transducer over the range of frequencies at the low voltage output. Once the data for the transducer responses collected, the frequency at which the minimum reactance occurs below anti-resonance is identified. The resistance at the minimum reactance is identified and the frequency setpoint is set to establish operation at this resistance. A real power setpoint for the frequency setpoint is established, which may be based on user input. The establishment of the operating setpoints, the method causes the power control signals to be output for the linear amplifier or the converter-inverter power supply.

The method performs a loop in which voltage and current are measured at the acoustic transducer, real power and resistance are calculated and provided to a proportional-integral (PI) controller. The output of the PI controller is used to adjust the amplitude and frequency of the signal supplied to the transducer. The loop is repeated, resulting in the amplitude of the power provided to the transducer being controlled and tracked, and the frequency of the power provided to the transducer being controlled and tracked. The loop permits the controller to dynamically adjust to changes in the system, including changes related to loading of the transducer and/or the transducer/acoustic cavity combination or changes related to temperature, as examples.

Figure 54:
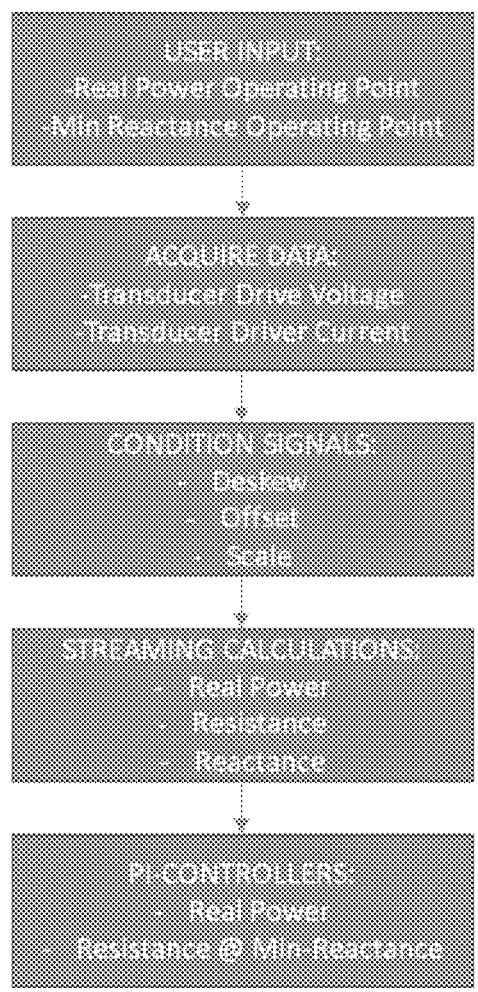
FIG. 54 is a flowchart illustrating components of a control technique for use with an acoustic transducer.

FIG. 54 illustrates an example method for processing information to implement a transducer control. The method uses desired operating points for real power and a minimum reactance, which may be obtained from user input. Data is received from the transducer, including drive voltage and drive current. The data received from the transducer is conditioned to improve the quality of the information and calculations derived there from. For example, the data representing drive voltage and drive current is deskewed, provided with an offset and scaled for use with subsequent calculations. The condition data is used to calculate real power, resistance and reactance of the transducer. These parameters are compared to operating points received in the method, and a PI controller is used to generate a signal that can adjust the real power and frequency of the drive signal provided to the transducer. Note that the conditioned feedback parameters can be used to generate an error signal in conjunction with the desired operating point information, with the error signal being provided to an amplifier that adjusts the signal provided to the RF driver power supply, whether linear amplifier or converter-inverter combination.

An LCL matching filter is discussed above, such as with respect to FIG. 43. According to another example, and LC matching filter is provided between the converter output and the PZT. The LC matching filter provides impedance scaling to obtain inappropriate load for the inverter drive. The LC combination can be considered a network, which is tuned to provide desired power transfer, such as optimized power transfer, through the transducer and into the resonant cavity. Considerations for implementing the LCL filter or the LC filter include the combined response of the transducer and the resonant cavity. According to one example, a filter is implemented to permit desired power transfer, such as optimized power transfer, when the acoustic transducer is operated in a multi-dimensional mode, or in a multi-mode, for example, with multiple overlaid vibrational modes that produce one or more primary or dominant vibrational modes. As discussed above, a desired mode of operation is at a frequency that corresponds to a minimum reactance point of the response of the transducer, and/or the response of the transducer/resonant cavity combination.

Figure 55:
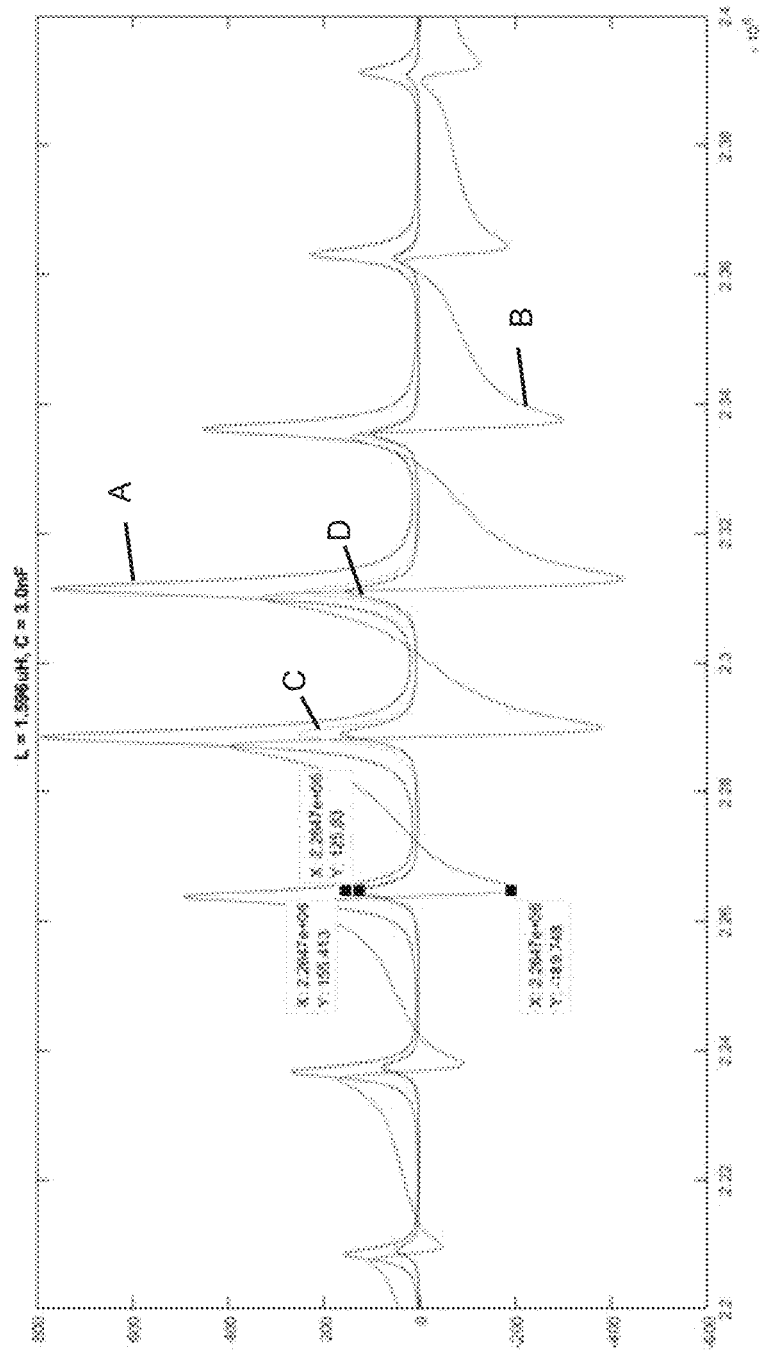
FIG. 55 is a graph illustrating a frequency response for an LC network.
Figure 56:
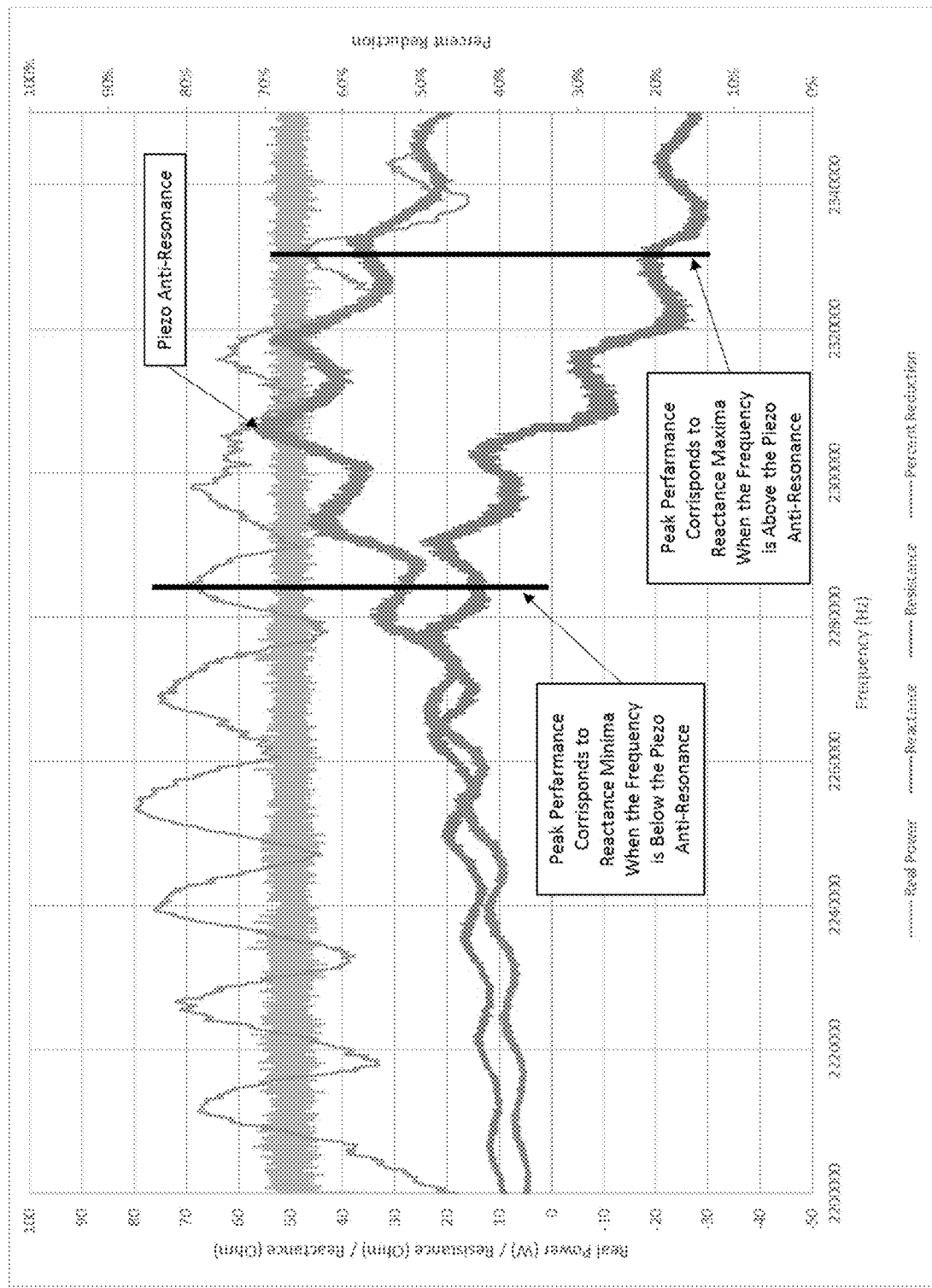
FIG. 56 is a graph illustrating power, reactance, resistance and peak performance for an acoustic transducer.

For a fixed resonant frequency, the LC network can deliver different amounts of power based on the system resonances residences in accordance with the combination of inductor and capacitor values that are used to form the LC network. FIG. 55 illustrates a response curve for an LC network with an inductor value of 1.596 uH and a capacitor value of 3.0 nF. The resonant frequency of the LC network is 2.3 MHz, the resistive impedance (A) is shown in blue, the reactive impedance (B) is shown in red, the input real power (C) is shown in yellow and the acoustic real power (D) into the cavity is shown in purple. With regard to the power delivered into the system, increasing the capacitor value with the same resonance increases power into the system. In general, changing the values of the inductor and/or capacitor can influence the resonant frequency of the LC network. Changing the resonant frequency of the LC network changes the frequency at which optimum power transfer occurs, and can impact the efficiency of the transfer. For example, the frequency for optimum power transfer relative to minimum reactance points (B) of the input impedance of the system is influenced by the resonance frequency of the LC network.

The plot in FIG. 55 shows the points on the input real power (C) and the acoustic real power (D) at a reactance minimum. The input real power and acoustic real power are fairly well matched, indicating efficient transfer of power. If the value of the inductor is changed to 0.8 uH and the value of the capacitor is changed to 6.0 nF, the same reactance minimum produces a greater power transfer with somewhat less efficiency. The power transfer becomes less efficient when the input real power (C) is significantly different (greater) than the acoustic real power (D). In some instances, depending on the inductor and capacitor values, power transfer can be highly efficient, however, the frequency operating point may not be at a minimum reactance point (B). Accordingly, trade of choices can be made between operating the transducer to obtain highly efficient separation in the acoustic chamber, implying a minimum reactance point, and obtaining efficient power transfer into the chamber. For a given material being separated and a given transducer, an LC network can be selected with a resonance frequency to obtain efficient power transfer into the acoustic cavity, improving overall system efficiency.

Figure 57:
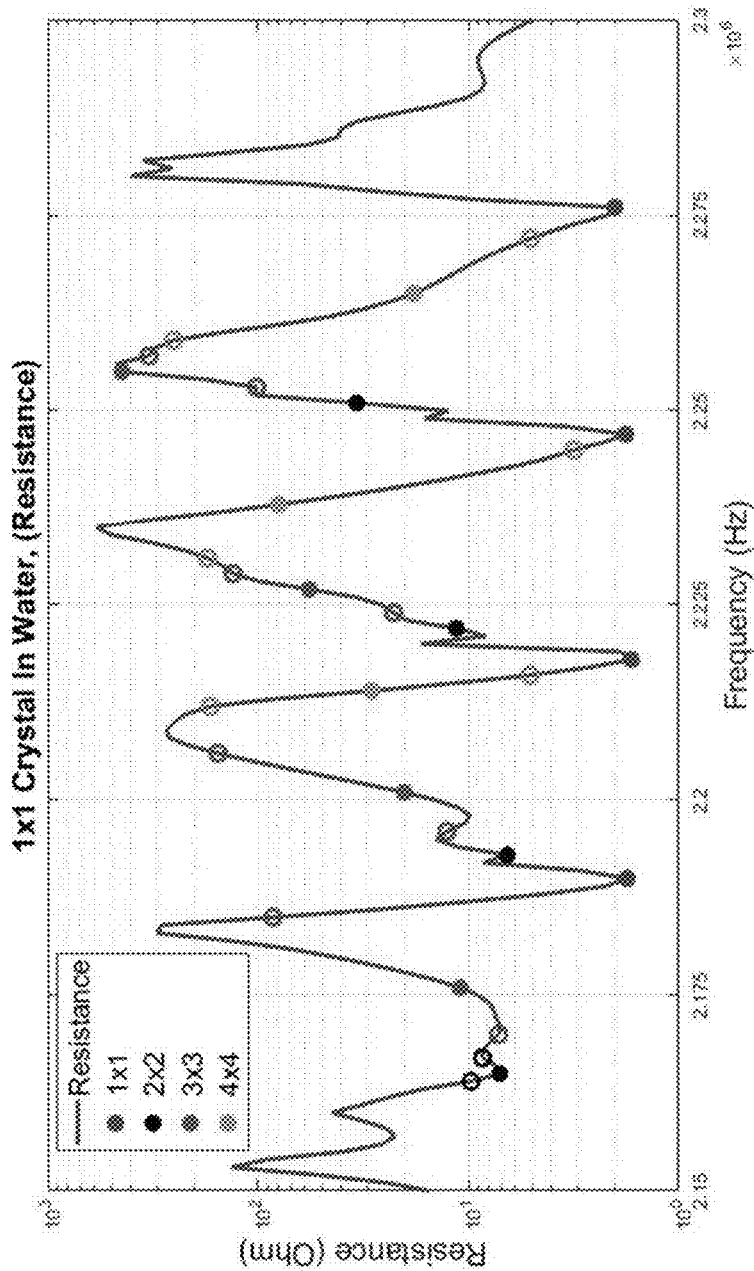
FIG. 57 is a graph illustrating a resistance curve versus frequency.
Figure 58:
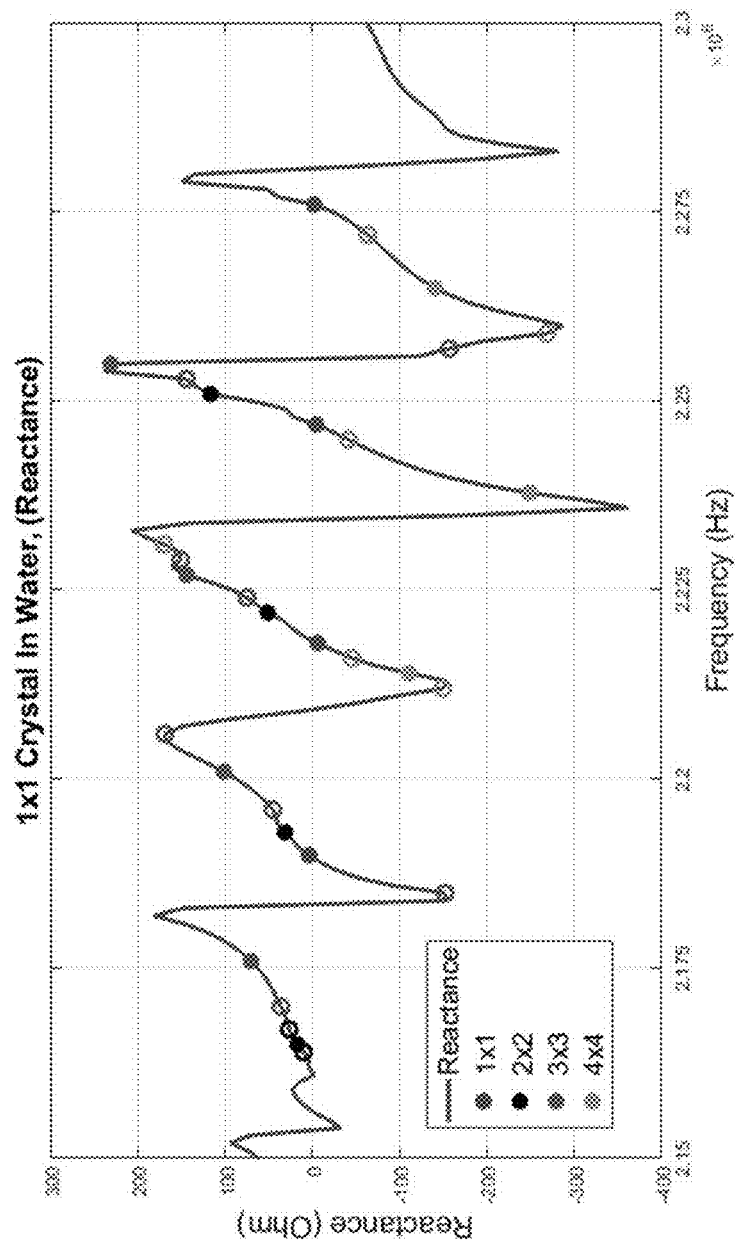
FIG. 58 is a graph illustrating reactance versus frequency, with a number of different modes identified.
Figure 59:
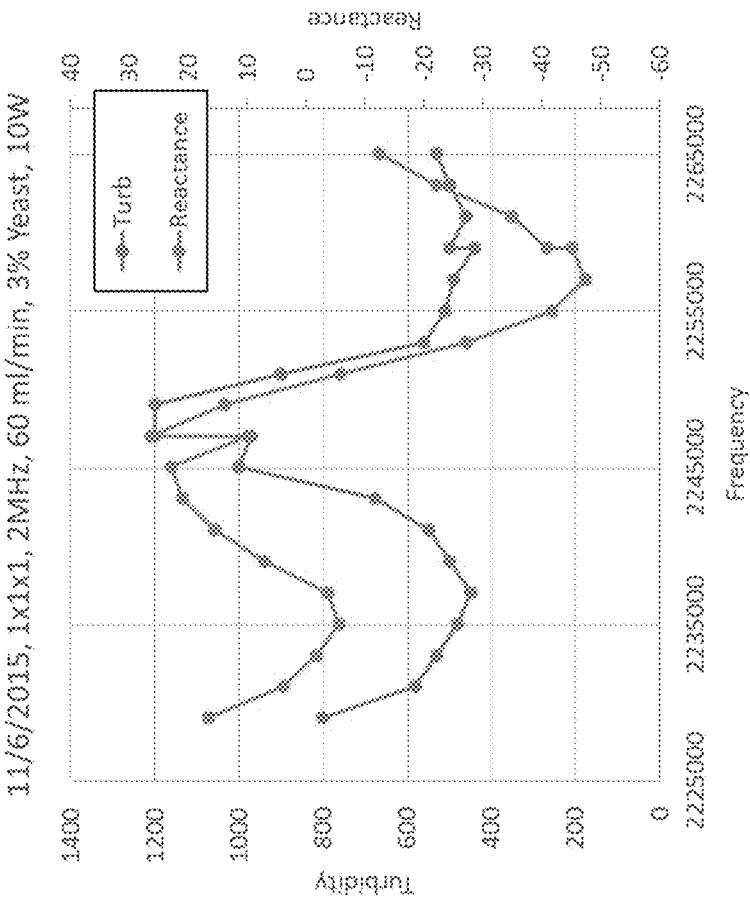
FIGS. 59, 60, 61 and 62 are graphs illustrating turbidity and reactance for a given example of acoustophoresis.
Figure 60:
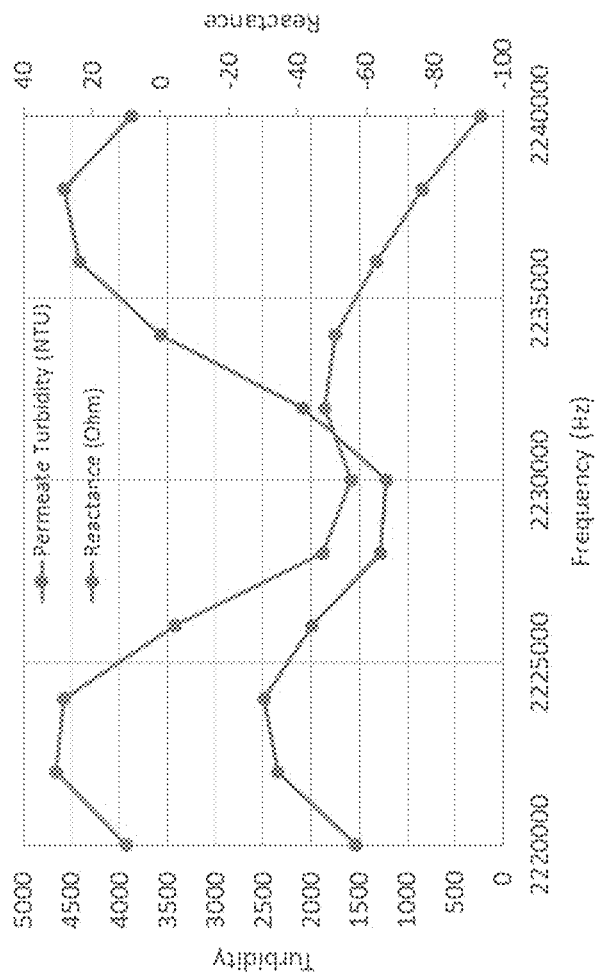
Figure 61:
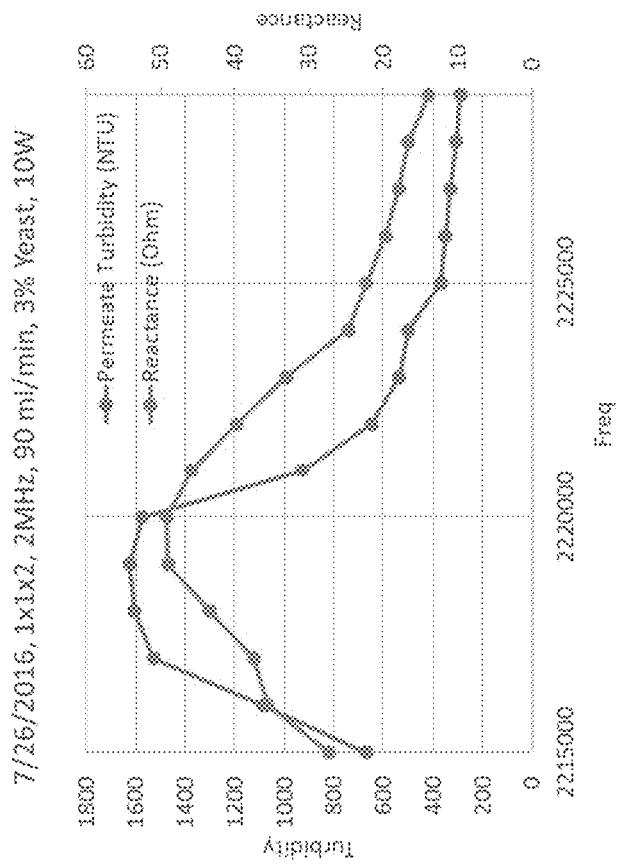
Figure 62:
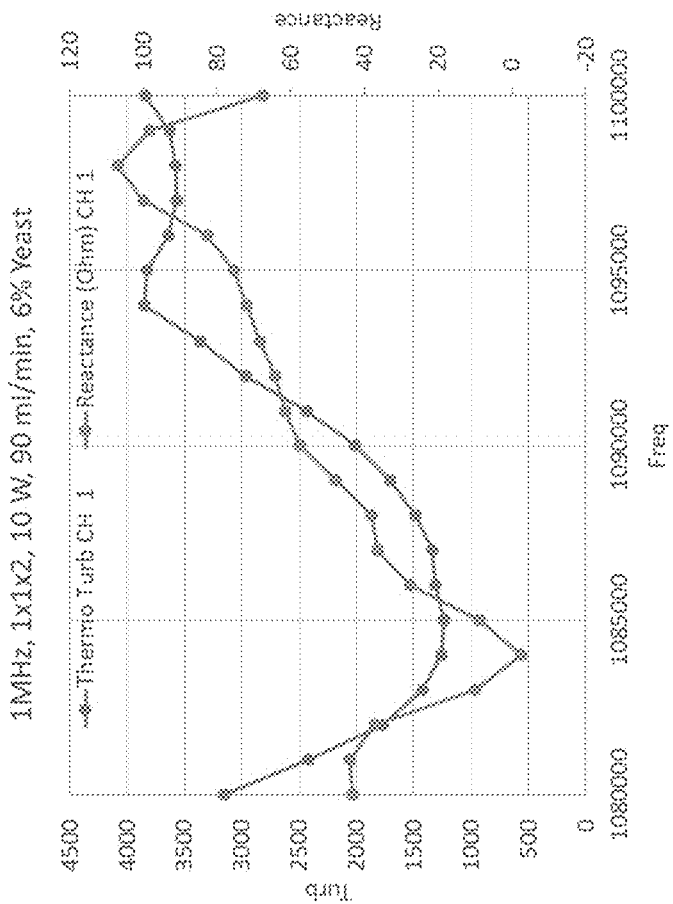

FIG. 57 is a graph illustrating a resistance curve versus frequency, with a number of different modes identified. Higher order modes are obtained along the graph line locations where resistance is above a minimum. FIG. 58 is a graph illustrating reactance versus frequency, with a number of different modes identified. Higher order modes are illustrated as available along a number of locations on the graph line. FIGS. 59, 60, 61 and 62 are graphs illustrating turbidity and reactance for a given example of acoustophoresis. The acoustic transducer in FIG. 62 was operated at 1 MHz.

The acoustic radiation force exerted on the particles in the fluid can be calculated and/or modeled. For example, a COMSOL model was created and used to predict linear acoustic standing wave fields. The model implemented models for piezo-electricity, elasticity and acoustics. The model was used to predict acoustic radiation forces on particles that are small compared to wavelength, which includes using the Gorkov equation, and larger particles, which includes using the Yurii-Zhenia equations. In some instances, it may be helpful to normalized the results, for example, by normalizing with respect to power. The effect on the particles of the acoustic radiation forces can be studied, and in particular used for determining transducer configurations, and for controlling the transducer and/or transducer/cavity combination.

Figure 63:
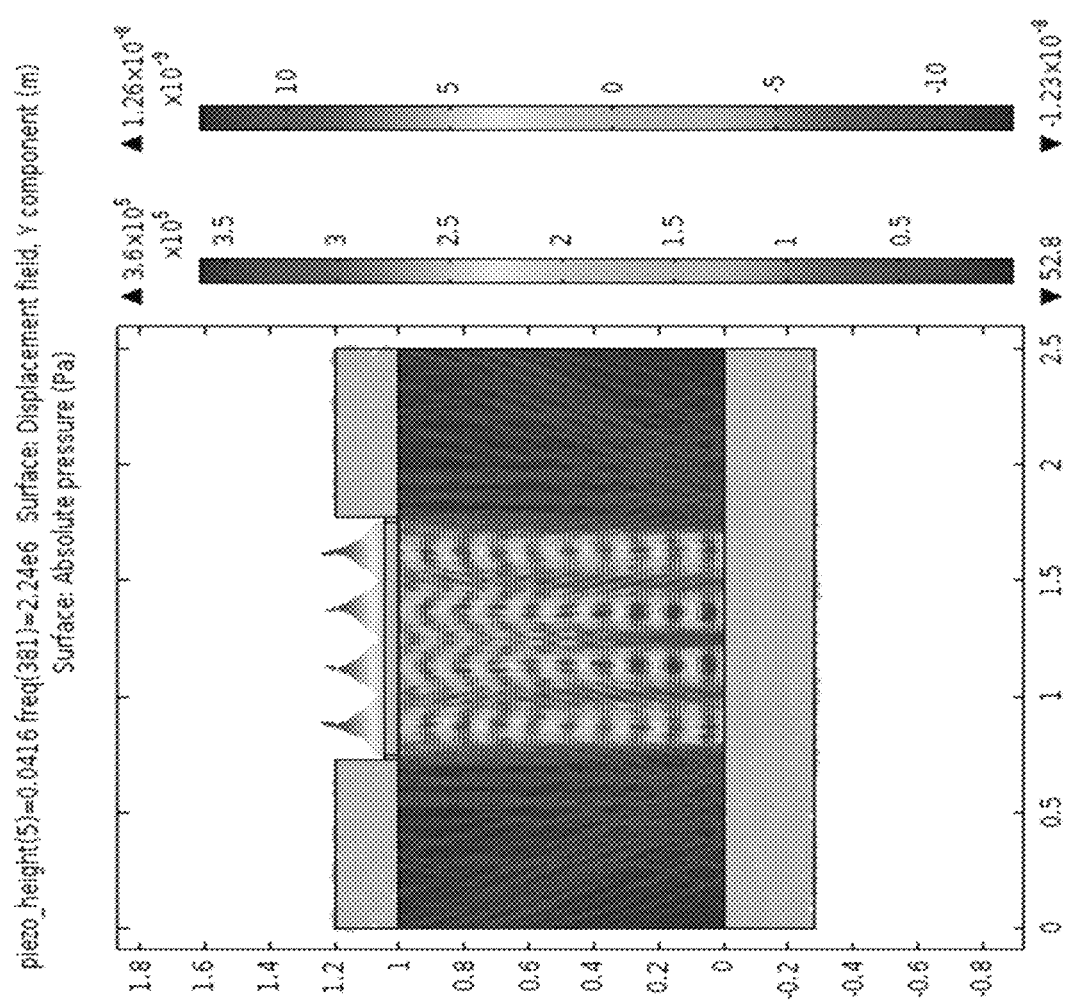
FIG. 63 is a graph illustrating piezoelectric displacement.
Figure 64:
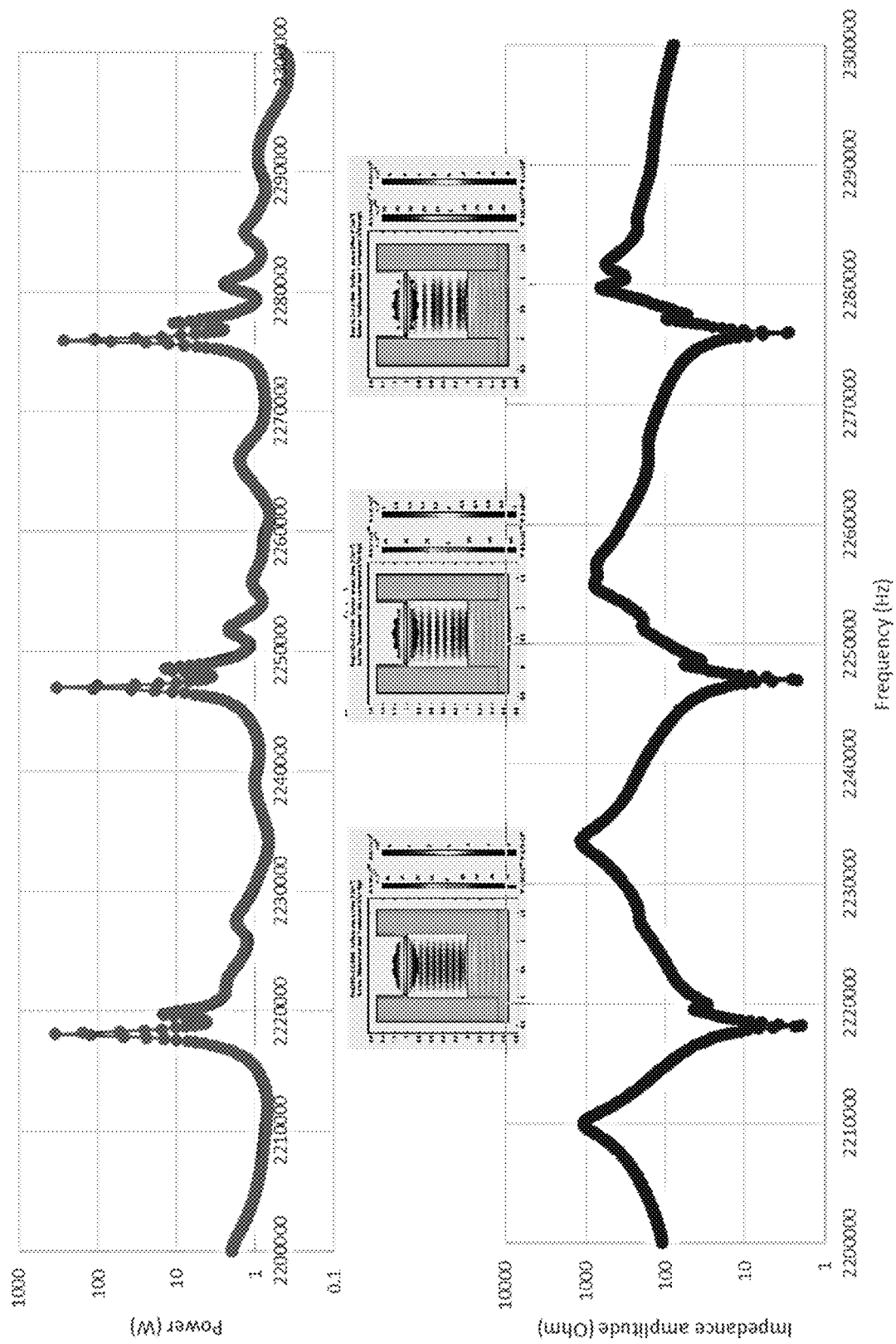
FIG. 64 is a graph illustrating power and impedance amplitude.
Figure 65:
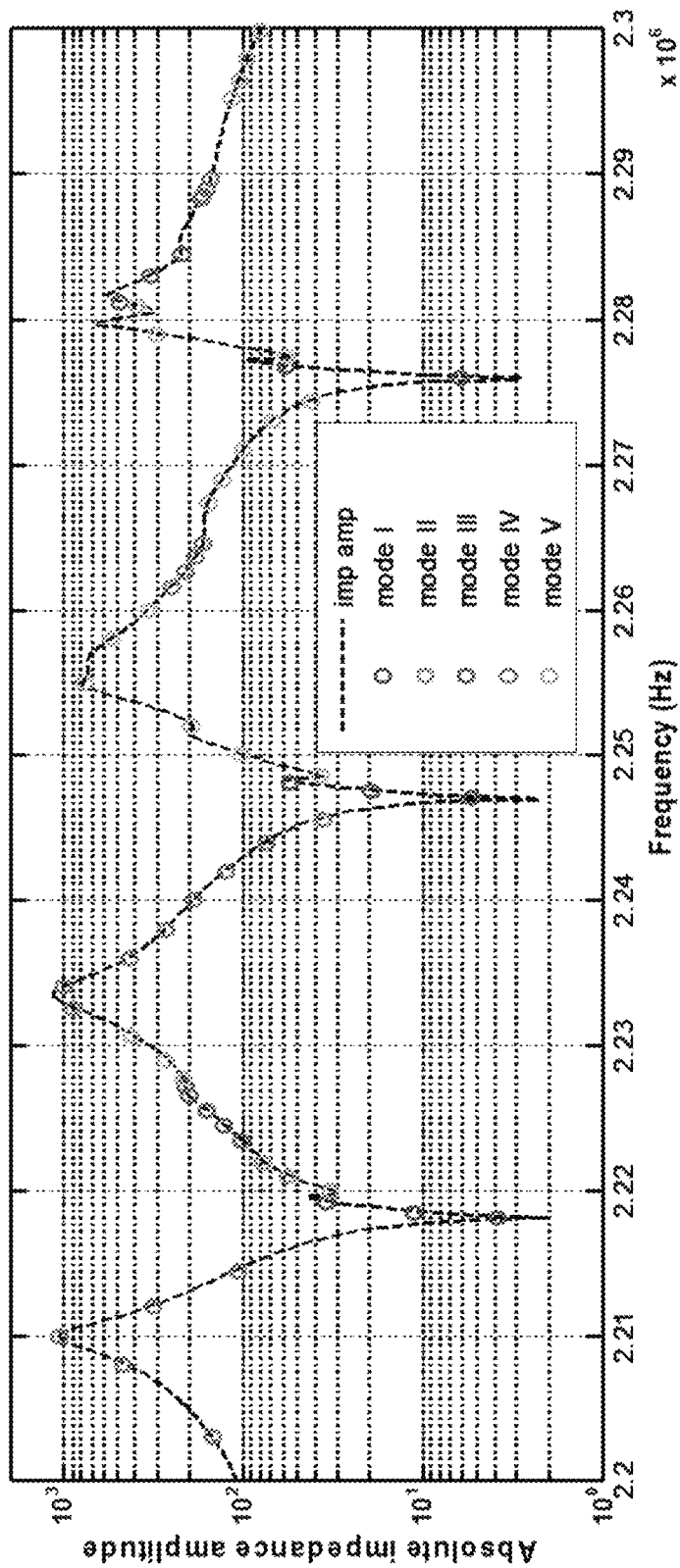
FIG. 65 is a graph illustrating absolute impedance amplitude.
Figure 66:
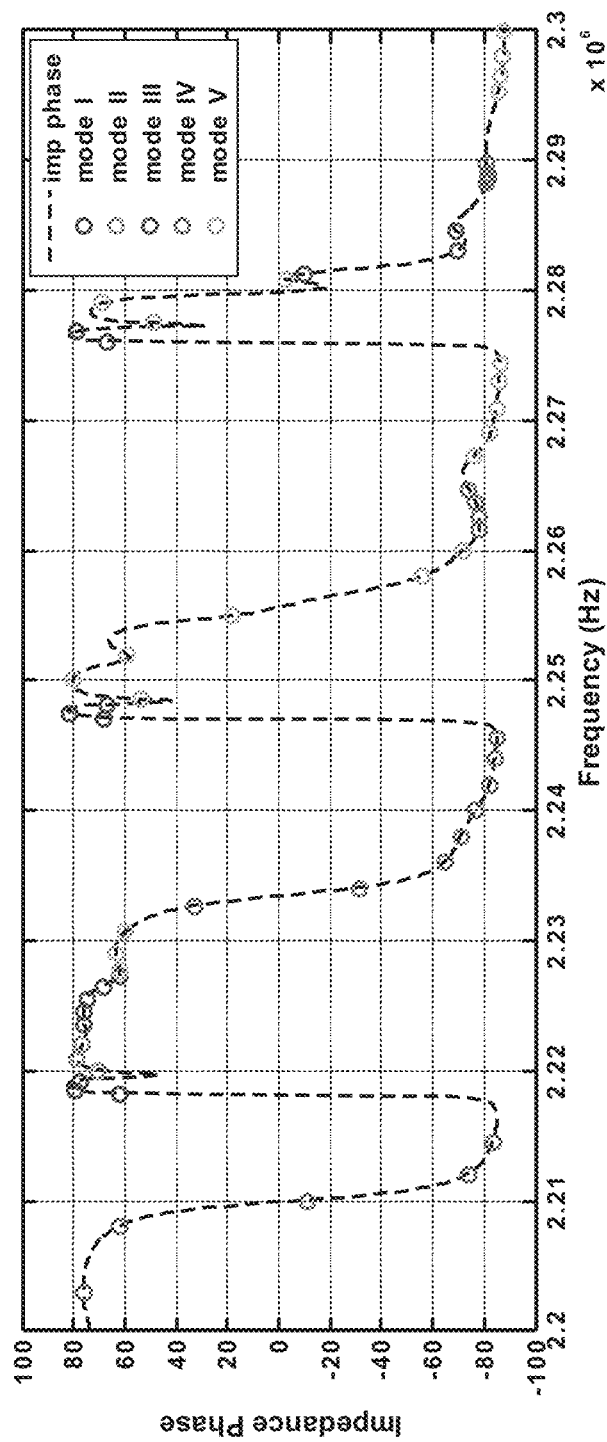
FIG. 66 is a graph illustrating impedance phase.
Figure 67:
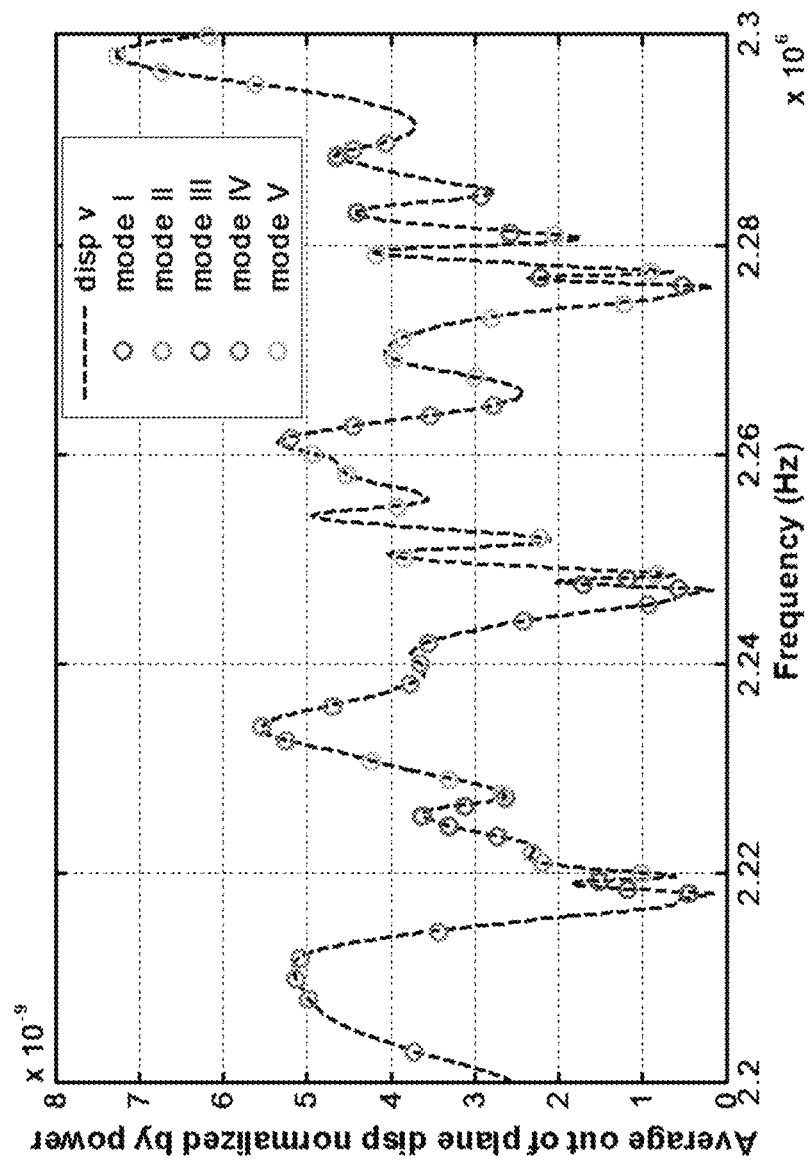
FIG. 67 is a graph illustrating displacement normalized by power.
Figure 68:
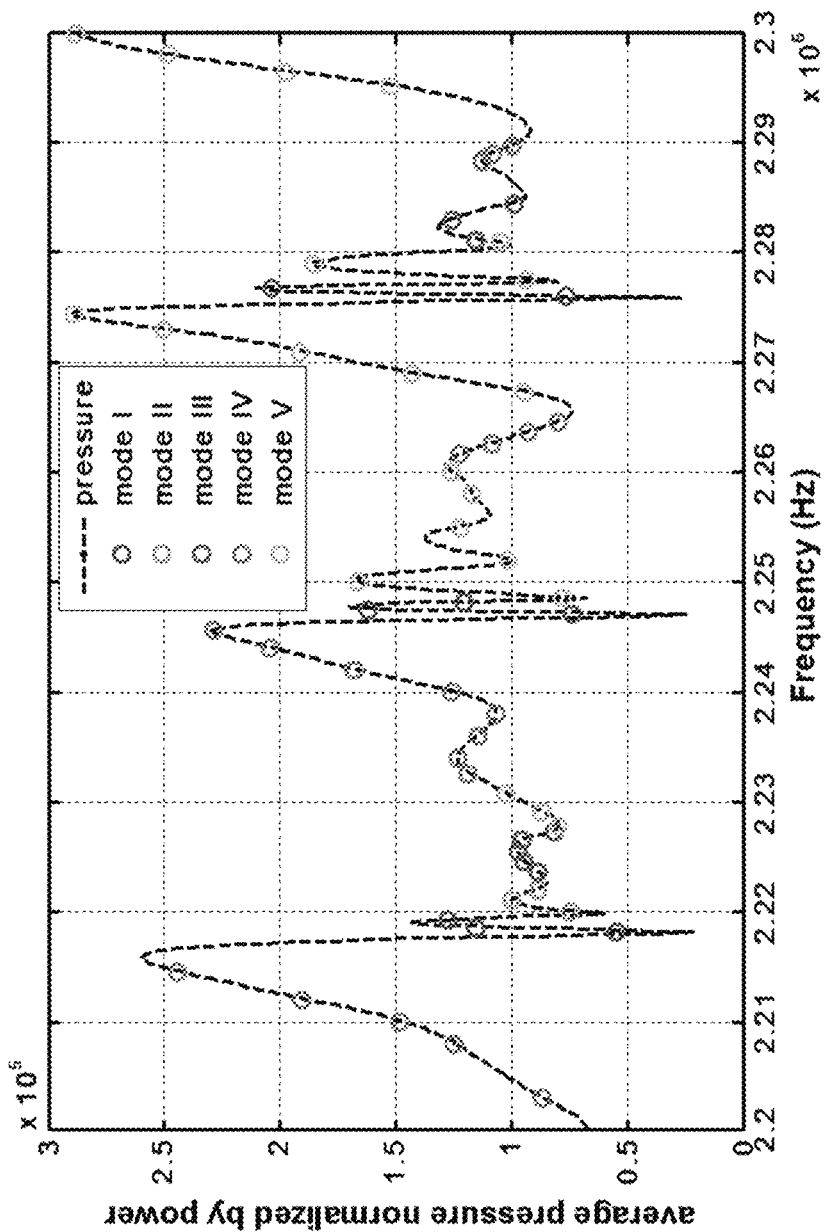
FIG. 68 is a graph illustrating average pressure normalized by power.
Figure 69:
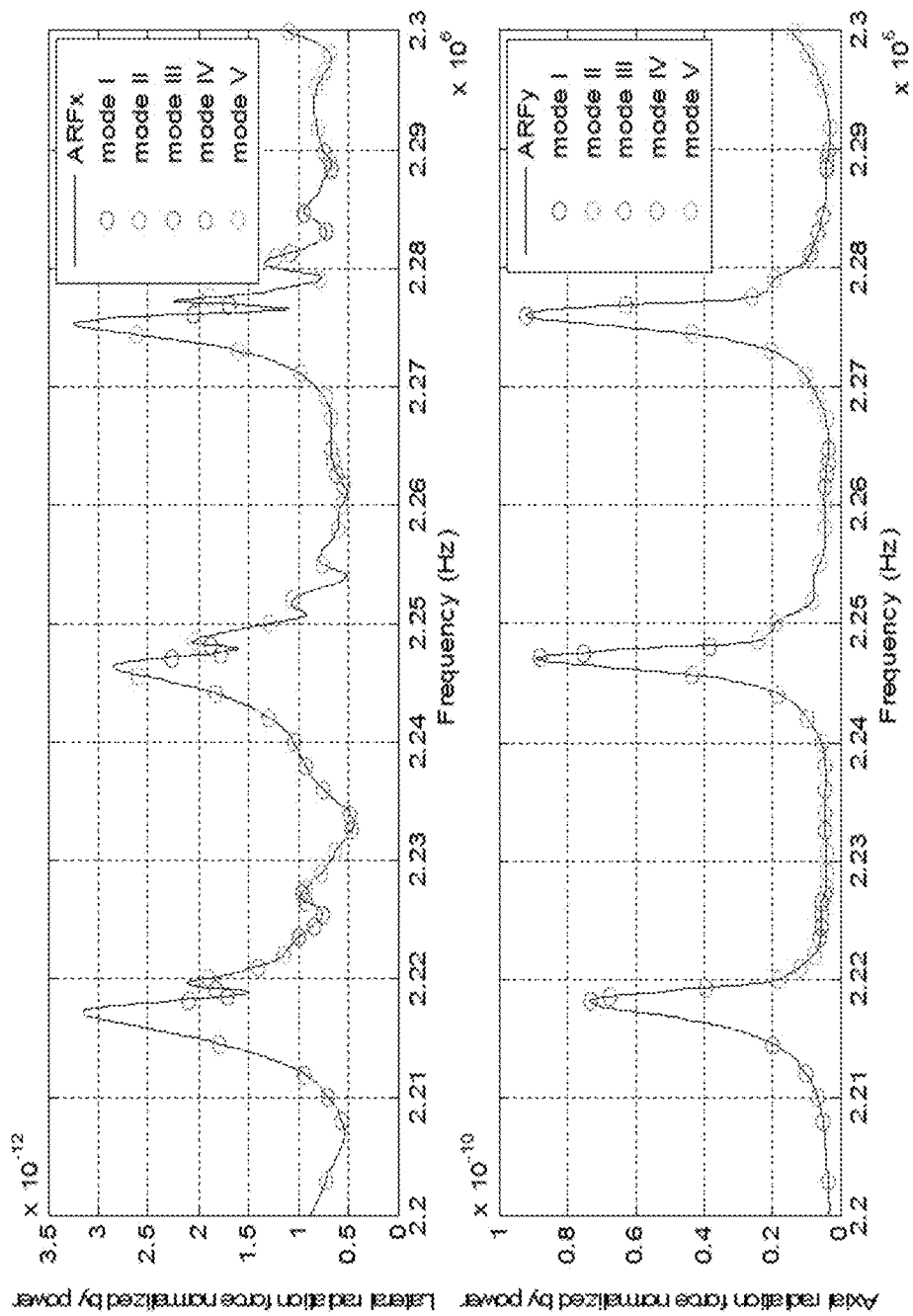
FIG. 69 shows two graphs illustrating axial and lateral radiation force.

FIG. 63 is a graph illustrating piezoelectric displacement. FIG. 64 is a graph illustrating power and impedance amplitude. FIG. 65 is a graph illustrating absolute impedance amplitude. A number of modes are identified along the line of the graph. Higher order modes can be attained near peak absolute impedance amplitudes. FIG. 66 is a graph illustrating impedance phase. Again, a number of modes are illustrated along the line of the graph. FIG. 67 is a graph illustrating displacement normalized by power. Again, a higher order multimode operation can be attained at higher displacement values. FIG. 68 is a graph illustrating average pressure normalized by power. FIG. 69 shows two graphs illustrating axial and lateral radiation force.

Figure 70:
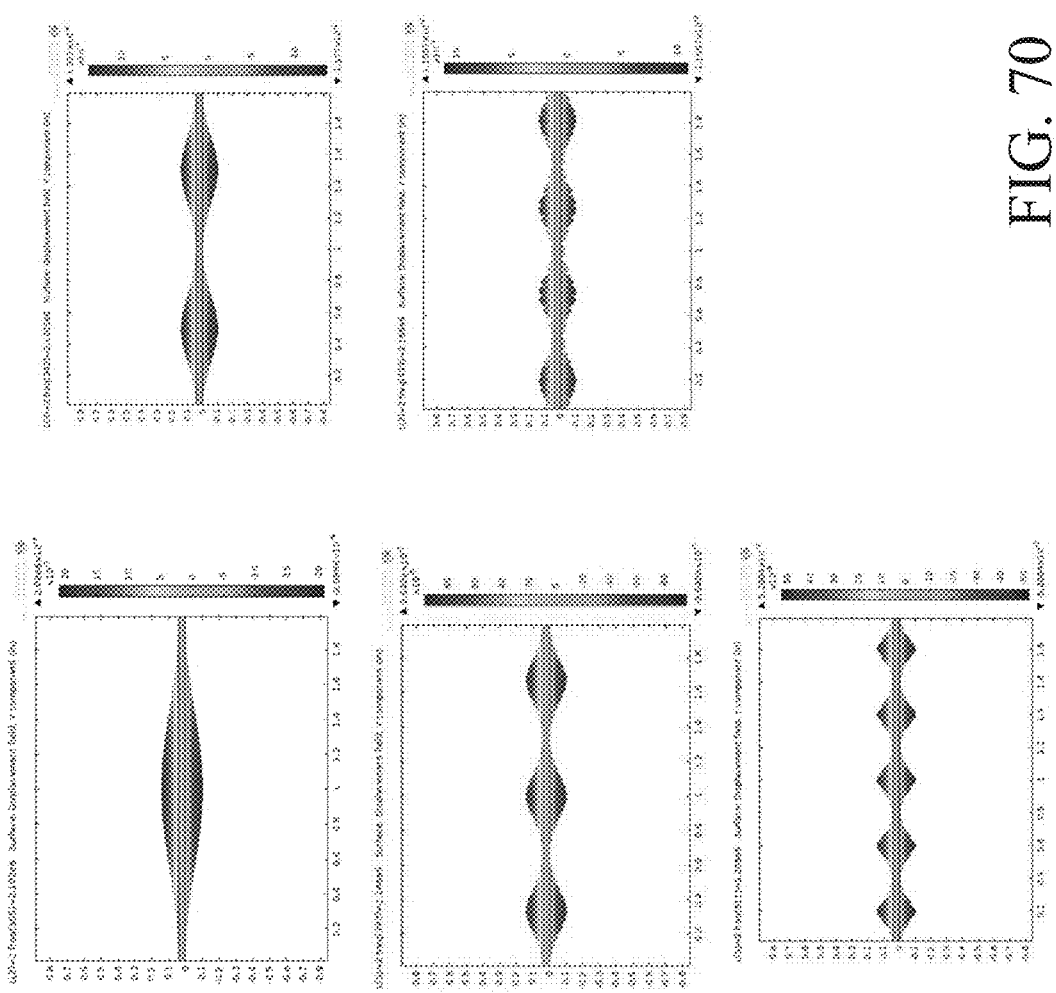
FIG. 70 shows five graphs illustrating displacement for various modes.
Figure 71:
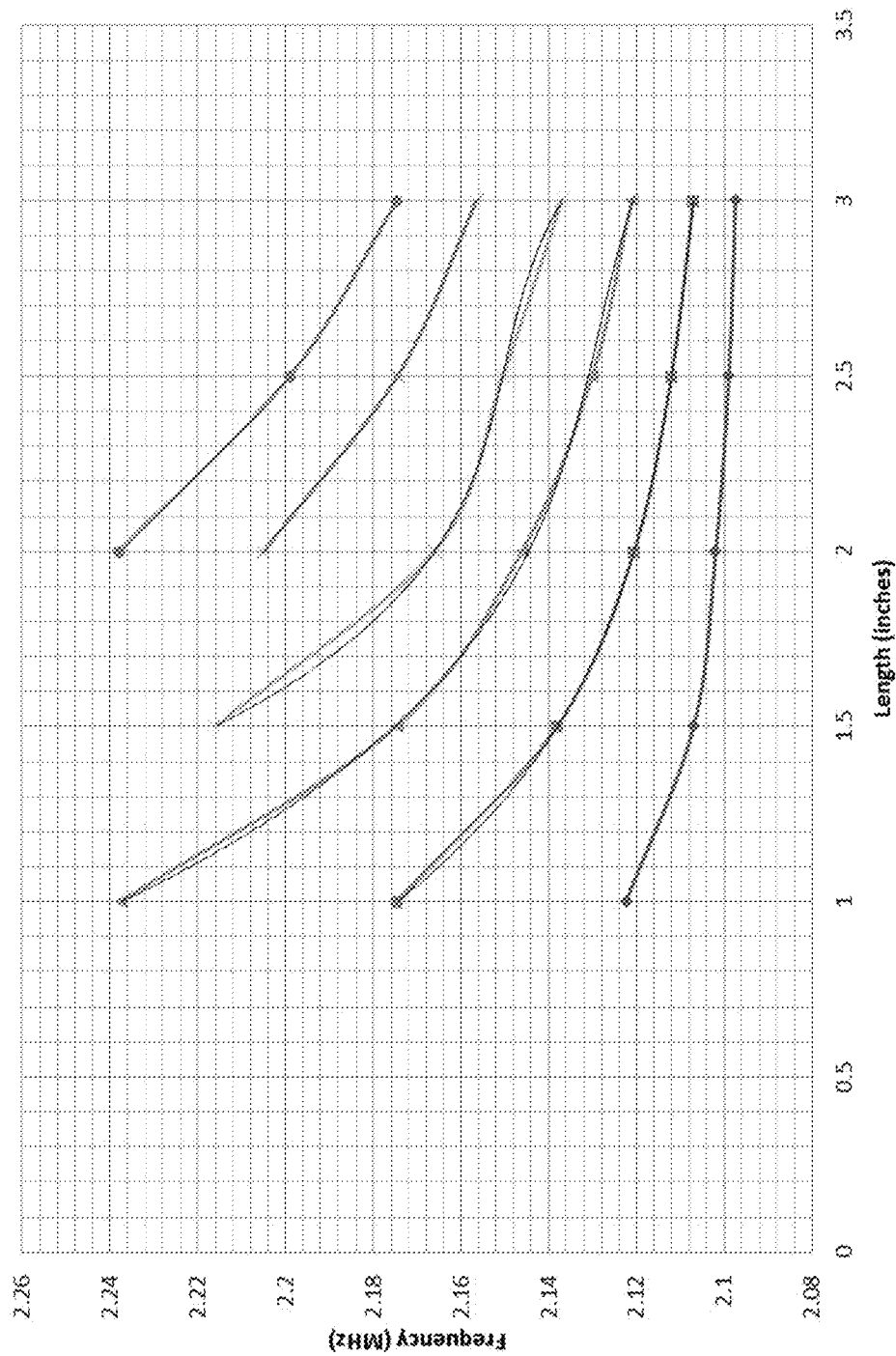
FIGS. 71, 72 are graphs illustrating relationships between dimensions of piezoelectric material and number of modes.
Figures 72, 73:
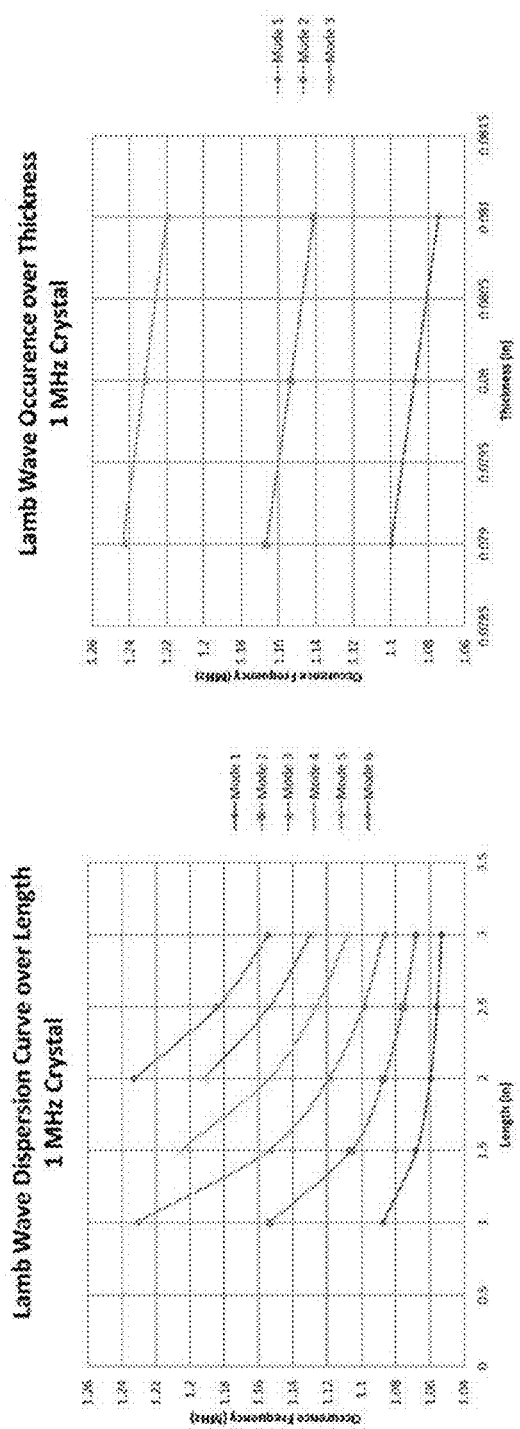
FIG. 73 is a graph illustrating turbidity, resistance, reactance and real power versus time for a planar wave.
Figure 74:
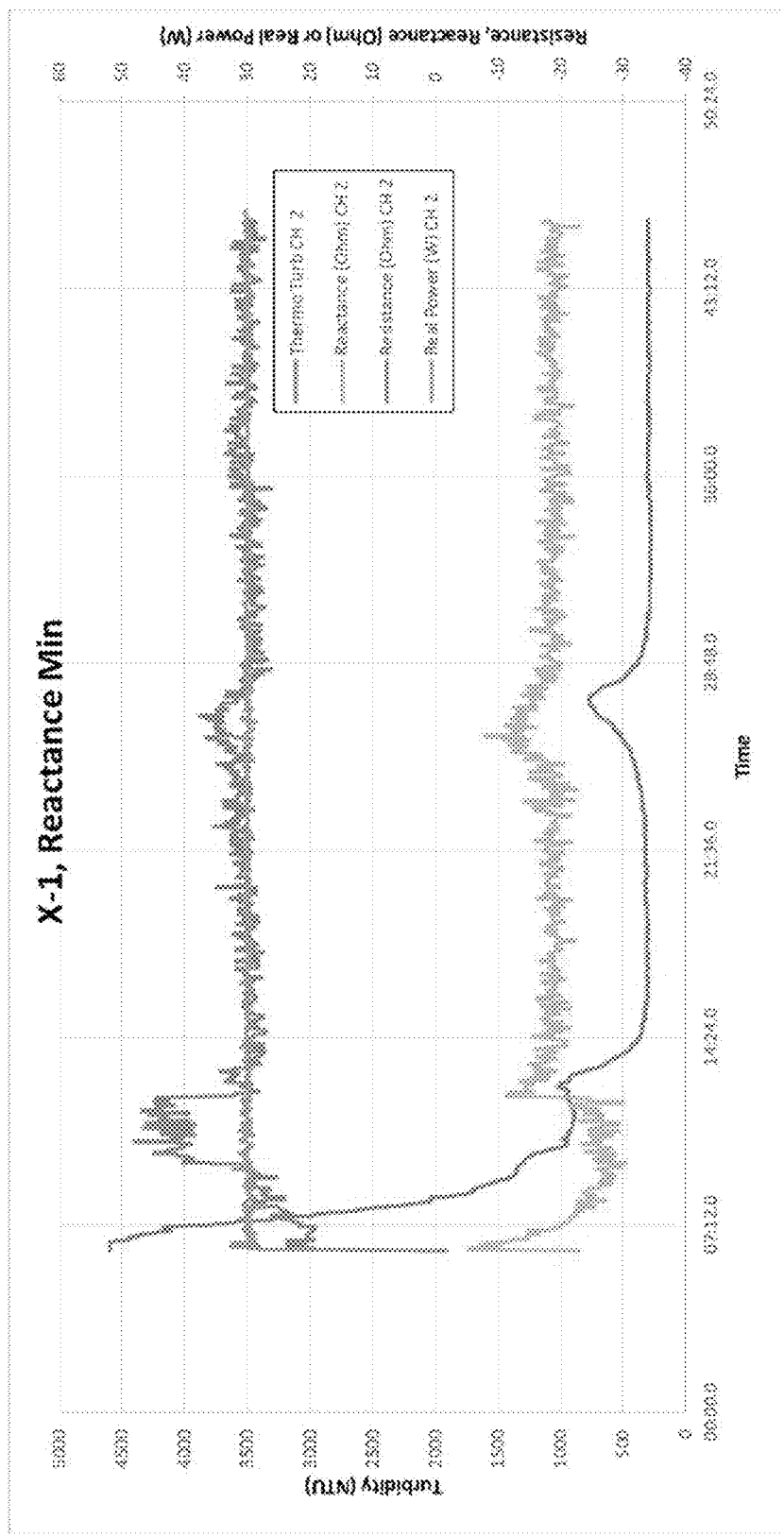
FIG. 74 is a graph illustrating turbidity, resistance, reactance and real power versus time for multimode operation at a minimum reactance point.
Figure 75:
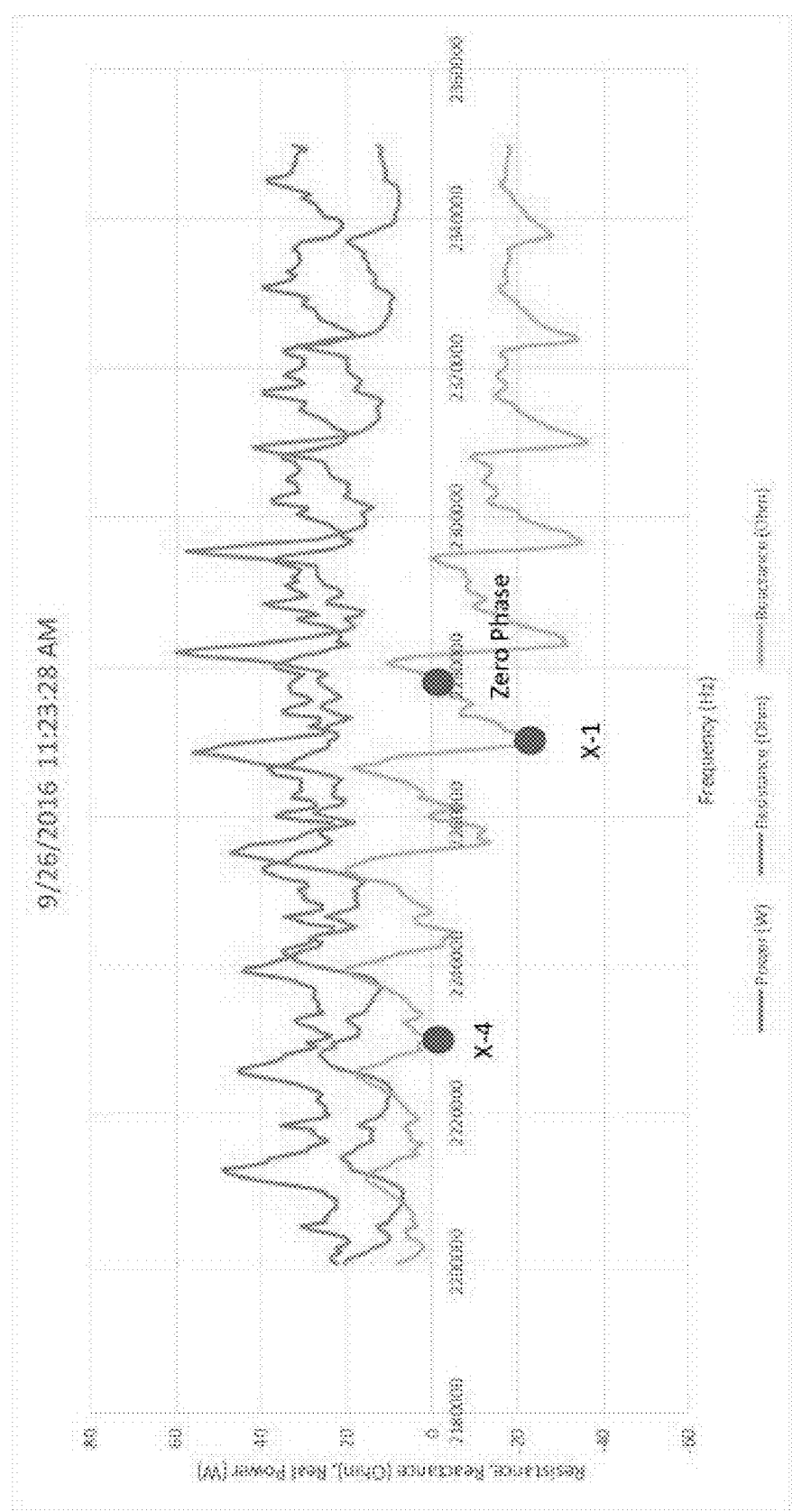
FIG. 75 is a graph illustrating resistance, reactance and real power versus frequency.
Figure 76:
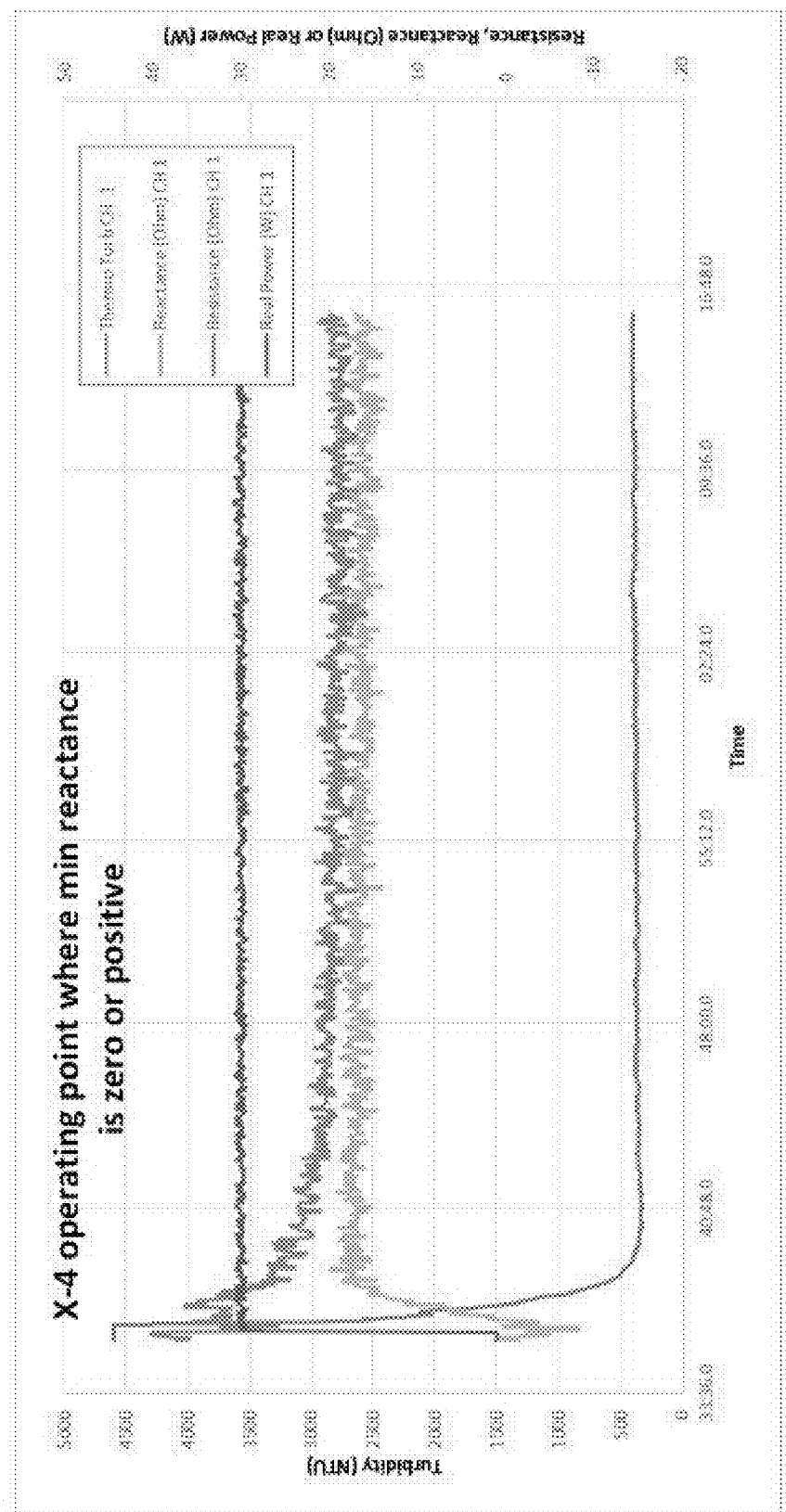
FIG. 76 is a graph illustrating turbidity, resistance, reactance and real power versus time for multimode operation at a minimum reactance point that is zero or positive.
Figure 77:
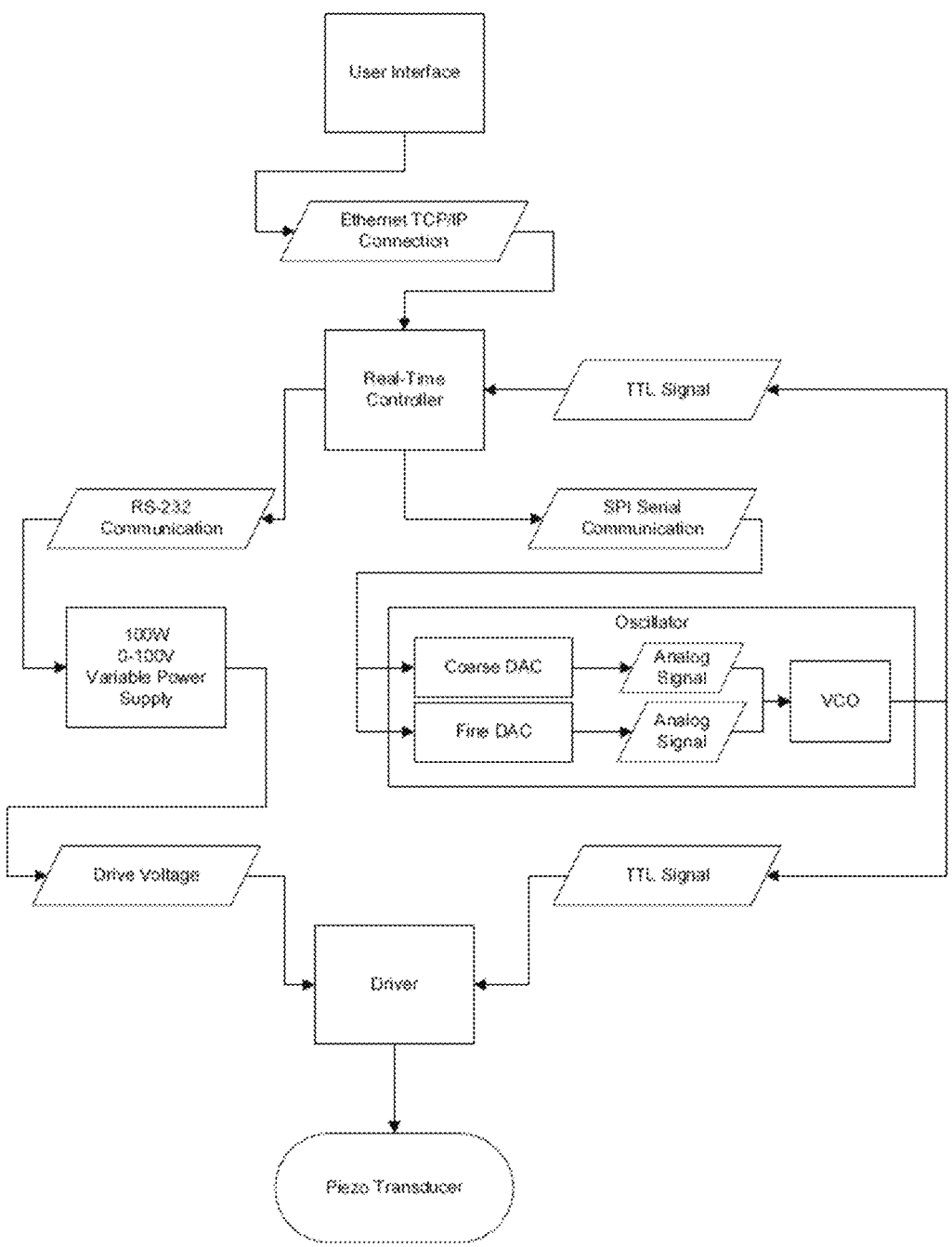
FIGS. 77, 78, 79 and 80 are flowcharts illustrating hardware and software configurations.
Figure 78:
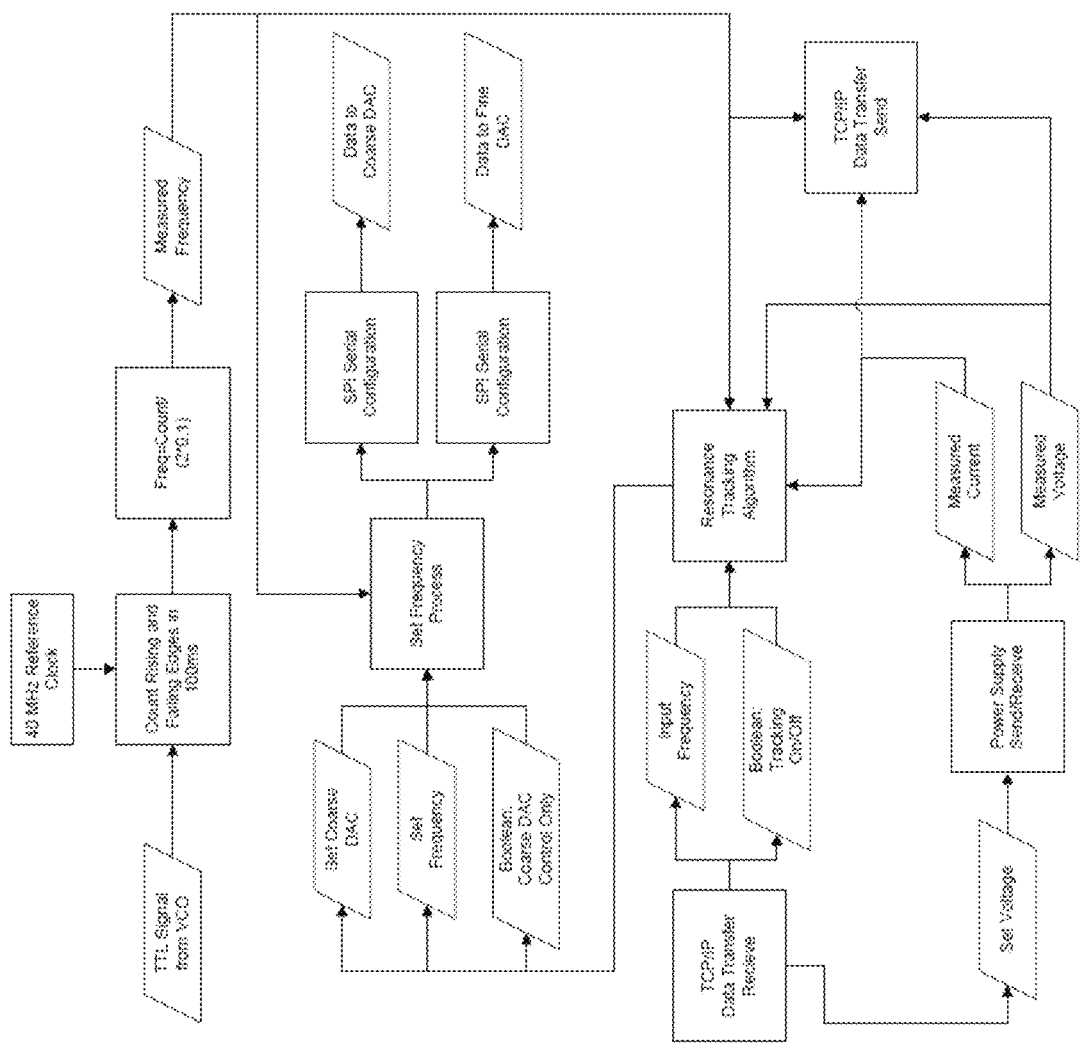
Figure 79:
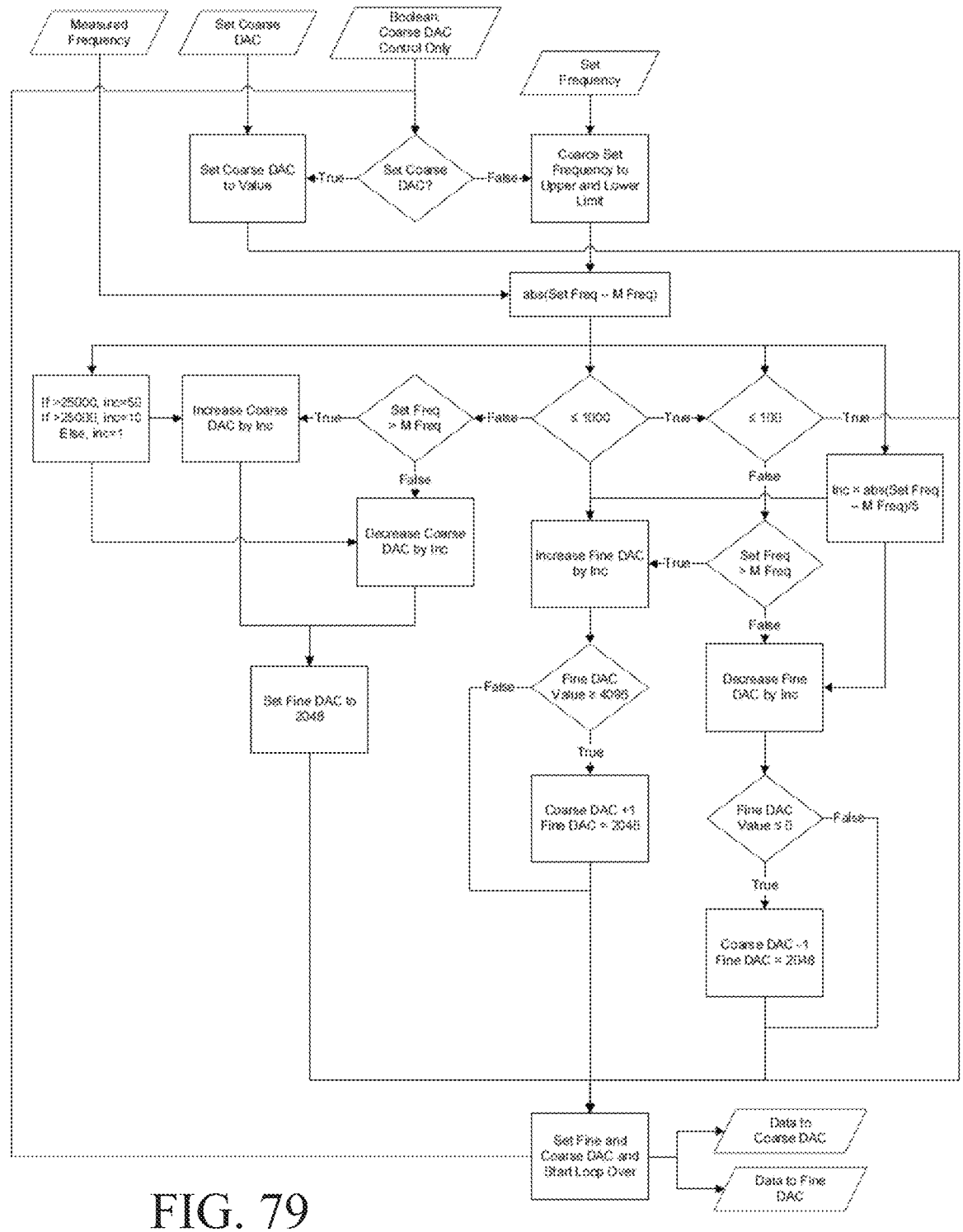

FIG. 70 shows five graphs illustrating displacement for various modes. FIGS. 71, 72 are graphs illustrating relationships between dimensions of piezoelectric material and number of modes. FIG. 73 is a graph illustrating turbidity, resistance, reactance and real power versus time for a planar wave. FIG. 74 is a graph illustrating turbidity, resistance, reactance and real power versus time for multimode operation at a minimum reactance point. FIG. 75 is a graph illustrating resistance, reactance and real power versus frequency. FIG. 76 is a graph illustrating turbidity, resistance, reactance and real power versus time for multimode operation at a minimum reactance point that is zero or positive.

The performance illustrated in FIG. 73 is fairly poor, with a minimum turbidity of approximately 1000, and typical turbidity performance being much higher. The performance illustrated in FIG. 73 is illustrated in FIG. 75 and zero phase. The acoustic transducer in this case is producing a planar mode acoustic standing wave, which can be envisioned as piston operation.

Figure 80:
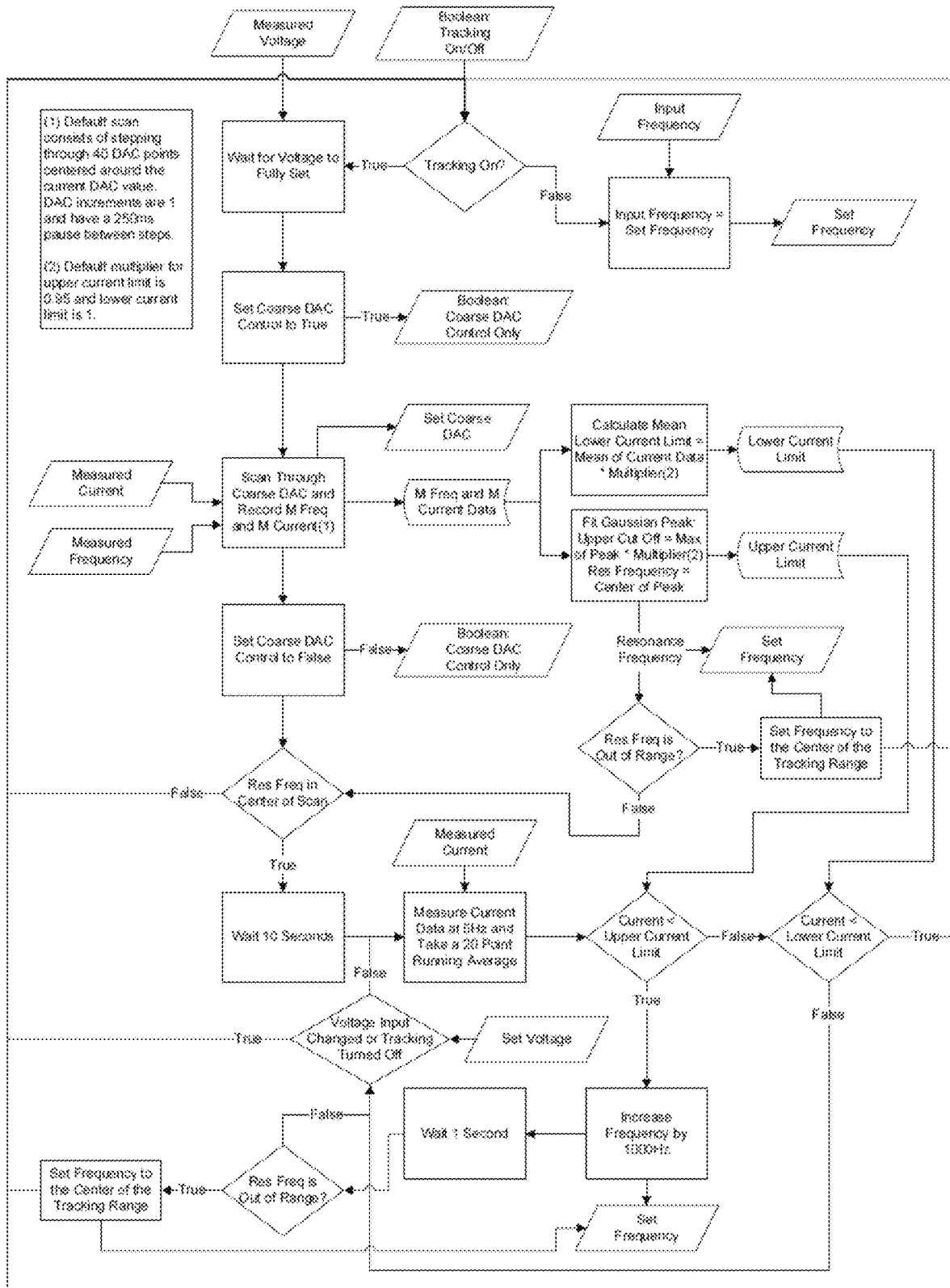
Figure 81:
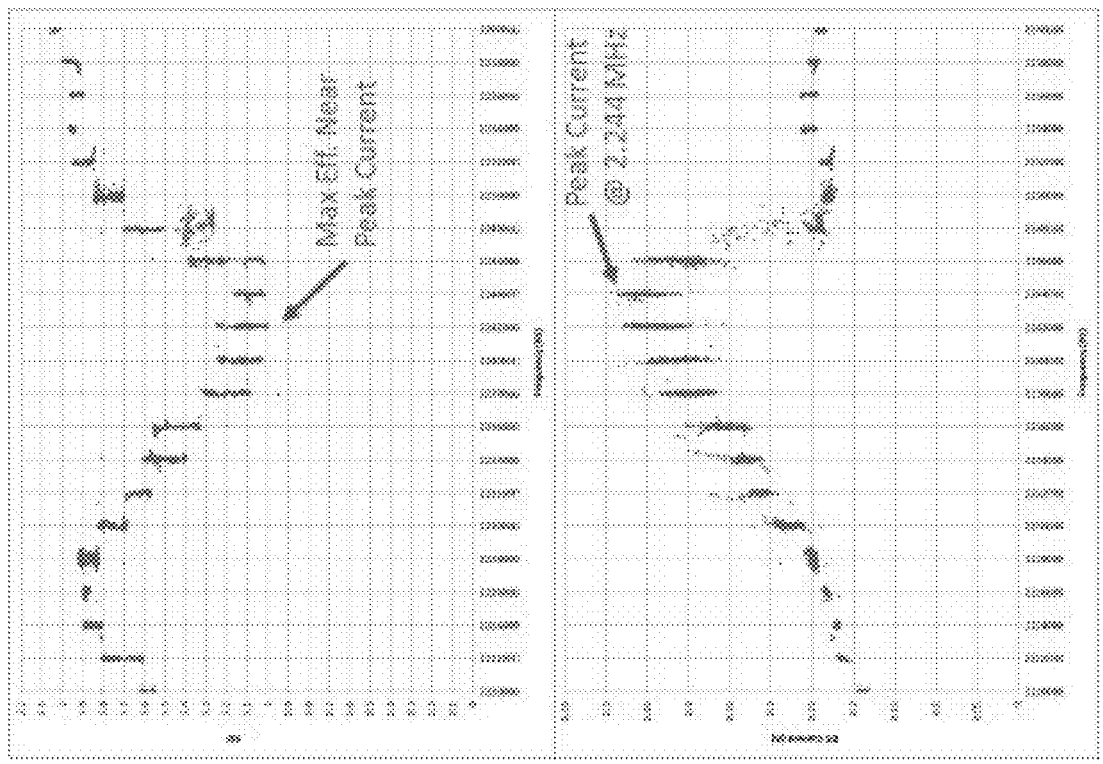
FIG. 81 shows graphs illustrating a frequency sweep response.
Figure 82:
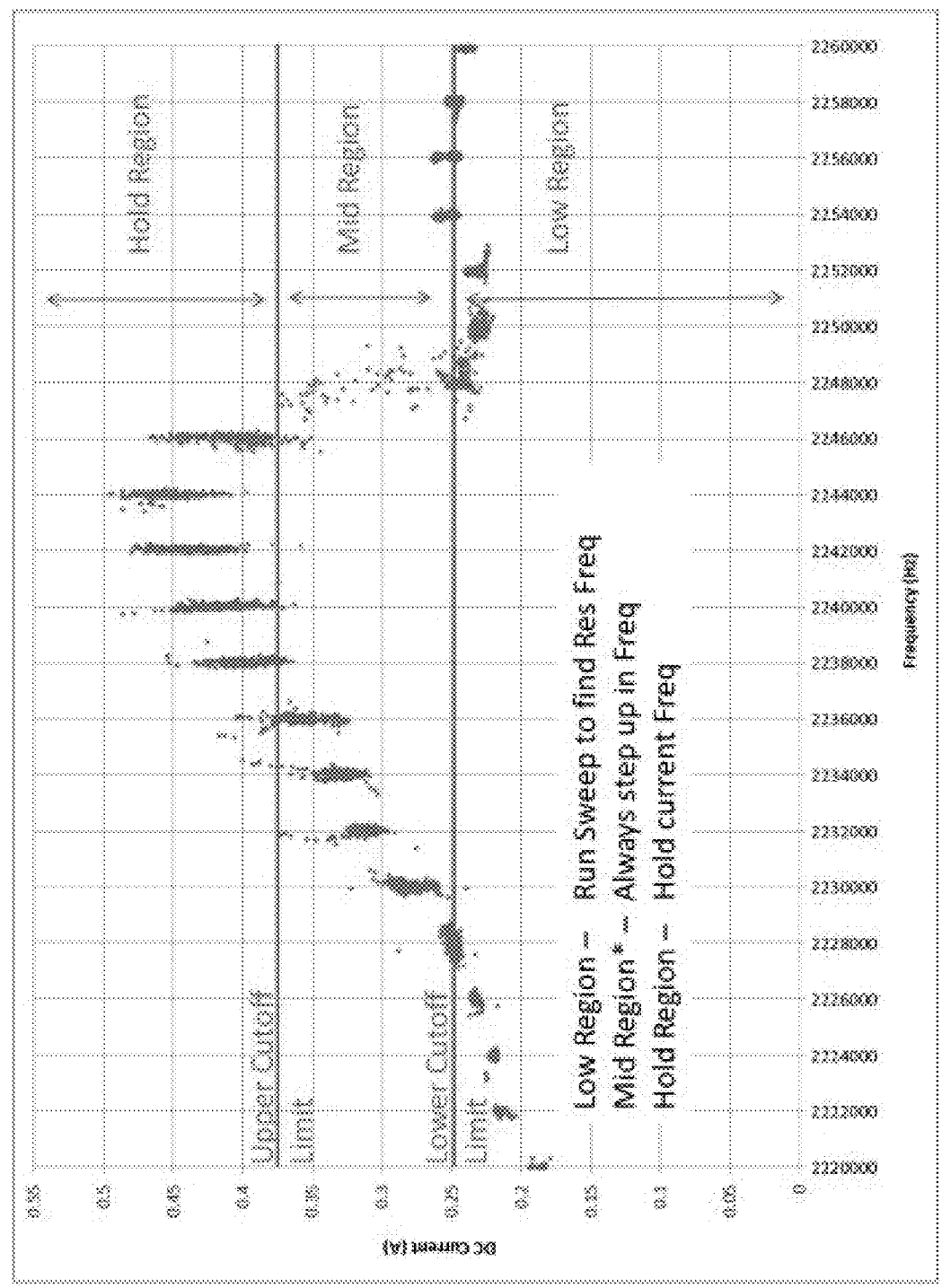
FIG. 82 is a graph illustrating regions of operation.
Figure 83:
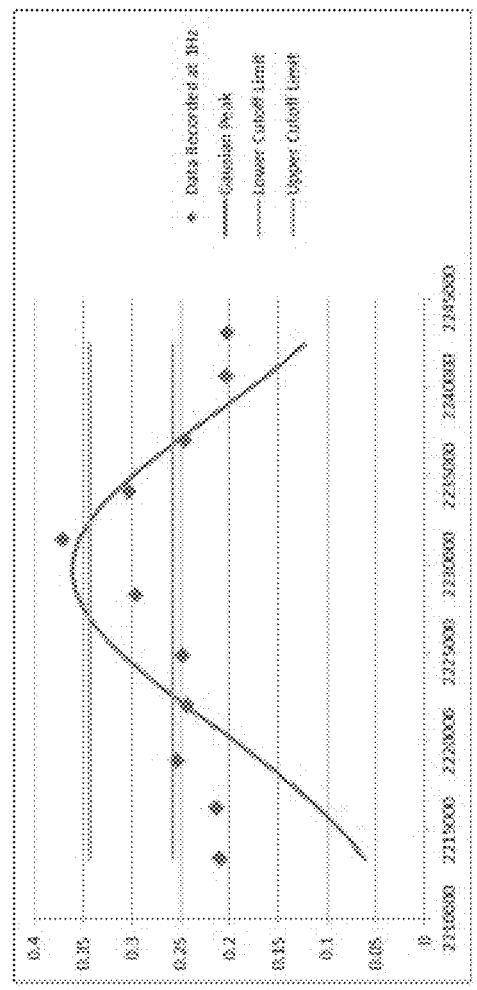
FIG. 83 is a graph and text illustrating a control technique.

The turbidity performance in FIG. 74 is a significant increase over that illustrated in FIG. 73, with minimum turbidity being often less than 500. The acoustic transducer in this case is operated at a reactance minimum, illustrated in the graph of FIG. 75 at point X-1. Point X-1 represents multimode operation, which can produce axial and lateral forces on particles in the fluid through which the acoustic standing wave passes. These acoustic forces are illustrated in an example in FIG. 69. Thus, providing a control technique for operating the acoustic transducer at a reactance minimum can attain desired performance. The desired performance can be attained even at zero phase when operating in multimode, as illustrated with point X-4 in FIG. 75. Point X-4 is a reactance minimum with zero phase, which can achieve desired performance due to multimode operation, unlike the zero phase planar wave operation. FIG. 76 is a graph illustrating turbidity, resistance, reactance and real power versus time for multimode operation at a minimum reactance point that is zero or positive;

FIGS. 77, 78, 79 and 80 are flowcharts illustrating hardware and software configurations. FIG. 80 shows graphs illustrating a frequency sweep response. FIG. 81 shows graphs illustrating a frequency sweep response. FIG. 82 is a graph illustrating regions of operation. FIG. 83 is a graph and text illustrating a control technique. FIG. 84 is text illustrating a control technique.

Figure 85:
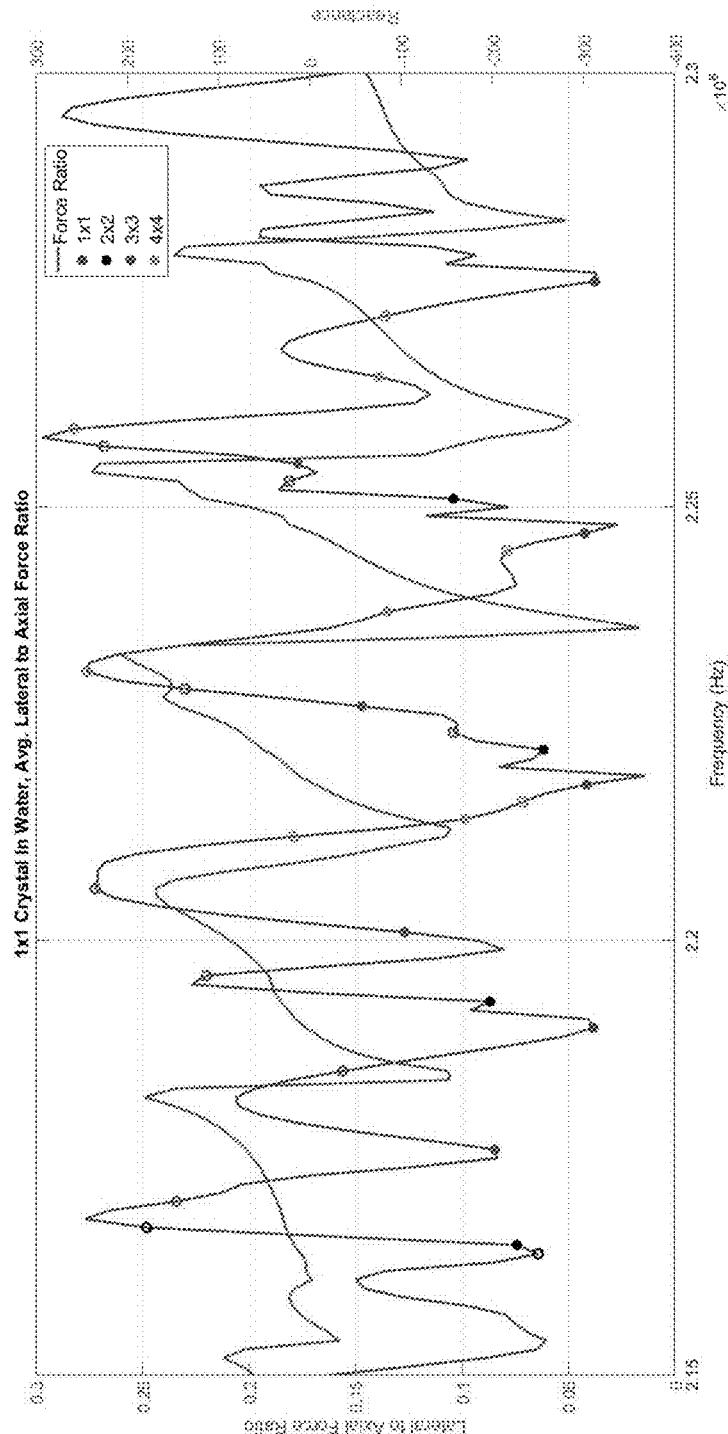
FIGS. 85, 86, 87 and 88 are graphs illustrating various parameters versus frequency.

FIGS. 85, 86, 87 and 88 are graphs providing plots of various parameters versus frequency. FIG. 85 is a graph with a left-hand scale measuring a ratio of lateral-to-axial forces for various frequencies (blue line), and a right-hand scale measuring reactance (red line). Identified on the ratio graph lines are locations and ranges for various modes of multimode operation. A range of a given mode for multimode operation is identified as existing between open circles, with a primary or dominant frequency for that mode being identified as a solid circle.

Figure 86:
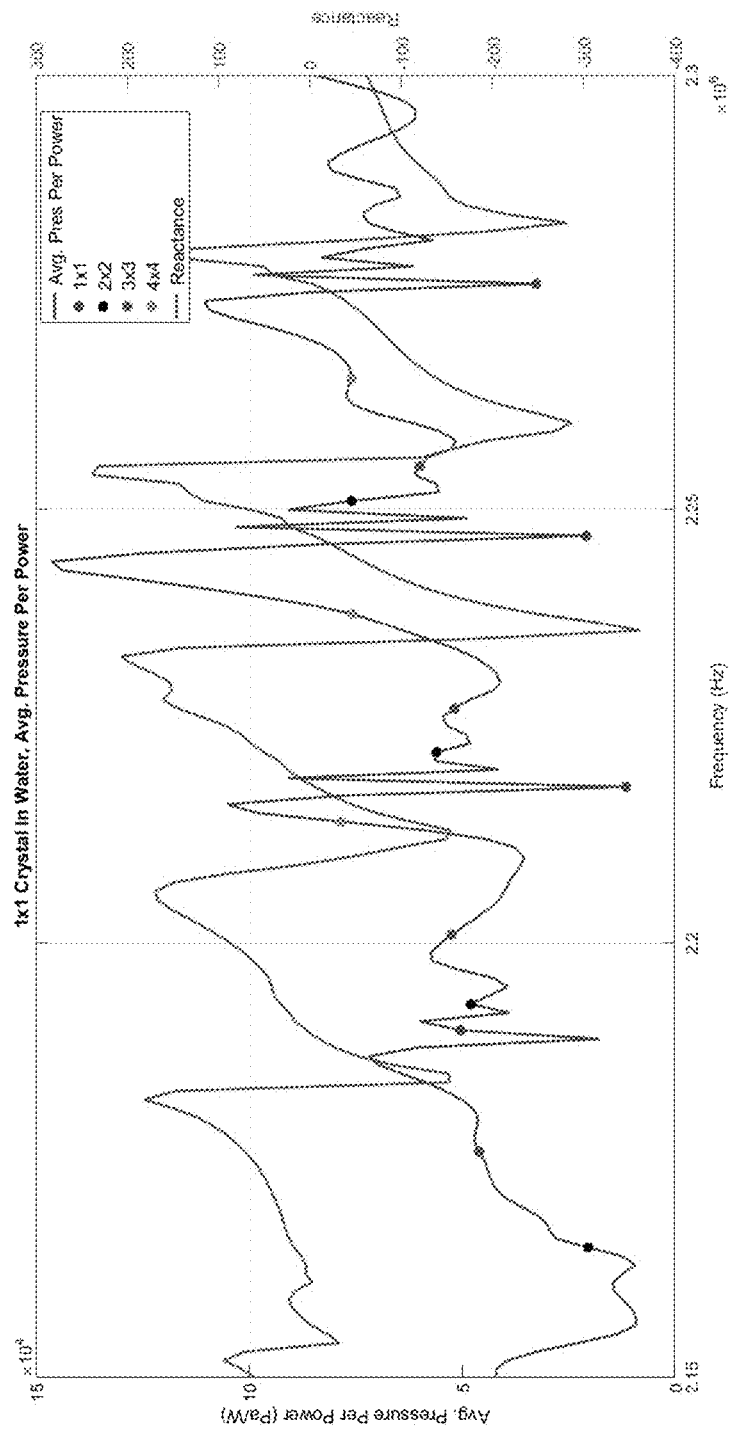

FIG. 86 is a graph with a left-hand scale measuring average pressure per power for various frequencies (blue line), and a right-hand scale measuring reactance (red line). Identified on the pressure graph line are locations and ranges for various modes of multimode operation. A given mode for multimode operation is identified as a circle that a primary or dominant frequency for that mode.

Figure 87:
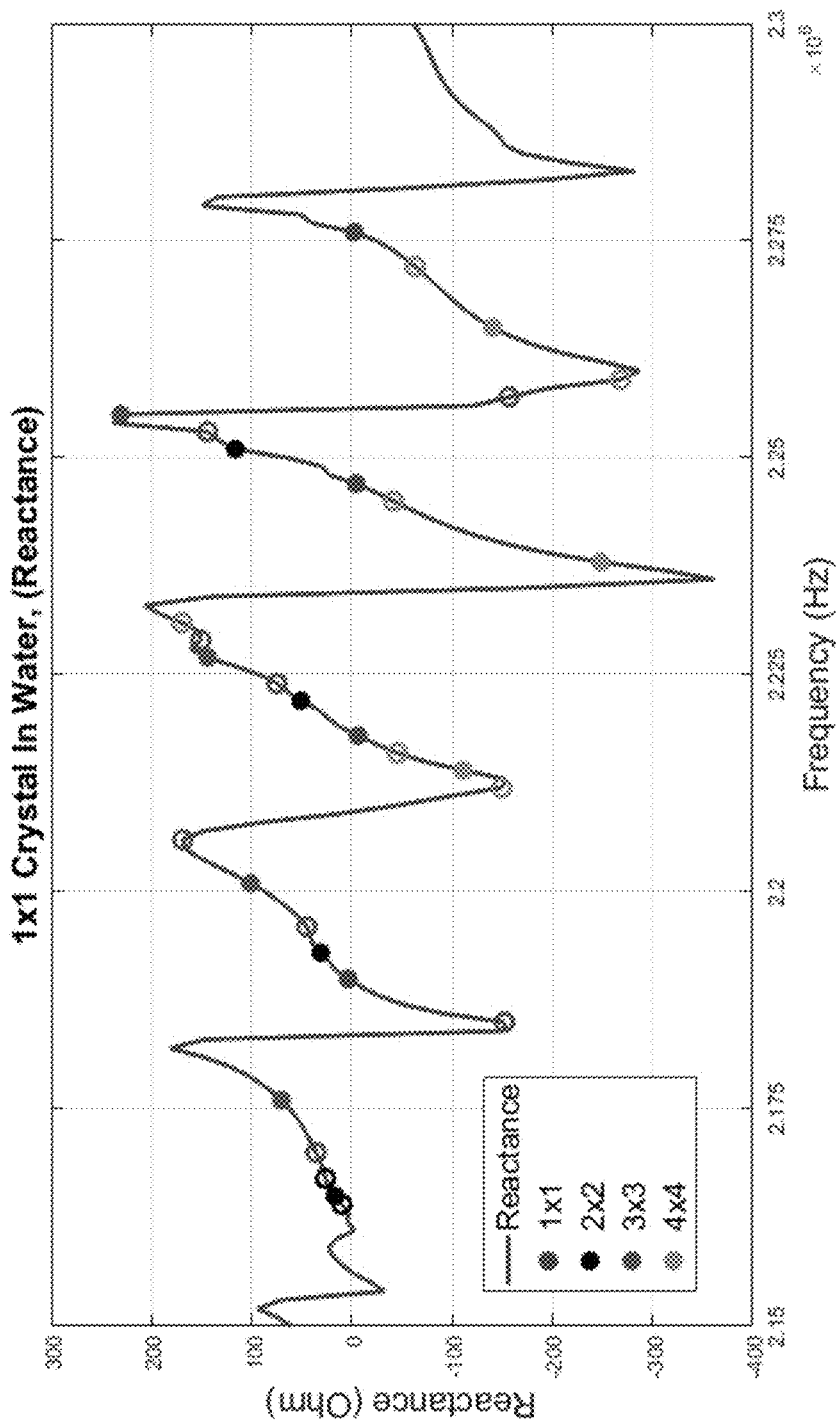

FIG. 87 is a graph showing reactance versus frequency, with a number of modes for multimode operation being identified as locations and ranges on the graph line. A range of a given mode for multimode operation is identified as existing between open circles, with a primary or dominant frequency for that mode being identified as a solid circle.

Figure 88:
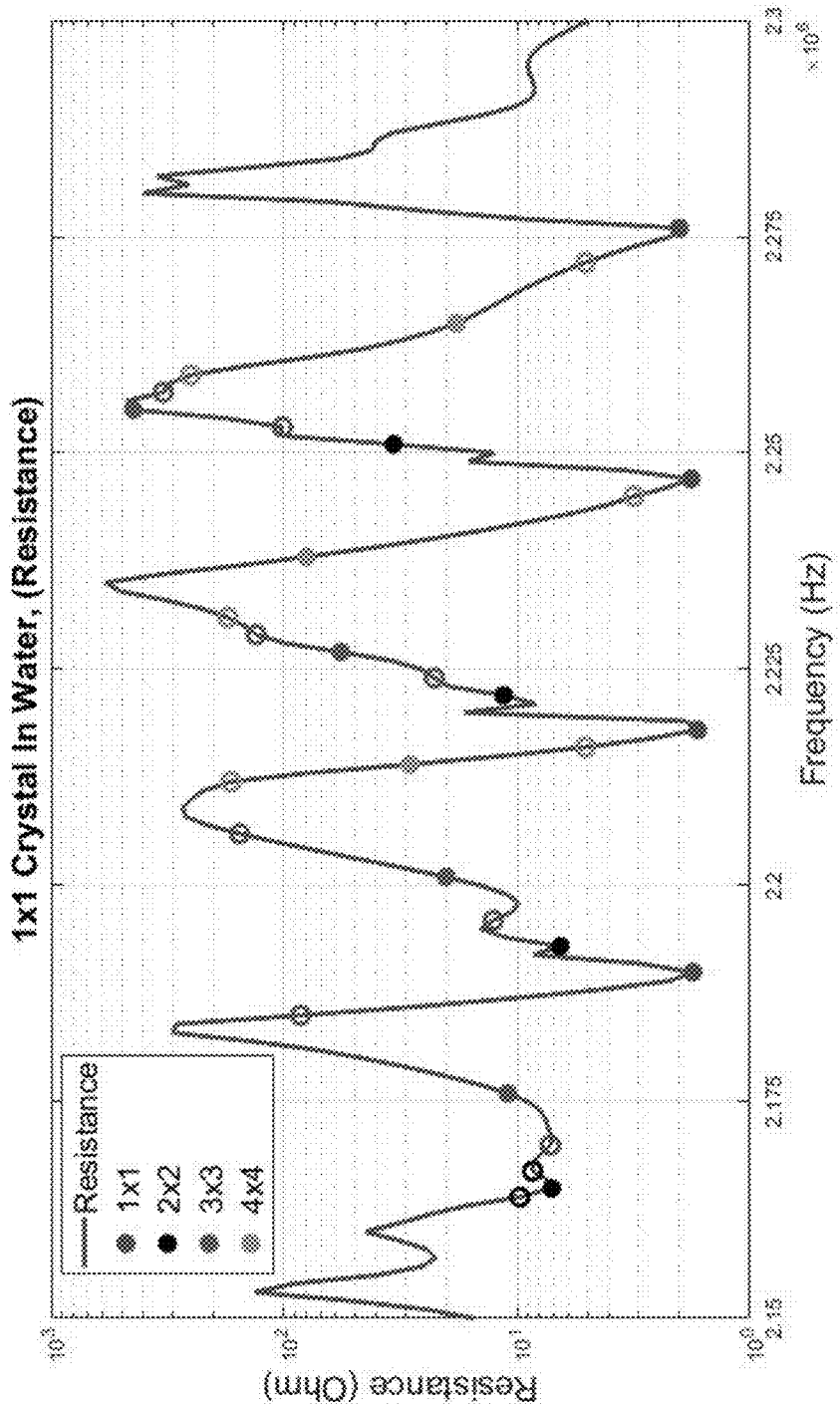

FIG. 88 is a graph showing resistance versus frequency, with a number of modes for multimode operation being identified as locations and ranges on the graph line. A range of a given mode for multimode operation is identified as existing between open circles, with a primary or dominant frequency for that mode being identified as a solid circle.

As can be seen with FIGS. 85-88, multimode operation is strong near minimum reactance. FIG. 85 shows a force ratio plot with a ratio of >0.1 at minimum reactance points. Along with these simulation results, experimental data showing minimum reactance gives the best performance. Note that the tests illustrated in FIGS. 85-88 reflect steady state tests.

The acoustophoretic devices of the present disclosure, can be used in a filter "train," in which multiple different filtration steps are used to clarify or purify an initial fluid/particle mixture to obtain the desired product and manage different materials from each filtration step. Each filtration step can be optimized to remove a particular material, improving the overall efficiency of the clarification process. An individual acoustophoretic device can operate as one or multiple filtration steps. For example, each individual ultrasonic transducer within a particular acoustophoretic device can be operated to trap materials within a given particle range. In particular, the acoustophoretic device can be used to remove large quantities of material, reducing the burden on subsequent downstream filtration steps/stages. Additional filtration steps/stages can be placed upstream or downstream of the acoustophoretic device. Multiple acoustophoretic devices can be used as well. Desirable biomolecules or cells can be recovered/separated after such filtration/purification.

The outlets of the acoustophoretic devices of the present disclosure (e.g. clarified fluid and concentrated cells) can be fluidly connected to any other filtration step or filtration stage. Such filtration steps can include various methods such as depth filtration, sterile filtration, size exclusion filtration, or tangential filtration. Depth filtration uses physical porous filtration mediums that can retain material through the entire depth of the filter. In sterile filtration, membrane filters with extremely small pore sizes are used to remove microorganisms and viruses, generally without heat or irradiation or exposure to chemicals. Size exclusion filtration separates materials by size and/or molecular weight using physical filters with pores of given size. In tangential filtration, the majority of fluid flow is across the surface of the filter, rather than into the filter.

Chromatography can also be used, including cationic chromatography columns, anionic chromatography columns, affinity chromatography columns, mixed bed chromatography columns. Other hydrophilic/hydrophobic processes can also be used for filtration purposes.

Desirably, flow rates through the devices of the present disclosure can be a minimum of 4.65 mL/min per cm2 of cross-sectional area of the acoustic chamber. Even more desirably, the flow rate can be as high as 25 mL/min/cm2, and can range as high as 40 mL/min/cm2 to 270 mL/min/cm2, or even higher. This is true for batch reactors, fed-batch bioreactors and perfusion bioreactors, with which the acoustophoretic devices and transducers discuss herein may be used. For example, the acoustophoretic devices may be interposed between a bioreactor and a downstream filtration device, such as those discussed above. The acoustophoretic devices may be configured to be downstream of a filtration device coupled to a bioreactor, and may be upstream of other filtration devices. In addition, the acoustophoretic devices and/or other filtration devices can be configured to have a feedback to the bioreactor.

The methods, systems, and devices discussed above are examples. Various configurations may omit, substitute, or add various procedures or components as appropriate. For instance, in alternative configurations, the methods may be performed in an order different from that described, and that various steps may be added, omitted, or combined. Also, features described with respect to certain configurations may be combined in various other configurations. Different aspects and elements of the configurations may be combined in a similar manner. Also, technology evolves and, thus, many of the elements are examples and do not limit the scope of the disclosure or claims.

Specific details are given in the description to provide a thorough understanding of example configurations (including implementations). However, configurations may be practiced without these specific details. For example, well-known processes, structures, and techniques have been shown without unnecessary detail to avoid obscuring the configurations. This description provides example configurations only, and does not limit the scope, applicability, or configurations of the claims. Rather, the preceding description of the configurations provides a description for implementing described techniques. Various changes may be made in the function and arrangement of elements without departing from the spirit or scope of the disclosure.

Also, configurations may be described as a process that is depicted as a flow diagram or block diagram. Although each may describe the operations as a sequential process, many of the operations can be performed in parallel or concurrently. In addition, the order of the operations may be rearranged. A process may have additional stages or functions not included in the figure.

Having described several example configurations, various modifications, alternative constructions, and equivalents may be used without departing from the scope of the disclosure. For example, the above elements may be components of a larger system, wherein other structures or processes may take precedence over or otherwise modify the application of the invention. Also, a number of operations may be undertaken before, during, or after the above elements are considered. Accordingly, the above description does not bound the scope of the claims.

A statement that a value exceeds (or is more than) a first threshold value is equivalent to a statement that the value meets or exceeds a second threshold value that is slightly greater than the first threshold value, e.g., the second threshold value being one value higher than the first threshold value in the resolution of a relevant system. A statement that a value is less than (or is within) a first threshold value is equivalent to a statement that the value is less than or equal to a second threshold value that is slightly lower than the first threshold value, e.g., the second threshold value being one value lower than the first threshold value in the resolution of the relevant system.

The invention claimed is:

1. A method for controlling an acoustophoretic device that uses an ultrasonic transducer to create a multi-dimensional acoustic standing wave, the method comprising:
   driving an amplifier electrically connected to the at least one ultrasonic transducer to send an output signal to the ultrasonic transducer;
   measuring a first voltage between the amplifier and a predetermined first impedance;
   measuring a second voltage between the first impedance and the at least one ultrasonic transducer;
   measuring a current from the output signal between the measured first and second voltages;
   determining an actual impedance of the ultrasonic transducer from the measured current and measured first and second voltages; and
   adjusting the output signal from the amplifier to obtain a desired impedance of the ultrasonic transducer.

2. The method of claim 1, wherein the actual impedance of the ultrasonic transducer is proportional to both the measured current and the first impedance and is inversely proportional to both the measured first and second voltages.

3. The method of claim 1, further comprising determining an electrical power consumed by the ultrasonic transducer from the measured second voltage and the impedance of the at least one ultrasonic transducer.

4. The method of claim 3, wherein the electrical power consumed by the ultrasonic transducer is proportional to the measured second voltage and is inversely proportional to the impedance of the at least one ultrasonic transducer.

5. The method of claim 1, wherein the amplifier is driven by a function generator that generates a low voltage sinusoidal voltage signal that is sent to the amplifier.

6. The method of claim 1, wherein the first and second voltages are measured by an oscilloscope.

7. The method of claim 1, further comprising characterizing the particles using a particle analyzer located downstream of the acoustophoretic device.

8. The method of claim 1, wherein the first impedance is predetermined across a power resistor electrically connected between the amplifier and the ultrasonic transducer.

9. The method of claim 8, wherein the predetermined first impedance across the power resistor is proportional to the first voltage and is inversely proportional to the second voltage.

10. The method of claim 1, further comprising determining the phase angle of the impedance of the ultrasonic transducer.

* * * * *